(12) United States Patent
Van Dongen et al.

(10) Patent No.: US 10,280,462 B2
(45) Date of Patent: May 7, 2019

(54) NUCLEIC ACID AMPLIFICATION PRIMERS FOR PCR-BASED CLONALITY STUDIES

(71) Applicants: Jacobus Johannes Maria Van Dongen, Vorden (NL); Anthonie Willem Langerak, Barendrecht (NL); Eduardus Maria Dominicus Schuuring, Groningen (NL); Jesus Fernando San Miguel, Salamanca (ES); Ramon Garcia Sanz, Salamanca (ES); Antonio Parreira, Lisbon (PT); John Lewis Smith, Wilts (GB); Frances Louise Lavender, Hants (GB); Gareth John Morgan, Surrey (GB); Paul Anthony Stuart Evans, West Yorkshire (GB); Michael Kneba, Westensee (DE); Michael Hummel, Berlin (DE); Elizabeth Anne Macintyre, Meudon (FR); Christian Bastard, Ardouval (FR); Frederic Bernard Louis Davi, Meudon (FR); Monika Brüggemann, Kiel (DE)

(72) Inventors: Jacobus Johannes Maria Van Dongen, Vorden (NL); Anthonie Willem Langerak, Barendrecht (NL); Eduardus Maria Dominicus Schuuring, Groningen (NL); Jesus Fernando San Miguel, Salamanca (ES); Ramon Garcia Sanz, Salamanca (ES); Antonio Parreira, Lisbon (PT); John Lewis Smith, Wilts (GB); Frances Louise Lavender, Hants (GB); Gareth John Morgan, Surrey (GB); Paul Anthony Stuart Evans, West Yorkshire (GB); Michael Kneba, Westensee (DE); Michael Hummel, Berlin (DE); Elizabeth Anne Macintyre, Meudon (FR); Christian Bastard, Ardouval (FR); Frederic Bernard Louis Davi, Meudon (FR); Monika Brüggemann, Kiel (DE)

(*) Notice: Subject to any disclaimer, the term of this patent is extended or adjusted under 35 U.S.C. 154(b) by 451 days.

(21) Appl. No.: 14/312,583

(22) Filed: Jun. 23, 2014

(65) Prior Publication Data
US 2015/0099646 A1   Apr. 9, 2015

Related U.S. Application Data

(63) Continuation of application No. 10/531,106, filed as application No. PCT/NL03/00690 on Oct. 13, 2003, now Pat. No. 8,859,748.

(60) Provisional application No. 60/417,779, filed on Oct. 11, 2002.

(51) Int. Cl.
C12Q 1/68 (2018.01)
C12Q 1/6883 (2018.01)
C12Q 1/6886 (2018.01)

(52) U.S. Cl.
CPC ........ C12Q 1/6883 (2013.01); C12Q 1/6886 (2013.01); C12Q 2600/112 (2013.01); C12Q 2600/156 (2013.01); C12Q 2600/16 (2013.01)

(58) Field of Classification Search
None
See application file for complete search history.

(56) References Cited

U.S. PATENT DOCUMENTS

| 5,472,693 A | 12/1995 | Mezes |
| 6,312,690 B1 | 11/2001 | Edelman |
| 2002/0150891 A1* | 10/2002 | Hood .................. C12Q 1/6883 435/6.16 |

FOREIGN PATENT DOCUMENTS

| EP | 1218542 B1 | 3/2004 |
| WO | WO 90/04648 A1 | 5/1990 |
| WO | WO 92/19775 A1 | 11/1992 |
| WO | WO 97/18330 A1 | 5/1997 |
| WO | WO 00/22111 A | 4/2000 |

(Continued)

OTHER PUBLICATIONS

Deane, et al., An Improved Method for Detection of B-Lymphoid Clonality Polimerase Chain Reaction, Leukemia, 1991.

(Continued)

*Primary Examiner* — Samuel C Woolwine
(74) *Attorney, Agent, or Firm* — Knobbe, Martens, Olson & Bear, LLP

(57) ABSTRACT

The invention relates to PCR-based clonality studies for among others early diagnosis of lymphoproliferative disorders. Provided is a set of nucleic acid amplification primers comprising a forward primer, or a variant thereof, and a reverse primer, or a variant thereof, capable of amplifying a rearrangement selected from the group consisting of a VH-JH IGH rearrangement, a DH-JH IGH rearrangement, a VK-Jκ IGK rearrangement, a VK/intron-Kde IGK rearrangement, a Vλ-Jλ IGL rearrangement, a Vβ-Jβ TCRB rearrangement, a Dβ-Jβ TCRB rearrangement, a Vγ-Jγ TCRG rearrangement, a Vδ-Jδ TCRD rearrangement, a Dδ-Dδ TCRD rearrangement, a Dδ-Jδ TCRD rearrangement, a Vδ-Dδ TCRD rearrangement, or a translocation selected from t(11;14)(BCL1-IGH) and t(14;18)(BCL2-IGH). The primers can be used in PCR-based clonality studies for early diagnosis of lymphoproliferative disorders and detection of minimal residual disease (MRD). Also provided is a kit comprising at least one set of primers of the invention.

Figure 1:
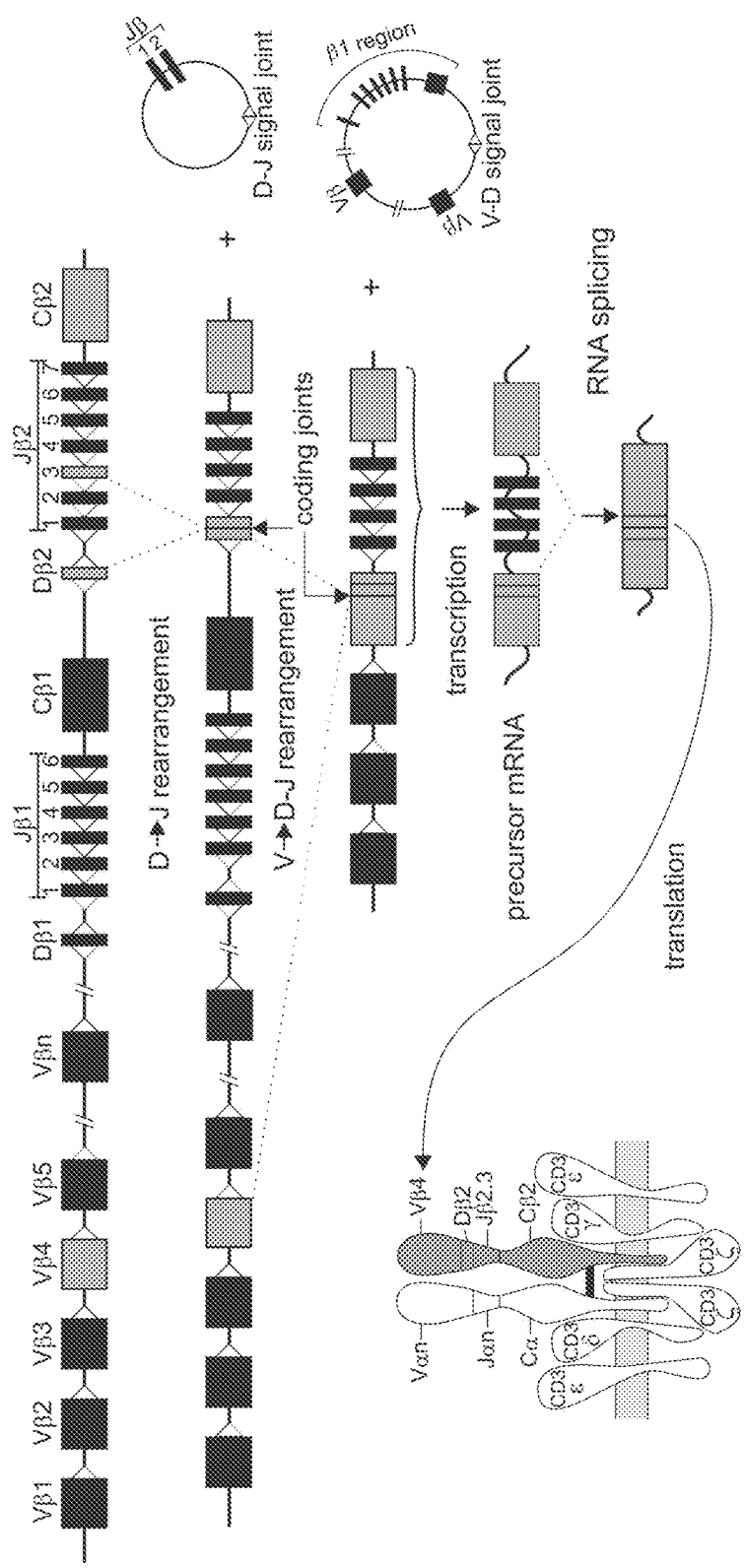
Figure 2A:
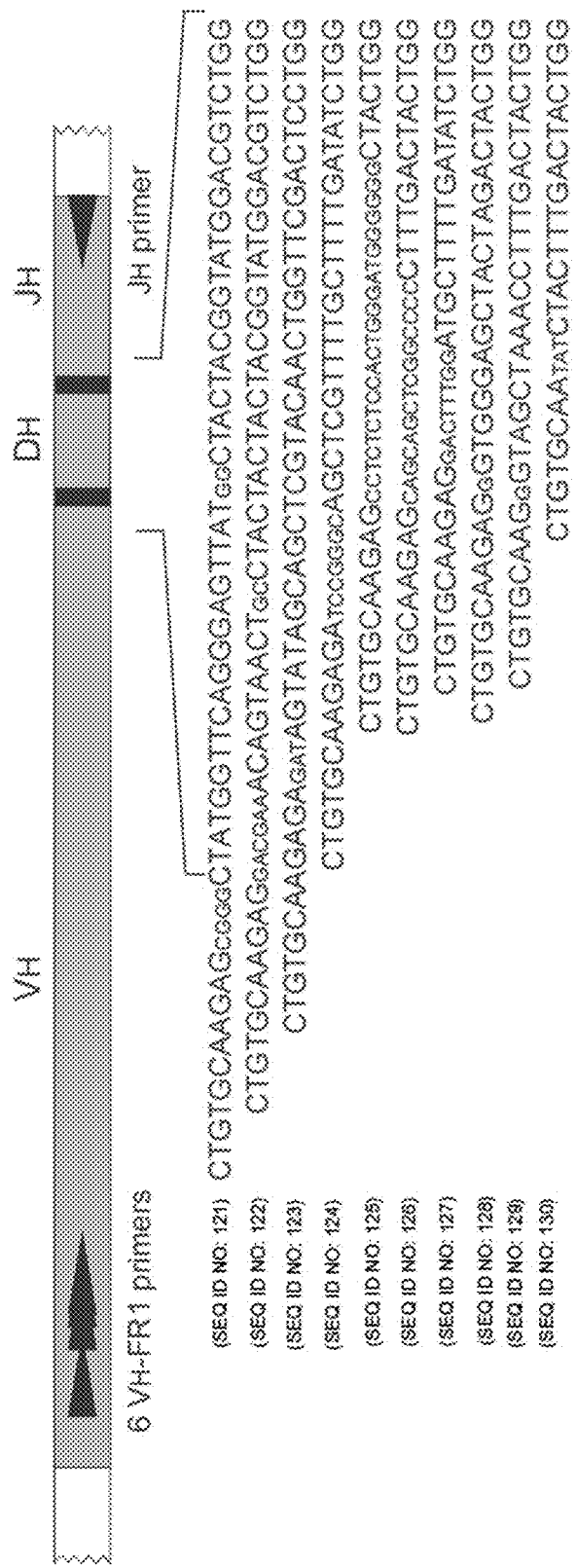
Figure 2B:
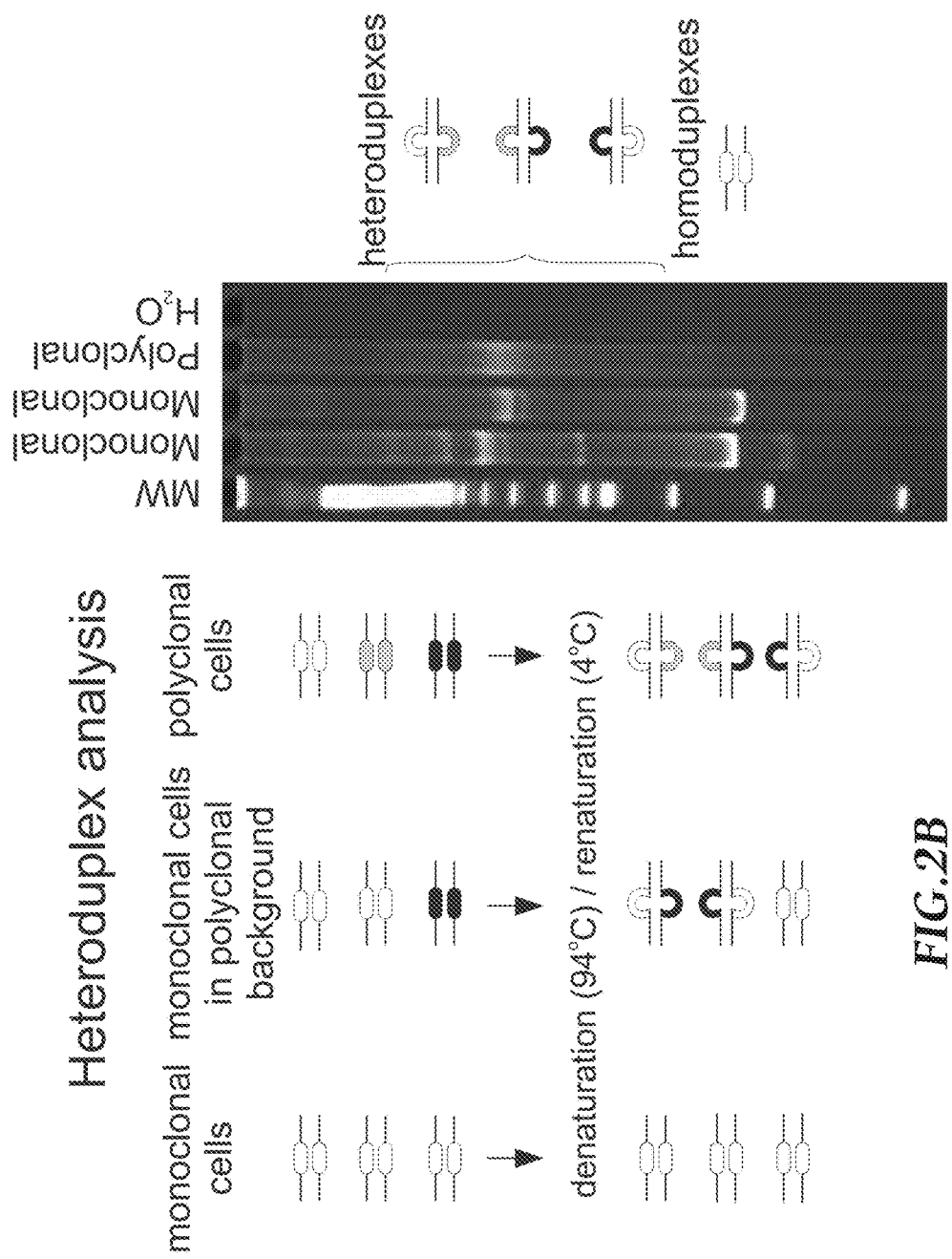
Figure 2C:
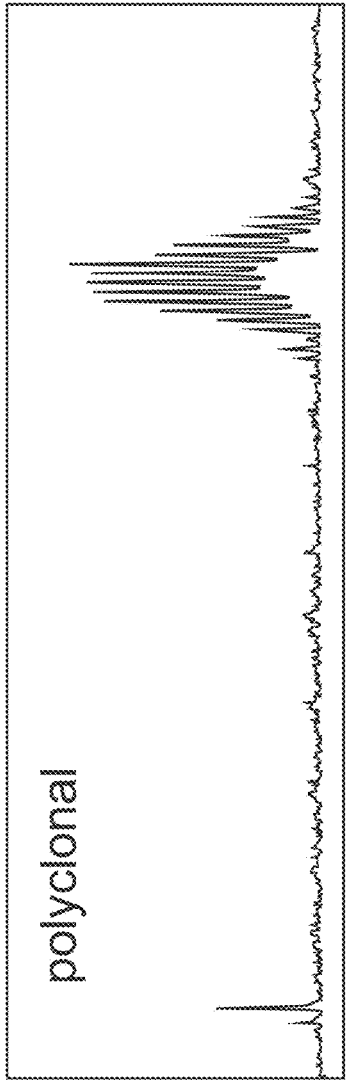
Figure 2C:
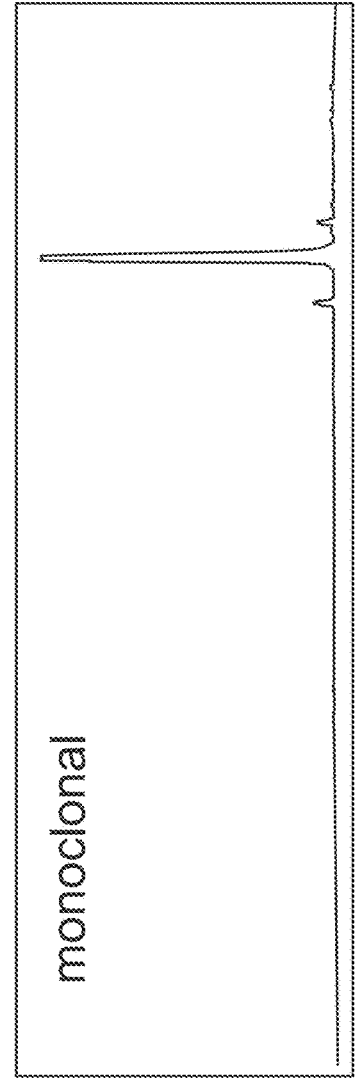

27 Claims, 42 Drawing Sheets
Specification includes a Sequence Listing.

(56) References Cited

FOREIGN PATENT DOCUMENTS

| WO | WO 00/28086 A1 | 5/2000 |
|---|---|---|
| WO | WO 02/00848 A | 1/2002 |

OTHER PUBLICATIONS

Derksen, et al., Comparison of Different Polymerase Chain Reaction-Based Approaches for Clonality Assessment of Immunoglobulin Heavy-Chain Gene Rearrangements in B-Cell Neoplasia, Mod. Pathol., 1999.
Segal, et al., Optimal Primer Selection for Clonality Assessment by Polymerase Chain Reaction Analysis, Hum. Pathol., 1994.
Aubin, et al., Description of a Novel FR1 IgH PCR Strategy and Its Comparison With Three Other Strategies for the Detection of Clonality in B Cell Malignancies, Leukemia, 1995.
Küppers, et al., Detection of Clonal B Cell Populations in Paraffin-Embedded Tissues by Polymerase Chain Reaction, AJP, 1993.
Height, et al., Analysis of Clonal Rearrangements of the Ig Heavy Chain Locus in Acute Leukemia, Blood, 1996.
Weirich, et al., PCR-Based Assays for the Detection of Monoclonality in non-Hodgkin's Lymphoma: Application to Formalin-Fixed, Paraffin-Embedded Tissue and Decalcified Bone Marrow Samples, J. Mol. Med., 1995.
Meier, et al., Simultaneous Evaluation of T- and B-Cell Clonality, t(11;14) and t(14;18), in a Single Reaction by a Four-Color Multiplex Polymerase Chain Reaction Assay and Automated High-Resolution Fragment Analysis, AJP, 2001.
Greiner, et al., Analysis of T Cell Receptor-y Gene Rearrangements by Denaturing Gradient Gel Electrophoresis of GO-Clamped Polymerase Chain Reaction Products, AJP, 1995.
Küppers and Dalla, Mechanisms of Chromosomal Translocations in B Cell Lymphomas, Oncogene, 2001.
Assaf, High Detection Rate of T-Cell Receptor Beta Chain Rearrangements in T-Cell Lymphoproliferations by Family Specific Polymerase Chain Reaction in Combination With the GeneScan Technique and DNA Sequencing, Blood, 2000.
Segal, et al., Optimal Primer Selection for Clonality Assessment by Polymerase Chain Reaction Analysis, Human Pathology, 1994, original contributions.
Affidavit of Mrs. Asuncion Olmo Sevilla, dated Jun. 30, 2011.
Redacted email to Asuncion Olmo, dated Oct. 3, 2003.
Attachment to email dated Oct. 3, 2003, Original Manuscript of Design and Standardization of PCR Primers and Protocols for Detection of Clonal Immunoglobulin and T-Cell Receptor Gene Recombinations in Suspect Lymphoproliferations.
Attachment to email dated Oct. 3, 2003, Figures.
Attachment to email dated Oct. 3, 2003. Section authors of BIOMED-2 Final Checklist.
Attachment to email dated Oct. 3, 2003. Letter from Erasmus MC to Section authors of BIOMED-2 Report, dated Sep. 24, 2003.
Diss, et al., Sources of DNA for Detecting B Cell Monoclonality Using PCR, J. Clin. Pathol., 1994.
Miettinen and Lasota, Polymerase Chain Reaction Based Gene Rearrangement Studies in the Diagnosis of Follicular Lymphoma-Performance in Formaldehyde-Fixed Tissue and Application in Clinical Problem Cases, Pathol. Res. Pract., 1997.
Gonzalez, et al., Heteroduplex Analysis of VDJ Amplified Segments From Rearranged IgH Genes for Clonality Assessments in B-Cell Non-Hodgkin's Lymphoma: A Comparison Between Different Strategies, Haematologica, 1999.
Child, et al., Molecular Analysis of the Immunoglobulin Heavy Chain Gene in the Diagnosis of Primary Cutaneous B Cell Lymphoma, J. Invest. Dermatol., 2001.

Trainor, et al., Monoclonality in B-Lymphoproliferative Disorders Detected at the DNA Level, Blood, 1990.
Extended European Search Report dated Jun. 6, 2012, received in connection with European Patent Application No. 10185191.3.
Kneba, M., et al., Analysis of Rearranged T-Cell Receptor Beta-Chain Genes by Polymerase Chain Reaction (PCR) DNA Sequencing and Automated High Resolution PCR Fragment Analysis, Blood 86(10:3930-3937, 1995.
Summons to Attend Oral Proceedings and Opinion dated May 30, 2012 received in connection with European Patent Application No. 03756746.8.
Van Dongen, J.J.M., et al., PCR-Based Clonality Studies for Early Diagnosis of Lymphoproliferative Disorders, Database Biosis [Online], Biosciences Information Service, Philadelphia, Nov. 16, 2001, Database Accession No. prev200200129978, Abstract.
Zemlin, et al., Improved Polymerase Chain Reaction Detection of Clonally Rearranged T-Cell Receptor Beta Chain Genes, Diagnostic Molecular Pathology 7(3):138-145, 1998.
Communication from the Examining Division dated Jun. 11, 2007 in connection with EP03756746.8.
Communication about intention to grant a European patent dated Feb. 19, 2010 in connection with EP03756746.8.
Barker, R.L., et al., Cytometric Detection of DNA Amplified With Fluorescent Primers: Applications to Analysis of Clonal BCL-2 and IGH Gene Rearrangements in Malignant Lymphomas, Blood 83(4):1079-1085, 1994.
Deane, et al., Immunoglobulin Gene Fingerprinting an Approach to Analysis of B Lymphoid Clonality in Lymphoproliferative Disorders, Brit. J. Haematol. 77:274-281, 1991.0.
Evans, et al., Significantly Improved PCR-Based Clonality Testing in B-Cell Malignancies by Use of Multiple Immunoglobulin Gene Targets, Report of the BIOMED-2 Concerted Action BHM4-CT98-3936, Leukemia 21:207-214, 2007.
European Search Report dated Jun. 6, 2012, issued in connection with EP 10185204.
International Search Report dated Aug. 12, 2004, issued in connection with PCT/NL2003/000690.
Kluin, P., and E. Schuuring, Molecular Cytogenetics of Lymphoma: Where Do We Stand in 2010?, Histopathol. 58:128-144, 2001.
Negrin, R.S., et al., Use of Polymerase Chain Reaction to Monitor the Effectiveness of Ex-Vivo Tumor Cell Purging, Blood 77(3):654-660, 1991.
Ngan, B-Y, et al., Detection of Chromosomal Translocation 14 18 Within the Minor Cluster Region of BCL-2 by Polymerase Chain Reaction and Direct Genomic Sequencing of the Enzymatically Amplified DNA in Follicular Lymphomas, Blood 73(7):1759-1762, 1989.
Segal, et al., Optimal Primer Selection for Clonality Assessment by Polymerase Chain Reaction Analysis: I. Low Grade B-Cell Lymphoproliferative Disorders of Nonfollicular Center Cell Type, Hum. Pathol. 25(12):1269-1275, 1994.
Van Krieken, et al., Improved Reliability of Lymphoma Diagnostics via PCR-Based Clonality Testing: Report of the BIOMED-2 Concerted Action BHM4-CT98-3936, Leukemia 21:201-206, 2007.
Decision Rejecting the Opposition issued by the Opposition Division on Oct. 18, 2012, in connection with European Patent Application No. 03756746.8.
Minutes of Oral Proceedings issued by the Opposition Division on Oct. 18, 2012, in connection with European Patent Application No. 03756746.8.
Opponent Letter dated Aug. 23, 2012, filed in connection with European Patent Application No. 03756746.8.
Oral Proceedings Notice issued May 30, 2012, in connection with European Patent Application No. 03756746.8.
Reply to Notice of Opposition dated Dec. 22, 2011, filed in connection with European Patent Application No. 03756746.8.

\* cited by examiner

FIG. 6A

SEQUENCE LISTING

<160> NUMBER OF SEQ ID NOS: 132

<210> SEQ ID NO 1
<211> LENGTH: 25
<212> TYPE: DNA
<213> ORGANISM: Homo sapiens

<400> SEQUENCE: 1
ggcctcagtg aaggtctcct gcaag                                    25

<210> SEQ ID NO 2
<211> LENGTH: 25

<212> TYPE: DNA
<213> ORGANISM: Homo sapiens

<400> SEQUENCE: 2
gtctggtcct acgctggtga aaccc            25

<210> SEQ ID NO 3
<211> LENGTH: 25
<212> TYPE: DNA
<213> ORGANISM: Homo sapiens

<400> SEQUENCE: 3 ctgggggtc cctgagactc tcctg            25

<210> SEQ ID NO 4
<211> LENGTH: 25
<212> TYPE: DNA
<213> ORGANISM: Homo sapiens

<400> SEQUENCE: 4
cttcggagac cctgtccctc acctg            25

<210> SEQ ID NO 5
<211> LENGTH: 25
<212> TYPE: DNA
<213> ORGANISM: Homo sapiens

<400> SEQUENCE: 5
cggggagtct ctgaagatct cctgt            25

<210> SEQ ID NO 6
<211> LENGTH: 25
<212> TYPE: DNA
<213> ORGANISM: Homo sapiens

<400> SEQUENCE: 6
tcgcagaccc tctcactcac ctgtg            25

<210> SEQ ID NO 7
<211> LENGTH: 25
<212> TYPE: DNA
<213> ORGANISM: Homo sapiens

<400> SEQUENCE: 7
ctgggtgcga caggcccctg gacaa            25

<210> SEQ ID NO 8
<211> LENGTH: 25
<212> TYPE: DNA
<213> ORGANISM: Homo sapiens

<400> SEQUENCE: 8
tggatccgtc agcccccagg gaagg            25

<210> SEQ ID NO 9
<211> LENGTH: 21
<212> TYPE: DNA
<213> ORGANISM: Homo sapiens

<400> SEQUENCE: 9
ggtccgccag gctccaggga a            21

<210> SEQ ID NO 10

<211> LENGTH: 25
<212> TYPE: DNA
<213> ORGANISM: Homo sapiens

<400> SEQUENCE: 10
tggatccgcc agcccccagg gaagg                                    25

<210> SEQ ID NO 11
<211> LENGTH: 25
<212> TYPE: DNA
<213> ORGANISM: Homo sapiens

<400> SEQUENCE: 11
gggtgcgcca gatgcccggg aaagg                                    25

<210> SEQ ID NO 12
<211> LENGTH: 25
<212> TYPE: DNA
<213> ORGANISM: Homo sapiens

<400> SEQUENCE: 12
tggatcaggc agtccccatc gagag                                    25

<210> SEQ ID NO 13
<211> LENGTH: 25
<212> TYPE: DNA
<213> ORGANISM: Homo sapiens

<400> SEQUENCE: 13
ttgggtgcga caggcccctg gacaa                                    25

<210> SEQ ID NO 14
<211> LENGTH: 25
<212> TYPE: DNA
<213> ORGANISM: Homo sapiens

<400> SEQUENCE: 14
tggagctgag cagcctgaga tctga                                    25

<210> SEQ ID NO 15
<211> LENGTH: 25
<212> TYPE: DNA
<213> ORGANISM: Homo sapiens

<400> SEQUENCE: 15
caatgaccaa catggaccct gtgga                                    25

<210> SEQ ID NO 16
<211> LENGTH: 25
<212> TYPE: DNA
<213> ORGANISM: Homo sapiens

<400> SEQUENCE: 16
tctgcaaatg aacagcctga gagcc                                    25

<210> SEQ ID NO 17
<211> LENGTH: 25
<212> TYPE: DNA
<213> ORGANISM: Homo sapiens

<400> SEQUENCE: 17
gagctctgtg accgccgcgg acacg                                    25

```
<210> SEQ ID NO 18
<211> LENGTH: 25
<212> TYPE: DNA
<213> ORGANISM: Homo sapiens

<400> SEQUENCE: 18
cagcaccgcc tacctgcagt ggagc                                    25

<210> SEQ ID NO 19
<211> LENGTH: 25
<212> TYPE: DNA
<213> ORGANISM: Homo sapiens

<400> SEQUENCE: 19
gttctccctg cagctgaact ctgtg                                    25

<210> SEQ ID NO 20
<211> LENGTH: 24
<212> TYPE: DNA
<213> ORGANISM: Homo sapiens

<400> SEQUENCE: 20
cagcacggca tatctgcaga tcag                                     24

<210> SEQ ID NO 21
<211> LENGTH: 22
<212> TYPE: DNA
<213> ORGANISM: Homo sapiens

<400> SEQUENCE: 21
cttacctgag gagacggtga cc                                       22

<210> SEQ ID NO 22
<211> LENGTH: 18
<212> TYPE: DNA
<213> ORGANISM: Homo sapiens

<400> SEQUENCE: 22
ggcggaatgt gtgcaggc                                            18

<210> SEQ ID NO 23
<211> LENGTH: 21
<212> TYPE: DNA
<213> ORGANISM: Homo sapiens

<400> SEQUENCE: 23
gcactgggct cagagtcctc t                                        21

<210> SEQ ID NO 24
<211> LENGTH: 20
<212> TYPE: DNA
<213> ORGANISM: Homo sapiens

<400> SEQUENCE: 24
gtggccctgg gaatataaaa                                          20

<210> SEQ ID NO 25
<211> LENGTH: 19
<212> TYPE: DNA
<213> ORGANISM: Homo sapiens

<400> SEQUENCE: 25
agatccccag gacgcagca                                           19
```

<210> SEQ ID NO 26
<211> LENGTH: 20
<212> TYPE: DNA
<213> ORGANISM: Homo sapiens

<400> SEQUENCE: 26
cagggggaca ctgtgcatgt                                            20

<210> SEQ ID NO 27
<211> LENGTH: 19
<212> TYPE: DNA
<213> ORGANISM: Homo sapiens

<400> SEQUENCE: 27 tgacccagc aagggaagg                                              19

<210> SEQ ID NO 28
<211> LENGTH: 18
<212> TYPE: DNA
<213> ORGANISM: Homo sapiens

<400> SEQUENCE: 28
cacaggcccc ctaccagc                                              18

<210> SEQ ID NO 29
<211> LENGTH: 25
<212> TYPE: DNA
<213> ORGANISM: Homo sapiens

<400> SEQUENCE: 29
tcaaggttca gcggcagtgg atctg                                      25

<210> SEQ ID NO 30
<211> LENGTH: 26
<212> TYPE: DNA
<213> ORGANISM: Homo sapiens

<400> SEQUENCE: 30
ggcctccatc tcctgcaggt ctagtc                                     26

<210> SEQ ID NO 31
<211> LENGTH: 27
<212> TYPE: DNA
<213> ORGANISM: Homo sapiens

<400> SEQUENCE: 31
cccaggctcc tcatctatga tgcatcc                                    27

<210> SEQ ID NO 32
<211> LENGTH: 27
<212> TYPE: DNA
<213> ORGANISM: Homo sapiens

<400> SEQUENCE: 32
caactgcaag tccagccaga gtgtttt                                    27

<210> SEQ ID NO 33
<211> LENGTH: 26
<212> TYPE: DNA
<213> ORGANISM: Homo sapiens

<400> SEQUENCE: 33
cctgcaaagc cagccaagac attgat                                     26

<210> SEQ ID NO 34
<211> LENGTH: 27
<212> TYPE: DNA
<213> ORGANISM: Homo sapiens

<400> SEQUENCE: 34
gaccgatttc accctcacaa ttaatcc                                    27

<210> SEQ ID NO 35
<211> LENGTH: 22
<212> TYPE: DNA
<213> ORGANISM: Homo sapiens

<400> SEQUENCE: 35
cgtggcaccg cgagctgtag ac                                         22

<210> SEQ ID NO 36
<211> LENGTH: 27
<212> TYPE: DNA
<213> ORGANISM: Homo sapiens

<400> SEQUENCE: 36
cttacgtttg atctccacct tggtccc                                    27

<210> SEQ ID NO 37
<211> LENGTH: 27
<212> TYPE: DNA
<213> ORGANISM: Homo sapiens

<400> SEQUENCE: 37
cttacgttta atctccagtc gtgtccc                                    27

<210> SEQ ID NO 38
<211> LENGTH: 27
<212> TYPE: DNA
<213> ORGANISM: Homo sapiens

<400> SEQUENCE: 38
cctcagaggt cagagcaggt tgtccta                                    27

<210> SEQ ID NO 39
<211> LENGTH: 22
<212> TYPE: DNA
<213> ORGANISM: Homo sapiens

<400> SEQUENCE: 39
attctctggc tccaagtctg gc                                         22

<210> SEQ ID NO 40
<211> LENGTH: 22
<212> TYPE: DNA
<213> ORGANISM: Homo sapiens

<400> SEQUENCE: 40
ggatccctga gcgattctct gg                                         22

<210> SEQ ID NO 41
<211> LENGTH: 22
<212> TYPE: DNA
<213> ORGANISM: Homo sapiens

<400> SEQUENCE: 41
ctaggacggt gagcttggtc cc                                              22

<210> SEQ ID NO 42
<211> LENGTH: 21
<212> TYPE: DNA
<213> ORGANISM: Homo sapiens

<400> SEQUENCE: 42
aactatgttt tggtatcgtc a                                               21

<210> SEQ ID NO 43
<211> LENGTH: 24
<212> TYPE: DNA
<213> ORGANISM: Homo sapiens

<400> SEQUENCE: 43
cacgatgttc tggtaccgtc agca                                            24

<210> SEQ ID NO 44
<211> LENGTH: 22
<212> TYPE: DNA
<213> ORGANISM: Homo sapiens

<400> SEQUENCE: 44
cagtgtgtcc tggtaccaac ag                                              22

<210> SEQ ID NO 45
<211> LENGTH: 21
<212> TYPE: DNA
<213> ORGANISM: Homo sapiens

<400> SEQUENCE: 45 aacccttat tggtaccgac a                                                21

<210> SEQ ID NO 46
<211> LENGTH: 22
<212> TYPE: DNA
<213> ORGANISM: Homo sapiens

<400> SEQUENCE: 46 atccctttt tggtaccaac ag                                               22

<210> SEQ ID NO 47
<211> LENGTH: 22
<212> TYPE: DNA
<213> ORGANISM: Homo sapiens

<400> SEQUENCE: 47 aacccttat tggtatcaac ag                                               22

<210> SEQ ID NO 48
<211> LENGTH: 21
<212> TYPE: DNA
<213> ORGANISM: Homo sapiens

<400> SEQUENCE: 48
cgctatgtat tggtacaagc a                                               21

<210> SEQ ID NO 49
<211> LENGTH: 25
<212> TYPE: DNA
<213> ORGANISM: Homo sapiens

<400> SEQUENCE: 49

```
ctcccgtttt ctggtacaga cagac                                              25

<210> SEQ ID NO 50
<211> LENGTH: 22
<212> TYPE: DNA
<213> ORGANISM: Homo sapiens

<400> SEQUENCE: 50
cgctatgtat tggtataaac ag                                                 22

<210> SEQ ID NO 51
<211> LENGTH: 26
<212> TYPE: DNA
<213> ORGANISM: Homo sapiens

<400> SEQUENCE: 51
ttatgtttac tggtatcgta agaagc                                             26

<210> SEQ ID NO 52
<211> LENGTH: 22
<212> TYPE: DNA
<213> ORGANISM: Homo sapiens

<400> SEQUENCE: 52
caaaatgtac tggtatcaac aa                                                 22

<210> SEQ ID NO 53
<211> LENGTH: 25
<212> TYPE: DNA
<213> ORGANISM: Homo sapiens

<400> SEQUENCE: 53
atacatgtac tggtatcgac aagac                                              25

<210> SEQ ID NO 54
<211> LENGTH: 23
<212> TYPE: DNA
<213> ORGANISM: Homo sapiens

<400> SEQUENCE: 54
ggccatgtac tggtatagac aag                                                23

<210> SEQ ID NO 55
<211> LENGTH: 24
<212> TYPE: DNA
<213> ORGANISM: Homo sapiens

<400> SEQUENCE: 55
gtatatgtcc tggtatcgac aaga                                               24

<210> SEQ ID NO 56
<211> LENGTH: 24
<212> TYPE: DNA
<213> ORGANISM: Homo sapiens

<400> SEQUENCE: 56
taacctttat tggtatcgac gtgt                                               24

<210> SEQ ID NO 57
<211> LENGTH: 21
<212> TYPE: DNA
<213> ORGANISM: Homo sapiens
```

<400> SEQUENCE: 57
ggccatgtac tggtaccgac a    21

<210> SEQ ID NO 58
<211> LENGTH: 22
<212> TYPE: DNA
<213> ORGANISM: Homo sapiens

<400> SEQUENCE: 58
tcatgtttac tggtatcggc ag    22

<210> SEQ ID NO 59
<211> LENGTH: 27
<212> TYPE: DNA
<213> ORGANISM: Homo sapiens

<400> SEQUENCE: 59
ttatgtttat tggtatcaac agaatca    27

<210> SEQ ID NO 60
<211> LENGTH: 21
<212> TYPE: DNA
<213> ORGANISM: Homo sapiens

<400> SEQUENCE: 60
caacctatac tggtaccgac a    21

<210> SEQ ID NO 61
<211> LENGTH: 22
<212> TYPE: DNA
<213> ORGANISM: Homo sapiens

<400> SEQUENCE: 61
taccctttac tggtaccggc ag    22

<210> SEQ ID NO 62
<211> LENGTH: 26
<212> TYPE: DNA
<213> ORGANISM: Homo sapiens

<400> SEQUENCE: 62
atacttctat tggtacagac aaatct    26

<210> SEQ ID NO 63
<211> LENGTH: 21
<212> TYPE: DNA
<213> ORGANISM: Homo sapiens

<400> SEQUENCE: 63
cacggtctac tggtaccagc a    21

<210> SEQ ID NO 64
<211> LENGTH: 21
<212> TYPE: DNA
<213> ORGANISM: Homo sapiens

<400> SEQUENCE: 64
cgtcatgtac tggtaccagc a    21

<210> SEQ ID NO 65
<211> LENGTH: 25
<212> TYPE: DNA
<213> ORGANISM: Homo sapiens

```
<400> SEQUENCE: 65
cttacctaca actgtgaatc tggtg                                      25

<210> SEQ ID NO 66
<211> LENGTH: 25
<212> TYPE: DNA
<213> ORGANISM: Homo sapiens

<400> SEQUENCE: 66
cttacctaca acggttaacc tggtc                                      25

<210> SEQ ID NO 67
<211> LENGTH: 25
<212> TYPE: DNA
<213> ORGANISM: Homo sapiens

<400> SEQUENCE: 67
cttacctaca acagtgagcc aactt                                      25

<210> SEQ ID NO 68
<211> LENGTH: 26
<212> TYPE: DNA
<213> ORGANISM: Homo sapiens

<400> SEQUENCE: 68
catacccaag acagagagct gggttc                                     26

<210> SEQ ID NO 69
<211> LENGTH: 25
<212> TYPE: DNA
<213> ORGANISM: Homo sapiens

<400> SEQUENCE: 69
cttacctagg atggagagtc gagtc                                      25

<210> SEQ ID NO 70
<211> LENGTH: 22
<212> TYPE: DNA
<213> ORGANISM: Homo sapiens

<400> SEQUENCE: 70
catacctgtc acagtgagcc tg                                         22

<210> SEQ ID NO 71
<211> LENGTH: 21
<212> TYPE: DNA
<213> ORGANISM: Homo sapiens

<400> SEQUENCE: 71
cttacccagt acggtcagcc t                                          21

<210> SEQ ID NO 72
<211> LENGTH: 21
<212> TYPE: DNA
<213> ORGANISM: Homo sapiens

<400> SEQUENCE: 72
ctcgcccagc acggtcagcc t                                          21

<210> SEQ ID NO 73
<211> LENGTH: 22
<212> TYPE: DNA
```

```
<213> ORGANISM: Homo sapiens

<400> SEQUENCE: 73
cttacctgta accgtgagcc tg                                            22

<210> SEQ ID NO 74
<211> LENGTH: 21
<212> TYPE: DNA
<213> ORGANISM: Homo sapiens

<400> SEQUENCE: 74
ccttcttacc tagcacggtg a                                             21

<210> SEQ ID NO 75
<211> LENGTH: 21
<212> TYPE: DNA
<213> ORGANISM: Homo sapiens

<400> SEQUENCE: 75
cccgcttacc gagcactgtc a                                             21

<210> SEQ ID NO 76
<211> LENGTH: 21
<212> TYPE: DNA
<213> ORGANISM: Homo sapiens

<400> SEQUENCE: 76
ccagcttacc cagcactgag a                                             21

<210> SEQ ID NO 77
<211> LENGTH: 16
<212> TYPE: DNA
<213> ORGANISM: Homo sapiens

<400> SEQUENCE: 77
cgcgcacacc gagcac                                                   16

<210> SEQ ID NO 78
<211> LENGTH: 21
<212> TYPE: DNA
<213> ORGANISM: Homo sapiens

<400> SEQUENCE: 78
gccaaacagc cttacaaaga c                                             21

<210> SEQ ID NO 79
<211> LENGTH: 20
<212> TYPE: DNA
<213> ORGANISM: Homo sapiens

<400> SEQUENCE: 79
tttccaagcc ccacacagtc                                               20

<210> SEQ ID NO 80
<211> LENGTH: 20
<212> TYPE: DNA
<213> ORGANISM: Homo sapiens

<400> SEQUENCE: 80
ggaaggcccc acagcrtctt                                               20

<210> SEQ ID NO 81
<211> LENGTH: 20
```

```
<212> TYPE: DNA
<213> ORGANISM: Homo sapiens

<400> SEQUENCE: 81
agcatgggta agacaagcaa                                              20

<210> SEQ ID NO 82
<211> LENGTH: 21
<212> TYPE: DNA
<213> ORGANISM: Homo sapiens

<400> SEQUENCE: 82
cggcactgtc agaaaggaat c                                            21

<210> SEQ ID NO 83
<211> LENGTH: 20
<212> TYPE: DNA
<213> ORGANISM: Homo sapiens

<400> SEQUENCE: 83
cttccacttc cactttgaaa                                              20

<210> SEQ ID NO 84
<211> LENGTH: 24
<212> TYPE: DNA
<213> ORGANISM: Homo sapiens

<400> SEQUENCE: 84
ttaccaggcg aagttactat gagc                                         24

<210> SEQ ID NO 85
<211> LENGTH: 22
<212> TYPE: DNA
<213> ORGANISM: Homo sapiens

<400> SEQUENCE: 85
gtgttgttcc actgccaaag ag                                           22

<210> SEQ ID NO 86
<211> LENGTH: 21
<212> TYPE: DNA
<213> ORGANISM: Homo sapiens

<400> SEQUENCE: 86
atgcaaaaag tggtcgctat t                                            21

<210> SEQ ID NO 87
<211> LENGTH: 23
<212> TYPE: DNA
<213> ORGANISM: Homo sapiens

<400> SEQUENCE: 87
ataccgagaa aaggacatct atg                                          23

<210> SEQ ID NO 88
<211> LENGTH: 21
<212> TYPE: DNA
<213> ORGANISM: Homo sapiens

<400> SEQUENCE: 88
gtaccggata aggccagatt a                                            21

<210> SEQ ID NO 89
```

```
<211> LENGTH: 21
<212> TYPE: DNA
<213> ORGANISM: Homo sapiens

<400> SEQUENCE: 89
atgaccagca aaatgcaaca g                                              21

<210> SEQ ID NO 90
<211> LENGTH: 21
<212> TYPE: DNA
<213> ORGANISM: Homo sapiens

<400> SEQUENCE: 90
accctgctga aggtcctaca t                                              21

<210> SEQ ID NO 91
<211> LENGTH: 21
<212> TYPE: DNA
<213> ORGANISM: Homo sapiens

<400> SEQUENCE: 91
ccctgcatta ttgatagcca t                                              21

<210> SEQ ID NO 92
<211> LENGTH: 21
<212> TYPE: DNA
<213> ORGANISM: Homo sapiens

<400> SEQUENCE: 92
gttccacagt cacacgggtt c                                              21

<210> SEQ ID NO 93
<211> LENGTH: 21
<212> TYPE: DNA
<213> ORGANISM: Homo sapiens

<400> SEQUENCE: 93
gttccacgat gagttgtgtt c                                              21

<210> SEQ ID NO 94
<211> LENGTH: 21
<212> TYPE: DNA
<213> ORGANISM: Homo sapiens

<400> SEQUENCE: 94
ctcacggggc tccacgaaga g                                              21

<210> SEQ ID NO 95
<211> LENGTH: 21
<212> TYPE: DNA
<213> ORGANISM: Homo sapiens

<400> SEQUENCE: 95
ttgtacctcc agataggttc c                                              21

<210> SEQ ID NO 96
<211> LENGTH: 21
<212> TYPE: DNA
<213> ORGANISM: Homo sapiens

<400> SEQUENCE: 96
agcgggtggt gatggcaaag t                                              21
```

```
<210> SEQ ID NO 97
<211> LENGTH: 21
<212> TYPE: DNA
<213> ORGANISM: Homo sapiens

<400> SEQUENCE: 97
tgggacccag ggtgaggata t                                          21

<210> SEQ ID NO 98
<211> LENGTH: 21
<212> TYPE: DNA
<213> ORGANISM: Homo sapiens

<400> SEQUENCE: 98
ggataaaggc gaggagcata a                                          21

<210> SEQ ID NO 99
<211> LENGTH: 22
<212> TYPE: DNA
<213> ORGANISM: Homo sapiens

<400> SEQUENCE: 99
cttacctgag gagacggtga cc                                         22

<210> SEQ ID NO 100
<211> LENGTH: 23
<212> TYPE: DNA
<213> ORGANISM: Homo sapiens

<400> SEQUENCE: 100
gaccagcaga ttcaaatcta tgg                                        23

<210> SEQ ID NO 101
<211> LENGTH: 25
<212> TYPE: DNA
<213> ORGANISM: Homo sapiens

<400> SEQUENCE: 101
actctgtggc attattgcat tatat                                      25

<210> SEQ ID NO 102
<211> LENGTH: 22
<212> TYPE: DNA
<213> ORGANISM: Homo sapiens

<400> SEQUENCE: 102
gcacctgctg gatacaacac tg                                         22

<210> SEQ ID NO 103
<211> LENGTH: 21
<212> TYPE: DNA
<213> ORGANISM: Homo sapiens

<400> SEQUENCE: 103
aaactagcag ggtgtggtgg c                                          21

<210> SEQ ID NO 104
<211> LENGTH: 23
<212> TYPE: DNA
<213> ORGANISM: Homo sapiens

<400> SEQUENCE: 104
gtaatgactg gggagcaaat ctt                                        23
```

```
<210> SEQ ID NO 105
<211> LENGTH: 22
<212> TYPE: DNA
<213> ORGANISM: Homo sapiens

<400> SEQUENCE: 105
actggttggc gtggtttaga ga                                              22

<210> SEQ ID NO 106
<211> LENGTH: 22
<212> TYPE: DNA
<213> ORGANISM: Homo sapiens

<400> SEQUENCE: 106
ccttctgaaa gaaacgaaag ca                                              22

<210> SEQ ID NO 107
<211> LENGTH: 22
<212> TYPE: DNA
<213> ORGANISM: Homo sapiens

<400> SEQUENCE: 107
tagagcaagc gcccaataaa ta                                              22

<210> SEQ ID NO 108
<211> LENGTH: 21
<212> TYPE: DNA
<213> ORGANISM: Homo sapiens

<400> SEQUENCE: 108
tgaatgccat ctcaaatcca a                                               21

<210> SEQ ID NO 109
<211> LENGTH: 23
<212> TYPE: DNA
<213> ORGANISM: Homo sapiens

<400> SEQUENCE: 109
ggtgacagag caaaacatga aca                                             23

<210> SEQ ID NO 110
<211> LENGTH: 22
<212> TYPE: DNA
<213> ORGANISM: Homo sapiens

<400> SEQUENCE: 110
cttacctgag gagacggtga cc                                              22

<210> SEQ ID NO 111
<211> LENGTH: 20
<212> TYPE: DNA
<213> ORGANISM: Homo sapiens

<400> SEQUENCE: 111
ggagcagcat tccatccagc                                                 20

<210> SEQ ID NO 112
<211> LENGTH: 20
<212> TYPE: DNA
<213> ORGANISM: Homo sapiens

<400> SEQUENCE: 112
catccatggg ccggacataa                                                 20
```

<210> SEQ ID NO 113
<211> LENGTH: 19
<212> TYPE: DNA
<213> ORGANISM: Homo sapiens

<400> SEQUENCE: 113
ccgcagcaag caacgaacc                                                19

<210> SEQ ID NO 114
<211> LENGTH: 19
<212> TYPE: DNA
<213> ORGANISM: Homo sapiens

<400> SEQUENCE: 114
gctttcctct ggcggctcc                                                19

<210> SEQ ID NO 115
<211> LENGTH: 21
<212> TYPE: DNA
<213> ORGANISM: Homo sapiens

<400> SEQUENCE: 115
tgcgatgtgg tcatcatggt g                                             21

<210> SEQ ID NO 116
<211> LENGTH: 21
<212> TYPE: DNA
<213> ORGANISM: Homo sapiens

<400> SEQUENCE: 116
cgtgtcattg tcgtctgagg c                                             21

<210> SEQ ID NO 117
<211> LENGTH: 20
<212> TYPE: DNA
<213> ORGANISM: Homo sapiens

<400> SEQUENCE: 117
tgttgactcg atccacccca                                               20

<210> SEQ ID NO 118
<211> LENGTH: 21
<212> TYPE: DNA
<213> ORGANISM: Homo sapiens

<400> SEQUENCE: 118
tgagctgcaa gtttggctga a                                             21

<210> SEQ ID NO 119
<211> LENGTH: 20
<212> TYPE: DNA
<213> ORGANISM: Homo sapiens

<400> SEQUENCE: 119
gcccgacatt ctgcaagtcc                                               20

<210> SEQ ID NO 120
<211> LENGTH: 19
<212> TYPE: DNA
<213> ORGANISM: Homo sapiens

<400> SEQUENCE: 120

```
ggtgttgccg ggaagggtt                                              19
```

<210> SEQ ID NO 121
<211> LENGTH: 58
<212> TYPE: DNA
<213> ORGANISM: Homo sapiens

<400> SEQUENCE: 121

```
ggtctgcagg tatggcatca tcggtattga gggacttggt atcgggcgag aacgtgtc   58
```

<210> SEQ ID NO 122
<211> LENGTH: 56
<212> TYPE: DNA
<213> ORGANISM: Homo sapiens

<400> SEQUENCE: 122

```
ggtctgcagg tatggcatca tcatcatccg tcaatgacaa agcaggagaa cgtgtc     56
```

<210> SEQ ID NO 123
<211> LENGTH: 50
<212> TYPE: DNA
<213> ORGANISM: Homo sapiens

<400> SEQUENCE: 123

```
ggtcctcagc ttggtcaaca tgctcgacga tatgatagag agaacgtgtc            50
```

<210> SEQ ID NO 124
<211> LENGTH: 44
<212> TYPE: DNA
<213> ORGANISM: Homo sapiens

<400> SEQUENCE: 124

```
ggtctatagt tttcgttttg ctcgacgggc ctagagaacg tgtc                  44
```

<210> SEQ ID NO 125
<211> LENGTH: 41
<212> TYPE: DNA
<213> ORGANISM: Homo sapiens

<400> SEQUENCE: 125

```
ggtcatcggg gggtagggtc acctctctcc gagaacgtgt c                     41
```

<210> SEQ ID NO 126
<211> LENGTH: 39
<212> TYPE: DNA
<213> ORGANISM: Homo sapiens

<400> SEQUENCE: 126

```
ggtcatcagt ttcccccggc tcgacgacga gaacgtgtc                        39
```

<210> SEQ ID NO 127
<211> LENGTH: 36
<212> TYPE: DNA
<213> ORGANISM: Homo sapiens

<400> SEQUENCE: 127

```
ggtctatagt tttcgtaggt ttcaggagaa cgtgtc                           36
```

<210> SEQ ID NO 128
<211> LENGTH: 34
<212> TYPE: DNA
<213> ORGANISM: Homo sapiens

<400> SEQUENCE: 128

```
ggtcatcaga tcatcgaggg tgggagaacg tgtc                          34

<210> SEQ ID NO 129
<211> LENGTH: 33
<212> TYPE: DNA
<213> ORGANISM: Homo sapiens

<400> SEQUENCE: 129
ggtcatcagt ttccaaatcg atgggaacgt gtc                           33

<210> SEQ ID NO 130
<211> LENGTH: 27
<212> TYPE: DNA
<213> ORGANISM: Homo sapiens

<400> SEQUENCE: 130
ggtcatcagt ttcatctata acgtgtc                                  27

<210> SEQ ID NO 131
<211> LENGTH: 20
<212> TYPE: DNA
<213> ORGANISM: Homo sapiens

<400> SEQUENCE: 131
gcactgtctg gatgcaccgc                                          20

<210> SEQ ID NO 132
<211> LENGTH: 19
<212> TYPE: DNA
<213> ORGANISM: Homo sapiens

<400> SEQUENCE: 132
accgaatatg cagtgcagc                                           19
```

US 10,280,462 B2

NUCLEIC ACID AMPLIFICATION PRIMERS FOR PCR-BASED CLONALITY STUDIES

CROSS-REFERENCE TO RELATED APPLICATIONS

This application is a continuation of U.S. patent application Ser. No. 10/531,106, filed Feb. 17, 2011, now U.S. Pat. No. 8,859,748, which is a U.S. National Phase under 35 U.S.C. § 371 of International Application No. PCT/NL2003/000690, filed Oct. 13, 2003, which claims priority to U.S. Provisional Patent Application No. 60/417,779, filed Oct. 11, 2002, each of which is hereby incorporated by reference in it entirety into this application.

The present invention relates to PCR-based clonality studies for among others early diagnosis of lymphoproliferative disorders. In most patients with suspect lymphoproliferative disorders, histomorphology or cytomorphology supplemented with immunohistology or flow cytometric immunophenotyping can discriminate between malignant and reactive lymphoproliferations. However, in 5 to 10% of cases, making the diagnosis is more complicated. The diagnosis of lymphoid malignancies can be supported by clonality assessment based on the fact that in principle all cells of a malignancy have a common clonal origin.

The majority of lymphoid malignancies belongs to the B-cell lineage (90 to 95%) and only a minority belongs to the T-cell lineage (5-7%) or NK-cell lineage (<2%). Acute lymphoblastic leukemias (ALL) are of T-cell origin in 15 to 20% of cases, but in the group of mature lymphoid leukemias and in non-Hodgkin lymphomas (NHL) T-cell malignancies are relatively rare, except for specific subgroups such as cutaneous lymphomas (Table 1). Consequently, the vast majority of lymphoid malignancies (>98%) contains identically (clonally) rearranged immunoglobulin (Ig) and/or T-cell receptor (TCR) genes and in 25 to 30% of cases also well-defined chromosome aberrations are found, all of which can serve as markers for clonality.[1,2]

The Ig and TCR gene loci contain many different variable (V), diversity (D), and joining (J) gene segments, which are subjected to rearrangement processes during early lymphoid differentiation.[3,4] The V-D-J rearrangements are mediated via a recombinase enzyme complex in which the RAG1 and RAG2 proteins play a key role by recognizing and cutting the DNA at the recombination signal sequences (RSS), which are located downstream of the V gene segments, at both sides of the D gene segments, and upstream of the J gene segments (FIG. 1). Inappropriate RSS reduce or even completely prevent rearrangement.

The rearrangement process generally starts with a D to J rearrangement followed by a V to D-J rearrangement in case of Ig heavy chain (IGH), TCR beta (TCRB), and TCR delta (TCRD) genes (FIG. 1) or concerns direct V to J rearrangements in case of Ig kappa (IGK), Ig lambda (IGL), TCR alpha (TCRA), and TCR gamma (TCRG) genes. The sequences between rearranging gene segments are generally deleted in the form of a circular excision product, also called TCR excision circle (TREC) or B cell receptor excision circle (BREC) (FIG. 1).

The Ig and TCR gene rearrangements during early lymphoid differentiation generally follow a hierarchical order. During B-cell differentiation: first the IGH genes rearrange, then IGK, potentially resulting in IgH/κ expression or followed by IGK deletion and IGL rearrangement, potentially followed by IgH/λ expression.[5] This implies that virtually all Igλ+ B-cells have monoallelic or biallelic IGK gene deletions. During T-cell differentiation: first the TCRD genes rearrange, then TCRG, potentially resulting in TCRγδ expression or followed by further TCRB rearrangement and TCRD deletion with subsequent TCRA rearrangement, potentially followed by TCRαβ expression. The Ig and TCR gene rearrangement patterns in lymphoid malignancies generally fit with the above-described hierarchical order, although unusual rearrangement patterns are found as well, particularly in ALL.[6]

The many different combinations of V, D, and J gene segments represent the so-called combinatorial repertoire (Table 2), which is estimated to be ~2×10$^6$ for Ig molecules, ~3×10° for TCRαβ molecules and ~5×10$^8$ for TCRγδ molecules. At the junction sites of the V, D, and J gene segments, deletion and random insertion of nucleotides occurs during the rearrangement process, resulting in highly diverse junctional regions, which significantly contribute to the total repertoire of Ig and TCR molecules, estimated to be >10$^{12}$.[5]

Mature B-lymphocytes further extend their Ig repertoire upon antigen recognition in follicle centers via somatic hypermutation, a process, leading to affinity maturation of the Ig molecules. The somatic hypermutation process focuses on the V-(D-)J exon of IGH and Ig light chain genes and concerns single nucleotide mutations and sometimes also insertions or deletions of nucleotides. Somatically-mutated Ig genes are also found in mature B-cell malignancies of follicular or post-follicular origin.[7]

Functionally rearranged Ig and TCR genes result in surface membrane expression of Ig, TCRαβ, or TCRγδ molecules. Based on the concept that only a single type of Ig or TCR molecule is expressed by a lymphocyte or lymphocyte clone, the clonally rearranged genes of mature lymphoid malignancies might be detectable at the protein level. Detection of single Ig light chain expression (Igκ or Igλ) has for a long time been used to discriminate between reactive (polyclonal) B-lymphocytes (normal Igκ/Igλ ratio: 0.7-2.8) versus aberrant (clonal) B-lymphocytes with Igκ/Igλ ratios of >4.0 or <0.5.[8-10] In the vast majority (>90%) of mature B-cell malignancies, single Ig light chain expression can support the clonal origin of the malignancy.

Also, the development of many different antibodies against variable domains of the various TCR chains allows detection of monotypic Vβ, Vγ and Vδ domains, when compared with appropriate reference values.[11-16] In the interpretation of monotypic Vβ results using 20 to 25 antibodies against different Vβ families (Table 2), one should realize that clinically-benign clonal TCRαβ+ T-cell expansions (frequently CD8+) are regularly found in peripheral blood (PB) of older individuals.[13,17] These clonal T-cell expansions in PB are however relatively small in size: <40% of PB T-lymphocytes and <0.5×10$^6$/ml PB.[13] It is not yet clear to what extent such clinically benign T-cell clones can also be found in lymphoid tissues.

The results of monotypic Vγ and Vδ domain expression should be interpreted with caution, because in healthy individuals a large fraction of normal polyclonal TCRγδ T-lymphocytes has been selected for Vγ9-Jγ1.2 and Vδ2-Jδ1 usage.[18,19] Consequently, high frequencies of Vγ9/Vδ2+ T-lymphocytes in PB should be regarded as a normal finding, unless the absolute counts are 1 to 2×10$^6$/ml PB. It should be noted that most TCRγδ+ T-cell malignancies express Vδ1 or another non-Vδ2 gene segment in combination with a single Vγ domain (generally not Vγ9).[15,20]

Detection of Igκ or Igλ restricted expression or monotypic Vβ, Vγ or Vδ expression is relatively easy in flow cytometric studies of PB and bone marrow (BM) samples of patients with mature B-cell or T-cell leukemias. However, this appears to be more difficult in tissue samples with suspect lymphoproliferative disorders that are intermixed with normal (reactive) lymphocytes.

In contrast to the antibody-based techniques, molecular techniques are broadly applicable for detection of clonally rearranged Ig/TCR genes as well as well-defined chromosome aberrations. This previously concerned Southern blot analysis, but nowadays particularly PCR techniques are used.

Difficulties in making a final diagnosis of lymphoid malignancy occur in a proportion of cases (5 to 10%) despite extensive immunophenotyping. Therefore, additional (molecular clonality) diagnostics is needed to generate or to confirm the final diagnosis, such as in case of:

any suspect B-cell proliferation where morphology and immunophenotyping are not conclusive;

all suspect T-cell proliferations (CAUTION: T-cell rich B-NHL);

lymphoproliferations in immunodeficient patients or transplanted patients;

evaluation of the clonal relationship between two lymphoid malignancies in one patient or discrimination between a relapse and a second malignancy;

further classification of a malignancy, e.g. via Ig/TCR gene rearrangement patterns or particular chromosome aberrations;

occasionally: staging of lymphomas.

For long time, Southern blot analysis has been the gold standard technique for molecular clonality studies. Southern blotting is based on the detection of non-germline ("rearranged") DNA fragments, obtained after digestion with restriction enzymes. Well-chosen restriction enzymes (resulting in fragments of 2 to 15 kb) and well-positioned DNA probes (particularly downstream J segment probes) allow detection of virtually all Ig and TCR gene rearrangements as well as chromosome aberrations involving J gene segments.[21,28] It should be noted that Southern blot analysis focuses on the rearrangement diversity of Ig/TCR gene segments and therefore takes advantage of the combinatorial repertoire.

Optimal Southern blot results for clonality assessment can particularly be obtained with the IGH, IGK, and TCRB genes, because these genes have an extensive combinatorial repertoire as well as a relatively simple gene structure which can be evaluated with only one or two DNA probes.[22,24,28] The IGL and TCRA genes are more complex and require multiple probe sets.[214] Finally, the TCRG and TCRD genes have a limited combinatorial repertoire, which is less optimal for discrimination between monoclonality and polyclonality via Southern blot analysis.[20,21]

Despite the high reliability of Southern blot analysis, it is increasingly replaced by PCR techniques, because of several inherent disadvantages: Southern blot analysis is time-consuming, technically demanding, requires 10 to 20 μg of high quality DNA, and has a limited sensitivity of 5 to 10%.[21]

Detection of rearranged Ig/TCR genes and chromosome aberrations by PCR techniques requires precise knowledge of the rearranged gene segments in order to design appropriate primers at opposite sides of the junctional regions and breakpoint fusion regions, respectively.

In routine PCR-based clonality studies, the distance between the primers should be less than 1 kb, preferably less than 500 bp. This is particularly important for discrimination between PCR products from monoclonal versus polyclonal Ig/TCR gene rearrangements, which is based on the diversity of the junctional regions (diversity in size and composition). So far, mainly IGH and TCRG gene rearrangements have been used for PCR-based clonality studies, because of the limited number of primers needed to detect $V_H$-$J_H$ and Vγ-Jγ rearrangements.

The main advantages of PCR techniques are their speed, the low amounts of DNA required, the possibility to use DNA of lower quality, and the relatively good sensitivity of 1 to 5%, for some types of rearrangements even <1%. Consequently, PCR techniques allow the use of small biopsies (e.g. fine needle aspiration biopsies), or the use of formaldehyde-fixed paraffin-embedded samples, which generally results in DNA of lower quality. Therefore also archival material might be used, if needed.

Molecular clonality studies can be highly informative, but several limitations and pitfalls might hamper the interpretation of the results obtained with conventional detection methods:

1. Limited Sensitivity, Related to Normal Polyclonal Background

The detection limit varies between 1% and 10% (or even 15%), dependent on the applied technique (Southern blot analysis or PCR techniques) and dependent on the relative size of the "background" of normal (polyclonal) B- and T-lymphocytes. A limited sensitivity might hamper the detection of small clonal cell populations with less than 5 to 10% clonal lymphoid cells.

2. Clonality is not Equivalent to Malignancy

Detection of clonality does not always imply the presence of a malignancy. Some clinically benign proliferations have a clonal origin, such as many cases of $CD8^+$ (or sometimes CD4+) T-lymphocytosis, benign monoclonal gammopathies, initial phases of $EBV^+$ lymphoproliferations (frequently being oligoclonal) in immunodeficient patients, and benign cutaneous T-cell proliferations, such as lymphomatoid papulosis, etc. This implies that results of molecular clonality studies should always be interpreted in the context of the clinical, morphological, and immunophenotypic diagnosis, i.e. in close collaboration with hematologists, cytomorphologists, pathologists and immunologists.

3. Ig and TCR Gene Rearrangements are not Markers for Lineage

In contrast to the initial assumption, it is now clear for more than a decade that Ig and TCR gene rearrangements are not necessarily restricted to B-cell and T-cell lineages, respectively. Cross-lineage TCR gene rearrangements occur relatively frequently in immature B-cell malignancies, particularly in precursor-B-ALL (>90% of cases),[30] but also acute myeloid leukemias (AML) and mature B-cell malignancies might contain TCR gene rearrangements.[31,33] Albeit at a lower frequency, also cross-lineage Ig gene rearrangement occur in T-cell malignancies and AML, mainly involving the Ig heavy chain (IGH) locus.[33,34]

Virtually all (>98%) TCRαβ$^+$ T-cell malignancies have TCRG gene rearrangements (generally biallelic) and many TCRγδ$^+$ T-cell malignancies have TCRB gene rearrangements, implying that the detection of TCRB or TCRG rearrangements is not indicative of T-cells of the αβ or γδ T-cell lineage, respectively, either.

In addition to these cross-lineage rearrangements, it has been established that several lymphoid malignancies have unusual Ig/TCR gene rearrangement patterns. This information is available in detail for precursor-B-ALL and T-ALL, but not yet for most other lymphoid malignancies.[6]

4. Pseudoclonality and Oligoclonality

The detection of a seemingly clonal or seemingly oligoclonal lymphoid cell population (pseudoclonality) is rare in Southern blot analysis, unless genes with a limited combinatorial repertoire are used, such as TCRG or TCRD. This might result in faint rearranged bands, e.g. representing Vγ9-Jγ1.2 or Vδ2-Jδ1 rearrangements derived from antigen-selected TCRγδ+ T-lymphocytes. Yet, this is a well-known pitfall of Southern blot analysis and will not result in rearranged bands of high density.

Pseudoclonality in PCR-based clonality studies is more difficult to recognize. The high sensitivity of PCR can cause amplification of the few Ig or TCR gene rearrangements derived from a limited number of B-cells or T-cells in the studied tissue sample. Particularly the few reactive (polyclonal) T-cells in a small needle biopsy or in a B-NHL sample with high tumor load might result in (oligo)clonal PCR products. Frequently the amount of such PCR products is limited. This is particularly seen when TCRG genes are used as PCR target. Duplicate or triplicate PCR analyses followed by mixing of the obtained PCR products should help to clarify whether the seemingly clonal PCR products are in fact derived from different lymphocytes.

Finally, reactive lymph nodes can show a reduced diversity of the Ig/TCR repertoire, caused by predominance of several antigen-selected subclones (oligoclonality). Particularly lymph nodes or blood samples of patients with an active EBV or CMV infection can show a restricted TCR repertoire or TCR gene oligoclonality. Also clinical pictures of immunosuppression are frequently associated with restricted TCR repertoires, e.g. in transplant patients or patients with hairy cell leukemia. Recovery from transplantation and hematological remission are followed by restoration of the polyclonal TCR repertoire.[36,37]

5. False-Positive Results

In Southern blot analysis, false-positive results are rare and can generally be prevented by checking for underdigestion and by excluding polymorphic restriction sites.[21]

False-positive PCR results comprise a serious problem, if no adequate analysis of the obtained PCR products is performed to discriminate between monoclonal or polyclonal PCR products. Such discrimination can be achieved via single-strand conformation polymorphism (SSCP) analysis,[38] denaturing gradient gel electrophoresis (DGGE),[39] heteroduplex analysis (HD),[40,41] or GeneScanning (GS).[42,43] These techniques exploit the junctional region diversity for discrimination between monoclonal cells with identical junctional regions and polyclonal cells with highly diverse junctional regions.

6. False-Negative Results

False-negative results are rare in Southern blot analysis if appropriate J gene segment probes are used. Nevertheless, some uncommon rearrangements (generally non-functional rearrangements) might be missed, such as V-D rearrangements or deletions of the J regions. PCR analysis of Ig and TCR genes might be hampered by false-negative results because of improper annealing of the applied PCR primers to the rearranged gene segments. This improper primer annealing can be caused by two different phenomena. Firstly, precise detection of all different V, D, and J gene segments would require many different primers (Table 1), which is not feasible in practice. Consequently, family primers are designed, which specifically recognize most or all members of a particular V, D, or J family. Alternatively, consensus primers are used, which are assumed to recognize virtually all V and J gene segments of the locus under study. Family primers and particularly consensus primers are generally optimal for a part of the relevant gene segments, but show a lower homology (70 to 80%) to other gene segments. This may eventually lead to false-negative results, particularly in Ig/TCR genes with many different gene segments. In TCRG and TCRD genes this problem is minimal, because of their limited number of different gene segments.

The second phenomenon is the occurrence of somatic hypermutations in rearranged Ig genes of follicular and poet-follicular B-cell malignancies, particularly B-cell malignancies with class-switched IGH genes.

Sufficient knowledge and experience can prevent the first four pitfalls, because they mainly concern interpretation problems. The last two pitfalls concern technical problems, which can be solved by choosing reliable techniques for PCR product analysis and by the design of better primer sets.

Optimization of Southern blot analysis of Ig/TCR genes during the last ten years has resulted in the selection of reliable combinations of restriction enzymes (fragments between 2 and 15 kb, avoiding polymorphic restriction sites) and probes (mainly downstream of J gene segments). Although Southern blot analysis is a solid "gold standard" technique, many laboratories have gradually replaced Southern blot analysis by PCR technology, because PCR is fast, requires minimal amounts of medium-quality DNA, and has an overall good sensitivity.

Despite the obvious advantages, replacement of Southern blot analysis by PCR techniques for reliable Ig/TCR studies is hampered by two main technical problems:
false negative results due to improper primer annealing;
difficulties in discrimination between monoclonal and polyclonal Ig/TCR gene rearrangements.

Several individual diagnostic laboratories tried to solve the problems of the PCR-based clonality studies, but thus far no reliably standardized PCR protocols were obtained. In contrast, many different primer sets are being used, which all differ in their sensitivity and applicability.

The present invention now provides sets of nucleic acid amplification primers and standardized PCR protocols for detecting essentially all relevant Ig and TCR loci and two frequently occurring chromosome aberrations. The primers sets according to the invention comprising a forward and a reverse primer are capable of amplifying clonal rearrangements of the Ig heavy chain genes (IGH), Ig kappa chain genes (IGK), Ig lamba chain genes (IGL), TCR beta genes (TCRB), TCR gamma genes (TCRG), and TCR delta genes (TCRD) or of amplifying chromosomal translocation t(11;14)(BCL1-IGH) and t(14;18)(BCL2-IGH). The primers of the invention allow that both complete and incomplete rearrangements are detectable and that gene segments from different V, (D), and J families can be recognized.

Two techniques which can be used in a method of the invention for discrimination between monoclonal and polyclonal Ig/TCR gene rearrangements are heteroduplex analysis and GeneScanning. Heteroduplex analysis uses double-stranded PCR products and takes advantage of the length and composition of the junctional regions, whereas in GeneScanning single-stranded PCR products are separated in a high-resolution gel or polymer according to their length only (FIG. 2).

107 different, specific primers for all the relevant Ig/TCR loci as well as for t(11;14) (BCL1-IGH) and t(14;18) (BCL2-IGH), or variants thereof are provided (see FIGS. 3 to 11). The term "variant" refers to a primer which differs in 1 to 5 nucleotides, preferably 1 to 3 nucleotides, from the size and/or position from the nucleotide of a primer sequence shown, provided that the nucleotide sequence of said variant primer contains at most 2 mismatches, at most 1 mismatch, most preferably no mismatches with the target locus. In addition, a variant primer comprises a (differentially) labeled primer, i.e. a primer having a label that can be identified or distinguished from other labels by any means, including the use of an analytical instrument. Examples of differentially labeled primers are primers provided with a fluorescent label such as a 6-FAM, HEX, TET or NED dye. Labeled primers of the invention are particularly advantageous for use in automated high resolution PCR fragment analysis (Gene Scanning technology) for detection of PCR products. As is exemplified below, differentially labeled primers according to the invention allow to distinguish different PCR amplification products of approximately the same length (size), preferably using multi-color GeneScanning. Of course, a variant nucleic acid amplification primer, be it a forward or a reverse (dye-labeled) primer, should not be capable of forming dimers with any other (variant) forward and/or reverse nucleic acid amplification primer that is used in an amplification reaction, since this can interfere with primer annealing to a target locus and thus with the amplification of the rearrangement or translocation of interest.

In one embodiment, the invention provides a nucleic acid amplification assay, preferably a PCR assay, using at least one set of primers according to the invention. Said PCR assay can be a single (monoplex) or a multiplex PCR. In a preferred embodiment, a set of primers according to the invention is used in a standardized multiplex PCR assay, using for example two or more forward primers, or three or four forward primers, or variants thereof (e.g. selected from a group of "family primers", for example from the $V_H$ family primers), together with one or more consensus reverse primer(s), or variant(s) thereof (e.g. a $J_H$ consensus primer). The family primers of the invention are designed in such a way that they recognize most or all gene segments of a particular family (see Table 2). In a specific embodiment, all 107 primers are used in only 18 multiplex PCR tubes: 5 for IGH (3× $V_H$-$J_H$ and 2× $D_H$-$J_H$), 2 for IGK, 1 for IGL, 3 for TCRB (2× Vβ-Jβ and 1× Dβ-Jβ), 2 for TCRG, 1 for TCRD, 3 for BCL2-IGH, and 1 for BCL1-IGH (FIGS. 3 to 11). Such an assay allows assessing clonal rearrangements and/or chromosome aberrations. Furthermore, it allows detection of a lymphoproliferative disorder. Multiplex PCR testing of the primers on about 90 Southern blot defined lymphoproliferations showed that in more than 95% of the samples the Southern blot and PCR results were concordant.

In another embodiment, a method is provided for detecting a rearrangement, preferably two or more rearrangements, selected from the group consisting of a $V_H$-$J_H$ IGH rearrangement, a $D_H$-$J_H$ IGH rearrangement, a Vκ-Jκ IGK rearrangement, a Vκ/intron-Kde IGK rearrangement, a Vλ-Jλ IGL rearrangement, a Vβ-Jβ TCRB rearrangement, a Dβ-Jβ TCRB rearrangement, a $V_\gamma$-$J_\gamma$ TCRG rearrangement, a Vδ-Jδ TCRD rearrangement, a Dδ-Jδ TCRD rearrangement, a Dδ-Dδ TCRD rearrangement, and a Vδ-Dδ TCRD rearrangement, using at least one set of primers according to the invention. Also provided is a method for detecting a t(11;14)(BCL1-IGH) translocation or a t(14;18)(BCL2-IGH) translocation, using at least one set of primers according to the invention. Furthermore, methods are provided for detecting at least one of the above rearrangements and at least one translocation, using at least two sets of primers as provided herein.

Figure 12A:
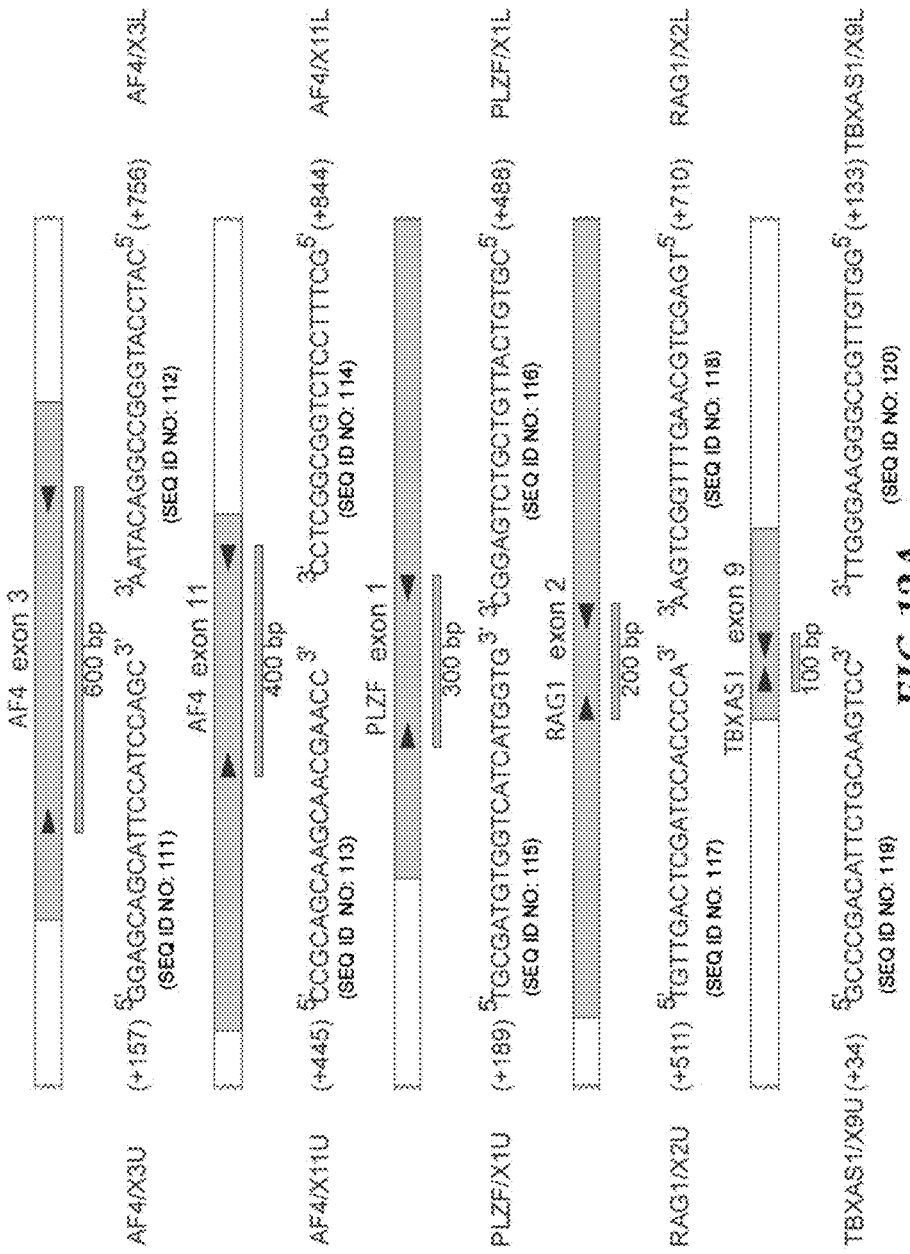
Figure 12B:
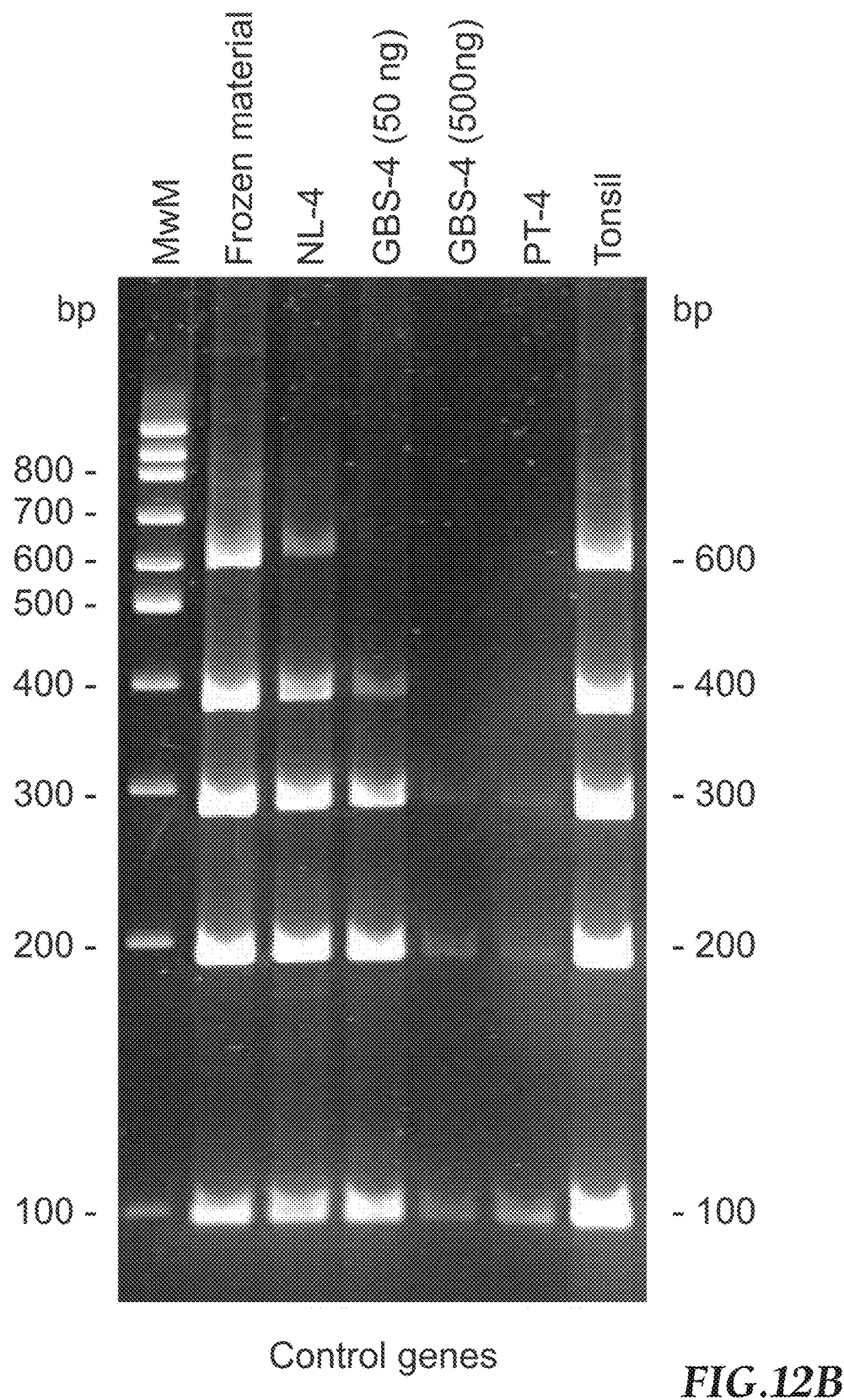

In a further aspect, a set of nucleic acid amplification primers capable of amplifying a human gene selected from the group consisting of the human AF4 gene (exon 3), the human AF4 gene (exon 11), the human PLZF1 gene, the human RAG1 gene and the human TBXAS1 gene is provided (see FIG. 12). Using one or more of these five primer sets consisting of a forward primer (or a variant thereof) and a reverse primer (or a variant thereof) in a nucleic acid amplification assay of the invention, it is possible to detect one or more "Control Gene(s)" selected from the group consisting of the human AF4 gene (exon 3), the human AF4 gene (exon 11), the human PLZF1 gene, the human RAG1 gene and the human TBXAS1 gene. Such a detection method is advantageously used to assess the quality (e.g. integrity and amplifiability) of a nucleic acid (DNA) sample extracted or isolated from a biological sample, for instance DNA extracted from a paraffin-embedded sample (see Example 10).

The ability of the different primer sets of the invention to amplify clonal rearrangements and/or chromosomal aberrations (translocations) has been tested in many different types of malignant lymphomas, among which follicular lymphoma, diffuse large B-cell lymphoma, and multiple myeloma. It was found that a set of primers is very useful for assessing clonal rearrangements and/or chromosomal tranalocations. It appeared that the detection rate of clonal rearrangements using the multiplex primer tubes according to the invention is unprecedentedly high, i.e at least 95%.

Parallel testing of available paraffin-embedded tissues of the above samples revealed largely identical results, if the DNA quality of these tissues is sufficiently high, meaning that fragments of at least 300 bp can be amplified in a specially-designed control gene PCR.

The applicability of the developed multiplex PCR assays according to the invention was evaluated on series of 50 to 100 cases per type of lymphoid malignancy. Following national pathology panel review, and central pathology panel review in case of difficulties, all included cases were defined according to the World Health Organization (WHO) classification. The studied diagnostic categories included malignancies such as follicular lymphoma, mantle cell lymphoma, marginal zone lymphoma, diffuse large B-cell lymphoma, angioimmunoblastic T-cell lymphoma, peripheral T-cell lymphoma, and anaplastic large cell lymphoma, as well as reactive lesions. The results show a very high level of clonality detection, even in entities, which are known to bear somatic hypermutations such as follicular lymphoma and diffuse large B-cell lymphoma. Particularly the usage of the three IGH $V_H$-$J_H$ tubes, supplemented with the two IGH $D_H$-$J_H$ tubes and the two IGK tubes appeared to be highly efficient in the detection of clonal Ig gene rearrangements. This high efficiency is obtained by the complementarity of the Ig tubes as well as by the fact that $D_H$-$J_H$ and IGK-Kde rearrangements are not (or rarely) somatically mutated. Such complementarity was also found for the TCRB and TCRG primers in case of T-cell malignancies.

Furthermore, interesting and unexpected rearrangement patterns, such as unusual cross-lineage rearrangements, were observed. Remarkably, in about 10% of reactive lesions clonal rearrangements were detected. These reactive lymphoproliferations included EBV-related lymphoproliferations and atypical hyperplasias like Castleman's disease, as well as lesions that were suspicious for a B- or T-cell clone.

In a specific embodiment, a method is provided for the detection of minimal residual disease (MRD). The term minimal residual disease (MRD) describes the situation in which, after chemotherapy for acute leukemia (AL), a morphologically normal bone marrow can still harbor a relevant amount of residual malignant cells. Detection of minimal residual disease (MRD) is a new practical tool for a more exact measurement of remission induction during therapy because leukemic blasts can be detected down to $10^{-4}$-$10^{-6}$. Known PCR-based MRD analysis uses clonal antigen receptor rearrangements detectable in ~90-95% of the investigated patient samples. However, amplification of polyclonal products often leads to false-positive PCR amplicons not suitable for MRD analysis. The invention now provides a method for the detection of identically (clonally) rearranged Ig and TCR genes or detection of well-defined and frequent chromosome aberrations, such as t(11;14), and t(14;18). Thus, the rearrangements and translocations detected using a set of primers of the invention not only serve as markers for clonality at diagnosis, but also as PCR targets for detection of MRD during follow-up.

In a further aspect, the invention provides a (diagnostic) kit for the detection of at least one rearrangement selected from the group consisting of a $V_H$-$J_H$ IGH rearrangement, a $D_H$-$J_H$ IGH rearrangement, a Vκ-Jκ IGK rearrangement, a Vκ/intron-Kde IGK rearrangement, a Vλ-Jλ IGL rearrangement, a Vβ-Jβ TCRB rearrangement, a Dβ-Jβ TCRB rearrangement, a $V_γ$-$J_γ$ TCRG rearrangement, a Vδ-Jδ TCRD rearrangement, a Dδ-Jδ TCRD rearrangement, a Dδ-Dδ TCRD rearrangement, a Vδ-Dδ TCRD rearrangement and/or at least one translocation selected from t(11;14)(BCL1-IGH) and t(14;18)(BCL2-IGH), comprising at least one set of primers according to the invention. A kit of the invention is highly suitable for PCR-based clonality diagnostics. Optionally, such a kit also comprises at least one set of primers capable of amplifying a human "control gene" as mentioned above. Inclusion of one, preferably at least two, more preferably at least three of these control gene primer sets in a Control Tube can be helpful in estimating the quality of the DNA sample to be diagnosed, for instance DNA extracted from paraffin-embedded tissue.

In a further aspect, the invention provides a method for rapid discrimination of different types of Ig/TCR gene rearrangements in the same multiplex PCR tube. GeneScanning allows the application of multiple different fluorochrome-conjugated primers in a single tube. Such differential labeling of primers can be used for extra discrimination between different types of Ig or TCR gene rearrangements.

Differential labeling of V primers generally has limited added value, but differential labeling of downstream primers can support the rapid and easy identification of the type of Ig/TCR gene rearrangement, which is useful for PCR-based detection of minimal residual disease.[44,45] Labeling of J primers is not regarded to be informative for IGH ($V_H$-$J_H$ or $D_H$-$J_H$), IGK (Vκ-Jκ), or IGL (Vλ-Jλ). For rapid identification of IGK-Kde rearrangements, it might be interesting to discriminate between Vκ-Kde and intron RSS-Kde rearrangements by differential labeling of the Kde and intron RSS primers (see FIG. 5B).

Figure 13A:
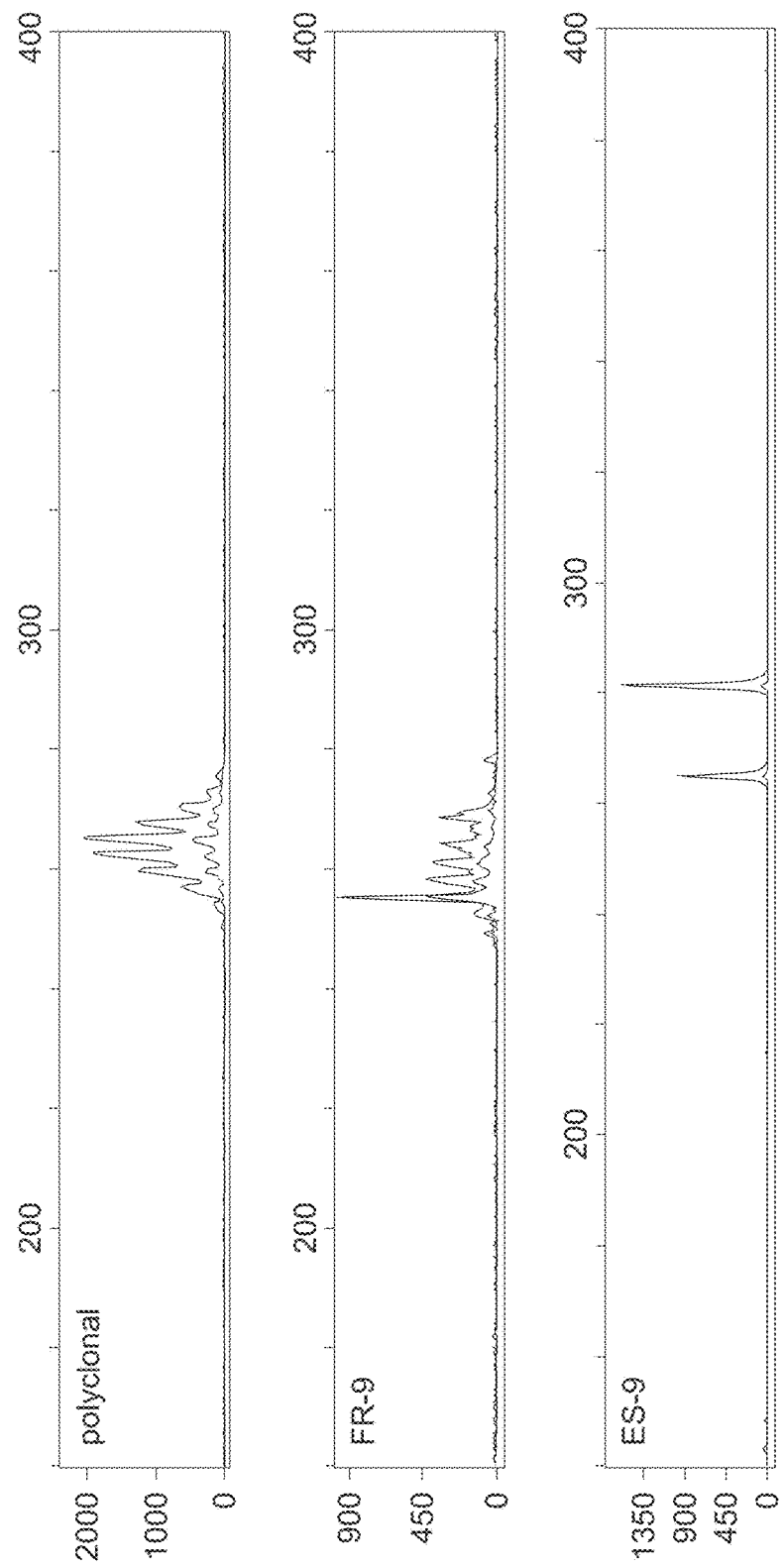
Figure 13B:
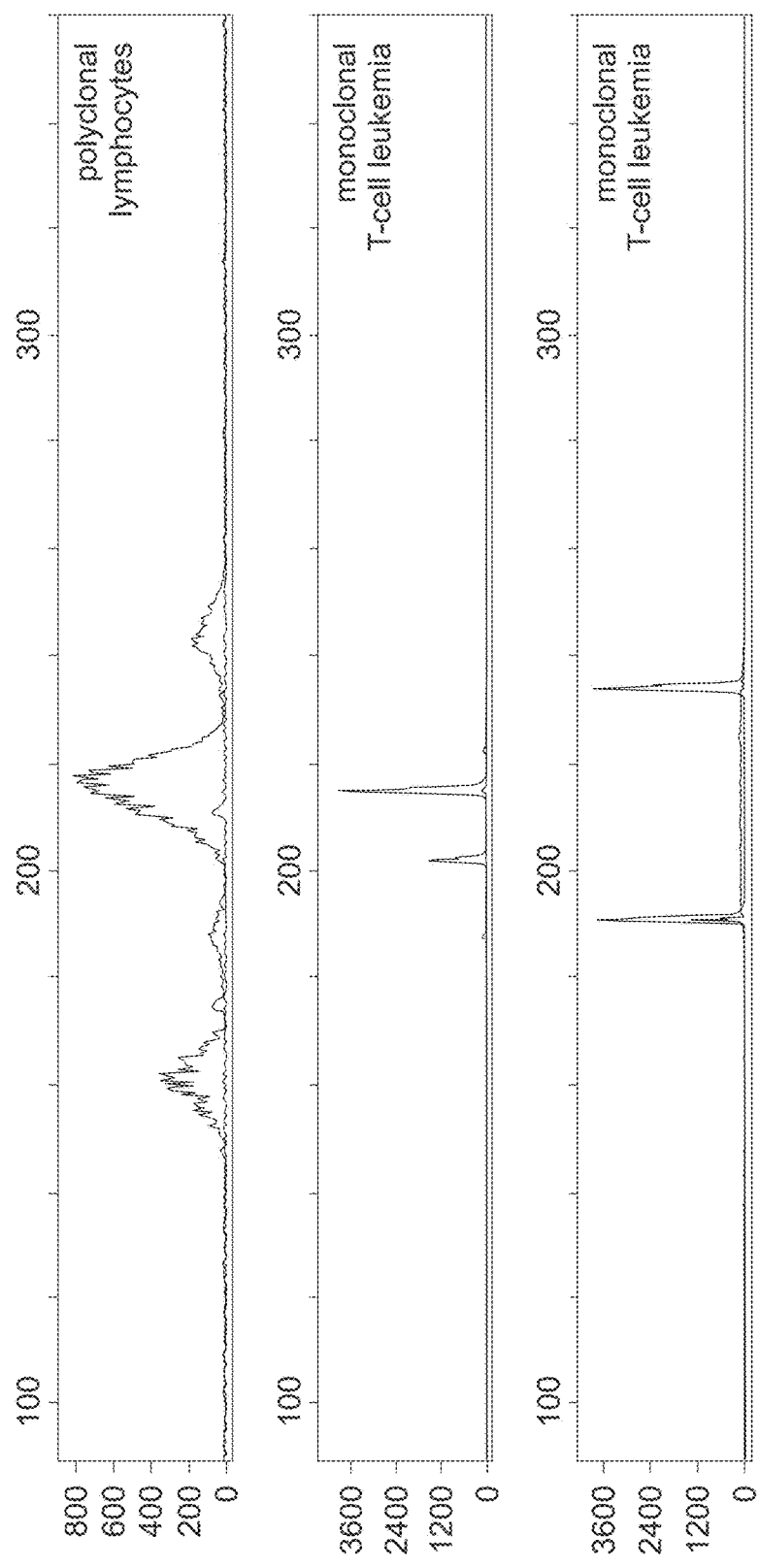
Figure 13C:
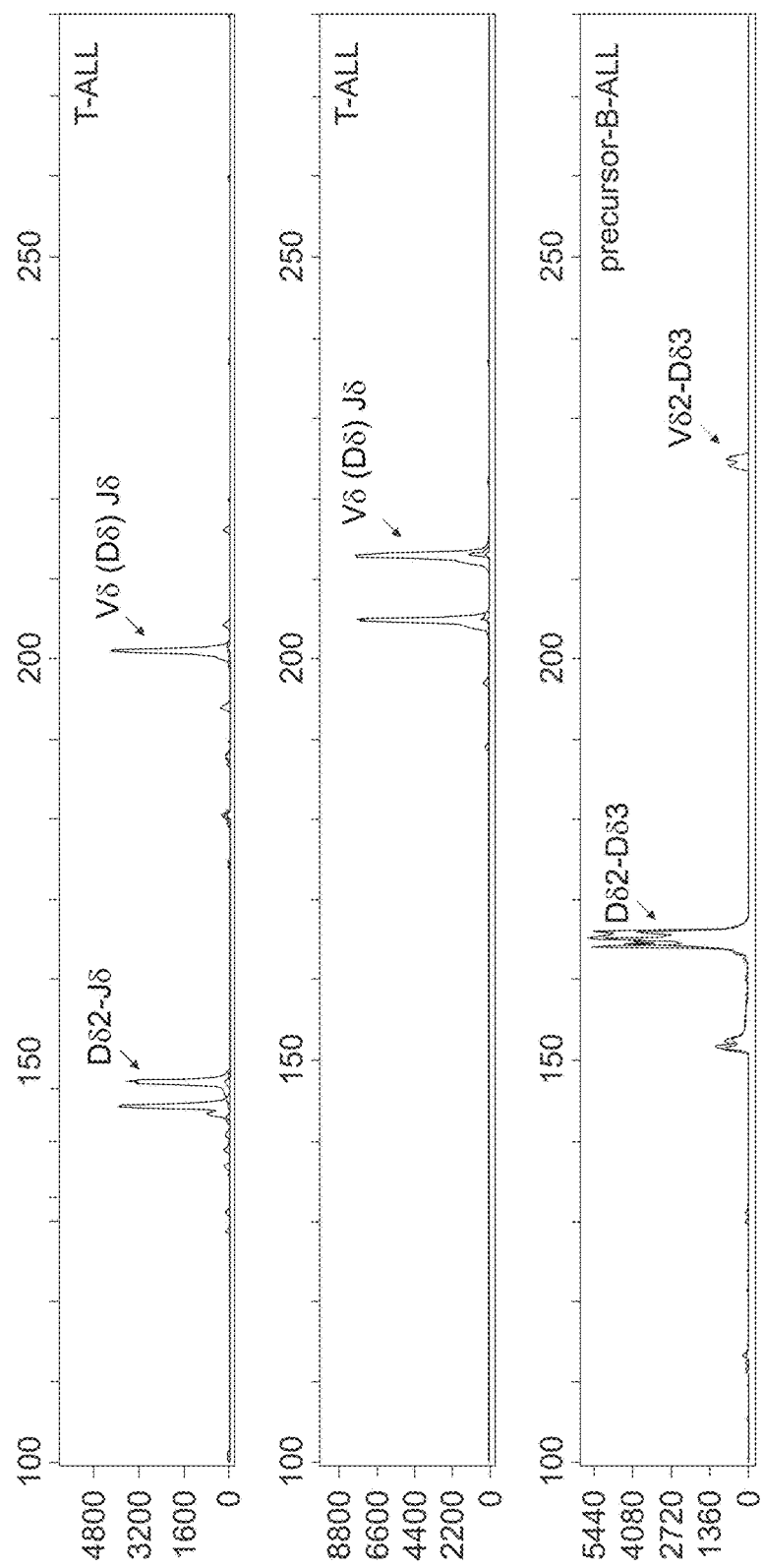

The most informative multicolor GeneScanning can be designed for TCR gene rearrangements, facilitating the rapid recognition of the different types of TCRB, TCRG, and TCRD gene rearrangements. For example, differential labeling of the Jβ1 and Jβ2 primers in TCRB tube A (see FIG. 7B) allows easy identification of the polyclonal and monoclonal Vβ-Jβ1 versus Vβ-Jβ2 rearrangements (FIG. 13A). Differential labeling of the Jγ1.3/2.3 and Jγ1.1/2.1 primers (FIG. 8B) results in easy identification of the different types of TCRG gene rearrangements (FIG. 13B). Differential labeling of the Jδ primers, Dδ2 primer, and Dδ3 primer in the TCRD tube (FIG. 9B) results in easy identification of the most relevant TCRD gene rearrangements, such as Dδ2-Jδ, Vδ-Jδ, Dδ2-Dδ3, and Vδ2-Dδ3 rearrangements (FIG. 13C).

These multi-color multiplex PCR tubes appear to be easy and convenient in daily practise of PCR based clonality diagnotics.

LEGENDS TO THE FIGURES

FIG. 1. Schematic Diagram of Sequential Rearrangement Steps, Transcription, and Translation of the TCRB Gene.

In this example first a Dβ2 to Jβ2.3 rearrangement occurs, followed by Vβ4 to Dβ2-Jβ2.3 rearrangement, resulting in the formation of a Vβ4-Dβ2-Jβ2.3 coding joint. The rearranged TCRB gene is transcribed into precursor mRNA, spliced into mature mRNA, and finally translated into a TCRβ protein chain. The two extrachromosomal TCR excision circles (TRECs) that are formed during this recombination process are indicated as well; they contain the D-J signal joint and V-D signal joint, respectively.

FIG. 2. Schematic Diagram of Heteroduplex Analysis and GeneScanning of PCR Products, Obtained from Rearranged Ig and TCR Genes.

A. Rearranged Ig and TCR genes (IGH in the example) show heterogeneous junctional regions with respect to size and nucleotide composition. Germline nucleotides of V, D, and J gene segments are given in large capitals and randomly inserted nucleotides in small capitals. The junctional region heterogeneity is employed in heteroduplex analysis (size and composition) and GeneScanning (size only) to discriminate between products derived from monoclonal and polyclonal lymphoid cell populations. B. In heteroduplex analysis, PCR products are heat-denatured (5 min, 94° C.) and subsequently rapidly cooled (1 hour, 4° C.) to induce duplex (homo- or heteroduplex) formation. In cell samples consisting of clonal lymphoid cells, the PCR products of rearranged IGH genes give rise to homoduplexes after denaturation and renaturation, whereas in samples which contain polyclonal lymphoid cell populations the single-strand PCR fragments will mainly form heteroduplexes, which result in a background smear of slowly migrating fragments upon electrophoresis. C. In GeneScanning fluorochrome-labeled PCR products of rearranged IGH genes are denatured prior to high-resolution fragment analysis of the resulting single-stranded fragments. Monoclonal cell samples will give rise to PCR products of identical size (single peak), whereas in polyclonal samples many different IGH PCR products will be formed, which show a characteristic Gaussian size distribution.

FIG. 3. PCR Analysis of IGH ($V_H$-$J_H$) Rearrangements.

A. Schematic diagram of IGH gene complex on chromosome band 14q32.3 (adapted from ImMunoGeneTics database).[46,47] Only rearrangeable non-polymorphic $V_H$ gene segments are included in blue (functional $V_H$), or in gray (rearrangeable pseudogenes). Recently discovered (generally truncated) $V_H$ pseudogenes are not indicated. B. Schematic diagram of IGH $V_H$-$J_H$ rearrangement with three sets of $V_H$ primers and one $J_H$ consensus primer, combined in three multiplex tubes. The relative position of the $V_H$ and $J_H$ primers is given according to their most 5' nucleotide upstream (−) or downstream (+) of the involved RSS. The $V_H$ gene segment used as representative $V_H$ family member for primer design is indicated in parentheses. C, D, and E. Heteroduplex analysis and GeneScanning of the same polyclonal and monoclonal cell populations, showing the typical heteroduplex smears and homoduplex bands (left panels) and the typical polyclonal Gaussian curves and monoclonal peaks (right panels). The approximate distribution of the polyclonal Gaussian curves is indicated in nt.

Figure 4A:
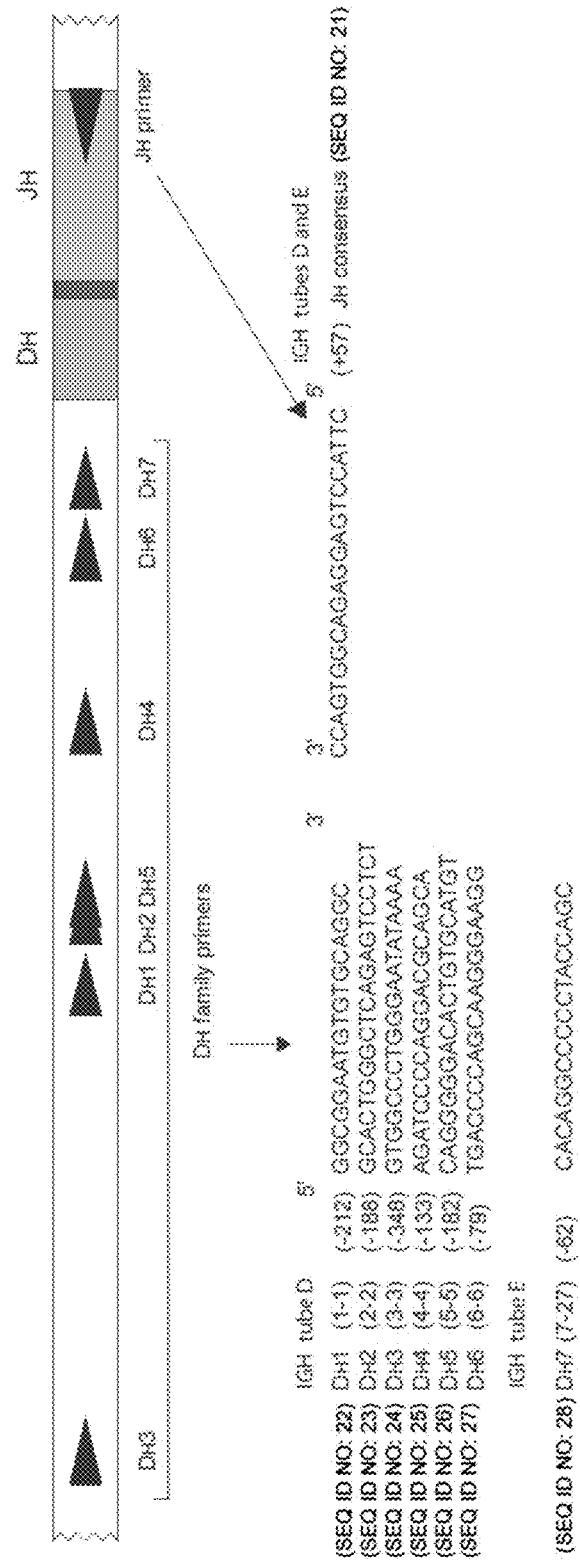
Figure 4B:
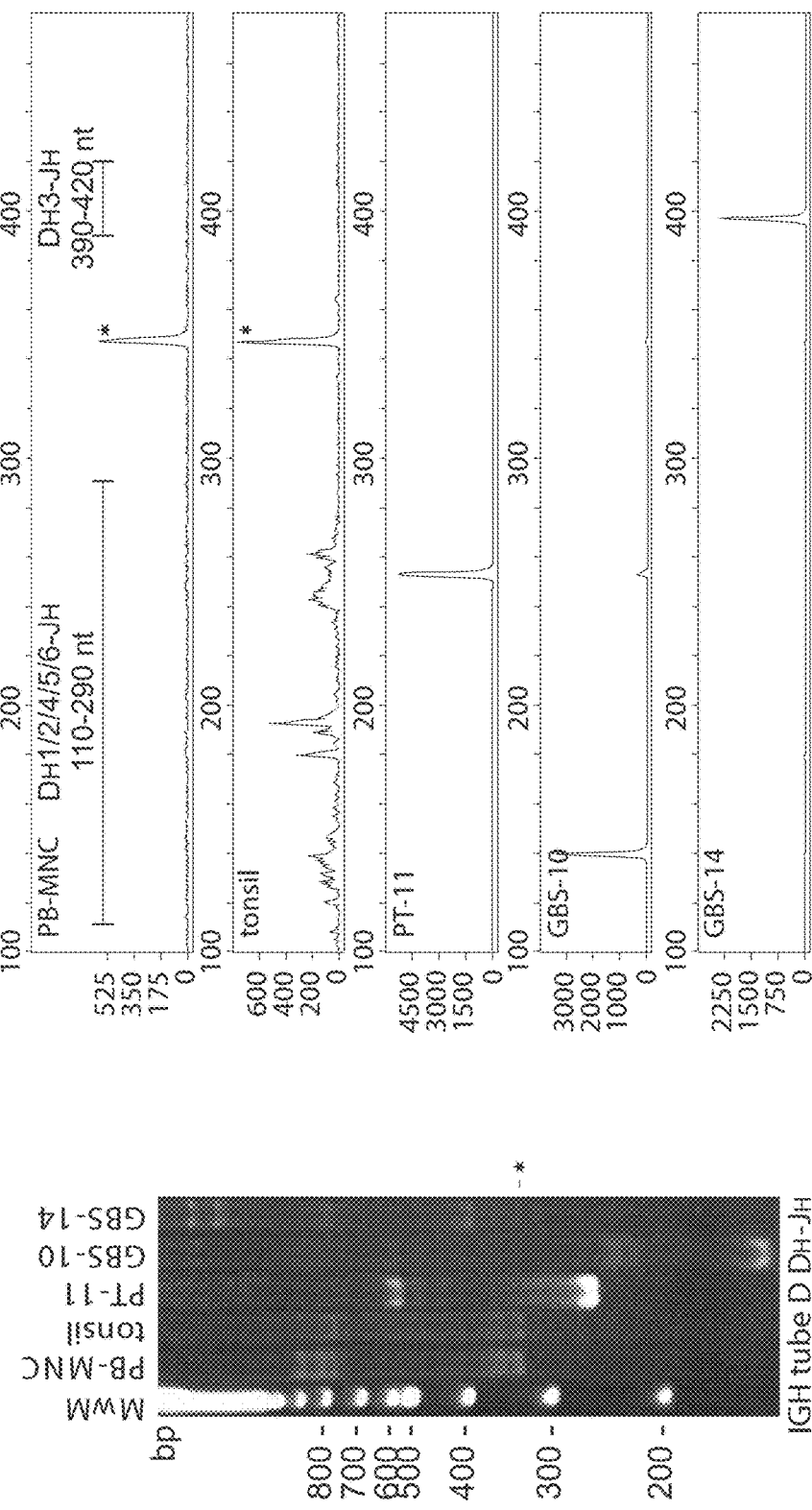
Figure 4C:
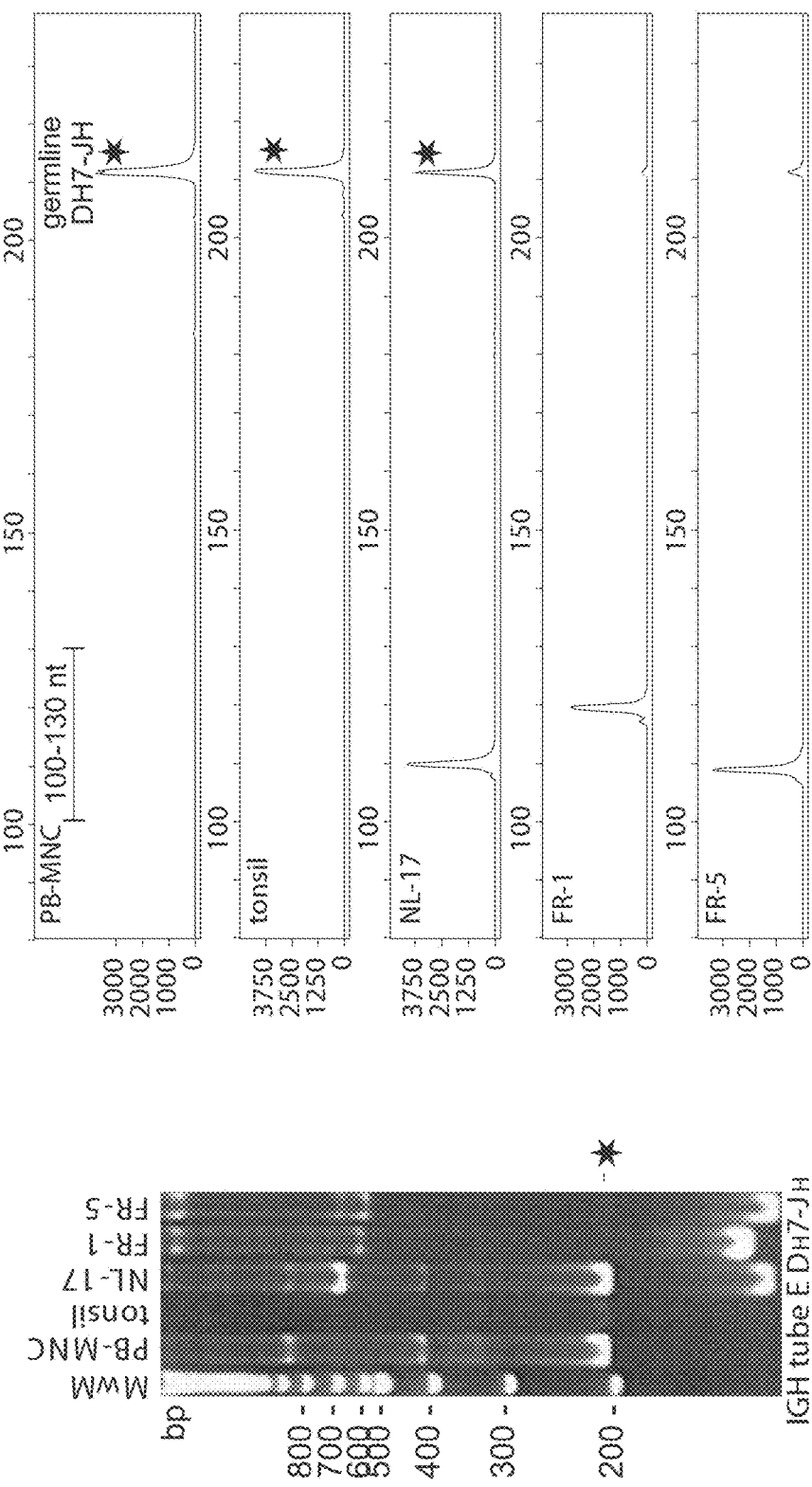

FIG. 4. PCR Analysis of IGH ($D_H$-$J_H$) Rearrangements.

A. Schematic diagram of IGH ($D_H$-$J_H$) rearrangement with seven $D_H$ family primers and one $J_H$ consensus primer, divided over two tubes (IGH tubes D and E). The $D_H$7 (7-27) primer was separated from the other six $D_H$ primers, because the $D_H$7 and $J_H$ consensus primer will give a germline PCR product of 211 nt. The relative position of the $D_H$ and $J_H$ primers is given according to their most 5' nucleotide upstream (−) or downstream (+) of the involved RSS. The $D_H$ gene segment used as representative $D_H$ family member for primer design is indicated in parentheses. B and C. Heteroduplex analysis (left panels) and GeneScanning (right panels) of the same polyclonal and monoclonal cell populations. The approximate distribution of the polyclonal and monoclonal peaks is indicated. The potential background band/peak in tube D is indicated with an asterisk and is located outside the expected range of $D_H$-$J_H$ rearrangements. The germline $D_H7$-$J_H$ band of tube E is also indicated with an asterisk.

FIG. 5. PCR Analysis of IGK Gene Rearrangements.

A. Schematic diagram of the IGK gene complex on chromosome band 2p11.2 (adapted from ImMunoGeneTics database).[46,47] Only rearrangeable non-polymorphic Vκ gene segments are indicated in blue (functional Vκ) or in grey (nonfunctional Vκ). The cluster of inverted Vκ gene segments (coded with the letter D) is located ~800 kb upstream of the non-inverted Vκ gene segments. These upstream Vκ gene segments are presented as a mirrored image to their corresponding non-inverted counterparts. B. Schematic diagrams of Vκ-Jκ rearrangement and the two types of Kde rearrangements (Vk-Kde and intron RSS-Kde). The relative position of the Vκ, Jκ, Kde and intron RSS (INTR) primers is given according to their most 5' nucleotide upstream (−) or downstream (+) of the involved RSS. The Vκ gene segment used as representative member of the Vκ1, Vκ2, and Vκ3 families are indicated in parentheses. Vκ4, Vκ5, and Vκ7 are single-member Vκ families. The primers are divided over two tubes: tube A with Vκ and Jκ primers and tube B with Vκ, intron RSS, and Kde primers. C and D. Heteroduplex analysis and GeneScanning of the same polyclonal and monoclonal cell populations, showing the typical heteroduplex smears and homoduplex bands (left panels) and the typical Gaussian curves and monoclonal peaks (right panels). The approximate distribution of the polyclonal Gaussian curves is indicated in nt.

Figure 6A:
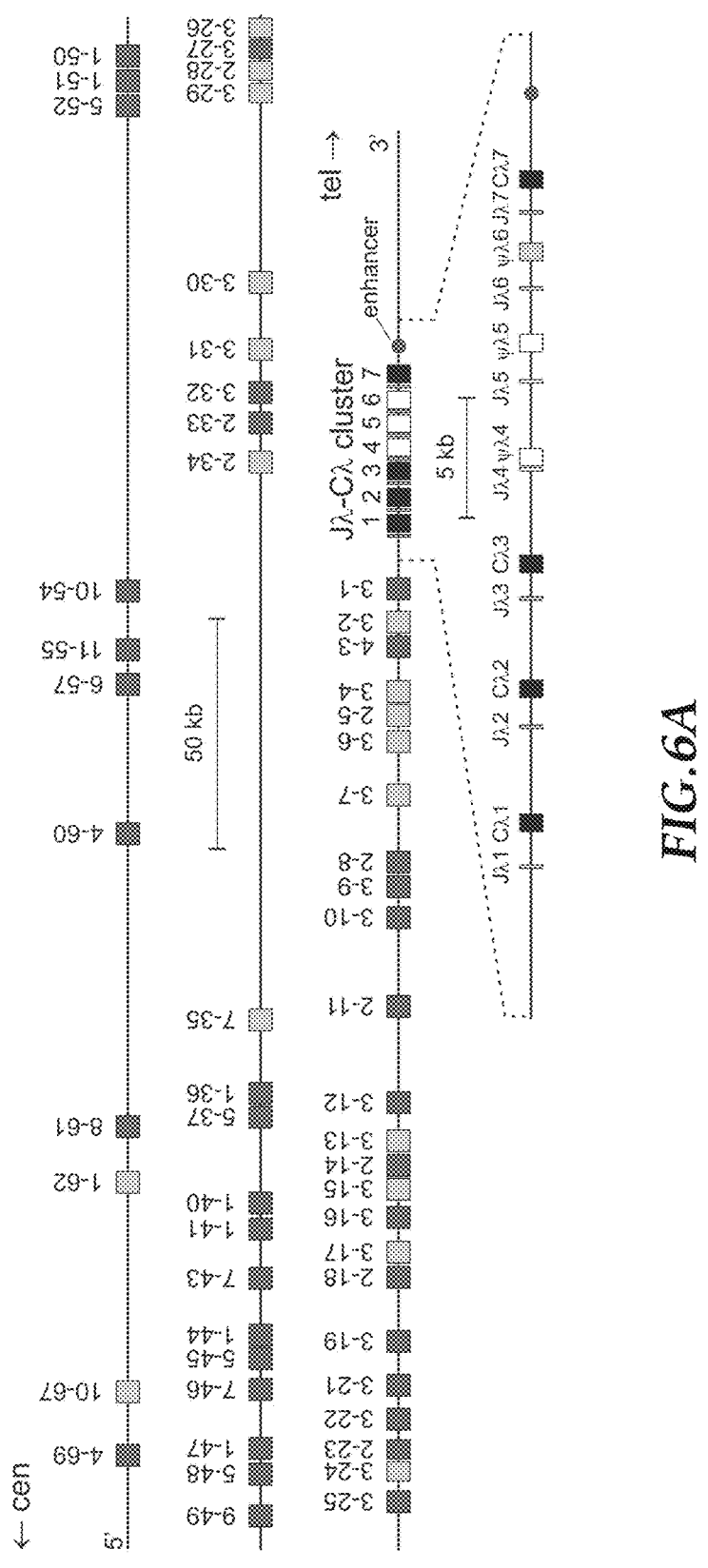
Figure 6B:
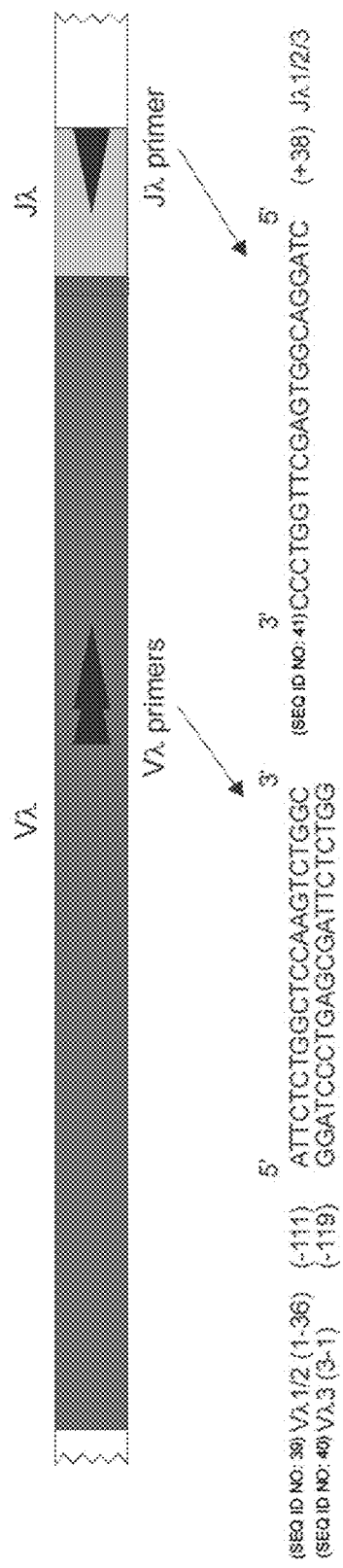
Figure 6C:
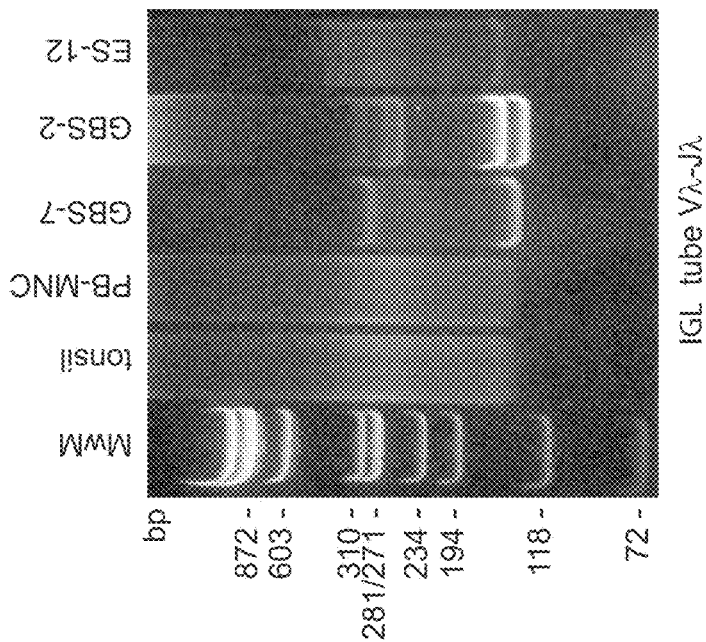
Figure 6C:
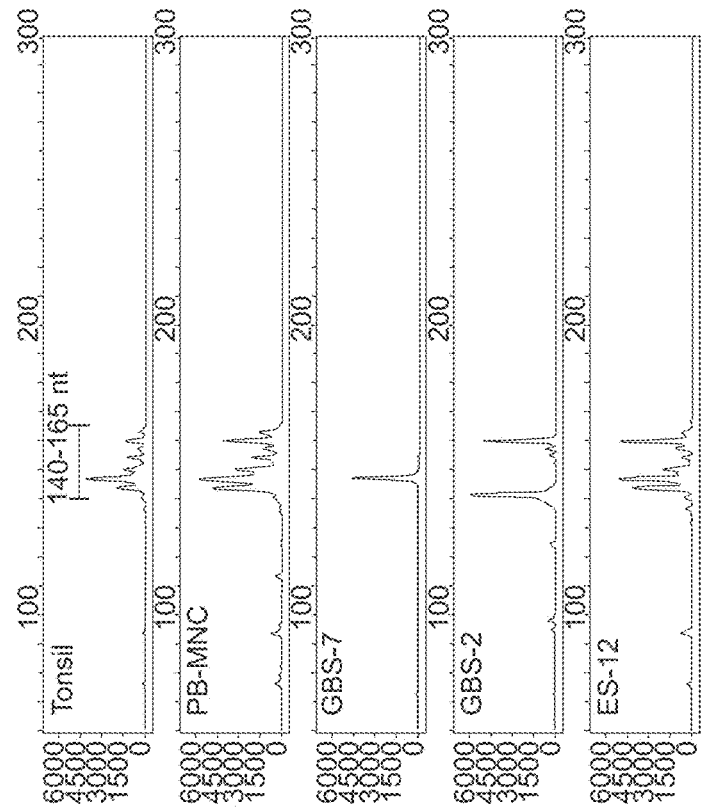

FIG. 6. PCR Analysis of IGL Gene Rearrangements.

A. Schematic diagram of IGL gene complex on chromosome band 22q11.2 (adapted from ImMunoGenetics database).[46,47] Only rearrangeable non-polymorphic Vλ gene segments are included in blue (functional Vλ) or in grey (nonfunctional VΔ) B. Schematic diagram of Vλ-Jλ rearrangement with two Vλ family primers and one Jλ consensus primer. Only two Vλ primers were designed for Vλ1 plus Vλ2 and for Vλ3, because these three Vλ families cover approximately 70% of rearrangeable Vλ gene segments and because approximately 90% of all IGL gene rearrangements involve Vλ1, Vλ2, or Vλ3 gene segments.[48] Although five of the seven Jλ gene segments can rearrange, only a single Jλ consensus primer was designed for Jλ1, Jλ2, and Jλ3, because 98% of all IGL gene rearrangements involve one of these three gene segments.[49] The relative position of the Vλ and Jλ primers is given according to their most 5' nucleotide upstream (−) or downstream (+) of the involved RSS. C. Heteroduplex analysis and GeneScanning of the same polyclonal and monoclonal cell populations, showing the typical heteroduplex smears and homoduplex bands (left panel) and the polyclonal Gaussian curves and monoclonal peaks (right panel). The approximate position of the polyclonal Gaussian curves is indicated in nt.

FIG. 7. PCR Analysis of TCRB Gene Rearrangements.

A. Schematic diagram of the human TCRB locus. The gene segment designation is according to Arden et al.[50] with the designation according to Rowen et al.[51] and Lefranc et al.[46,47] in parentheses. The figure is adapted from the international ImMunoGeneTics database.[46,47] Only the rearrangeable non-polymorphic Vβ gene segments are depicted in blue (functional Vβ), in half blue/half gray (potential functional, but no protein expression found) and in grey (non-functional Vβ). B. Schematic diagram of Vβ-Jβ and Dβ-Jβ rearrangements. The 23 Vβ primers, 13 Jβ primers and two Dβ primers are combined in three tubes: tube A with 23 Vβ primers and nine Jβ primers, tube B with 23 Vβ primers and four Jβ primers, and tube C with two Dβ primers and 13 Jβ primers. The 23 Vβ primers and the 13 Jβ primers are aligned in order to obtain comparably sized PCR products (see panels C and D). The Vβ primers cover approximately 90% of all Vβ gene segments. The relative position of the Vβ, Dβ, and Jβ primers is given according to their most 5' nucleotide upstream (−) or downstream (+) of the involved RSS. C, D, and E. Heteroduplex analysis and GeneScanning of the same polyclonal and monoclonal cell populations, showing the typical heteroduplex smears and homoduplex bands (left panels) and the typical polyclonal Gaussian curves and monoclonal peaks (right panels). The approximate distribution of the polyclonal Gaussian curves is indicated in nt.

FIG. 8. PCR Analysis of TCRG Gene Rearrangements.

A. Schematic diagram of the human TCRG locus on chromosome band 7p14. Only the rearrangeable Vγ gene segments are depicted in blue (functional Vγ) or in gray (non-functional Vγ). For the Jγ gene segments, both nomenclatures are used.[46,47,52] B. Schematic diagram of TCRG Vγ-Jγ rearrangement with four Vγ primers and two Jγ primers, which are divided over two tubes. The relative position of the Vγ and Jγ primers is indicated according to their most 5' nucleotide upstream (−) or downstream (+) of the involved RSS. C and D. Heteroduplex analysis and GeneScanning of the same polyclonal and monoclonal cell populations, showing the typical heteroduplex smears and homoduplex bands (left panels) and the typical polyclonal Gaussian curves and monoclonal peaks (right panels). The approximate distribution of the polyclonal Gaussian curves is indicated in nt.

FIG. 9. PCR Analysis of TCRD Gene Rearrangements.

A. Schematic diagram of human TCRD locus on chromosome band 14q11.2. The six "classical" Vd gene segments are indicated in blue, scattered between the Vα gene segments in black. Since Vδ4, Vδ5, and Vδ6 are also recognized as Vα gene segments, their Vα gene code is given in parenthesis. B. Schematic diagram of Vδ-Jδ, Dδ2-Jδ, Dδ2-Dδ3, and Vδ-Dδ3 rearrangements, showing the positioning of six Vδ, four Jδ, and two Dδ primers, all combined in a single tube. The relative position of the Vδ, Dδ, and Jδ primers is indicated according to their most 5' nucleotide upstream (−) or downstream (+) of the involved RSS. C. Heteroduplex analysis (left panel) and GeneScanning (right panel) of the same polyclonal and monoclonal cell populations. The polyclonal cell populations show a vague smear in heteroduplex analysis and a complex and broad peak pattern in GeneScanning. The monoclonal bands and peaks are clearly visible. The approximate position of the PCR products of the different types of rearrangements in GeneScanning is indicated.

Figure 10A:
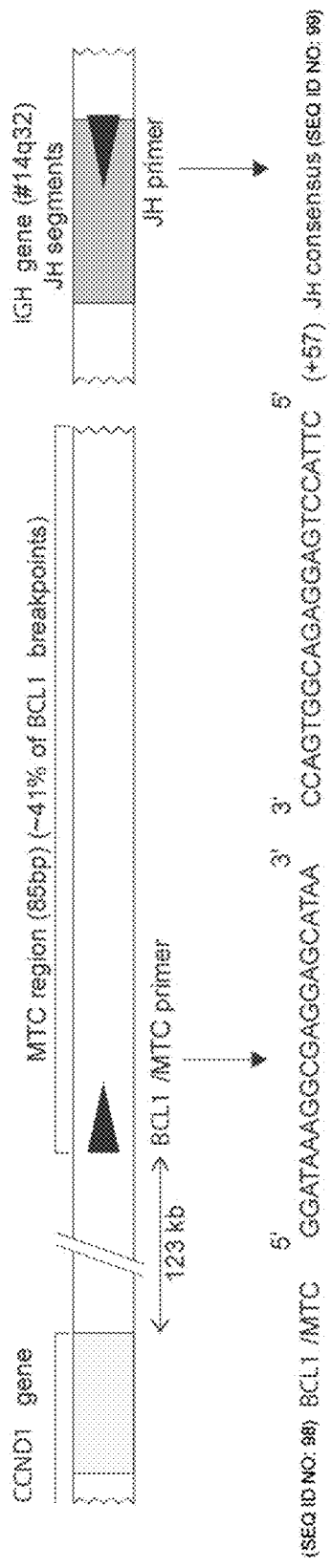
Figure 10B:
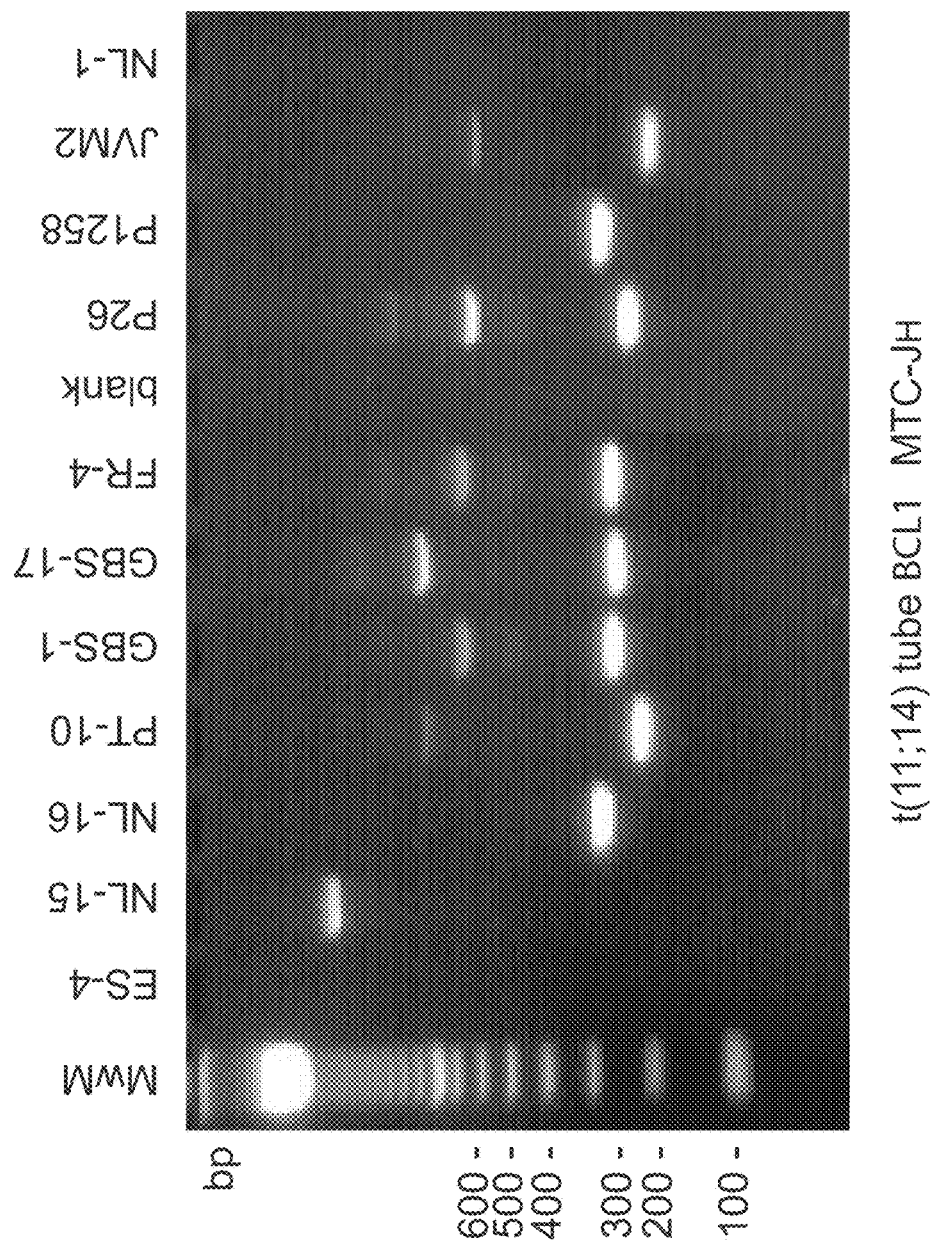

FIG. 10. Detection of BCL1-IGH rearrangements. A. Schematic diagram of the CCND1 gene and the BCL1 breakpoint region MTC on chromosome band 11q13 as well as the $J_H$ gene segment on chromosome band 14q32. For the primer design in the BCL1-MTC region an artificial BCL1-MTC/$J_H$4 junctional sequence was composed (as partially reported for JVM2[53]): the first 50-nucleotides as reported by Williams[54] were linked to nucleotide 1-439 from MTC-sequence present at NCBI (accession-number S77049[55]); the N-region "GCCC" of JVM2[53] was added followed by nucleotide 1921-3182 representing the $J_H4$-$J_H6$ genomic region (accession-number J00256). B. Agarose gel electrophoresis of a series of BCL1-IGH PCR products from different MCL patients and the positive control cell line JVM2. The PCR products differ is size, indicating different positions of the BCL1-MTC breakpoints. The larger bands of lower density represent PCR products that extend to the next downstream germline $J_H$ gene segment.

FIG. 11. PCR Detection of BCL2-IGH Rearrangements.

A. Schematic diagram of the BCL2 gene on chromosome band 18q21. The majority of the BCL2 breakpoints cluster in three regions: MBR, 3' MBR, and mcr. Consequently, multiplex primers have been designed to cover the potential breakpoints in these three regions: two MBR primers, four 3' MBR primers, and three mcr primers. The relative position of the BCL2 primers is indicated according to their most 5' nucleotide upstream (−) or downstream (+) to the 3' end of BCL2 exon 3 (according to NCBI accession no. AF325194S1), except for two BCL2-mcr primers; their position is indicated downstream of the first nucleotide of the AF275873 sequence. B, C, and D. Agarose gel electrophoresis of PCR products from different FCL patients and several positive control cell lines (DoHH2, K231, OZ, and SC1). Panel B and D contain the same samples and show complementarity in positivity, illustrating that tube C (mcr tube) has added value. The PCR products differ in size, related to different position of the BCL2 breakpoints. The larger bands of lower density in the same lanes represent PCR products that extend to the next downstream germline $J_H$ gene segment or to the next upstream BCL2 primer.

FIG. 12. Control Gene PCR for Assessment of Amplifiability and Integrity of DNA Samples.

A. Schematic diagram of five control genes exons and the five primer sets for obtaining PCR products of 600 bp, 400 bp, 300 bp, 200 bp, and 100 bp. The relative position of the control gene primers is given according to their most 5' nucleotide downstream of the 5' splice site of the involved control gene exon. B. Control gene PCR products of six DNA samples, separated in a 6% polyacrylamide gel. Two control samples contained high molecular weight DNA (outer lanes) and four DNA samples were obtained from paraffin-embedded tissue samples, showing reduced amplifiability (e.g. GBS-4 50 ng versus GBS-4 500 ng) or reduced integrity of the DNA (PT-4).

FIG. 13. Multicolor GeneScanning for supporting the rapid and easy identification of TCR gene rearrangements. A. Two-color analysis of TCRB tube A with differential labeling of Jβ1 primers (TET-labeled; green) and Jβ2 primers (FAM labeled; blue). The top panel nicely shows the two polyclonal Jβ1 and Jβ2 rearrangement patterns (c.f FIG. 7C), whereas the other two panels show clonal Jβ2 rearrangements. B. Two-color analysis of TCRG tube A with differential labeling of the Jγ1.3/2.3 primer (FAM-labeled; blue) and the Jγ1.1/2.1 (TET-labeled; green). The top panel nicely shows the polyclonal rearrangement patterns (c.f. FIG. 8C), whereas the other two panels show clonal Jγ1.3/2.3 and clonal Jγ1.1/2.1 rearrangements, respectively. C. Three-color analysis of TCRD gene rearrangements with differential labeling of Jδ primers (FAM-labeled; blue), Dδ2 primer (HEX-labeled; green) and Dδ3 primer (NED-labeled; black). Within the complex rearrangement patterns of the TCRD tube (FIG. 9C), the three-color analysis allows direct detection of Vδ-Jδ rearrangements (blue peaks), Dδ2-Jδ rearrangements (blue and green peaks, not fully comigrating because of differences in migration speed of the two fluochromosomes), Vδ2-Dδ3 rearrangement (black peaks), and Dδ2-Dδ3 rearrangement (comigrating green and black peaks).

MATERIALS AND METHODS

Selection of PCR Targets: Aiming for Complementarity

It was decided to aim for the availability of at least one PCR-detectable clonality target in each lymphoid malignancy. In mature B-cell malignancies this aim might be hampered by the occurrence of somatic hypermutations in Ig genes, which are particularly found in follicular and post-follicular B-cell malignancies. Therefore it was decided to include PCR targets that have some degree of complementarity.

Several rationales were used for target selection:
IGH genes: not only complete $V_H$-$J_H$ rearrangements but also incomplete $D_H$-$J_H$ rearrangements were included as PCR targets, because $D_H$-$J_H$ rearrangements are probably not affected by somatic hypermutations;
IGK and IGL genes: both Ig light chain genes were included as PCR targets, because this increases the chance of finding a PCR-detectable Ig gene rearrangement in each mature B-cell malignancy;
IGK genes: not only Vκ-Jκ rearrangements were included, but also rearrangements of the kappa deleting element (Kde), because they occur on one or both alleles in (virtually) all Igλ$^+$ B-cell malignancies and in one third of Igκ B-cell malignancies and because Kde rearrangements are probably not affected by somatic hypermutation;
TCRB genes: both complete Vβ-Jβ and incomplete Dβ-Jβ rearrangements, because complete and incomplete TRCB gene rearrangements occur in all mature TCRαβ$^+$ T-cell malignancies and also in many TCRγδ$^+$ T-cell malignancies;
TCRG genes: this classical PCR clonality target is useful in all T-cell malignancies of the TCRγδ and the TCRαβ lineage.
TCRD genes: this is a potentially useful target in immature T-cell malignancies as well as in TCRγδ$^+$ T-cell malignancies;
TCRA gene: this gene was not included as PCR target, because of its high degree of complexity with ~50 V and 61 J gene segments. Furthermore, all T-cell malignancies with TCRA gene rearrangements contain TCRB gene rearrangements and generally also have TCRG gene rearrangements;
functional gene segments: most suspect lymphoproliferations concern mature lymphocytes, which consequently have functional Ig or TCR gene rearrangements. Therefore PCR primer design aimed at inclusion of (virtually) all functional Ig/TCR gene segments.
well-defined chromosome aberrations: t(11;14) with BCL1-IGH and t(14;18) with BCL2-IGH were included as additional targets, because these two aberrations are PCR-detectable at relatively high frequencies in lymphomas i.e. in 30% of mantle cell lymphoma (MCL) and in 60 to 70% of follicular cell lymphomas (FCL), respectively.

Primer Design for Multiplex PCR

Precise detection of all V, D, and J gene segments in rearranged Ig and TCR genes would require many different primers (Table 2). For some gene complexes this might be possible (e.g. TCRG and TCRD), but for other loci in practice this is impossible because of the high number of different gene segments. To solve this problem, family primers can be designed, which recognize most or all gene segments of a particular family (Table 2). Alternatively, consensus primers can be made, which recognize conserved sequences that occur in many or all involved gene segments.

The design of family primers and consensus primers balances between a limited number of primers and maximal homology with all relevant gene segments. In this study, we aimed at maximal homology with all relevant gene segments (particularly functional gene segments) in order to prevent suboptimal primer annealing, which might cause false-negative results. Furthermore, we aimed at the design of specific family primers without cross-annealing to other families In order to limit the number of PCR tubes per locus, multiplexing of PCR primers became important for practical reasons. Consequently, special guidelines were developed to ensure maximal possibilities for designing primers useful in multiplex PCR tubes. For this purpose dr. W. Rychlick (Molecular Biology Insights, Cascade, Colo., USA) provided his specially-adapted OLIGO 6.2 software program and supported the development of the guidelines for optimal primer design.

The general guidelines for primer design were as follows:
the position of the primers should be chosen in such a way that the size of the PCR products would preferably be <300 bp (preferably 100 to 300 bp) in order to be able to use paraffin-embedded material;
a minimal distance to the junctional region of preferably >10-15 bp should be taken into account (in order to avoid false-negativity due to impossibility of the 3' end of the primer to anneal to the rearranged target because of nucleotide deletion from the germline sequence);
primers preferably should not be too long (e.g. <25 nucleotides).

The following parameters were used for primer design with the OLIGO 6.2 program:
search for primers should be performed with moderate stringency;
primer efficiency (PE) value should preferably be ~400 (and >630, if the primer is to be used as consensus primer for other gene segments as well);
the most stable 3' dimer of upper/upper, lower/lower, or upper/lower primers should not exceed −4 Kcal (moderate search strategy); the most stable dimer overall being less important;
in view of multiplex PCR, the following guidelines were taken into account: a common primer would have to be designed in the most consensus region (i.e. high PE in consensus search), whereas individual primers (family or member) have to be designed in the least consensus region (i.e. low PE value of that primer for gene segments that should not be covered) to avoid cross-annealing to other gene segments and thereby multiple (unwanted) PCR products.

PCR Protocol

A standardised PCR protocol was developed based on pre-existing experience from earlier European collaborative studies. After initial testing and approval, the protocol was accepted as summarized in Table 3.

Techniques for Analysis of PCR Products Obtained from Ig/TCR Gene Rearrangements The PCR products obtained from Ig and TCR gene rearrangements have to be analysed for discrimination between monoclonal lymphoid cells with identical junctional regions and polyclonal lymphoid cells with highly diverse junctional regions.

Based on the combined experience of the participating laboratories, two techniques were selected: heteroduplex (HD) analysis and Gene Scanning (GS) analysis. HD analysis uses double-stranded PCR products and takes advantage of the length and composition of the junctional regions, whereas in GS single-stranded PCR products are separated in a high resolution gel or polymer according to their length only (FIG. 2).

Heteroduplex Analysis of PCR Products

PCR products obtained with unlabeled primers are denatured at high temperature (~95° C. for 5 min), followed by rapid random renaturation at low temperature (preferably at 4° C. for 1 hour). This enforced duplex formation results in many different heteroduplexes with different migration speed in case of polyclonal lymphoproliferations, but resulting in homoduplexes with identical rapid migration in case of monoclonal lymphoproliferations. Electrophoresis of the homoduplexes in a 6% polyacrylamide gel results in a single band of predictable size, whereas the heteroduplexes form a smear at a higher position (FIG. 2). The heteroduplex technique is rapid, simple and cheap (see Table 4 for technical details) and has a detection limit of ~5%.[40,41] The detection limit is influenced by the frequency of polyclonal lymphocytes, because the formation of many heteroduplexes will also consume a part of the monoclonal PCR products.[41]

Genescanning Analysis of PCR Products

The PCR primers for GeneScanning analysis need to be labeled with a fluorochrome to allow detection of the PCR products with automated sequencing equipment (FIG. 2).

The fluorochrome labeled single-strand (denatured) PCR products are size-separated in a denaturing polyacrylamide sequencing gel or capillary sequencing polymer and detected via automated scanning with a laser (see Table 5 for technical details). This results in a Gausian distribution of multiple peaks, representing many different PCR products in case of polyclonal lymphoproliferations, but gives a single peak consisting of one type of PCR product in case of a fully monoclonal lymphoproliferation (FIG. 2).

GeneScanning is rapid and relatively simple, but needs expensive equipment. GeneScanning is generally more sensitive than heteroduplex analysis and can reach sensitivities of 0.5 to 1% of clonal lymphoid cells.

Control Genes and Paraffin-Embedded Tissues

In several European countries, fresh tissue material is not easily available for molecular diagnostics such as PCR-based clonality studies. Therefore one of the aims of the present study was to develop a strategy for PCR-based clonality studies in paraffin-embedded tissues.

To control for the quality and amplifiability of DNA from paraffin-embedded material, a special multiplex control gene PCR was developed, resulting in a ladder of five fragments (100 bp, 200 bp, 300 bp, 400 bp, and 600 bp). From 45 of the above described 90 cases sufficient paraffin-embedded tissue was available for DNA extraction. These DNA samples were tested in parallel to the freshly-obtained DNA samples, using the Control Gene multiplex tube as well as the Ig/TCR/BCL1/BCL2 multiplex tubes for clonality diagnostics (see Example 10).

Example 1. Complete IGH Gene Rearrangements: $V_H$-$J_H$

Background

The functional rearrangement of the IGH gene, first $D_H$ to $J_H$ and subsequently V to $D_H$-$J_H$, is followed by antibody expression, the hallmark of mature B-cells. The IGH gene is located on chromosome 14q32.3 in an area covering approximately 1250 kilobases. 46 to 52 functional $V_H$ segments (depending on the individual haplotype) have been identified, which can be grouped according to their homology in six or seven $V_H$ subgroups. In addition approximately 30 non-functional $V_H$ segments have been described. Furthermore, 27 $D_H$ segments and functional six $J_H$ segments have been consistently found (Table 2 and FIG. 3A).[56]

Figure 3A:
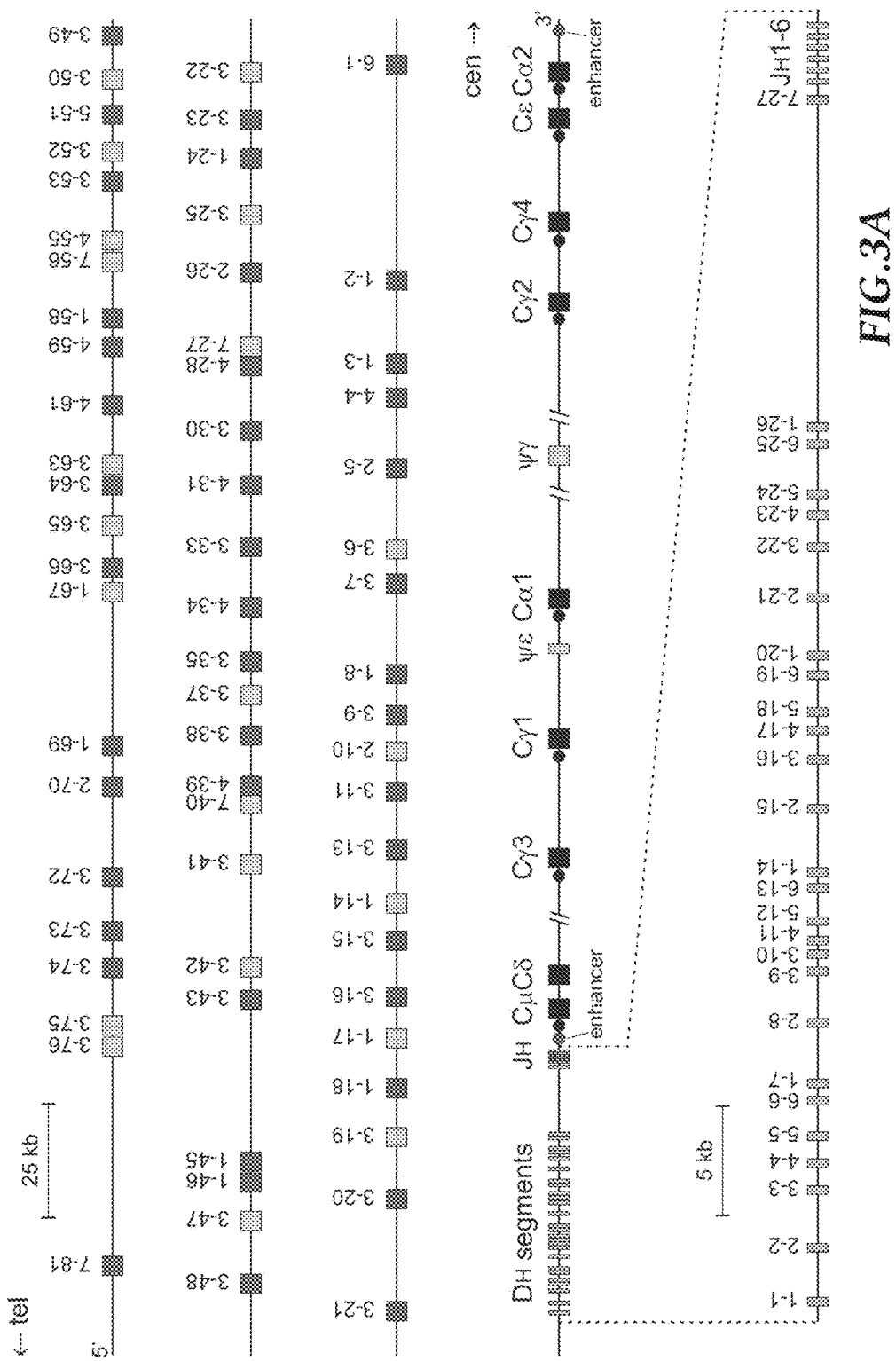
Figure 3B:
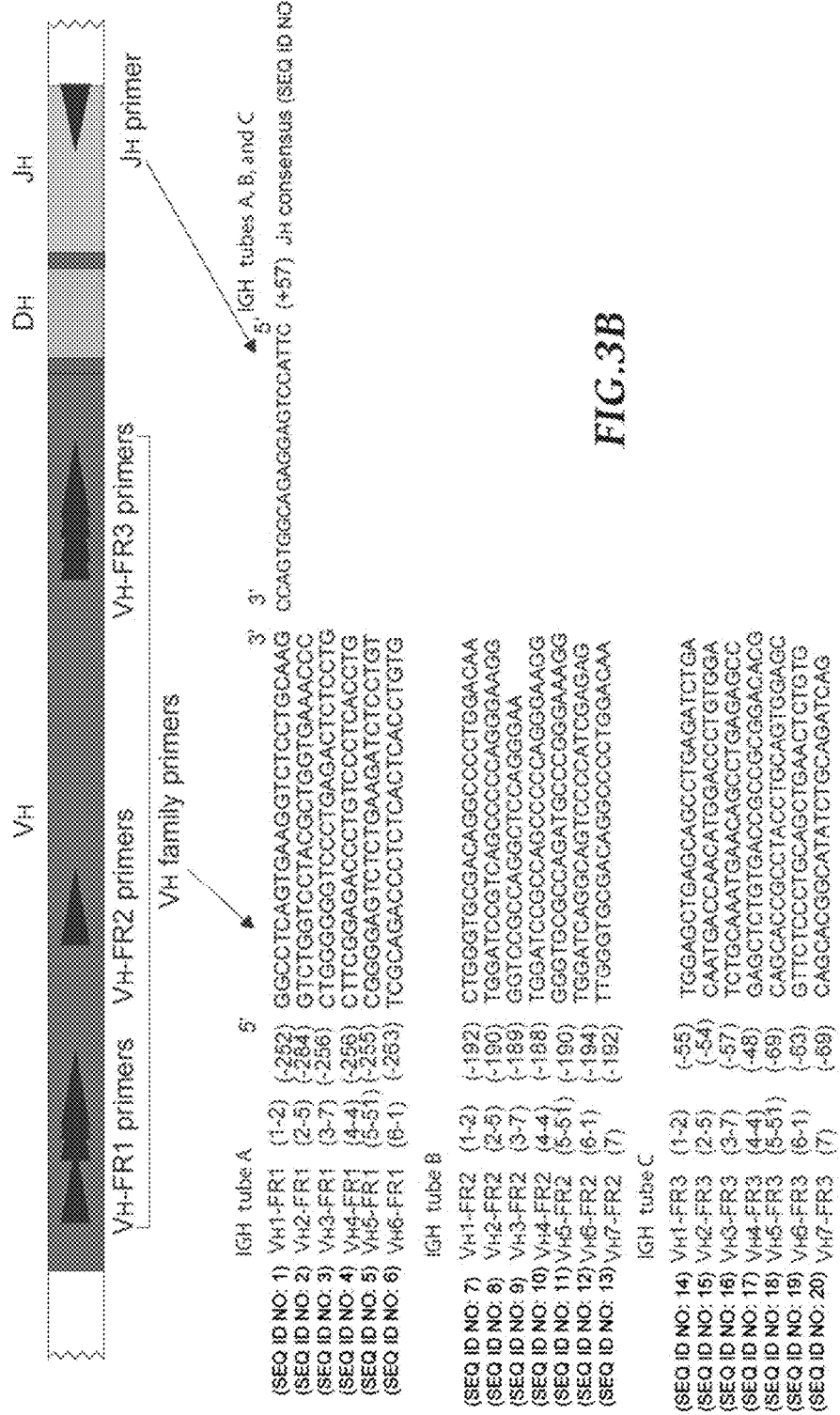

The $V_H$ segments contain three framework (FR) and two complementarity determining regions (CDR) (FIG. 3B). The FRs are characterized by their similarity among the various $V_H$ segments whereas the CDRs are highly different even within the same $V_H$ family. Furthermore, the CDRs represent the preferred target sequences for somatic hypermutations in the course of the germinal center reaction, which increase the variability within those regions. Although the FRs are usually less affected by somatic mutations, nucleotide substitutions may also occur within these regions, especially in B-cells under a heavy mutational process.

The highly variable V-D-$J_H$ regions can be amplified by PCR to detect clonal B-cell populations indicative of the presence of a malignant B-cell disorder. Clonal B-cells can be discriminated from polyclonal B-cells (i.e. normal or reactive lymphoid tissues) based on the identical size and composition of the clonal PCR products as compared to the many different polyclonal PCR products with a size range of approximately 60 bp, arranged in a Gaussian distribution. PCR-based strategies for detection of clonal B-cell populations in histological sections and cell suspensions have already been established in the early nineties. However, the initial PCR protocols used single $V_H$ consensus primers which were able to bind to one of the three framework regions, mainly FR3. Such consensus primers were not suitable to amplify all $V_H$ segments with the same efficiency leading to non-detectability of a significant number of clonal rearrangements. In addition, somatic mutations introduced in the course of the germinal center reaction are not restricted to the CDRs, but can also occur in FRs, thereby preventing primer annealing and consequently leading to absence of clonal PCR products despite the presence of a neoplastic B-cell population. This is especially true for follicular lymphomas, diffuse large B-cell lymphomas, and multiple myelomas which usually contain high numbers of somatic mutations.

To further increase the detection rate of the IGH PCR, several attempts have been made to design family-specific primers to overcome the limitations of consensus primers. However, these family-specific primers are largely based on the sequences of the previous consensus primers. Although these PCR strategies have helped to improve the detection rate, there is still a need of primer systems which are less sensitive to somatic hypermutations, thus allowing amplification of (virtually) all possible V-D-$J_H$ rearrangements.

Primer Design

According to the guidelines of the invention, three sets of $V_H$ primers were designed with the help of the OLIGO-6.2 program corresponding to the three $V_H$ frame work regions (FR1, FR2 and FR3) (FIG. 3B). Each set of primers consisted of six or seven oligonucleotides capable to anneal to their corresponding $V_H$ segments ($V_{H_1}$ to $V_{H_7}$) with no mismatches for most $V_H$ segments and one or at most two mismatches for some rare $V_H$ segments. The design was such that mismatches would be located at the very 5'-end of the primer. These $V_H$ primer sets were used in conjunction with a single $J_H$ consensus primer, designed to anneal to the most homologous 3'-end of the six $J_H$ segments, approximately 35 bp downstream of the $J_H$ RSS. This ensures that all $J_H$ segments are detectable with the same binding efficiency and that the primer binding will not easily be affected by extensive nucleotide deletion in the course of the rearrangement process. In addition, there was no cross-annealing between the $V_H$ primers and the $J_H$ primer as evaluated by the OLIGO-6.2 program.

The $J_H$ primer was also designed to be used for amplification of other PCR targets, such as incomplete $D_H$-$J_H$ rearrangements as well as t(11;14) (BCL1-IGH) and t(14; 18) (BCL2-IGH). This allows the detection of different PCR products by GS analysis employing the same labeled $J_H$ primer.

Results of Initial Testing Phase

The initial testing of the newly designed $V_H$-$J_H$ PCR was done by separate application of each $V_H$ primer together with the $J_H$ primer in an individual PCR. For this purpose, DNA extracted from B-cell lines as well as well-defined clonal patient samples was used. Furthermore, clonal rearrangements were tested for sensitivity by serial dilution in DNA extracted from reactive tonsils. Clonal control samples were not available for each possible IGH rearrangement, but all major $V_H$ segments and several rarely rearranged $V_H$ segments have been included in the initial testing phase.

Figure 3C:
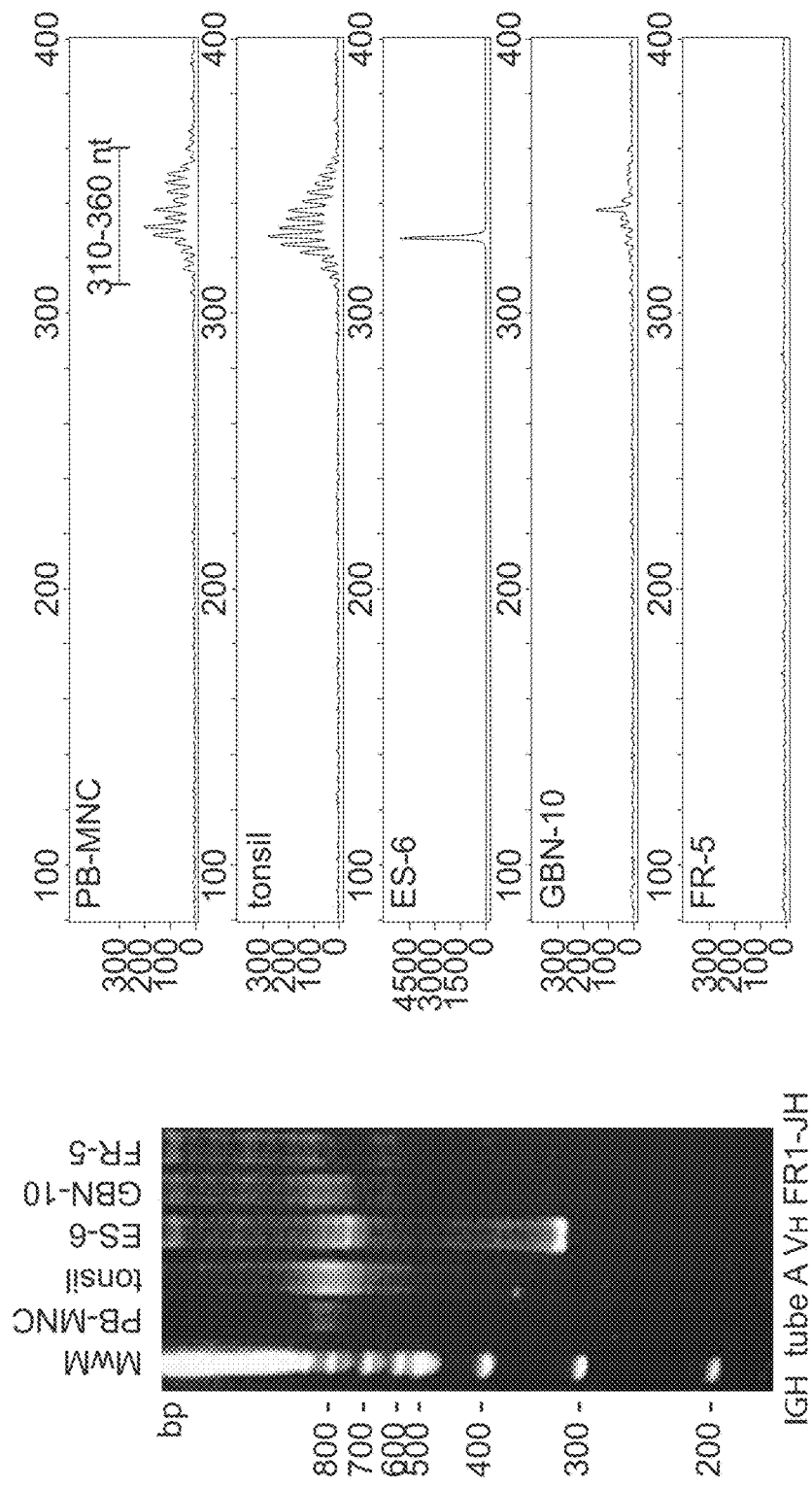
Figure 3D:
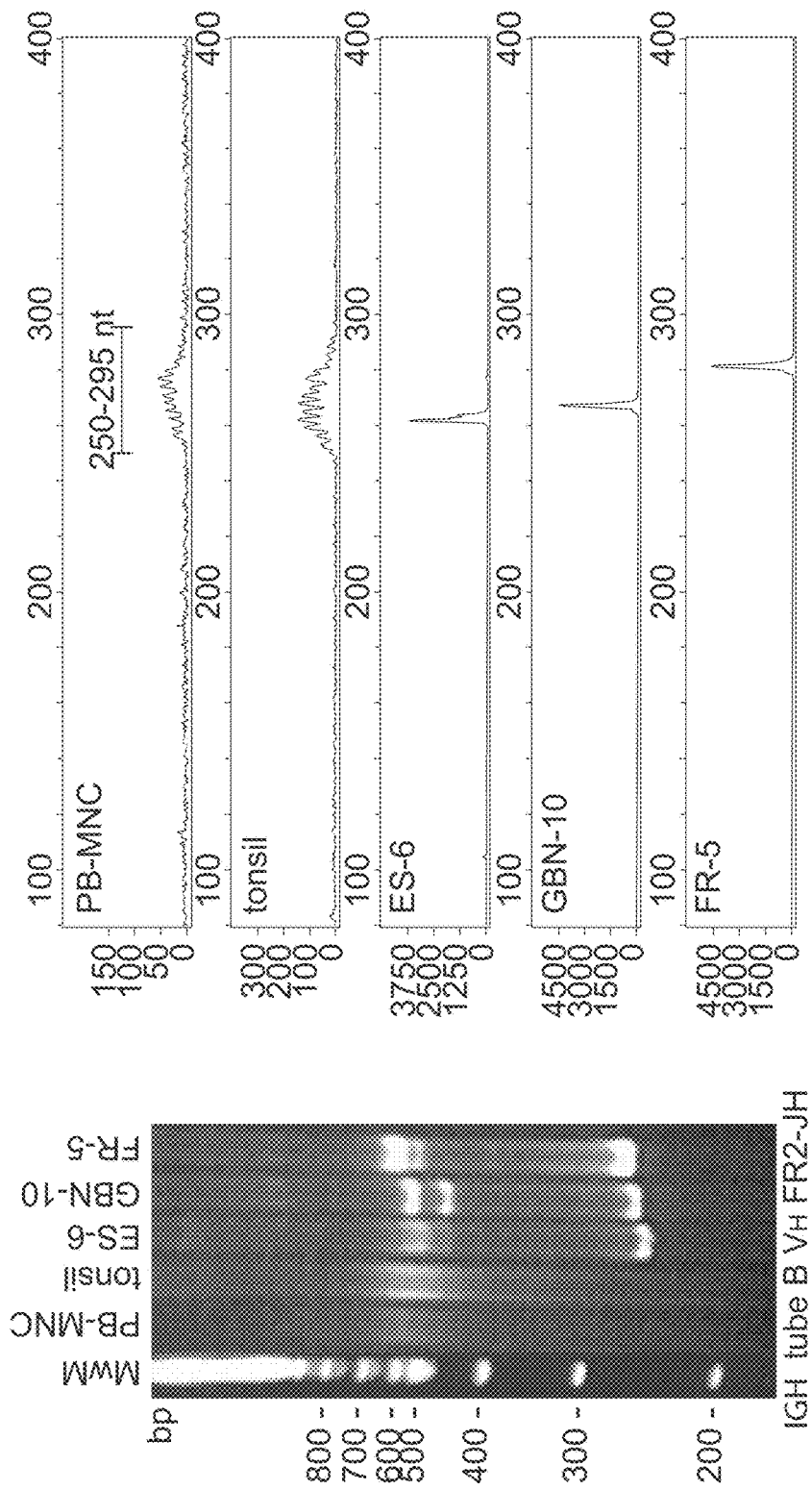
Figure 3E:
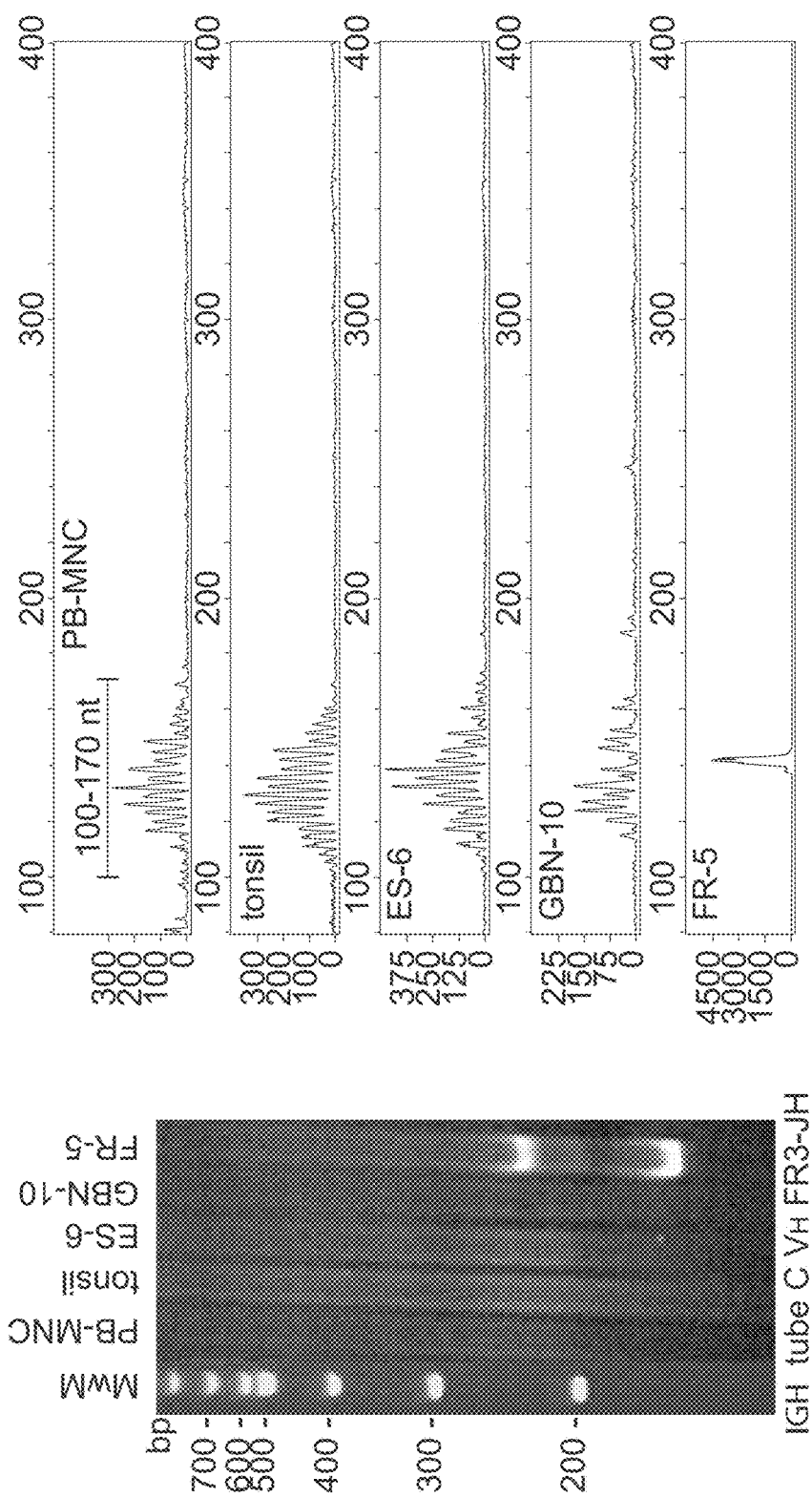

All primer pairs worked with high efficiency and sensitivity. The expected clonal $V_H$ rearrangements were detectable and the sensitivity was at least 1% ($10^{-2}$). There was no background within the expected size range and the amplification of tonsillar DNA gave the expected Gaussian distribution curve. (FIGS. 3C, D, and E)

Based on these results we started the next phase of the initial primer testing by combining the $V_H$ primers into three sets, each specific for one of the three framework regions, which were used together with the common $J_H$ primer (FIG. 3B). The results were the same as those obtained with single primer pairs, but with a slightly lower sensitivity. In addition, no nonspecific products were amplified within the expected size range, with the exception of a 340 bp PCR product which appeared in the FR1 multiplex PCR. This PCR product was generated irrespective of the source of the DNA (lymphoid and non-lymphoid) used for PCR, whereas no PCR product was obtained when no DNA template was applied. Furthermore, this amplicon was only detectable in heteroduplex analysis, not in GeneScanning. This indicates that the fluorescent labeled $J_H$ primer was not involved in the generation of this PCR product. Sequence analysis of this PCR product disclosed a $V_H$4 fragment amplified by the FR1 $V_H$4 primer in conjunction with the $FR_1$ $V_H$2 primer which apparently acted as a downstream primer by binding to the intronic $V_H$4 sequence. This problem could be solved by designing a new FR1 $V_H$2 primer which was located 25 bp upstream to the previous primer binding site.

Results of General Testing Phase

The approved IGH PCR was applied to the 90 Southern blot defined DNA samples, which were derived from well-characterized cases. Six of the 11 laboratories involved in the general testing phase performed GS analysis of the PCR products and five performed HD analysis. In addition several polyclonal as well as monoclonal samples (cell line DNA) were included as controls. 45 of these cases displayed dominant PCR products after GS analysis and 40 cases after HD detection, indicating the presence of a monoclonal B-cell population. The clonal rearrangements were detectable with all three FR primer sets in 33 of the 45 clonal cases (GS) and in the remaining 12 with one or two of the three FR primer sets. It was concluded that most negative results were caused by somatic hypermutations in the primer binding site, preventing primer annealing and thus amplification.

The comparison of the $V_H$-$J_H$ PCR results with the Southern blot results revealed a high degree of concordance. 85% (46 out of 55) and 76% (42 out of 55) of the samples with rearranged $V_H$ genes by Southern blot analysis showed a dominant amplification product by GS analysis and HD analysis, respectively. Vice versa, all but two samples harboring germline $V_H$ genes by Southern blot displayed a polyclonal pattern by GS and HD analysis.

Conclusion

In conclusion, the three multiplex PCRs for detection of clonal $V_H$-$J_H$ rearrangements provide a new and reliable assay to identify clonal B-cell proliferations. The combined use of standardized primers in the three different FRs helps to decrease the rate of false-negative results due to somatic hypermutation in primer binding sites of the involved $V_H$ gene segments.

Example 2. Incomplete IGH Gene Rearrangements: $D_H$-$J_H$

Background

The formation of complete V-D-J rearrangements in the IGH locus on chromosome 14q32.3 is a sequential process that occurs in two steps: $V_H$ coupling is generally preceded by an initial rearrangement between $D_H$ and $J_H$ gene segments in early precursor-B cells (reviewed by[57]). In addition to the many distinct $V_H$ gene segments and the six functional $J_H$ gene segments (see Example 1), the human IGH locus also contains 27 $D_H$ gene segments.[58] Based on sequence homology, the 27 $D_H$ segments can be grouped into seven families: $D_H$1 (formerly known as DM), $D_H$2 (DLR), $D_H$3 (DXP), $D_H$4 (DA), $D_H$5 (DK), $D_H$6 (DN), and $D_H$7 (DQ52); all families comprise at least four members, except for the seventh which consists of the single $D_H$7-27 segment just upstream of the $J_H$ region (FIG. 3A).[58,59]

Recombination between any of the $D_H$ and $J_H$ segments will result in the formation of incomplete $D_H$-$J_H$ joints, which can easily be detected in bone marrow-derived CD10$^+$/CD19$^-$ precursor B-cells[60,61] and hence also in a subset (20-25%) of precursor B-cell acute lymphoblastic leukemias, which show an immature genotype.[62] Sequencing revealed a predominance of $D_H$2 ($D_H$2-2), $D_H$3 ($D_H$3-9), and $D_H$7-27 gene segments in precursor B-ALL, comprising 36%, 33%, and 19% of all identified segments, respectively.[62]

However, also in mature B-cell malignancies incomplete $D_H$-$J_H$ rearrangements have been reported.[61,63] Moreover, even in a subset of IgH-negative multiple myelomas, which can be considered as the most mature type of B-lineage malignancy, $D_H$-$J_H$ joints were observed.[64] These $D_H$-$J_H$ rearrangements were derived from the non-coding second allele and involved segments from $D_H$1 to $D_H$4 families.[84] Based on the description of $D_H$-$J_H$ joints in precursor-B-ALL and multiple myelomas, it is assumed that incomplete $D_H$-$J_H$ rearrangements are also present in other types of B-cell leukemias and lymphomas. In immature T-cell malignancies $D_H$-$J_H$ couplings have been identified as cross-lineage rearrangements;[34] interestingly, these almost exclusively occurred in the more immature non-TCRαβ$^+$ T-ALL subset and mainly involved the more downstream $D_H$6-19 and $D_H$7-27 segments. The latter segment is frequently (up to 40%) used in fetal B cells but rarely in adult B cells.[65,66] Human adult precursor and mature B cells mainly seem to use $D_H$2 and $D_H$3 family segments, as evidenced from sequences of complete $V_H$-$D_H$-$J_H$ rearrangements.[66]

Although the exact frequencies of incomplete $D_H$-$J_H$ couplings in different types of mature B-cell malignancies are largely unknown, it is clear that they will at least be lower than those of $V_H$-$J_H$ joinings. Nevertheless, $D_H$-$J_H$ rearrangements might still represent an important complementary target for PCR-based clonality assessment. This presumed contribution of $D_H$-$J_H$ rearrangements as PCR target is based on the assumption that incomplete rearrangements in the IGH locus will not to contain somatic hypermutations, because transcription starting from the promoters in the V gene segments does not occur, which is regarded as an essential prerequisite for somatic hypermutation to take place.[67,68] Especially in those types of B-lineage proliferations in which somatic hypermutations are frequent, PCR analysis of a possible $D_H$-$J_H$ recombination product might therefore be relevant, and sometimes even the only possibility to detect the B-cell clone.

Primer Design

Based on the high degree of homology within each $D_H$ family, seven family-specific $D_H$ primers were designed (FIG. 4) in combination with the consensus $J_H$ primer that is also used for detection of $V_H$-$J_H$ rearrangements (see Example 1) and t(11;14) (BCL1-IGH) and t(14;18) (BCL2-IGH) (Examples 8 and 9). Primers were designed such that cross-annealing to other $D_H$ family segments would be minimal or preferably absent, resulting in distinct positions for the various family primers relative to the RSS elements (FIG. 4). The expected PCR product sizes of $D_H$-$J_H$ joints range from 110-130 bp (for $D_H$7-$J_H$ joinings) to 395-415 bp (for $D_H$3-$J_H$ rearrangements). Of note, due to the position of the $D_H$7-27 segment close to the segments in the $J_H$ region, PCR products of 211 bp (and also 419,1031,1404,1804, and 2420 bp in case of primer annealing to downstream $J_H$ gene segments) will be amplified from non-rearranged alleles and will be detected as a ladder of germline bands in virtually every sample.

Results of Initial Testing Phase

For initial testing of the individual $D_H$ primers, high tumor load precursor B-ALL or T-ALL samples with well-defined clonal $D_H$-$J_H$ rearrangements were used. Under standard PCR conditions using 1.5 mM $MgCl_2$ and AmpliTaq Gold buffer, all seven primer combinations appeared to detect the clonal $D_H$-$J_H$ targets with product lengths within the expected size ranges. Cross-annealing of the $D_H$ primers to rearranged gene segments from other $D_H$ families was only very weak or not observed at all. Furthermore, also in healthy control tonsillar or MNC DNA PCR products of the correct size ranges were observed. Nonspecific annealing of the primers was not observed for virtually all primers sets, using non-template specific control DNA; only in case of the $D_H$2/$J_H$ primer set a (sometimes faint) 340-350 bp product was observed in HeLa DNA. Further sequencing revealed that this nonspecific product was due to false priming of the $D_H$2 primer to a DNA sequence upstream of the $J_H$4 segment. However, as the size of this nonspecific product was so different from the sizes of any of the true $D_H$-$J_H$ PCR products, it was decided not to design a new $D_H$2 primer. In fact, the nonspecific 350 bp band can be employed as an internal marker for successful DNA amplification and hence the quality of the template DNA, being hardly or only faintly visible when enough clonal or polyclonal $D_H$-$J_H$ template is available (e.g. in tonsillar DNA or DNA from particular leukemic samples), but being especially strong in samples containing low numbers of lymphoid cells with $D_H$-$J_H$ rearrangements.

Serial dilutions of DNA from the clonal reference samples into tonsillar DNA generally resulted in sensitivities of 5% or lower (0.5-1% in case of the $D_H$6-$J_H$ rearrangement) using HD analysis; sensitivities in GS analysis were generally 1-2 dilution steps better, i.e. 1% or lower. The clonal $D_H7$-$J_H$ target could only be detected with a sensitivity of ~10%, which is most probably caused by primer consumption in PCR amplicons involving the non-rearranged germline $D_H7$ and $J_H$ gene segments.

Although the initial multiplex strategy, as suggested from the OLIGO 6.2-assisted primer design, was to divide the various $D_H$ primers over two tubes, it was decided after testing various multiplex approaches to combine all primers into one multiplex tube (tube D of IGH clonality assay), except for the $D_H7$ primer, which was included in a separate tube (tube E of IGH clonality assay). The reason to exclude the $D_H7$ primer was the complicated germline pattern, due to easy amplification of alleles with non-rearranged $D_H7$ segments. Using this two-tube multiplex approach, all clonal reference samples were still detectable. Under multiplex conditions the detection limits for these various clonal targets were logically less optimal as compared to the single assays, ranging from ~5% ($D_H3$, $D_H4$, and $D_H6$) to ~10% ($D_H2$, and $D_H5$). For the $D_H1$ clonal reference sample that was available, a sensitivity of ~20% was observed, at a later stage the $D_H1$-$J_H$ rearrangement of cell line KCA was found to be detectable down to 10% in the multiplex assay. As tube E only contains the $D_H7$ primer, the 10% sensitivity for this tube was the same as mentioned before. The same multiplex analysis performed with 500 ng instead of 100 ng DNA of the serial dilutions, resulted in slightly better sensitivities. The use of serial dilutions in MNC DNA instead of tonsillar DNA did not clearly affect detection limits of the assays for $D_H$-$J_H$ recombinations.

Results of General Testing Phase

Following initial testing in the three laboratories involved in primer design, the developed IGH $D_H$-$J_H$ multiplex PCR assay was further evaluated using the 90 Southern blot-defined samples. Every sample was analyzed in parallel in four laboratories by HD analysis and in five laboratories by GS analysis; in another two laboratories all samples were analyzed by both techniques. All together a total of six HD and seven GS analysis results were obtained per sample per tube. Despite concordant results (>80% of laboratories with identical results) in the vast majority of samples, nine showed inter-laboratory discordancies in tube D. Further analysis revealed that these could be explained by either the presence of a small clone with weak clonal products, or by large size products (~390 and larger). In a few cases the products were so large, that only after sequencing it became clear that they concerned true but extended $D_H$-$J_H$ rearrangements, either from upstream $D_H$ (e.g. $D_H6$-25-$D_H1$-26-$J_H$ in NL-12) or from downstream $J_H$ gene segments (e.g. $D_H6$-25-$J_H4$-$J_H5$ in PT-14). In all three cases (NL-17, mycosis fungoides; FR-1, B-CLL; FR-5, FCL) in which clonal products were found using tube E, the results were completely concordant between laboratories.

When evaluating results from HD and GS analysis, it appeared that these were comparable, although in general the number of laboratories showing identical results was slightly higher upon HD as compared to GS analysis (FIGS. 4B and C).

Direct comparison of $D_H$-$J_H$ multiplex PCR results with SB data is virtually impossible, as hybridization with a single probe (IGHJ6) in the $J_H$ region does not allow discrimination between $V_H$-$J_H$ and $D_H$-$J_H$ rearrangements. In three samples it was clear that detection of clonal products of the combined $V_H$-$J_H$ and $D_H$-$J_H$ assays did not fit with configuration of the IGH locus in SB analysis. Remarkably, no clonal $D_H$-$J_H$ PCR products were observed in the pre-follicular B-cell malignancies. In contrast, 11/16 B-CLL samples and 12/25 (post-)follicular B-cell malignancy samples did contain clonally rearranged $D_H$-$J_H$ PCR products. In three of the eighteen T-cell malignancy cases clonal $D_H$-$J_H$ rearrangements were seen; these concerned T-LBL (ES-9) and mycosis fungoides (NL-17) cases with SB-detected IGH rearrangements, and a case of T-NHL/EATL (PT-4) without SB-detected IGH rearrangements, probably because of the low tumor load of <15%. All 15 reactive cases only showed polyclonal $D_H$-$J_H$ PCR products, in accordance with SB results. In category D with difficult diagnoses, three samples (PT-12, GBS-10, and GBN-8) showed clonal IGH $D_H$-$J_H$ PCR products, which was in line with SB data as well as IGK PCR data in two of three cases; in another two samples (PT-6 and GBS-9), both T-cell rich B-NHL cases, clonal $D_H$-$J_H$ products were found in addition to clonal IGK and/or IGL products, but without evidence for clonality from SB analysis, which might best be explained by the small size of the B-cell clone in these samples.

In order to determine the additional value of $D_H$-$J_H$ PCR analysis, the results were compared to those of $V_H$-$J_H$ PCR analysis. In five (NL-4, PT-14, GBN-2, FR-7, NL-12) B-cell malignancies clonal $D_H$-$J_H$ PCR products were found, whereas only polyclonal $V_H$-$J_H$ PCR products were observed.

Conclusion

In conclusion, based on the initial and general testing phases, $D_H$-$J_H$ PCR analysis appears to be of added value for clonality assessment. Although HD analysis results might be interpreted slightly more easily, there is no clear preference for either HD or GS analysis as they are both suitable for analyzing amplified PCR products. A potential difficulty in $D_H$-$J_H$ PCR analysis is the relatively large size range of expected PCR products, due to scattered primer positions and to extended amplifications from upstream $D_H$ or downstream $J_H$ gene segments, implying that long runs are recommended for GS analysis. Finally, the remarkable position of the $D_H7$-27 gene segment in the IGH locus causes a ladder of germline amplification products in tube E, with clonal products being easily recognizable as much smaller bands/peaks.

Example 3. IGK Gene Rearrangements: Vκ-Jκ, Vκ-Kde/intronRSS-Kde

Background

The human IGK light chain locus (on chromosome 2p11.2) contains many distinct Vκ gene segments, grouped into seven Vκ gene families, as well as five Jκ gene segments upstream of the Cκ region. Originally, the Vκ gene segments were designated according to the nomenclature as described by Zachau et al.[69] An alternative nomenclature groups the Vκ gene segments in seven families and is used in the ImMunoGeneTics database.[46] Here we follow the latter nomenclature. The Vκ1, Vκ2, and Vκ3 families are multi-member families including both functional and pseudo gene segments, whereas the other families only contain a single (Vκ4, Vκ5, Vκ7) or a few segments (Vκ6).[70] Remarkably, all Vκ gene segments are dispersed over two large duplicated clusters, one immediately upstream and in the same orientation as the Jκ segments, and the other more distal and in an inverted orientation (FIG. 5A).[71] The latter implies that so-called inversion rearrangements are required to form Vκ-Jκ joints involving Vκ genes of the distal cluster. In addition to the Vκ and Jκ segments, there are other elements in the IGK locus that can be involved in recombination. The kappa deleting element (Kde), approximately 24 kb downstream of the Jκ-Cκ region, can rearrange to Vκ gene segments (Vκ-Kde), but also to an isolated RSS in the Jκ-Cκ intron (intronRSS-Kde).[24,72] Both types of rearrangements lead to functional inactivation of the IGK allele, through deletion of either the Cκ exon (intronRSS-Kde rearrangement) or the entire Jκ-Cκ area (Vκ-Kde rearrangement).

As human IGK recombination starts in precursor B-cells in the bone marrow, IGK rearrangements can also be detected in precursor B-cell acute leukemias (30-45% of alleles, depending on age). Although VK-Jκ joinings are present, these IGK rearrangements mainly concern recombinations involving Kde (25-35% of alleles). In childhood precursor B-ALL Vκ-Kde recombination predominates over intron-Kde, whereas in adult ALL the deletions exclusively concern Vκ-Kde couplings.[24,73,74] In chronic B-cell leukemias IGK rearrangements are even more frequent, being detectable on 75% (Igκ$^+$ cases) or even 95% (Ig)λ$^+$ cases) of all IGK alleles. By definition, functional Vκ-Jκ rearrangements are found on at least one allele in Igκ$^+$ B-cell leukemias; the non-coding second allele is either in germline configuration, or inactivated through Vκ-Kde (8% of alleles) or intronRSS-Kde (8% of alleles) recombination. Kde rearrangements are frequent in Igλ$^+$ B-cell leukemias (~85% of alleles), with a slight predominance of intronRSS-Kde recombinations over Vκ-Kde rearrangements. This implies that virtually all Igλ$^+$ leukemias contain a Kde rearrangement, while potentially functional Vκ-Jκ couplings are relatively rare.[24,75] Several studies have shown that Vκ gene segment usage is almost identical between various normal and malignant B-cell populations and largely reflects the number of available gene segments within each family. Both in Vκ-Jκ as well as in Vκ-Kde rearrangements, Vκ gene segments from the first four families (Vκ1 to Vκ4) predominate. Vκ2 gene usage appeared to be higher in precursor B-ALL than in more mature B-cell lymphoproliferations or normal B cells. Remarkably, the distal inverted Vκ cluster was rarely used in Vκ-Jκ rearrangements, whereas Vκ pseudogene segments were never involved, also not in Igλ$^+$ cases.[76] Little is known about Jκ gene segment usage, but sparse data show that Jκ1, Jκ2, and Jκ4 are the most frequently used Jκ gene segments.[75]

Vκ-Jκ rearrangements can be important complementary PCR target for those types of B-cell proliferations in which somatic hypermutations may hamper amplification of the $V_H$-$J_H$ target, but recombinations involving Kde are probably even more valuable. Deletion of intervening sequences in the Jκ-Cκ intron results in the removal of the IGK enhancer, which is thought to be essential for the somatic hypermutation process to occur. Rearrangements involving Kde are therefore assumed to be free of somatic hypermutations, and hence should be amplified rather easily.

Primer Design

Figure 5A:
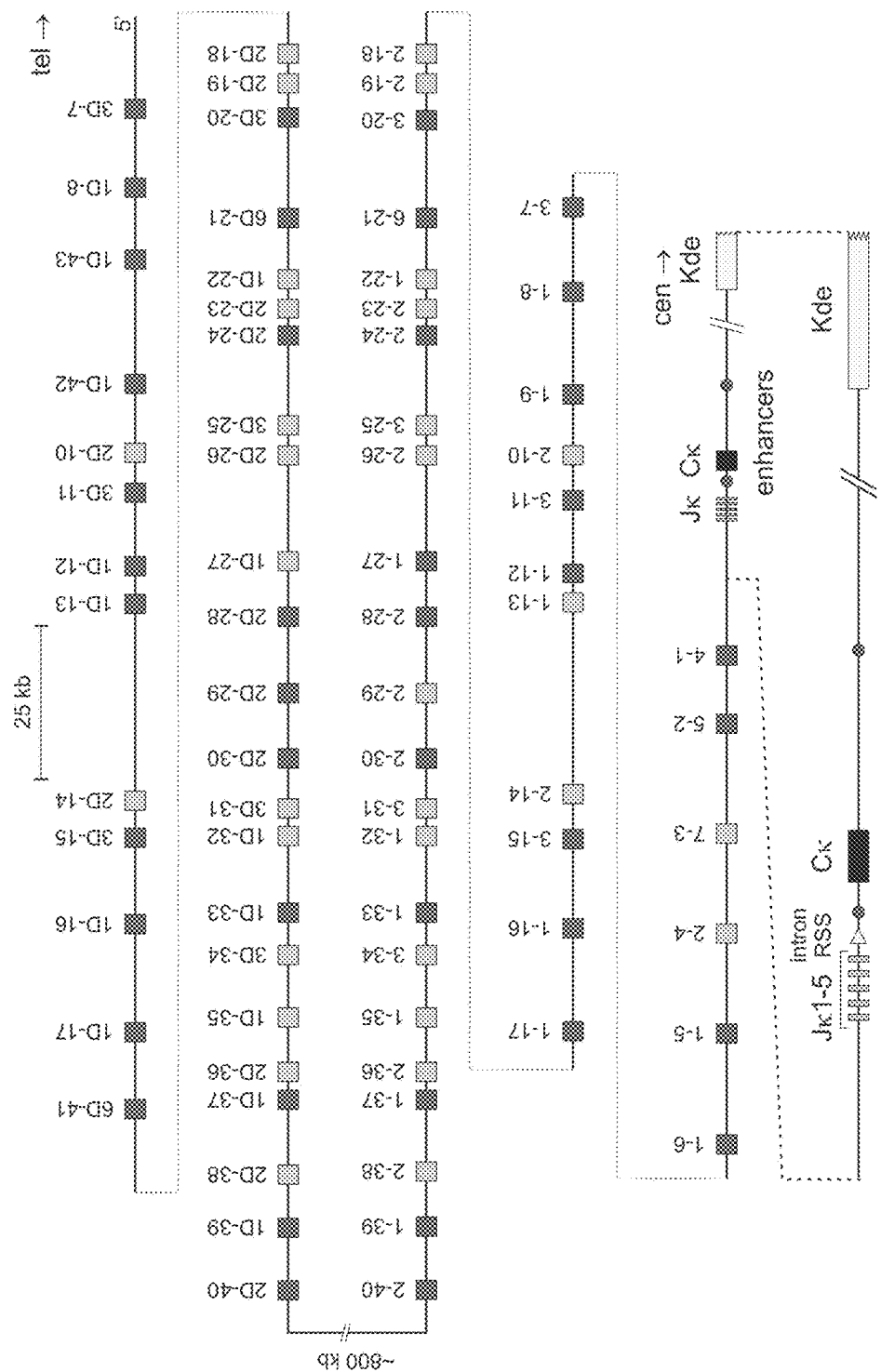
Figure 5B:
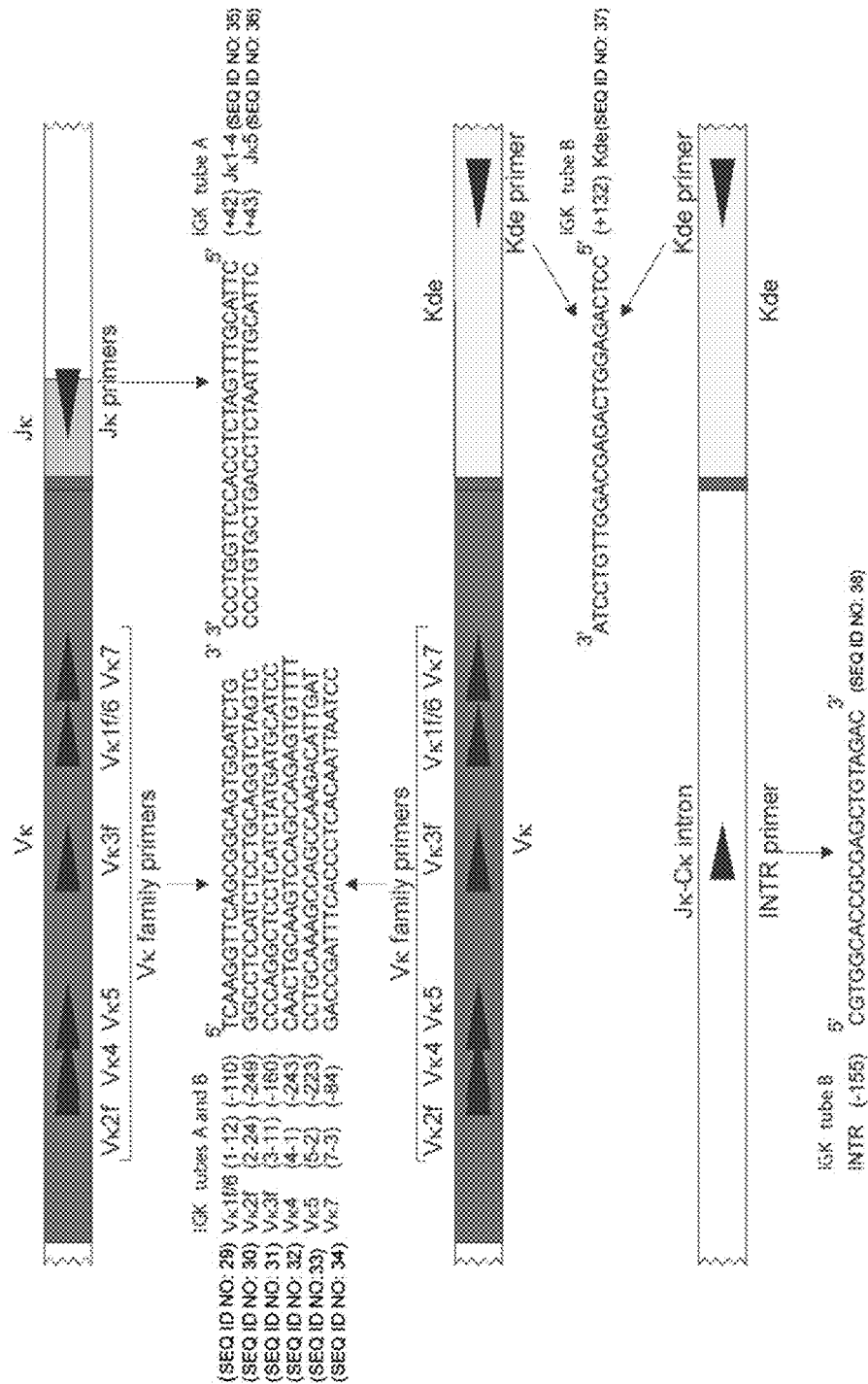

Using OLIGO 6.2 software, six family-specific Vκ primers were designed to recognize the various Vκ gene segments of the seven Vκ families; the Vκ6 family gene segments were covered by the Vκ1 family primer (FIG. 5B). In case of the relatively large Vκ1, Vκ2, and Vκ3 families only the functional Vκ gene segments were taken into consideration, as the less homologous pseudo gene segments complicated optimal primer design too much. The family-specific Vκ primers were designed to be used in combination with either a set of two Jκ primers (Jκ1-4, covering the first four Jκ segments and Jκ5 covering the fifth) or a Kde primer (FIG. 5B). For analysis of Kde rearrangements an additional forward primer recognizing a sequence upstream of the intronRSS was made. In order to show minimal cross-annealing to other Vκ family segments and still be useful in multiplex reactions, the various primers could not be designed at similar positions relative to RSS elements (FIG. 5B). The expected PCR product sizes of Vκ-Jκ joints range from ~115-135 bp (for Vκ7-Jκ joints) to ~280-300 bp (Vκ2-Jκ rearrangements). For the Kde rearrangements, product size ranges are from ~195-215 bp (Vκ7-Kde) to ~360-380 bp (Vκ2-Kde), whereas the intronRSS-Kde products are ~275-295 bp.

Results of Initial Testing Phase

For initial testing of the individual primers, several cell lines and patient samples with precisely defined clonal V-Jκ, or Vκ-Kde/intronRSS-Kde rearrangements were used. The patient samples with Vκ-Jκ joints mostly concerned chronic B-cell leukemias, which were additionally selected on basis of a high tumor load for easy and sensitive detection of the involved rearrangement. Unfortunately, clonal reference samples were not available for all Vκ-Jκ targets; especially the more rare types of rearrangements involving Vκ5, Vκ7 and/or Jκ5 were not represented in the series of reference samples. For these targets and also for the targets for which clonal reference samples were available, healthy control tonsillar or MNC DNA samples were employed, in which PCR products of the correct expected sizes were indeed observed. The only exception was the Vκ7/Jκ5 primer combination; most probably Vε7-Jκ5 joinings are so rare in normal B cells, that these PCR products were hardly or not detectable in tonsils. Rearranged products within the expected size ranges could be detected in all clonal reference samples, under standard PCR conditions using 1.5 mM MgCl$_2$ and either ABI Gold Buffer or ABI Buffer II. However, in a few cases weak amplification of particular VK-Jκ rearrangements was observed with other Vκ family/Jκ primer sets, due to slight cross-annealing of the Vκ3 primer to a few Vκ1 gene segments. Furthermore, in a few of the clonal reference samples clear additional clonal PCR products were seen with other Vκ/Jκ or even Vκ/Kde and intronRSS/Kde primer sets; in most samples this could be explained by the complete configuration of the two IGK alleles. This occurrence of multiple clonal PCR products illustrates the complexity of IGK rearrangement patterns in a given cell sample, mainly caused by the potential occurrence of two clonal rearrangements on one allele (Vκ-Jκ and intron RSS-Kde). This complexity does not hamper but support the discrimination between polyclonality and monoclonality.

No nonspecific annealing of the primers was observed for any of the VK-Jκ and V-Kde/intron RSS-Kde primer sets, when using HeLa DNA as a non-template specific control Serial dilutions of DNA from the clonal reference samples into tonsillar DNA generally resulted in sensitivities of 5-10% for Vκ-Jκ rearrangements and 1-10% for Vκ-Kde rearrangements, using HD analysis. In general, the sensitivities in GS analysis were approximately one dilution step better. The only slightly problematic target was the intronRSS-Kde target that could only be detected down to the 10% serial dilution in the employed patient sample. This is probably caused by the fact that intronRSS-Kde rearrangements are abundant in DNA from both Igκ$^+$ and Igλ$^+$ tonsillar B cells, which were used in the dilution experiments.

The multiplex strategy that was chosen after testing several approaches consisted of two different multiplex PCR reaction tubes. In the Vκ-Jκ tube (tube A) all Vκ primers were combined with both Jκ primers, whereas tube B contained all Vκ primers plus the intronRSS primer in combination with the Kde reverse primer (FIG. 5B). All beforementioned clonal reference samples were detectable using this two-tube multiplex approach. Of note is the observation that in non-clonal tonsil samples a predominant, seemingly clonal band of ~150 bp was detected using the Vκ-Jκ multiplex tube A analysis. The presence of this product, which is seen in HD analysis but especially in GS analysis, can be explained by the limited heterogeneity of Vκ-Jκ junctional regions leading to a high frequency of products of an average size of ~150 bp. Furthermore, in some samples a sometimes weak 404 bp nonspecific band was observed in tube B. Although sensitivities were on average slightly better in other multiplex approaches in which the Vκ primers were further subdivided over multiple tubes, the feasibility of having only two tubes to analyze all relevant IGK rearrangements, finally was the most important argument for choosing the two-tube multiplex strategy as given in FIG. 5B. Detection limits for the various clonal targets in the two-tube multiplex approach were ~10% for most of the clonal Vκ-Jκ rearrangements (Vκ1-Jκ4, Vκ2-Jκ4, Vκ3-Jκ4) derived from informative samples with a high tumor load; several of the Vκ-Kde targets were detectable with a still reasonable sensitivity of ~10%, but a few other samples containing Vκ2-Kde, Vκ5-Kde, and also intronRSS-Kde targets showed detection limits above 10%. Even the use of 500 ng serially diluted DNA instead of 100 ng hardly resulted in better sensitivities, whereas serial dilutions in MNC DNA did not affect the detection limits either. Nevertheless, detection limits of serial dilutions of reference DNA in water were all in the order of 0.5-1%, which shows that the chosen multiplex IGK PCR assay as such is good. It is important to note that potential clonal cell populations in lymph nodes or peripheral blood in practice will have to be detected within a background of polyclonal cells, which can hamper sensitive clonality detection, especially in samples with a relatively high background of polyclonal B-cells.

Results of General Testing Phase

Following initial testing in the four laboratories involved in primer design, the developed IGK multiplex PCR assay was further evaluated using 90 Southern blot-defined samples. Every sample was analyzed in parallel via HD (five laboratories) and GS (two laboratories) analysis; in another four laboratories all samples were analyzed by both techniques. Taken together, eight HD and five GS analysis results were available per sample per tube. In the vast majority of samples >80% of laboratories produced identical results, i.e. either clonal bands/peaks or polyclonal smears/curves in one or both tubes. However, in nine (~10%) samples discordancies were found between laboratories, which remained after repetitive analysis of these samples. More detailed analysis revealed that in at least six cases the approximately 150 and 200 bp sizes of the clonal products in tube A could not easily be discriminated from polyclonal products of roughly the same size. This is an inherent difficulty in especially Vκ-Jκ analysis, which is caused by the relatively limited junctional heterogeneity of these rearrangements. In two samples the results from tube B were however so clear in all laboratories with both techniques that in fact no discrepancy prevailed. In one sample (ES-8) a large product of around 500 bp appeared to be the reason for discrepant inter-laboratory results; further sequencing revealed that amplification starting from the downstream Jκ segment caused production of an extended Vκ1-Jκ3-Jκ4 PCR product.

Figure 5C:
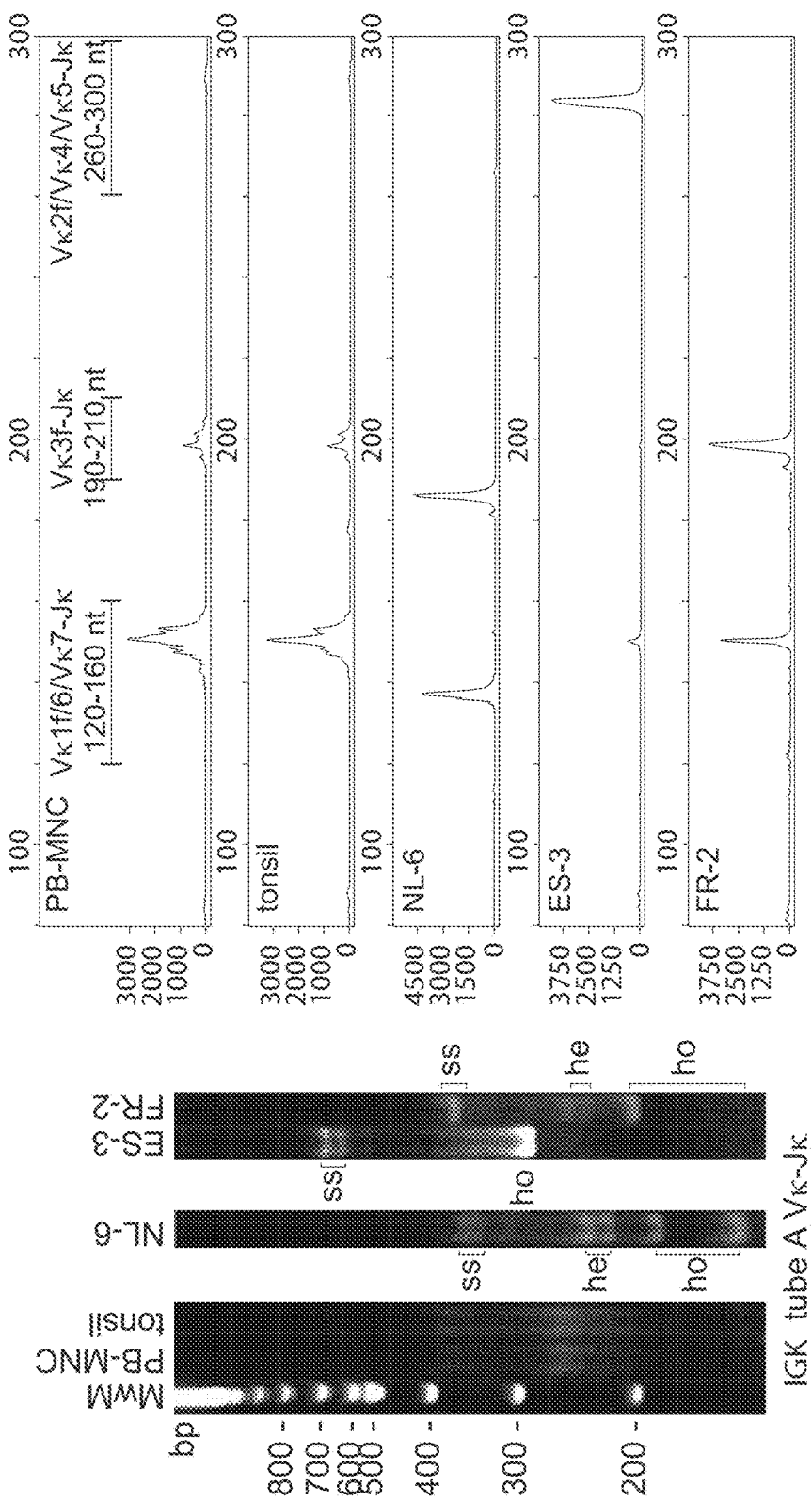
Figure 5D:
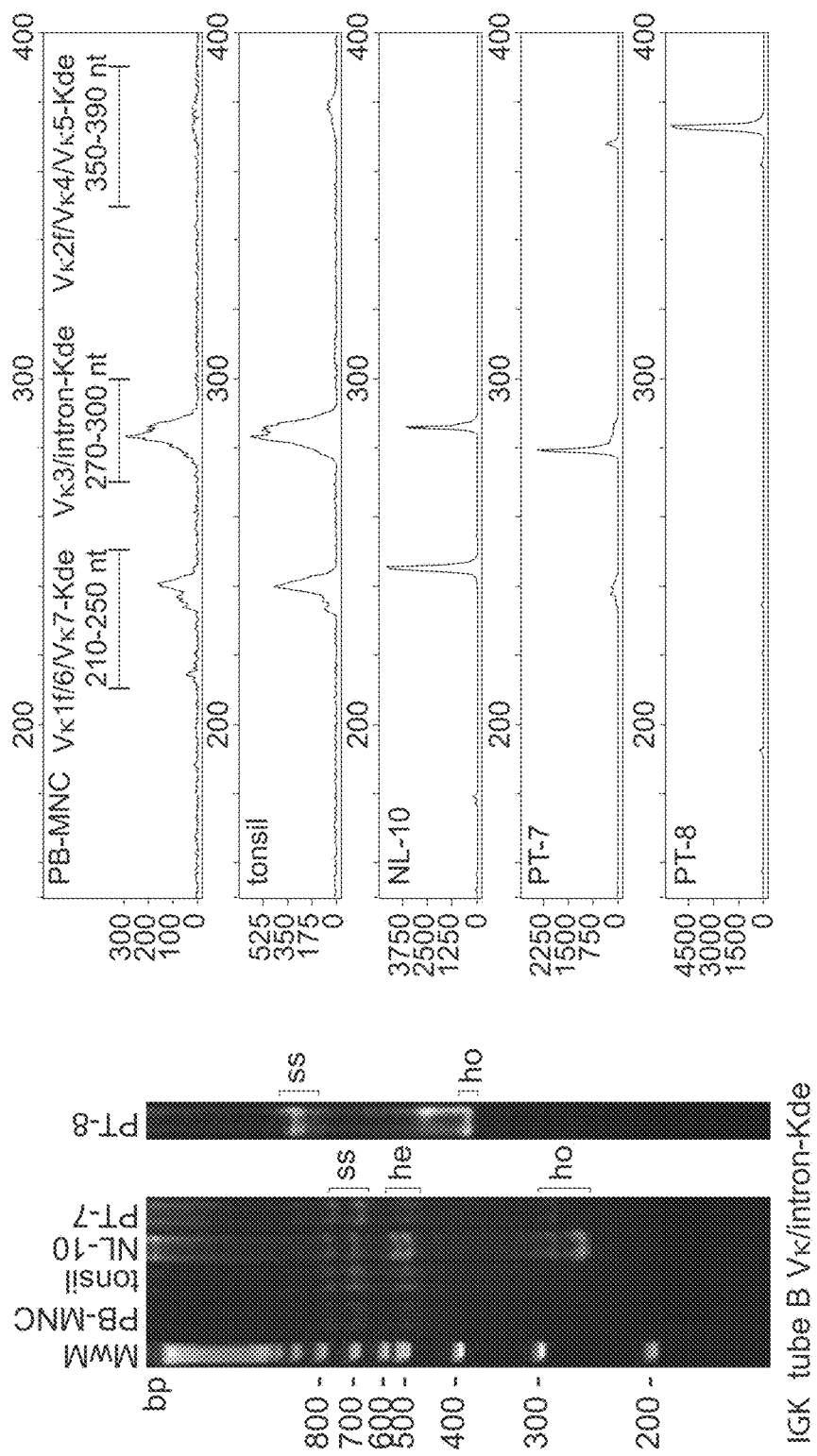

When evaluating results from HD and GS analysis, it appeared that these were rather comparable, although in general the number of laboratories showing identical results was slightly higher upon HD as compared to GS analysis (FIGS. 5C and D). Remarkably, in one sample (GBS-4) HD analysis revealed a clear product in both tubes, whereas GS analysis only showed polyclonality. Cloning of the HD product showed a peculiar Vκ3-Vκ5 PCR product, which was not observed in any other sample; the Vκ-Vκ configuration of this product explained why it was not detected with labeled Jκ primers in GS analysis.

Comparison of PCR results with SB data revealed no SB-PCR discrepancies in the pre-follicular B-cell malignancies and B-CLL samples; in line with the presence of rearranged IGK bands in SB analysis, all samples contained clonal IGK PCR products. In contrast, in the 25 (post-)follicular B-cell malignancy samples clonal IGK PCR products were missed in four DLCL cases (ES-5, PT-13, PT-14, FR-7) and one PC leukemia (NL-19) with both techniques and in another DLCL case (GBS-4, see above) with GS analysis only. In all cases this was most probably caused by somatic hypermutation. Interestingly, in one FCL case (NL-4), a clonal PCR product was found, whereas SB analysis revealed a germline band in case of the IGK genes and weak clonal bands upon IGH analysis. In all 18 T-cell malignancy cases and all 15 reactive cases (category C) polyclonal IGK PCR products were found in accordance with SB results, except for one peripheral T-NHL case (FR-10). Next to the clonal TCR and IGK products this sample also showed clonal IGH and IGL PCR products, but no clonal Ig rearrangements in SB analysis, probably reflecting the presence of a small additional B-cell clone in this sample. Finally, in the category with difficult diagnoses (D), two samples (GBS-10 and GBN-8) showed clonal IGK PCR products, in line with SB data; however, in another two samples (PT-6 and GBS-9), both T-cell rich B-NHL cases, clonal IGK PCR products were found as well as clonal IGH and/or IGL products, but without evidence for clonality from SB analysis. Also this discrepancy can probably be explained by the small size of the B-cell clone in these two patient samples.

To determine the additional value of analyzing the IGK locus, we compared the results of IGK PCR analysis to those of IGH PCR analysis. In five (ES-2, NL-4, PT-8, GBN-2, ES-8) of the nine samples in which no clonal $V_H$-$J_H$ PCR products were found, clonal products were readily observed in IGK analysis. When taking into account both $V_H$-$J_H$ and $D_H$-$J_H$ analysis, IGK PCR analysis was still complementary to IGH PCR analysis in three of these cases in detecting clonal Ig PCR products.

Conclusion

In conclusion, based on the initial and general testing phases as well as preliminary evidence from use of these multiplex assays in pathologically well-defined series of lymphoproliferations, PCR analysis of the IGK locus has clear (additional) value for clonality detection. Nevertheless, care should be taken with interpretation of seemingly clonal bands in especially tube A, due to the inherent restricted IGK junctional heterogeneity. As this problem is especially apparent in GS analysis, HD analysis is slightly preferred over GS analysis, although it should be marked that in some cases GS analysis may facilitate proper interpretation of results. Another potential pitfall is the relatively large size range of expected rearranged IGK products, due to scattered primer positions, and to extended amplifications from downstream Jκ gene segments. This implies that long runs are recommended for GS analysis. Finally, the inherent complexity of multiple rearrangements in the IGK locus (Vκ-Jκ and Kde rearrangements on the same allele), together with a low level of cross-annealing of Vκ primers, may occasionally result in patterns with multiple bands or peaks, resembling oligoclonality. However, with these considerations in mind, the two-tube IGK multiplex PCR system can be valuable in PCR-based clonality diagnostics.

Example 4. IGL Gene Rearrangements

Background

IGL gene rearrangements are present in 5 to 10% of Igκ+ B-cell malignancies and in all Igλ+ B-cell malignancies.[75] Therefore Vλ-Jλ rearrangements potentially represent an attractive extra PCR target for clonality studies to compensate for false-negative IGH $V_H$-$J_H$ PCR results, mainly caused by somatic mutations. The IGL locus spans 1 Mb on chromosome 22q11.2.[77-79] There are 73-74 Vλ genes over 900 kb, among which 30-33 are functional (FIG. 6A). Upon sequence homology, the Vλ genes can be grouped in 11 families and three clans. Members of the same family tend to be clustered on the chromosome. The Jλ and Cλ genes are organized in tandem with a Jλ segment preceding a Cλ gene. Typically there are 7 J-Cλ gene segments, of which J-Cλ1, J-Cλ2, J-Cλ3, and J-Cλ7 are functional and encode the four Igλ isotypes (FIG. 6A).[80,81] There is however a polymorphic variation in the number of J-CA gene segments, since some individual may carry up to 11 of them, due to an amplification of the Cλ2-Cλ3 region.[82,83]

Several studies have shown that the IGL gene repertoire of both normal and malignant B cells is biased.[48,49,84,85] Thus over 90% of Vλ genes used by normal B cells belong to the Vλ1, Vλ2 and Vλ3 families, which comprise 60% of the functional genes. Moreover, three genes (2-14, 1-40, 2-8) account for about half of the expressed repertoire. While normal B cells use J-Cλ1, J-Cλ2 and J-Cλ3 gene segments in roughly equivalent proportions, neoplastic B cells tend to use predominantly J-Cλ2 and J-Cλ3 gene segments.[49] In both normal and malignant B cells the J-Cλ7 is used very rarely (1%). This latter finding was however challenged by a single-cell study of normal cells which found that more than half of the rearrangements employed the J-Cλ7 gene segments.[86] In contrast to the mouse, there is some junctional diversity due to exonuclease activity and N nucleotide addition in human IGL gene rearrangements.[82,85-87] It is however much less extensive than that of the IGH locus, and a number of rearrangements result from the directly coupling of germline Vλ and Jλ gene segments. Nevertheless, the IGL locus might represent an alternative complementary locus to IGH for B-cell clonality studies.

Primer Design

Considering the biased Vλ repertoire, we chose to amplify only rearrangements which used the Vλ1, Vλ2 and Vλ3 gene segments. A single consensus primer recognizing both Vλ1 and Vλ2 gene segments, as well as a Vλ3 primer, were designed in regions of high homology between members of the same family (FIG. 6B). Initial experiments showed that they worked as well in multiplex as separately. In fact, cross annealing of Vλ3 primer hybridizing to some Vλ1 or Vλ2 genes (or vice versa) could be observed when Vλ primers were used separately; it was not seen however in multiplex PCR.

A single consensus primer was designed for the Jλ1, Jλ2 and Jλ3 gene segments and has one mismatch in its central portion compared to each of the germline sequences. In preliminary experiments it was found to give rather better results than a combination of perfectly matched Jλ1 and Jλ2-Jλ3 primers. Since a single study reported the frequent usage of the Jλ7 gene in normal B cells,[86] we also designed a Jλ7 specific primer. When tested on various polyclonal B cell samples, we could hardly detect any signal in HD analysis, in contrast to amplifications performed on the same samples using the Jλ1, Jλ2-Jλ3 or the Jλ consensus primers. Similarly, we could not detect any rearrangement with this primer when analyzing a collection of monoclonal B-cell tumors. Based on these results as well as the other reports in the literature[49], we concluded that the non-confirmed high frequency of Jλ7 rearrangements (in a single study)[86] had been caused by a technical pitfall and consequently, we decided not to include the Jλ7 primer. The PCR assay for the detection of IGL gene rearrangements in clonality study therefore consists of a single tube containing three primers (FIG. 6B). This single tube was expected to detect the vast majority of the rearrangements.

Results of Initial Testing Phase

Initial testing on a set of monoclonal and polyclonal samples showed they could very well be differentiated upon HD analysis of PCR products on 10% polyacrylamide gel electrophoresis (FIG. 6C). Clonal IGL rearrangements were seen in the homoduplex region, with one or sometimes two weaker bands in the heteroduplex region, while polyclonal rearrangements appeared as a smear in the heteroduplex region (FIG. 6C). Nonspecific bands were not observed. It should be noted that because of the limited size of the junctional region, it is extremely difficult to distinguish polyclonal from monoclonal rearrangements by running a simple polyacrylamide gel without performing a heteroduplex formation. Along this line, analysis of PCR products by GS proved to be less straightforward (FIG. 6C). While monoclonal rearrangements were clearly identified, the polyclonal rearrangement pattern had an oligoclonal aspect due to the limited junctional diversity. The interpretation was more difficult, particularly to distinguish polyclonal cases from those with a minor clonal B-cell population in a background of polyclonal B-cells. We therefore recommend HD analysis as the method of choice to analyze IGL gene rearrangements.

The sensitivity of the assay, performed on several cases, proved to be about 5% (2.5%-10%) when dilution of tumor DNA was done in PB-MNC and about 10% (5%-20%) when diluted in lymph node DNA Results of General Testing Phase The single-tube IGL PCR assay was evaluated on the series of 90 Southern blot defined lymphoid proliferations. This testing was done by nine laboratories, four with HD analysis only, one with GS analysis only, and four using both techniques. Clonal IGL gene rearrangements were detected in 19 cases. In 15 of them more than 70% concordance was obtained within the nine laboratories. In four cases less than 70% concordancy was obtained, which could be explained by minor clonal IGL gene rearrangements in three of them (ES-12, GB-10, and FR-10). This discordancy in the fourth case (PT-11) remains unexplained, particularly because no IGL gene rearrangements were detected by Southern blotting. As concluded from the initial testing, interpretation of GS analysis was more difficult than HD analysis, especially in the case of minor clonal populations. Of these 19 clonal IGL gene cases, 17 were B-cell proliferations (16 mature and one precursor B-cell). One case (ES12) corresponded to Hodgkin's disease and another (FR-10) to a T-NHL. Both had only a minor clonal IGL gene rearrangement, and FR-10 also displayed a clonal IGK gene rearrangement.

Comparison with Southern blot data showed some discrepancies. Six cases with clonal IGL gene rearrangements by PCR appeared as polyclonal by Southern blot analysis. Three of them (PT-6, ES-12, FR-10) concerned minor clonal populations which may have been below the sensitivity level of the Southern blot technique. In the three other cases (NL-19, ES-1, PT-11) a clonally rearranged band may have been missed by the fairly complex rearrangement pattern of the IGL locus on Southern blot.[26,49] Conversely the PCR assay failed to detect clonal rearrangements which were seen by Southern blot analysis in two cases (GBS-6, FR-5). However these were follicular lymphomas in which a high degree of somatic hypermutations may have prevented annealing of the IGL gene primers.

Conclusion

In conclusion, a single-tube PCR assay for the detection of IGL gene rearrangements containing only three primers (FIG. 6B) allows to detect the vast majority of IGL gene rearrangements (Vλ1, Vλ2, and V3 gene rearrangements). Heteroduplex analysis is the preferred analytic method, though GeneScan analysis can be used, but maximal caution is recommended to avoid overinterpretation of clonality due to the limited junctional diversity.

Example 5: TCRB Gene Rearrangements: Vβ-Jβ, Dβ-Jβ

Background

Molecular analysis of the TCRB genes is an important tool for assessment of clonality in suspect T-cell proliferations. TCRB gene rearrangements occur not only in almost all mature T-cell malignancies but also in about 80% of the CD3 negative T-cell acute lymphoblastic leukemias (T-ALL) and 95% of the CD3 positive T-ALL.[20] TCRB rearrangements are not restricted to T-lineage malignancies as about one third of precursor-B-ALL harbor rearranged TCRB genes.[30] Their frequency is much lower (0 to 7%) in mature B cell proliferations.[21]

The human TCRB locus is located on the long arm of chromosome 7, at band 7q34 and spans a region of 685 kb. In contrast to the TCRG and TCRD loci the V region gene cluster of the TCRB locus is far more complex (FIG. 7A).[1] It contains about 65 Vβ gene elements for which two different nomenclatures are used: the one summarized by Arden et al.[50] follows the gene designation of Wei et al.[88] and groups the Vβ genes into 34 families. The alternative nomenclature proposed by Rowen et al.[51] subdivides 30 Vβ gene subgroups and was later adopted by IMGT, the international ImMunoGeneTics database http://imgt.cines.fr (initiator and coordinator: Marie-Paule Lefranc, Montpellier, France). [Lefranc, 2003 #212; Lefranc, 2003 #219] The largest families, Vβ5, Vβ6, Vβ8 and Vβ13 (Arden nomenclature) reach a size of seven, nine, five and eight members, respectively. Twelve Vβ families contain only a single member. In general, the families are clearly demarcated from each other.[60] In this report we follow the Arden nomenclature.[50]

39-47 of the Vβ gene elements are qualified as functional and belong to 23 families. 7-9 of the nonfunctional Vβ elements have an open reading frame but contain alterations in the splice sites, recombination signals and/or regulatory elements. 10-16 are classified as pseudogenes. In addition, a cluster of six non-functional orphan Vβ genes have been reported that are localized at the short arm of chromosome 9 (9p21).[89,90] They are not detected in transcripts.[50,51]

Figure 7A:
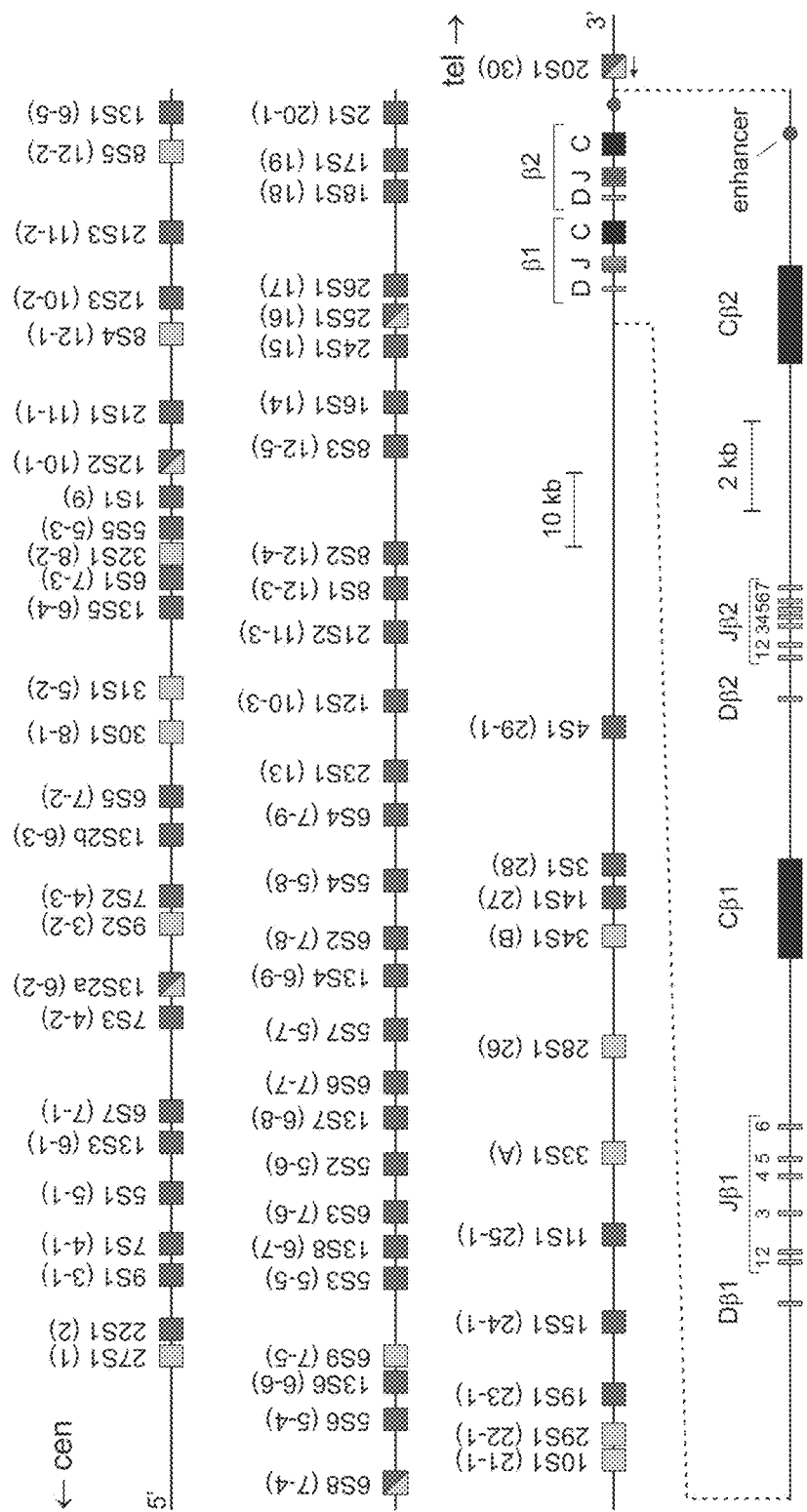

All but one Vβ genes are located upstream of two Dβ-Jβ-Cβ clusters. FIG. 7A illustrates that both Cβ gene segments (Cβ1 and Cβ2) are preceded by a Dβ gene (Dβ1 and Dβ2) and a Jβ cluster which comprises six (Jβ1.1 to Jβ1.6) and seven (Jβ2.1 to Jβ2.7) functional Jβ segments. Jβ region loci are classified into two families according to their genomic localization, not to sequence similarity.[51,89,91]

Due to the large germline encoded repertoire, the combinatorial diversity of TCRB gene rearrangements is extensive compared to the TCRG and TCRD rearrangements. The primary repertoire of the TCRβ molecules is further extended by an addition of an average of 3.6 (V-D junction) and 4.6 (D-J junction) nucleotides and deletion of an average of 3.6 (V), 3.8 (5' of D), 3.7 (3' of D) and 4.1 (J) nucleotides.[51] The complete hypervariable region resulting from the junction of the V, D and J segments comprises characteristically nine or ten codons. Size variation is limited, as 7 to 12 residues account for more than 80% of all functional rearrangements in contrast to the broad length repertoire of the IGH CDR3 region.[92]

During early T-cell development the rearrangement of the TCRB gene consists of two consecutive steps: Dβ to Jβ rearrangement and Vβ to D-Jβ rearrangement with an interval of one to two days between these two processes.[93] The Dβ1 gene segment may join either Jβ1 or Jβ2 gene segments but the Dβ2 gene segment generally joins only Jβ2 gene segments because of its position in the TCRB gene locus.[28,51] Due to the presence of two consecutive TCRB D-J clusters, it is also possible that two rearrangements are detectable on one allele: an incomplete TCRB Dβ2-Jβ2 rearrangement in addition to a complete or incomplete rearrangement in the TCRB Dβ1-Jβ1 region.[1]

In TCRB gene rearrangements, a non-random distribution of gene segment usage is seen. In healthy individuals, some Vβ families predominate in the peripheral blood T-cell repertoire (e.g Vβ1-Vβ5), while others are only rarely used (e.g. Vβ11, Vβ16, Vβ18, Vβ23). Mean values of the Vβ repertoire seem to be stable during aging, although the standard deviation increase in the elderly.[13,94] Also in the human thymus some Vβ gene segments dominate: the most prevalent seven Vβ genes (Vβ3-1, Vβ4-1, Vβ5-1, Vβ6-7, Vβ7-2, Vβ8-2, Vβ13-2) cover nearly half of the entire functional TCRB repertoire.[95] The representation of J segments is also far from even. The Jβ2 family is used more frequently than the Jβ1 family (72% vs. 28% of TCRB rearrangements).[96] In particular, the proportion of Jβ2.1 is higher than expected (24%) followed by Jβ2.2 (11%) and Jβ2.3 and Jβ2.5 (10% each).[95]

TCRB gene rearrangement patterns differ between categories of T cell malignancies. Complete TCRB Vβ-Jβ1 rearrangements and incompletely rearranged alleles in the TCRB D-Jβ2 cluster are seen more frequently in TCRαβ+ T-ALL as compared to CD3− T-ALL and TCRγδ+ T-ALL.[28] In the total group of T-ALL the TCRB D-Jβ1 region is relatively frequently involved in rearrangements in contrast to cross-lineage TCRB gene rearrangements in precursor-B-ALL which exclusively involve the TCRB Dβ-Jβ2 region.[30,73]

The development of monoclonal antibodies against most Vβ domains has helped to identify Vβ family expansions.[13] However, TCR gene rearrangement analysis is essential for clonality assessment in T cell lymphoproliferative disorders. As the restricted germline encoded repertoire of the TCRG and TCRD loci facilitates DNA based PCR approaches, various PCR methods have been established for the detection of TCRG and TCRD gene rearrangements.[97-99] Nevertheless, the limited junctional diversity of TCRG rearrangements leads to a high background amplification of similar rearrangements in normal T cells (Example 5). The TCRD gene on the other hand is deleted in most mature T cell malignancies. Therefore DNA based TCRB PCR techniques are needed for clonality assessment. In addition, TCRB rearrangements are of great interest for follow-up studies of lymphoproliferative disorders, because the extensive combinatorial repertoire of TCRB rearrangements and the large hypervariable region enables a highly specific detection of clinically occult residual tumor cells. However, the extensive germline encoded repertoire renders PCR assays more difficult. Some published PCR approaches use the time consuming procedure of multiple tube approaches with a panel of family- or subfamily-specific primers.[96,100] Usage of highly degenerated consensus primers limits the number of detectable rearrangements that are theoretically covered by the primers because there is no single common sequence of sufficient identity to allow a reliable amplification of all possible rearrangements.[42,101,102] Some published assays use a nested PCR requiring an additional PCR reaction.[42,102] Other assays focus on analysis of the TCRB Vβ-Dβ-Jβ-Cβ transcripts to limit the number of primers needed.[16,100,103] However, a major drawback of these mRNA based approaches is the need for fresh or frozen material and a reverse transcription step before the PCR amplification.

We tried to overcome these limitations by creating a completely new and convenient DNA based TCRB PCR. We designed multiple Vβ and Jβ primers, covering all functional Vβ and Jβ gene segments and being suitable for combination in multiplex PCR reactions. In addition the assay is applicable for HD and GS analysis and also detects the incomplete TCRB D-Jβ rearrangements with the same set of Jβ primers. In order to avoid problems due to cross priming we decided to design all Vβ and Jβ primers at the same conserved region of each gene segment.

Primer Design

Initially a total of 23 Vβ, 2 Dβ (Dβ1 and Dβ2) and 13 Jβ (Jβ1.1 to 1.6 and Jβ2.1 to 2.7) primers were designed with all the Vβ and Jβ primers positioned in the same conserved region of each Vβ and Jβ gene segment so that the effects of cross-annealing in a multiplex reaction could be neglected. In addition, rare polyclonal TCRB V-J rearrangements would not be mistaken for a clonal rearrangement even if they do not produce a fully polyclonal Gaussian peak pattern, because PCR products of all possible rearrangements are situated in the same size range.

Figure 7B:
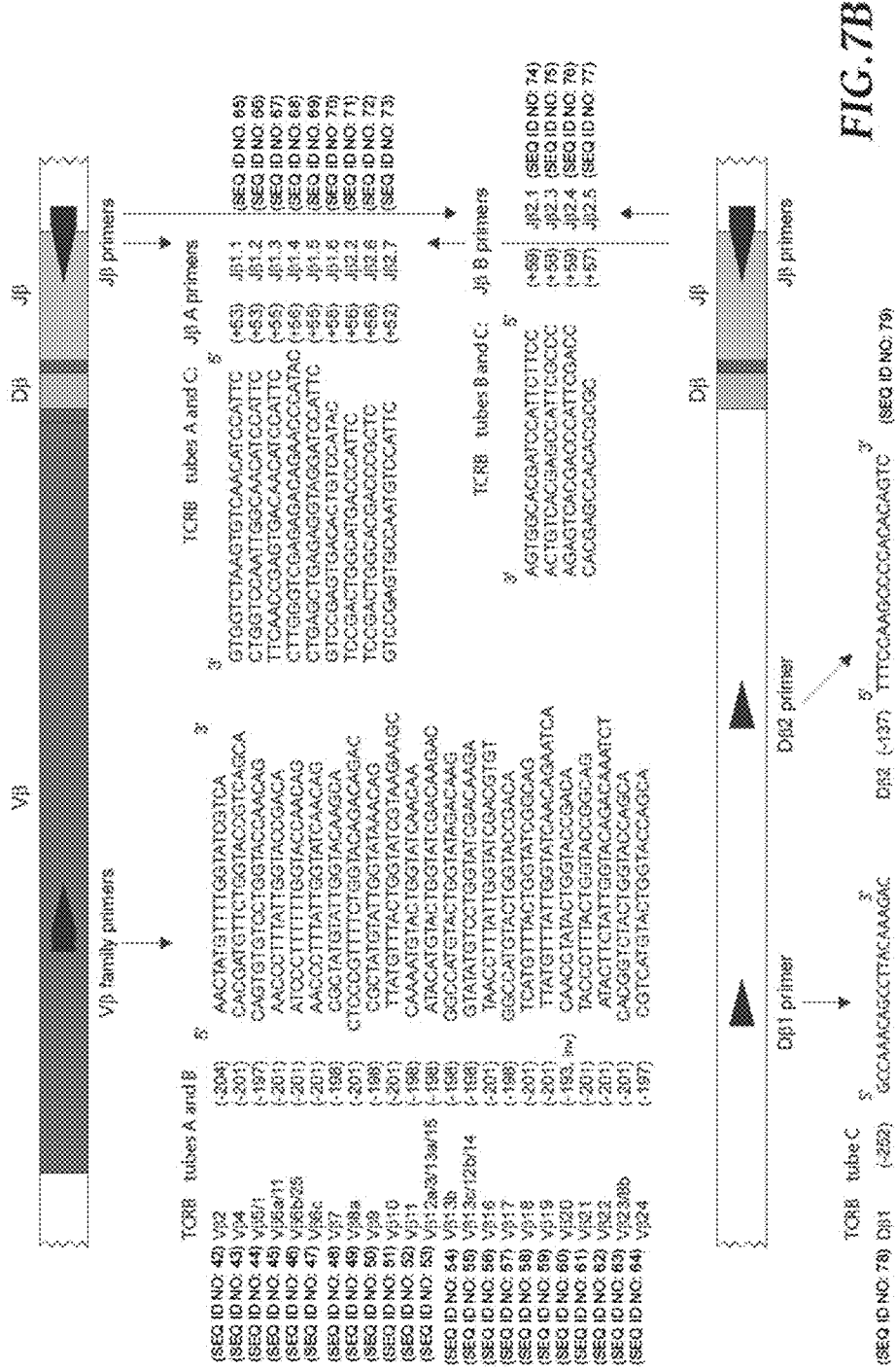
Figure 7C:
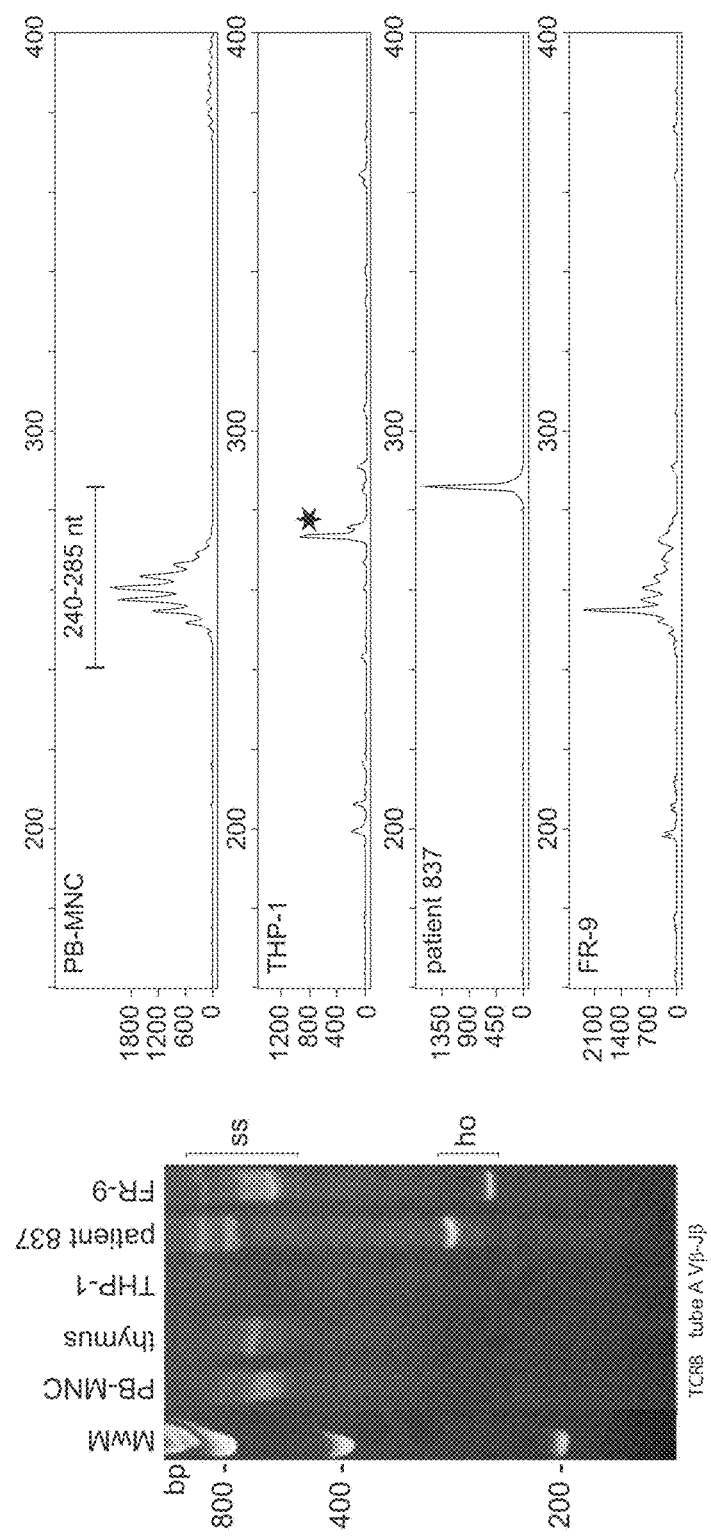
Figure 7D:
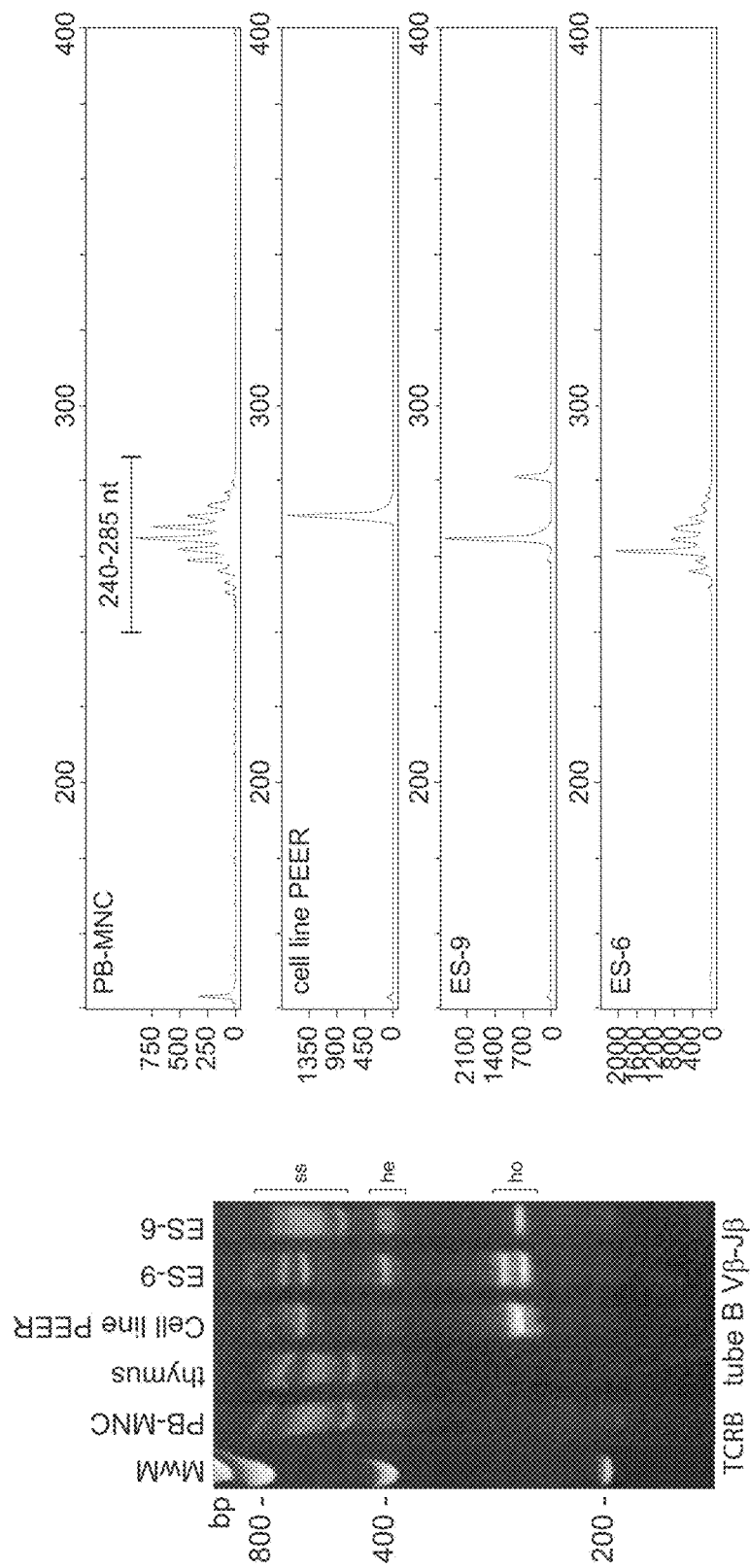

For primer design, the rearrangeable pseudogenes or open reading frame genes with alterations in splicing sites, recombination signals and/or regulatory elements or changes of conserved amino acids were taken into consideration whenever possible. However, the main objective was to cover all functional Vβ genes. The priming efficiency of each Vβ primer was checked for every Vβ gene using OLIGO 6.2 software. This led to primers that were not strictly Vβ family specific and some of which covered Vβ gene segments of more than one family (FIG. 7B). Since the 13 Jβ primers annealed to the same segment of each Jβ gene primer, dimerization made it necessary to split the J primers into two tubes. Initially, it was planned to use the primers in four sets of multiplex reactions as follows: all 23 Vβ primers in combination with the six Jβ1 family primers (240-285 bp), all 23 Vβ primers with the seven Jβ2 family primers (240-285 bp), Dβ1 (280-320 bp) with the six Jβ1 primers, and Dβ1 (280-320 bp) plus Dβ2 (170-210 bp) with the seven Jβ2 family primers.

Results of Initial Testing Phase

Initial monoplex testing of each possible primer combination was done using samples with known monoclonal TCRB rearrangements and polyclonal controls. PCR products of the expected size range were generated with differences in product intensity and signal profile for polyclonal samples depending on the frequency of usage of distinct Vβ and Jβ gene segments. However, when the primers were combined in a multiplex reaction some Jβ2 rearrangements in particular were missed and nonspecific products in the tubes B and D were observed. In addition cross-priming between the Jβ1 and Jβ2 primers resulted in interpretation problems. As a consequence the Jβ2 primers had to be redesigned and the primer combinations in the different tubes had to be rearranged: Jβ primers Jβ2.2, 2.6 and 2.7 were slightly modified and added to tube A. The localization of the primers Jβ2.1, 2.3, 2.4 and 2.5 was shifted by 4 bp downstream to avoid primer dimerization and cross priming with the remaining Jβ primers. Only nonspecific bands with varying intensity outside the expected size range persisted in tube B (banda<150 bp, 221 bp) and tube C (128 bp, 337 bp) using specific template DNA. However, because all nonspecific amplification products were outside the size ranges of the TCRB specific products, they did not affect interpretation and were considered not to be a problem. However, using nonspecific template controls one additional faint 273 bp aspecific peak in tube A was visible by GS analysis. This product is completely suppressed when the DNA contains enough clonal or polyclonal TCRB rearrangements but can appear in samples comprising low numbers of lymphoid cells. In the initial testing phase relatively faint V-D-J PCR products were generated. Thus we optimized PCR conditions for complete V-D-J rearrangements by increasing $MgCl_2$ concentration and the amount of Taq polymerase. Also usage of highly purified primers and application of ABI Buffer II instead of ABI Gold Buffer turned out to be very important. For detection of the incomplete Dβ-Jβ rearrangements, it was finally possible to mix all Jβ primers into one tube without loss of sensitivity or information. Consequently, the total number of multiplex reactions could be reduced to three tubes.

The finally approved primer set is (FIG. 7B):
tube A: 23 Vβ primers and 9 Jβ primers: Jβ1.1-1.6, 2.2, 2.6 and 2.7
tube B: 23 Vβ primers and 4 Jβ primers: Jβ2.1, 2.3, 2.4 and 2.5
tube C: Dβ1, Dβ2 and all 13 Jβ primers.

As tubes A and C contain Jβ1 and Jβ2 primers, differential labeling of Jβ1 and Jβ2 primers with different dyes (TET for Jβ1.1-1.6 and FAM for Jβ2.1-2.7 primers) allows GS discrimination of Jβ1 or Jβ2 usage in tube A and C reactions (see FIG. 13A).

Sensitivity testing was performed via dilution experiments with various cell lines and patient samples with clonally rearranged TCRB genes in MNC. Single PCR dilution experiments generally reached sensitivity levels of at least 0.1% to 1%. As expected, the sensitivity decreased in multiplex testing, probably due to an increase of background amplification. Especially in GS analysis this background hampered interpretation due to the relative small length variation of the TCRB PCR products. Nevertheless, in 40 of 46 positive controls tested a sensitivity of at least 1% to 10% was reached using heteroduplex or GeneScanning (Table 6).

Results of General Testing Phase

Figure 7E:
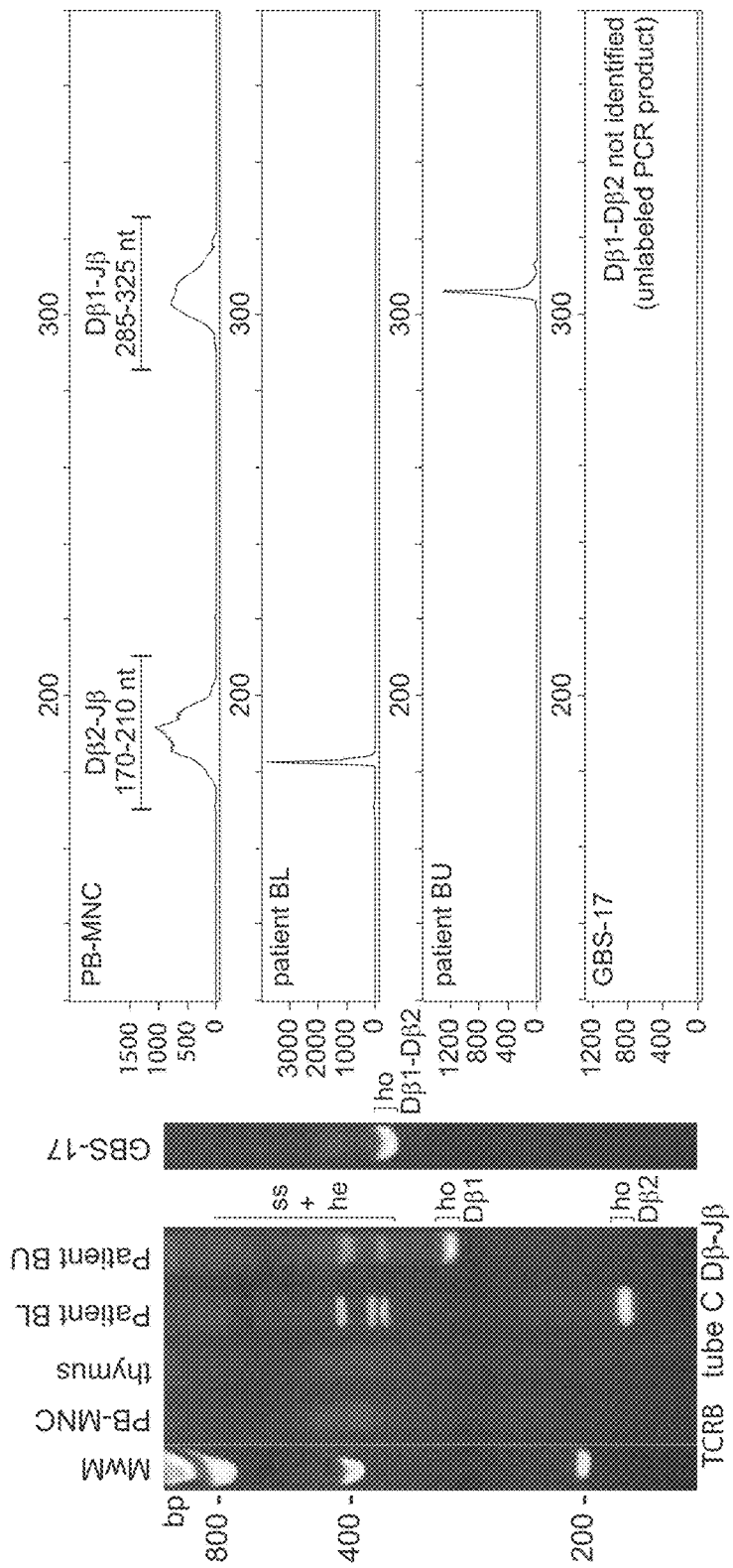

Eleven groups participated in the analysis of DNA from a series of 90 Southern blot-defined malignant and reactive lymphoproliferative disorders using the TCRB multiplex protocol. Every sample was analysed by HD in two laboratories and in six laboratories using GS analysis. Another three laboratories used both techniques for PCR analysis (FIGS. 7C, D, and E). This testing phase as well as experience from use of these TCRB PCR assays raised some general issues about the protocol that were in part already described in the initial testing phase: 1. The limited length variation of the TCRB PCR products may hamper GS detection of clonal signals within a polyclonal background 2. Only bands/peaks within the expected size range represent clonal TCRB gene rearrangements. Especially for tube A a nonspecific control DNA must be included to define the aspecific 273 bp peak that may occur in situations without competition. 3. It is extremely important to use highly purified primers and ABI Buffer II (and not ABI Gold Buffer) for good PCR results as well as the recommended PCR product preparation protocol for HD analysis. Of the 90 Southern blot-defined cases submitted, 29 were SB positive for monoclonal TCRB rearrangements. 25 of these clonal rearrangements (86%) were also detectable by the TCRB PCR. 23 rearrangements were disclosed by GS and HD analysis, two additional cases only by HD. One of the GS negative HD positive cases (FR-9) was interpreted as monoclonal on GS analysis by four of the nine laboratories involved in the general testing phase (FIG. 7C). However, due to a significant polyclonal background, interpretation of the GS patterns was difficult in this particular case. The other GS negative HD positive case displayed an atypical PCR product in tube C with a size of about 400 bp (FIG. 7E). The PCR product was clearly visible in agarose gels and HD analysis but not by GS. After DNA sequencing of this fragment a TCRB Dβ1-Dβ2 amplification product was identified explaining the unlabelled PCR product. Four SB positive cases (NL-15, NL-16, GBN-2 and FR-6) were neither detected by GS nor by HD analysis all of them with an underlying B lymphoid malignancy. Possible explanations for this failure are atypical rearrangements (e.g. incomplete Vβ-Dβ rearrangements),[28,104] sequence variations of the rearranged Vβ gene segments[51] or a lack of sensitivity for particular rearrangements.

62 of the samples were considered to be polyclonal by SB. For 61 (98%) of these cases PCR results were concordant with at least one method of analysis, for 57 (92%) cases results were concordant using both methods. The one SB negative sample (ES-14) found to be monoclonal by HD and GS analysis showed an incomplete Dβ2-rearrangement. For four samples non-uniform results were obtained: one sample was considered to be clonal by GS but only by 50% of the labs analyzing the PCR products by HD (GBS-4). Three samples were found to produce weak clonal signals only by HD analysis (ES-6, GBS-9 and DE-2). TCRB rearranged subclones being too small to be detected by SB analysis may only be seen by the more sensitive PCR methodology. In B cell malignancies the detected rearrangements may also represent clonal or oligoclonal expansions of residual T cells.[105] In this case these weak clonal PCR products should not be regarded as evidence of a clonal T cell disorder. This stresses the importance of the interpretation of the PCR results in context with other diagnostic tests and the clinical picture of the patients. Optimal PCR assessment of TCRB rearrangements is obtained by the combined use of HID and GS analysis. Sensitivity may differ between the two detection methods as a function of clonal PCR product size compared to the polyclonal size distribution: on the one hand HD analysis disperses the polyclonal background from the clonal products and on the other hand PCR products outside the main size range allow a more sensitive GS detection. Also the risk of false-positive results is reduced in the combined use of HD and GS analysis. Furthermore, HD analysis allows detection of some additional atypical TCRB Dβ1-Dβ2 rearrangements that cannot be detected by GS analysis of the PCR product as no labeled primer is involved in amplification. However, GS analysis is in general the more informative method for samples with a high tumor load because the exact size of the monoclonal PCR product is indicated, which may be used for monitoring purposes and differentially labeled Jβ primers provide additional information about Jβ gene usage.

Conclusion

In conclusion, the three-tube TCRB multiplex PCR system provides a new and convenient assay for clonality assessment in suspect T-cell proliferations with an unprecedentedly high clonality detection rate.

Example 6: TCRG Gene Rearrangements

Background

TCRG gene rearrangements have long been used for DNA PCR detection of lymphoid clonality and represent the "prototype" of restricted repertoire targets. It is a preferential target for clonality analyses since it is rearranged at an early stage of T lymphoid development, probably just after TCRD,[106] in both TCRαβ and TCRγδ lineage precursors. It is rearranged in greater than 90% of T-ALL, T-LGL and T-PLL, in 50-75% of peripheral T-NHL and mycosis fungoïdes but not in true NK cell proliferations. It is also rearranged in a major part of B lineage ALLs, but much less so in B-NHL.[1,30,73] Unlike several other Ig/TCR loci, the complete genomic structure has been known for many years. It contains a limited number of Vγ and Jγ segments. Amplification of all major Vγ-Jγ combinations is possible with limited number of four Vγ and three Jγ primers.

Figure 8A:
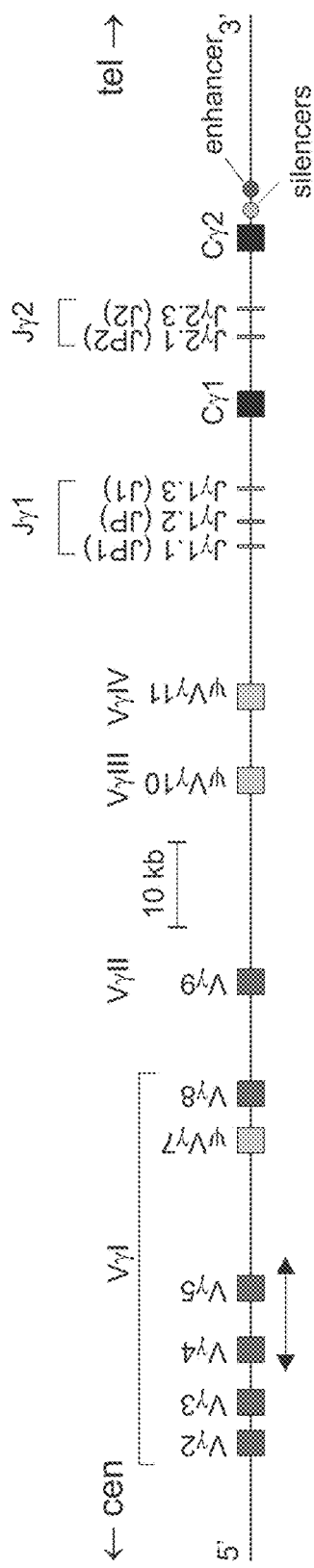

The human TCRG locus on chromosome 7p14 contains 14 Vγ segments, only ten of which have been shown to undergo rearrangement (FIG. 8A). The expressed Vγ repertoire includes only six Vγ genes (Vγ2, Vγ3, Vγ4, Vγ5, Vγ8 and Vγ9) but rearrangement also occurs with the ψVγ7, ψVγ10, γψVγ11 segments.[107,108] Rearrangement of ψVγB (also known as Vγ12)[107] is so exceptional that it is rarely used in diagnostic PCR strategies. Rearranging Vγ segments can be subdivided into those belonging to the VγI family (VγfI: Vγ2, Vγ3, Vγ4, Vγ5, ψVγ7 and Vγ8; overall homology >90% and highest between Vγ2 and Vγ4 and between Vγ3 and Vγ5) and the single member Vγ9, ψVγ10, ψVγ11 families. The TCRG locus contains five Jγ segments: Jγ1.1 (JγP1), Jγ1.2 (JγP), Jγ1.3 (Jγ1), Jγ2.1 (JγP2), Jγ2.3 (Jγ2), of which Jγ1.3 and Jγ2.3 are highly homologous, as are Jγ1.1 and Jγ2.1.

Whilst the restricted TCRG germline repertoire facilitates PCR amplification, the limited junctional diversity of TCRG rearrangements complicates distinction between clonal and polyclonal PCR products. The TCRG locus does not contain D segments and demonstrates relatively limited nucleotide additions. TCRG V-J junctional length therefore varies by 20-30 bp, compared to approximately 60 bp for IGH and TCRD. The capacity to distinguish clonal from polyclonal TCRG rearrangements depends on the complexity of the polyclonal repertoire. In general, minor clonal populations using frequent Vγ-Jγ rearrangements such as VγfI-Jγ1.3/2.3 are at risk of being lost amidst the polyclonal repertoire, whereas rare combinations will be detected with greater sensitivity. However, occasional polyclonal T lymphocytes demonstrating rare Vγ-Jγ rearrangements may be mistaken for a clonal rearrangement, due to absence of a polyclonal background for that type of rearrangement. A further possible source of false positivity results from the presence of TCRγδ expressing T lymphocytes demonstrating "canonical" TCRG rearrangements, which do not demonstrate N nucleotide additions. The most commonly recognized human canonical TCRG rearrangement involves the Vγ9-Jγ1.2 segments and occurs in approximately 1% of blood T-lymphocytes.[110,111] It is therefore extremely important to analyze TCRG PCR products using high resolution electrophoretic techniques or to separate PCR products on criteria other than purely on size, in order to reduce the risk of false positive results. It is also important to be aware of the profile of canonical rearrangements and the situations in which they most commonly occur. Canonical Vγ9-Jγ1.2 rearrangements, for example, are found predominantly in peripheral blood and increase in frequency with age, since they result from accumulation of TCRγδ+ T-lymphocytes.[19]

Unlike TCRD, TCRG is not deleted in TCRαβ lineage cells. Since TCRG rearrangements occur in both TCRαβ and TCRγδ lineage precursors, their identification cannot be used for determination of the type of T cell lineage. Similarly, TCRG rearrangements occur in 60% of B lineage ALL,[30] implying that they can not be used for assessment of B vs. T cell lineage in immature proliferations. However, they occur much less frequently in mature B lymphoproliferative disorders, including the majority of B-NHL,[1] and might therefore be used, in combination with clinical and immunophenotypic data, to determine lineage involvement in mature lymphoproliferative disorders.

The limited germline repertoire allows determination of Vγ and Jγ segment utilization, either by Southern blot or PCR analysis. Identification of Vγ and Jγ usage is not of purely academic interest, since specific amplification is required for MRD analysis.[112]

We undertook to develop a minimal number of multiplex TCRG strategies which would maintain optimal sensitivity and informativity, minimize the risk of false positive results and allow simple Vγ and Jγ identification, including by HD analysis or monofluorescent GS strategies. We chose to include Vγ primers detecting all rearranging segments other than ψVγB (ψVγ12), given its rarity. In order to reduce the risk of falsely identifying canonical rearrangements as clonal products, we excluded the Jγ1.2 primer, since it is rarely involved in lymphoid neoplasms and is usually, although not always, associated with a TCRG rearrangement on the other allele.[113]

Primer Design

We initially developed 3Vγ and 2 Jγ primers, to be used in two multiplex reactions, as follows: one tube with Jγ1.3/2.3 with Vγ9 specific (160-190 bp), VγfI consensus (200-230 bp) and Vγ10/11 consensus (220-250 bp) and a second tube with Jγ1.1/2.1 with Vγ9 specific (190-220 bp), VγfI consensus (230-260 bp) and Vγ10/11 consensus (250-280 bp). Vγ usage was to be identified by PCR product size by HD analysis. No distinction between Jγ1.3 and Jγ2.3 or Jγ1.1 and Jγ2.1 was attempted.

Results of Initial Testing Phase

While all Vγ-Jγ combinations gave the expected profiles on single PCR amplification, multiplex amplification led to competition of larger PCR products, with preferential amplification of smaller fragments, and failure to detect some VγfI and Vγ10/11 rearrangements. This was further complicated by significant primer dimer formation between the Vγ10/11 consensus and the VγfI primers. Competition between differently sized fragments and primer dimer formation both led to unsatisfactory sensitivity and informativity and this strategy was therefore abandoned.

Figure 8B:
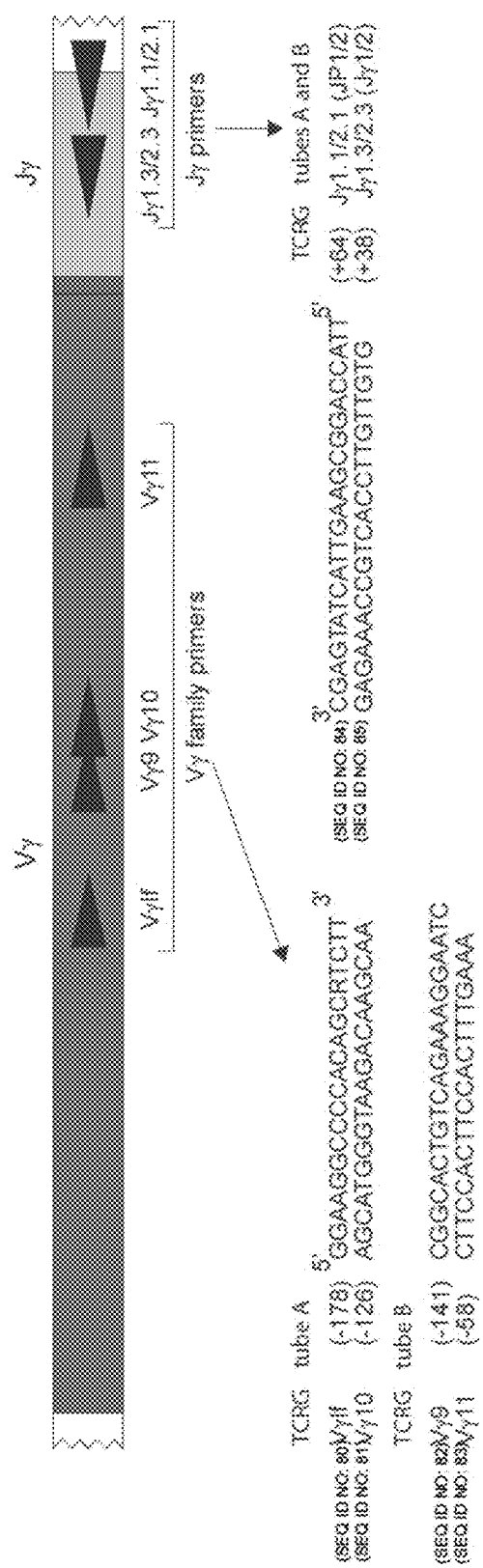
Figure 8C:
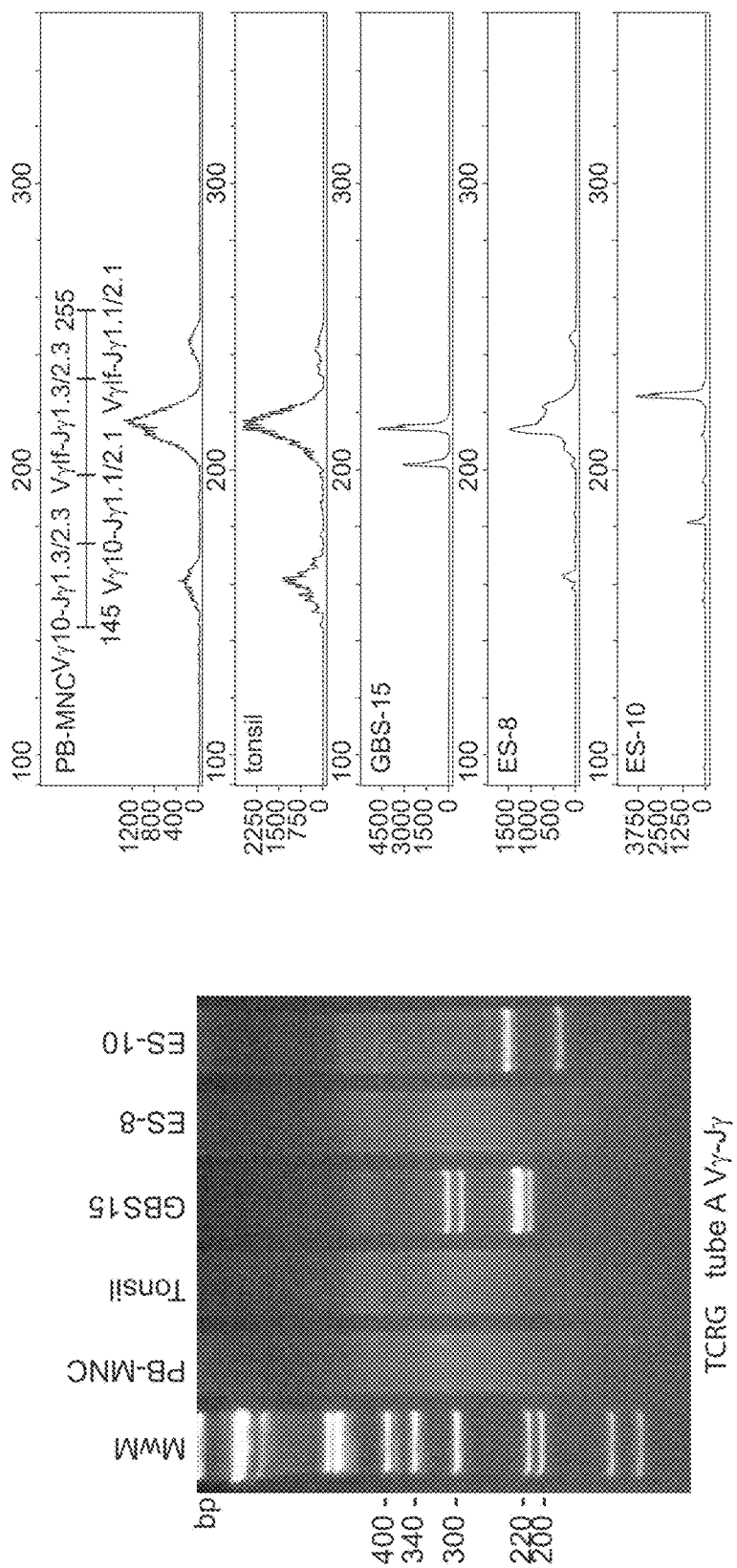
Figure 8D:
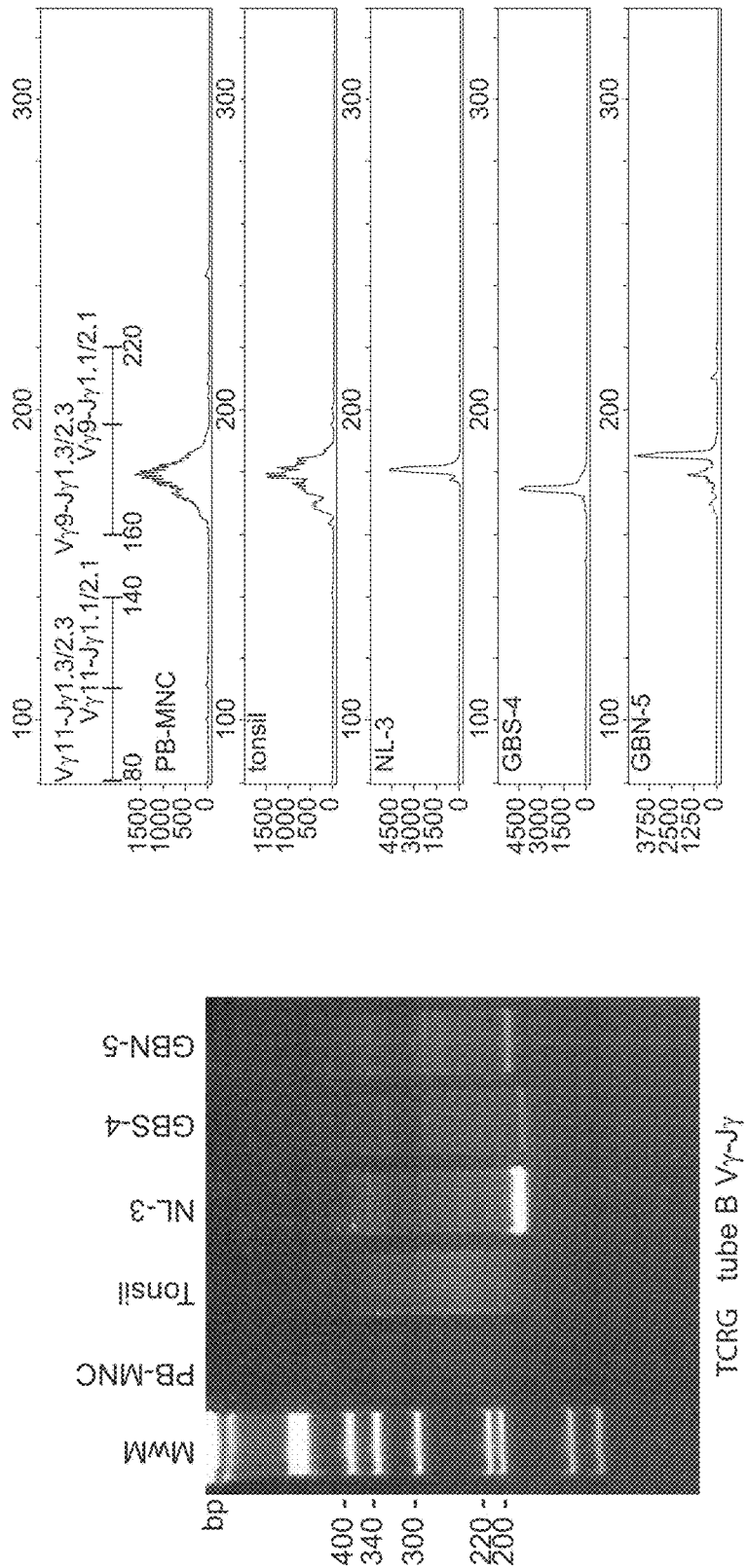

We reasoned that competition would be minimized by separating the most frequently used Vγ primers (VγfI and Vγ9) and combining them with Vγ10 and Vγ11 specific primers, respectively. The latter rearrangements are rarely used and therefore minimize competition for the predominant repertoires. The Vγ10/11 consensus primer was therefore replaced by two specific Vγ primers which generated smaller PCR products (FIG. 8B). By mixing Jγ1.3/2.3 and Jγ1.1/2.1 it was possible to maintain a two-tube multiplex which allows approximate identification on the basis of product size of Vγ usage by HD analysis and of both Jγ and Vγ usage by GS analysis.

The approved set of multiplex TCRG PCR tubes with four Vγ and two Jγ primers includes (FIG. 8B):
Tube A: VγfI+Vγ10+Jγ1.1/2.1+Jγ1.3/2.3
Tube B: Vγ9+Vγ11+Jγ1.1/2.1+Jγ1.3/2.3

The position and the sequence of the primers are shown in FIG. 8B. These primers gave satisfactory amplification in both single and multiplex PCR formats and allowed detection of virtually all known Vγ-Jγ combinations. The competition of larger PCR fragments was no longer seen, although it cannot be excluded that some competition of Vγ9 or VγfI rearrangements may occur if these are present in a minority population.

Sensitivity of detection varied between 1% and 10%, as a function of the complexity of the polyclonal repertoire and the position of the clonal rearrangement relative to the polyclonal Gaussian peak.[114] Interpretation of ψVγ11 rearrangements can be difficult, since the normal repertoire is extremely restricted and since these primitive rearrangements are often present in subclones.

Since the Vγ4 segment is approximately 40 bp longer than the other VγfI members and Vγ4 rearrangements are relatively common in both physiological and pathological lymphoid cells, the polyclonal repertoire can be skewed towards larger sized fragments, and clonal Vγ4-Jγ1.3/2.3 rearrangements could theoretically be mistaken for VγfI-Jγ1.1/2.1 rearrangements. The proximity of the different repertoires also makes Vγ and Jγ identification much more reliable if differently labeled Jγ primers are used. For example, the use of a TET-labeled Jγ1.1/2.1 and a FAM labeled Jγ1.3/2.3 was tested in a single center and was shown to give satisfactory results (FIG. 13B). It is, however, possible to estimate Vγ and Jγ usage following GS analysis on the basis of size alone (FIGS. 8C and D).

Results of General Testing Phase

Given the limited germline TCRG repertoire and the restricted junctional diversity, reactive T lymphocytes which have undergone TCRG rearrangements using a single Vγ and Jγ segment with variable CDR3 sequences which are of uniform length, will migrate as an apparent clonal population by GS analysis. HD formation will disperse these rearrangements more easily and will therefore prevent their erroneous interpretation as evidence of lymphoid clonality. In contrast, GS analysis provides improved resolution and sensitivity compared to HID analysis. For these reasons, optimal assessment of TCRG rearrangements requires both HD and GS analysis. If this is not possible, HD analysis alone is probably preferable, since it might be associated with a risk of false-negative results, whereas GS analysis alone will increase the risk of false-positive results.

Of the 18 TCRG rearrangements detected by Southern blotting in the 90 cases, 16 were also detected by PCR. The minor VγfI-Jγ1.3/2.3 rearrangement detected by Southern in the NL-1 oligoclonal case, was only detected by PCR in a proportion of laboratories performing GS analysis. A major Vγ9-Jγ1.3/2.3 rearrangement detected in GBS-6 was found to be polyclonal by both HD and GS in all laboratories and, as such, probably represents a false-negative result.

Comparison of allele identification showed that, for all alleles identified by Southern blotting, PCR Vγ and Jγ identification on the basis of size gave concordant results. Seven rearrangements were detected by Southern blotting but precise allele identification was not possible. Six of these were due to Jγ1.1/2.1 usage, suggesting that PCR allows preferential detection of this type of rearrangement.

Seventy two samples were considered to be polyclonal by Southern. Sixteen (22%) of these demonstrated a total of 24 rearrangements by TCRG PCR. Of these, 13 (81%) were B lymphoid proliferations. Sixteen of the 24 clonal rearrangements were minor, with 15 only being detected by GS in the majority of laboratories. It is worth noting that, of these minor rearrangements, nine (39%) involved the ψVγ10 segment and eight (33%) Vγ9. ψVγ11 rearrangements were not detected. No ψVγ10 rearrangements were detected by Southern blot analysis. PCR therefore allowed more sensitive detection of minor clonal ψVγ10 rearrangements, particularly by GS analysis. It is likely that these rearrangements represent residual, predominantly TCRαβ lineage, T lymphocytes with a restricted repertoire, which may or may not be related to the underlying B lymphoid malignancy. These minor peaks should obviously not be interpreted as evidence of a clonal T cell disorder. They emphasize the importance of understanding the nature of TCRG rearrangements before using this locus as a PCR target in the lymphoid clonality diagnostic setting. Consequently, it is also extremely important to interpret TCRG gene results within their clinical context.

Conclusion

In conclusion, the two TCRG multiplex tubes allow detection of the vast majority of clonal TCRG rearrangements. The potential risk of false positive results due to overinterpretation of minor clonal peaks can be minimized by the combined use of heteroduplex analysis and GeneScanning and by interpreting results within their clinical context, particularly when the apparent clonality involved the ψVγ10 and ψVγ11 segments. The relative merits of TCRG compared to TCRB analysis for the detection of clonal T lymphoproliferative disorders should be studied prospectively. They are likely to represent complementary strategies.

Example 7. TCRD Gene Rearrangements:
Vδ-Dδ-Jδ, Dδ-Dδ, Vδ-Dδ, and Dδ-Jδ

Background

Figure 9A:
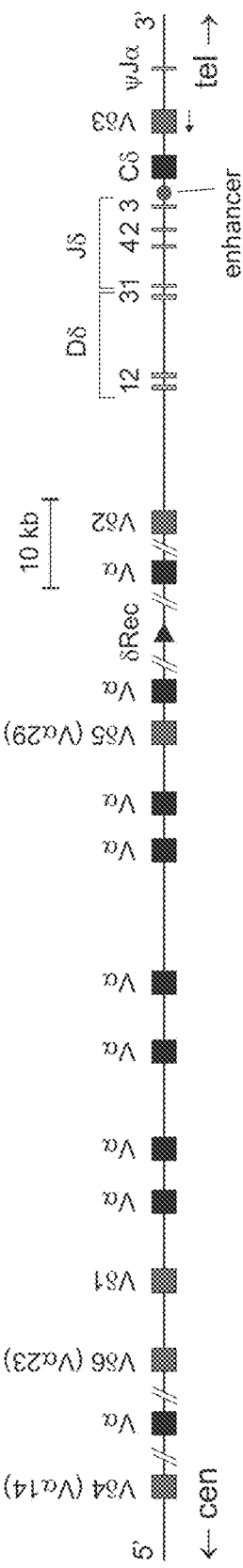

The human TCRD gene locus is located on chromosome 14q11.2 between the Vα and Jα gene segments. The major part of the TCRD locus (Dδ-Jδ-Cδ) is flanked by TCRD-deleting elements, ψJα and δREC such that rearrangement of the deleting elements to each other or rearrangement of Vα to Jα gene segments causes deletion of the intermediate TCRD gene locus (FIG. 9A). The germline encoded TCRD locus consists of 8Vδ, 4Jδ, and 3Dδ gene segments, of which at least five of the eight Vδ gene segments can also rearrange to Jα gene segments.[115] Other Vα gene segments may also be utilized in TCRD gene rearrangements in rare cases. The WHO-IUIS nomenclature[110] for TCR gene segments uses a different numbering system for those V genes used mainly or exclusively in TCRδ chains from those which can be used in either TCRα or TCRδ chains. Thus TCRDV101S1 (Vδ1), TCRDV102S1 (Vδ2) and TCRDV103S1 (Vδ3) are used almost exclusively in TCRD rearrangements, whereas TCRADV6S1 (Vδ4), TCRADV21S1 (Vδ5) and TCRADV17S1 (Vδ6) can be used in either TCRδ or α chains. TCRADV28S1 (Vδ7) and TCRADV14S1 (Vδ8) are used extremely rarely in TCRD rearrangements.

The germline-encoded repertoire of the TCRγδ+ T cells is small compared to the TCRαβ+ T cells and the combinatorial repertoire is even more limited due to preferential recombination in peripheral blood and thymocyte TCRγδ+ T cells. At birth, the repertoire of cord blood TCRγδ+ T cells is broad, with no apparent restriction or preferred expression of particular Vγ/Vδ combinations. During childhood, however, the peripheral blood TCRγδ+ T cell repertoire is strikingly shaped so that Vγ9/Vδ2 cells clearly dominate in adults.[117] Studies have shown that Vδ1 and Vδ2 repertoires become restricted with age leading to the appearance of oligoclonal Vδ1+ and Vδ2+ cells in blood and intestine.[118] TCRγδ+ T cells are evenly distributed throughout human lymphoid tissues but there is preferential expression of particular Vδ segments in specified anatomical localizations. Notably, most intraepithelial TCRγδ T cells occurring in the small intestine and in the colon express Vδ1. Similarly, Vδ1 is expressed by normal spleen TCRγδ+ T cells, but TCRγδ+ T cells in the skin express the Vδ2 gene.

Although the small number of V, D and J gene segments available for recombination limits the potential combinatorial diversity, the CDR3 or junctional diversity is extensive due to the addition of N regions, P regions and random deletion of nucleotides by recombinases. This diversity is also extended by the recombination of up to three Dδ segments and therefore up to four N-regions within the rearranged TCRD locus. This limited germline diversity encoded at the TCRD locus in conjunction with extensive junctional diversity results in a useful target for PCR analysis and TCRD recombination events have been used most extensively as clonal markers in both T and B cell acute lymphoblastic leukemia (ALL).[119,120] The TCRD locus is the first of all TCR loci to rearrange during T cell ontogeny. The first event is a Dδ2-Dδ3 rearrangement, followed by a Vδ2-(Dδ1-Dδ2)-Dδ3 rearrangement, and finally Vδ-Dδ-Jδ rearrangement. Immature rearrangements (Vδ2-Dδ3 or Dδ2-Dδ3) occur in 70% of precursor B-ALL (and are therefore non lineage restricted)[30] while there is a predominance of mature rearrangements comprising incomplete Dδ2-Jδ1 and complete Vδ1, Vδ2, Vδ3 to Jδ1 found in T-ALL.[23,121] Thus specific primer sets can be used to identify different types of complete and incomplete rearrangements corresponding to different types of ALL.[122]

TCRγδ+ T-ALL form a relatively small subgroup of ALL, representing 10-15% of T-ALL but still only constitute 2% of all ALL. Vδ1-Jδ1 rearrangements predominate in TCRγδ+ T ALL; interestingly Vδ1 is never found in combination with Jδ segments other than Jδ1.[15,20] Other recombinations occur in less than 25% of alleles. Furthermore, Vδ1-Jδ1-Cδ chains are almost always disulfide linked to either VγI or VγII gene families recombined to Jγ2.3-Cγ2. Such gene usage is consistent with the immature thymic origin of these leukemic cells.

Most T cell lymphomas express TCRαβ while the minority express TCRγδ and comprise of several distinct entities. Peripheral T cell lymphomas (PTCL) expressing TCRγδ comprise 8-13% of all PTCL and Vδ1-Jδ1 as well as other Vδ to Jδ1 recombinations have been documented.[123,124] Hepatosplenic γδ T-cell lymphoma is derived from splenic TCRγδ T cells which normally express Vδ1. It is an uncommon entity that exhibits distinctive clinicopathologic features and gene usage analysis has indicated clonal Vδ1-Jδ1 rearrangements associated with these lymphomas.[125] Furthermore, the rare type of cutaneous TCRγδ+ T cell lymphomas express Vδ2 and therefore appear to represent a clonal expansion of TCRγδ+ T cells which normally reside in the skin.[126] Other clonal TCRγδ proliferations include CD3+ TCRγδ+ large granular lymphocyte (LGL) proliferations which comprise about 5% of all CD3+ LGL and often show Vδ1-Jδ1 rearrangements.[127]

The development of monoclonal antibodies towards framework regions of TCRγδ and more recently to specific Vδ gene segments has helped identify TCRγδδ+ T cell populations by flow cytometric analysis,[15] but PCR clonality studies are still required to identify whether these populations represent clonal or polyclonal expansions.[128]

Primer Design

Figure 9B:
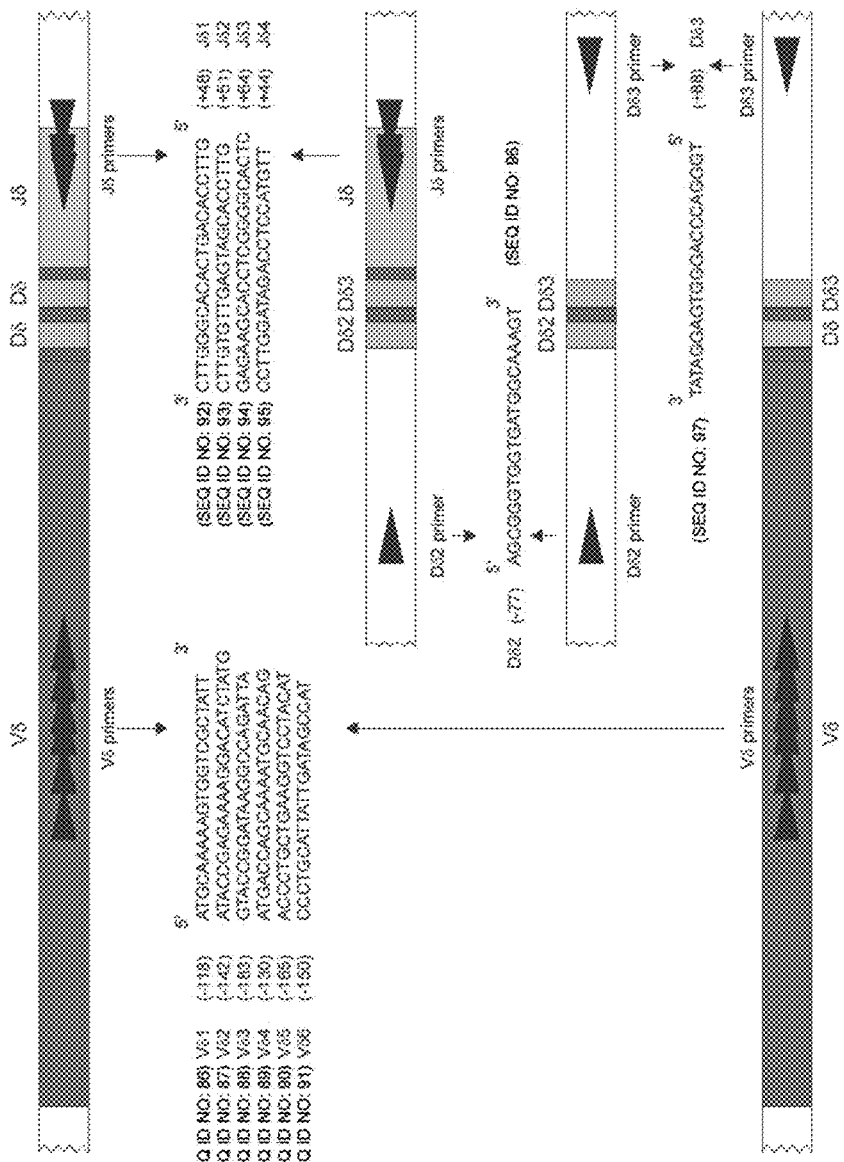
Figure 9C:
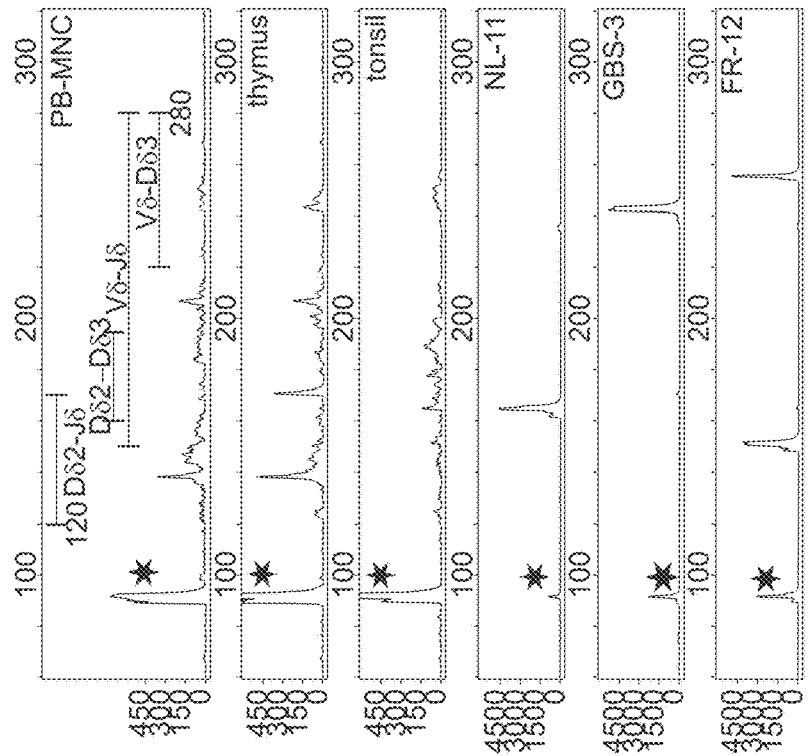
Figure 9C:
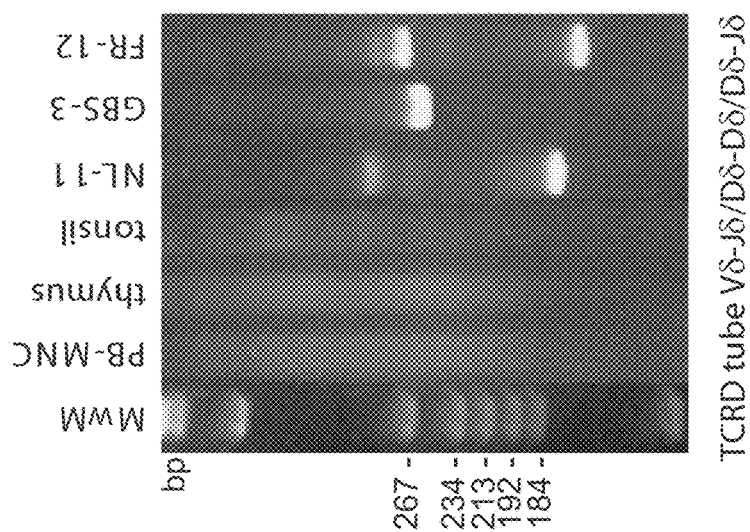

The TCRD gene segments, consisting of eight V, four Jδ and three Dδ gene segments, show little or no homology to each other and so segment-specific primers were designed which would not cross-anneal with other gene segments. Usage of Vδ7 and Vδ8 gene segments was considered too rare to justify inclusion of primers for these segments and so, following the general guidelines according to the invention for primer design, a total of 16 primers were designed: 6 Vδ, 4 Jδ and 5' and 3' of the 3 Dδ gene segments (FIG. 9B). All primers were designed for multiplex together in any combination, but originally it was planned to have one tube (A) with all V and all J primers which would amplify all the complete V(D)J rearrangements and a second tube (B) with Vδ2, Dδ2-5', Dδ3-3' and Jδ1 primers to amplify the major partial rearrangements (Vδ2-Dδ3, Dδ2-Dδ3 and Dδ2-Jδ1). Together these tubes should amplify 95% of known rearrangements. The other primers (Dδ1-5', Dδ3-5', Dδ1-3' and Dδ2-3) could be used to amplify other Dδ-Jδ, Vδ-Dδ or Dδ-Dδ rearrangements, but were always intended to be optional.

Results of Initial Testing Phase

All primer pair combinations were tested using polyclonal DNA (tonsil and MNC). Most gave products of the expected size, but some (Dδ1-5', Dδ1-3' and Dδ2-3) gave no visible product in combination with any other primer. Rearrangements involving these primer regions are likely to be extremely rare and so these, and Dδ3-5', were excluded from subsequent testing. Clonal cases for the six main rearrangements (Vδ1-Jδ1, Vδ2-Jδ1, Vδ3-Jδ1, Dδ2-Dδ3, Vδ2-Dδ3 and Dδ2-Jδ1) were tested initially in monoplex PCR and then in multiplex tubes A and B (see above). Serial dilutions of clonal DNA in polyclonal DNA (tonsil or MNC) showed detection sensitivities of at least 5% in all cases. However, in clonal cases with biallelic rearrangements, which were clearly detected in single PCR reactions, the second, usually larger, allele often failed to amplify on multiplexing. In addition, it was found, using a different set of clonal cases that several of the Vδ2-Jδ1 rearrangements failed to amplify. A polymorphic site was subsequently identified at the position of the original Vδ2 primer;[129] the frequency of this polymorphism in the general population unknown, and so this primer was redesigned to a new region of the Vδ2 gene segment, retested and found to amplify all cases. The problem with the failure to amplify the second allele was overcome by increasing the MgCl$_2$ concentration from 1.5 mM to 2.0 mM.

We also tested the possibility of combining the two tubes into a single multiplex reaction. Twelve clonal cases were tested, which had a total of 21 gene rearrangements between them. A single multiplex tube containing 12 primers (6 Vδ, 4 Jδ, Dδ2-5' and Dδ3-3) was used with ABI Gold buffer and 2.0 mM MgCl$_2$ to amplify all the cases. All gene rearrangements were indeed detected with a sensitivity of 0.5-10% by HD analysis when diluted in polyclonal MNC DNA (Table 7). The only problem with combining all TCRD primers in a single tube was the appearance of a nonspecific band at about 90 bp in all amplifications, which was not present when the two separate multiplex tubes were used. Since the band was outside the size range of the TCRD products and did not interfere with interpretation, it was not considered to be a problem.

Results of General Testing Phase

The testing of the 90 Southern blot-defined samples in ten laboratories raised some general issues about the TCRD protocol: Interpretation of some GS results was difficult. Because of the large size range of products for the TCRD locus, there is no classical Gaussian distribution for polyclonal samples (see FIG. 9C) and this, coupled with the low usage of TCRD in many samples meant that in some cases it was hard to determine whether a sample was polyclonal or clonal. The same problem did not arise with HD analysis and so the recommendation is that GS should only be used for TCRD with extreme care and awareness of the potential problems.

The 90 bp nonspecific band was quite intense in some laboratories, but less so in others. It appeared to be weaker when using Buffer II rather than Gold buffer (confirmed by subsequent testing) and is also sensitive to MgCl$_2$ concentration, becoming more intense as MgCl$_2$ concentration increases. This product has now been sequenced and found to be an unrelated gene utilizing the Dδ2 and Jδ3 primers.

The results of the general testing of the 90 Southern blot defined samples showed that the overall concordance of all the PCR groups doing the testing was very high (95%). Of the 90 cases, six were Southern blot positive for TCRD clonal rearrangements, five of which were found to be clonal by PCR. The remaining case (DE-10, a T-ALL with high tumor load) was found to be polyclonal by all labs. Of the 84 Southern blot negative cases, 75 were found to be polyclonal by PCR, four were found to be clonal and the remaining five cases showed discordance between the GS and HD results. Of the clonal cases, two (DE-2 and GBS-9) were T-rich B-NHLs with presumably low tumor load and so the results may reflect the increased sensitivity of PCR over Southern blotting. The other two clonal cases (GBS-15 and ES-7) had high tumor load. Of the five cases, which showed discrepancy between the GS and HD results, one (NL-1) was a difficult oligoclonal case, which caused problems for several other loci. The remaining four were found to be polyclonal by HD and clonal by GS. In three of the cases (NL-13, NL-15 and NL-18) this may reflect the greater sensitivity of GS over HD analysis, but the remaining case (PT-1, a reactive lymph node) may be attributed to "pseudoclonality" on GS analysis because of the limited repertoire of TCRD usage in some samples.

Conclusion

In conclusion, the recommended protocol for detection of TCRD gene rearrangements is a single tube assay containing 12 primers for detection of all major Vδ(D)Jδ, Vδ-Dδ, Dδ-Dδ and Dδ-Jδ rearrangements using Buffer II and 2.0 mM MgCl$_2$ to ensure maximum specificity and detection. The preferred analysis method is HD, but GS may be used with care if consideration is given to the problems of pseudoclonality caused by the limited usage of TCRD in some samples. However, the use of multi-color GeneScanning (see FIG. 13C) can be helpful in rapid recognition of the different types of complete and incomplete TCRD gene rearrangements in the different types of ALL. With these limitations in mind, TCRD can nevertheless be a valuable target for the more immature T-cell leukemias as well as TCRγδ+ T-cell proliferations.

Example 8. T(11;14) with BCL1-IGH Rearrangement

Background

The t(11;14)(q13;q32) is characteristic for mantle cell lymphoma (MCL) because this cytogenetic reciprocal translocation was observed in 60-70% of MCL cases and only sporadically in other B-cell NHL.[130] The breakpoint region was originally cloned by Tsujimoto et al (1983) and referred to as the BCL1-region.[131] However in only few cases with a cytogenetic t(11;14) a genomic breakpoint in the BCL1-region was identified. Using fiber and interphase FISH with probes covering the approximately 750 kb 11q13-BCL1 region, in almost all MCL (33 out of 34) a breakpoint was observed and all breakpoints were confined to a region of 360 kb 5' of the cyclin D1 gene.[132,133] In nearly half of MCL cases (41%) the breakpoints were clustered within an 85 bp region that was referred to as the major translocation cluster region, BCL1-MTC.[130,134,135] In most if not all cases of MCL the break at the IGH locus located at 14q32 involves the $J_H$ genes juxtaposing the IGH-Eµ enhancer to chromosome 11q13 sequences and consequently resulting in transcriptional activation of the cyclin D1 gene.[136] Cyclin D1 together with $CDK_4$ phosphorylates (and inactivates) pRB and allows for progression through the G1 phase of the cell cycle. Because cyclin D1 is silent in B-lymphocytes and B-cell NHL other than MCL, and the presence of this translocation correlates well with cyclin D1 expression, this gene is considered to be the biological relevant target in MCL. Both expression of cyclin D1 and/or the presence of t(11;14)(q13;q32) is used as an additional tool in the differential diagnosis of NHL.[2] The gold standard detection strategy for the presence of the t(11;14) that will identify almost all breakpoints is interphase FISH using breakpoint-flanking probes in fresh or frozen material[133] as well as in archival specimens.[137] However, a PCR based detection strategy for the t(11;14) might be useful for e.g. residual disease monitoring. Many groups have developed PCR based assays to detect the BCL1/$J_H$-breakpoints, in general using a consensus $J_H$-primer in combination with primers in the BCL1-MTC region that were all located in a region of 392 bp.[54,55] Breaks within the BCL1-MTC region can occur up to 2 kb downstream of the MTC region, but the majority of breakpoints are tightly clustered within an 85 bp segment, immediately downstream of the reported most 3'-primer ("primer B" in[54,134]). Because breaks in this BCL1-MTC-region account for only part of the breakpoints in the 11q13-BCL1 region in MCL cases (41%), the PCR based strategy for t(11;14) seriously impairs the diagnostic capability with an high rate of false-negative results as compared to FISH.

The t(11;14)(q13;q32) has also been reported to be observed in other B-cell proliferative diseases such as multiple myeloma (20%), SLVL (30%), B-PLL (33%) and B-CLL (8%).[130,138,139] One reason for the presence of the t(11;14) in B-CLL in some studies might be due to the incorrect classification of B-CLL.[130] In myeloma the breakpoints are quite different from those in MCL because (i) the frequency is much lower; (ii) most breaks involve switch-class recombination sites; and (iii) although all tested cases are located in the same 360 kb BCL1-region there seems to be no preferential clustering within the BCL1-MTC region. On the other hand, in all cases with a break the cyclin D1 gene is activated. Of note, in a subgroup of multiple myelomas with a IGH-switch-break myeov, an additional region in the 11q13-BCL1 region, is involved.[138]

Primer Design

Based on the location of the reported most-far 51-breakpoint and available nucleotide sequences from the BCL1-MTC region (GenBank accession number S77049), we designed a single BCL1 primer (5'-GGATAAAGGCGAG-GAGCATAA-3') (SEQ ID NO:98) in the 472-bp region 5' of this breakpoint by using the primer design program OL1GO6.2 relative to the consensus $J_H$ primer.

Results of Initial Testing Phase

Using the consensus JH-primer in combination with the single BCL1-MTC-primer on a small series of MCL (n=5) previously identified as positive with an in-house BCL1/JH-PCR using a similar consensus JH18-primer (18 nt) and 51-GCACTGTCTGGATGCACCGC-3' (SEQ ID NO:131) as BCL1-MTC-primer, we initially compared both assays in parallel. In contrast to the analysis of Ig/TCR gene rearrangements via GS and/or HD analysis, the BCL1-JH PCR products (as for BCL2-JH products) are identified via agarose gel electrophoresis using ethidium bromide staining only. The results on the five positive arid two negative samples were identical except that the PCR products were significantly weaker. To evaluate whether we could increase the sensitivity of the PCR, we determined the effect of different concentrations of $MgCl_2$ and primers, and different temperatures in a Stratagene-Robocycler PCR-machine (all other PCR were done on ABI-480 or ABI-9700). Most intriguing was the variation due to small changes in $MgCl_2$ concentration. At 2.0 mM a weak nonspecific product of 550 bp became apparent whereas at 2.5 mM and higher this nonspecific product was very prominent in all DNAs including non-template DNA controls. At lower concentrations (less than 1.5 mM) no nonspecific fragments were observed but the expected specific products were very weak. Hybridizations with a BCL1-MTC-internal oligo-probe (5'-ACCGAATATGCAGTGCAGC-3') (SEQ ID NO: 132) did not show hybridization to this 550 bp product. PCRs with each of the primers separately revealed that the 550 bp product could be generated by using the JH-consensus primer only. In some MCL cases, in addition to the PCR-products ranging from 150-350 bp (FIG. 10B), larger specific PCR-products might be apparent due to annealing of the consensus JH-primer to downstream JH5 and JH6 segments as described for BCL2/JH.[140] From the initial testing phase the most optimal PCR-conditions for the BCL1-MTC/JH-PCR were: annealing temperature of 60° C., 2.0 mM $MgCl_2$ and 10 pmol of each primer (for 35 PCR-cycles in the ABI 9700).

To evaluate the specificity of the PCR on a larger series of cases, the BCL1-MTC/JH-PCR was performed in three laboratories on DNA from in total 25 cases MCL that were all previously identified as positive with in-house BCL1/JH-PCR, and from 18 negative controls. None of the negative cases revealed a PCR-product whereas 22 of 25 positive cases showed products of the expected size. In the three cases that did not reveal a product on agarose-gel, a product was detected with GS suggesting that the sensitivity is lower when compared to in-house PCR.

The sensitivity of the PCR was evaluated by amplifying DNA dilutions of a MCL in normal tonsillar DNA. A sensitivity between $10^{-3}$ and $10^{-4}$ was observed on agarose gel using the developed PCR-primers. An in-house PCR performed in parallel on the same samples was at least 10× more sensitive. Hybridizations with the in-house BCL1-MTC-oligo-probe revealed a 10-100× higher sensitivity of both PCRs. Dilutions with DNA of an established cell line JVM2 (available through DSMZ; http://www.dsmz.de) with an BCL1-MTC/JH4-breakpoint[53] is used as our standard positive control. As a negative control normal tonsillar tissue or peripheral blood cells might be used, but almost any non-MCL B-cell NHL should be suitable because of the very low frequency of this aberration.[130]

Results of General Testing Phase

To evaluate inter-laboratory variations for the detection of breakpoints at the BCL1-MTC region, ten groups participated in the analysis of DNA from a series of 90 histologically defined malignant and reactive lymphoproliferations using the BCL1-MTC/JH-PCR protocol. All cases were defined for their status at the Ig and TCR loci using Southern hybridization techniques. Of the 90 cases, seven were histologically characterized as MCL. All seven MCL cases were shown to have a clonal IGH rearrangement by Southern hybridization. Assessment of rearrangements within the BCL1-MTC-region at chromosome 11q13 by either Southern hybridization or FISH was not performed in all cases. In six of the seven MCL cases the PCR-product was identified in all ten laboratories. In MCL case NL-15 in six of the laboratories the expected 1.8 kb PCR product was identified. This particular case carries an exceptional breakpoint with an uncommon large PCR-product (normally ranging from 150 to 350 bp) and represents the 3'-most-far detectable BCL1-MTC-breakpoint to our knowledge. In two of six labs the PCR product was observed but initially considered as nonspecific because of its uncommon size. In ES-4, characterized histologically as MCL in none of the ten labs a PCR-product could be detected suggesting that this case carries a breakpoint outside the BCL1-MTC. It should be stressed that the MCL cases submitted to this series for the general testing phase were selected and thus are expected to carry breaks at the BCL1-MTC region at an higher incidence than normal Importantly, except for one single case (FR-1), in all 83 other non-MCL cases including 16 cases that were histologically characterized as B-CLL, no BCL1-MTC/JH-PCR product was detected in any laboratory. In case FR-1 histologically characterized as B-CLL, in three of the ten labs a product was identified indicating that the number of cells with this break is low. The IGH status determined by Southern blot analysis revealed that this sample was composed of 90% clonal B-cells in good agreement with the histological examination. PCR-based B-cell clonality analyses for IGH and IGK (sensitivity of approximately 1%) revealed a single clone and Southern blot analysis for IGK showed a single major IGK rearrangement only. In addition, Northern blot analysis for expression of cyclin D1 did not show overexpression. All these data suggested that the very small number (less than 1%) t(11;14)-positive cells represent either (i) a subclone derived from the B-CLL, (ii) an independent second B-malignancy or (iii) normal B-cells as described for t(14;18)-positive B-cells in normal individuals.[140] However, with the available data of this patient at present we can not discriminate between these three alternatives. In summary, the analysis by the ten laboratories illustrates the high specificity of the BCL1-MTC/$J_H$-PCR strategy.

To evaluate the presence of possible false-negative cases due to the relative low sensitivity of the PCR, in one laboratory the previously described in-house PCR (with about 10-fold higher sensitivity) was performed on DNA of all 90 cases and the PCR products of both assays were also hybridized with an internal-BCL1-MTC oligo-probe that increases the sensitivity another 10-100-fold. This analysis revealed no PCR products in other cases.

Conclusion

We conclude that also the sensitivity of the BCL1-MTC/$J_H$ PCR (between $10^{-3}$ and $10^{-4}$) is sufficiently high for the detection of the BCL1-MTC/$J_H$-breakpoint in diagnostic material. The results of this approach are very encouraging and suggest that the definition of common approaches and reaction conditions can minimize erroneous results. However, it should be remembered that maximally about 50% of the t(11;14) breakpoints in MCL will be detected and that for diagnosis additional detection tools are recommended.

Example 9. t(14;18) with BCL2-IGH Rearrangement

Background

The t(14; 18) is one of the best characterized recurrent cytogenetic abnormalities in peripheral B cell lymphoproliferative disease.[141] It is detectable in up to 90% of follicular lymphomas and 20% of large cell B-cell lymphomas depending upon the diagnostic test used.[142] As a consequence of the translocation the BCL2 gene from 18q32 is placed under the control of the strong enhancers of the IGH locus resulting in deregulation of its normal pattern of expression.[143,144] BCL2 is located on the outer mitochondrial membrane and its normal function is to antagonize apoptosis and when deregulated it is intimately involved in the pathogenesis of the tumor.[145-148] As a consequence of this role in pathogenesis the t(14;18) provides an ideal target for both diagnosis and molecular monitoring of residual disease.

The IGH locus is located at 14q32.3 with the Vs regions lying telomeric and the $D_H$, $J_H$ and constant regions placed more centromeric. The transcriptional orientation is from telomere to centromere with enhancers located 5' of the V regions and between each of the constant regions. The most common form of the translocation involves the process of VDJ recombination and one of the six germline $J_H$ regions is closely opposed to BCL2. Most PCR based detection strategies have utilized a consensus $J_H$ primer that will detect the majority of translocations.[149,150] In contrast to the IGH locus, the pattern of breaks in BCL2 is more complicated. BCL2 is located on chromosome 18q21 and is orientated 5' to 3' from centromere to telomere. The majority of breakpoints fall within the 150 bp MBR located in the 3' untranslated region of exon 3.[151] As a consequence of the translocation, the Sµ enhancer located 3' of the $J_H$ regions is placed in close proximity to the BCL2 gene leading to its deregulation. As more translocations have been investigated it has become apparent that there are a number of other breakpoint regions which must be taken into account for an efficient PCR detection strategy. Positioned 4 kb downstream of the MBR is a further breakpoint region, the 3'MBR subcluster, encompassing a region of 8.8 kb.[152] The mcr is located 20 kb 3' of the MBR and covers a region of 500 bp.[153] However, though analogous to the MBR, the mcr is more extensive than was initially envisaged and a region 10 kb upstream of the mcr, the 5' mcr subcluster, has been described.[154,155] In addition to these classical breakpoints a number of variant translocations are described where the breaks occur 5' of BCL2.[156] These are, however, rare and thus can not be taken into account using a PCR based detection strategy.

There is no single gold standard detection strategy for the t(14;18) and a combination of cytogenetics and Southern blotting have been generally used.[157,158] Interphase FISH detection strategies offer an applicable alternative that have the potential to pick up more translocations.[159] In contrast DNA based fiber FISH has been very informative for defining variant translocations but is unsuitable for routine application.[100] For molecular diagnostic laboratories PCR based detection strategies offer rapid results, are generally applicable and can be used for residual disease monitoring. However, the primers commonly used have been derived on an ad hoc basis and have not been designed to take into account recent information on the molecular anatomy of the breakpoints. As a consequence when compared to gold standard approaches, PCR based techniques only detect up to 60% of translocations which seriously impairs the diagnostic capability of PCR. Compounding this high percentage of false negative results is the problem of false positive results arising from contamination from other samples and previously amplified PCR products.

Primer Design

We initially evaluated a two tube multiplex system, one tube designed to detect breakpoints within the MBR and a second tube used to identify breakpoints outside this region. The MBR strategy contained three primers MBR1, MBR2 and the consensus $J_H$ primer. The second multiplex reaction contained five primers, MCR1, MCR2, 5'mcr, 3' MBR1 and the consensus $J_H$ (FIG. 11A) and was designed to detect breakpoints within the mcr, 5'mcr and 3' MBR regions.

Results of Initial Testing Phase

The evaluation of these primers was performed in three laboratories on DNA derived from a total of 124 cases of follicular lymphoma known to carry a t(14;18). 109 cases (88%) were identified with an BCL2-IGH fusion, 83/124 (67%) were positive using the MBR multiplex and 26/124 (21%) were positive using the non-MBR multiplex strategy. In 15/124 (12%) cases there was no amplifiable PCR product. Further examination of the cases identified with the non-MBR multiplex showed that 11 (9%) had a breakpoint within the mcr, five cases (4%) within the 5'mcr and 10/124 (8%) within the 3'MBR.

To further investigate the value of this set of primers for the detection of breakpoints within the 5'mcr and 3'MBR sub-cluster regions a series of 32 cases of t(14;18) positive follicular lymphomas known to be germline at the MBR and mcr by Southern hybridization were analyzed in one laboratory. Five of the cases had breakpoints within the 5'mcr (260-490 bp) and were amplified using both the 5'mcr primer in isolation and with the multiplex reaction. None of the remainder of cases showed a positive result. Of the series of 32 cases, nine were already known to have breakpoints within the 3'MBR region and the multiplex approach was able to detect 5/9 of these cases.

In order to improve the sensitivity of the assay within this region we designed three further primers that spanned the 3'MBR sub-cluster region; 3'MBR2, 3'MBR3 and 3'MBR4 and combined them. with 3'MBR1 and the consensus JH in an additional multiplex reaction; 3'MBR multiplex (FIG. 11). This new approach confirmed that eight of the 32 cases were positive but missed the ninth case. The primers were then used individually and in this experiment 11 of the 32 cases were positive. The breakpoints were distributed as follows; 2/11 cases had a breakpoint present between primer 3'MBR1 and 3'MBR2, 3/11 cases between primers 3'MBR2 and 3'MBR3, 2/11 cases between primers 3'MBR3 and 3'MBR4 and the remaining four cases amplified using primer 3'MBR4 and were distributed 200-1000 bp 3' of this primer. In this series of cases there were three false negative results using the 3'MBR multiplex. One of the cases was a true false negative where the break occurred in the middle of the 3'MBR, in proximity to an Alu repeat sequence. The translocation was detected using the 3'MBR3 primer when used in isolation and a product of 450 bp was generated suggesting a reduced sensitivity of the multiplex. The remaining two false negative cases generated products larger than 1000 bp with the 3'MBR4 primer, placing them in the far 3'MBR not fully covered by this approach. Further improvement in the sensitivity of the 3'MBR assay has been achieved following the general testing phase of this study. Substituting primer 3'MBR3 with a new downstream primer 5'-GGTGACAGAGCAAAACATGAACA-3' (see FIG. 11A) significantly improved both the sensitivity and specificity of the 3'MBR assay.

Based on this, the 3'MBR multiplex was incorporated into our diagnostic strategy. Analysis of the Southern blot defined cases was therefore carried out using the three tube multiplex system presented in FIG. 11A.

Results of General Testing Phase

Figure 11A:
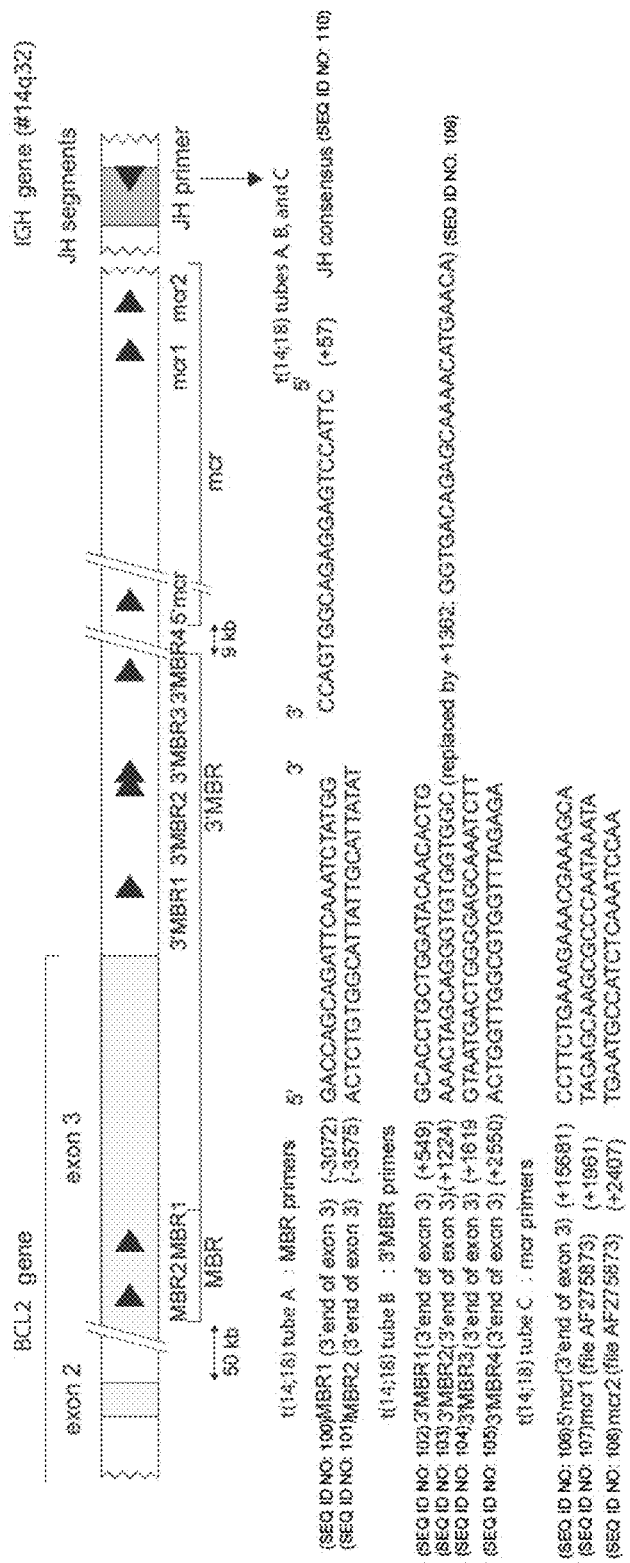
Figure 11B:
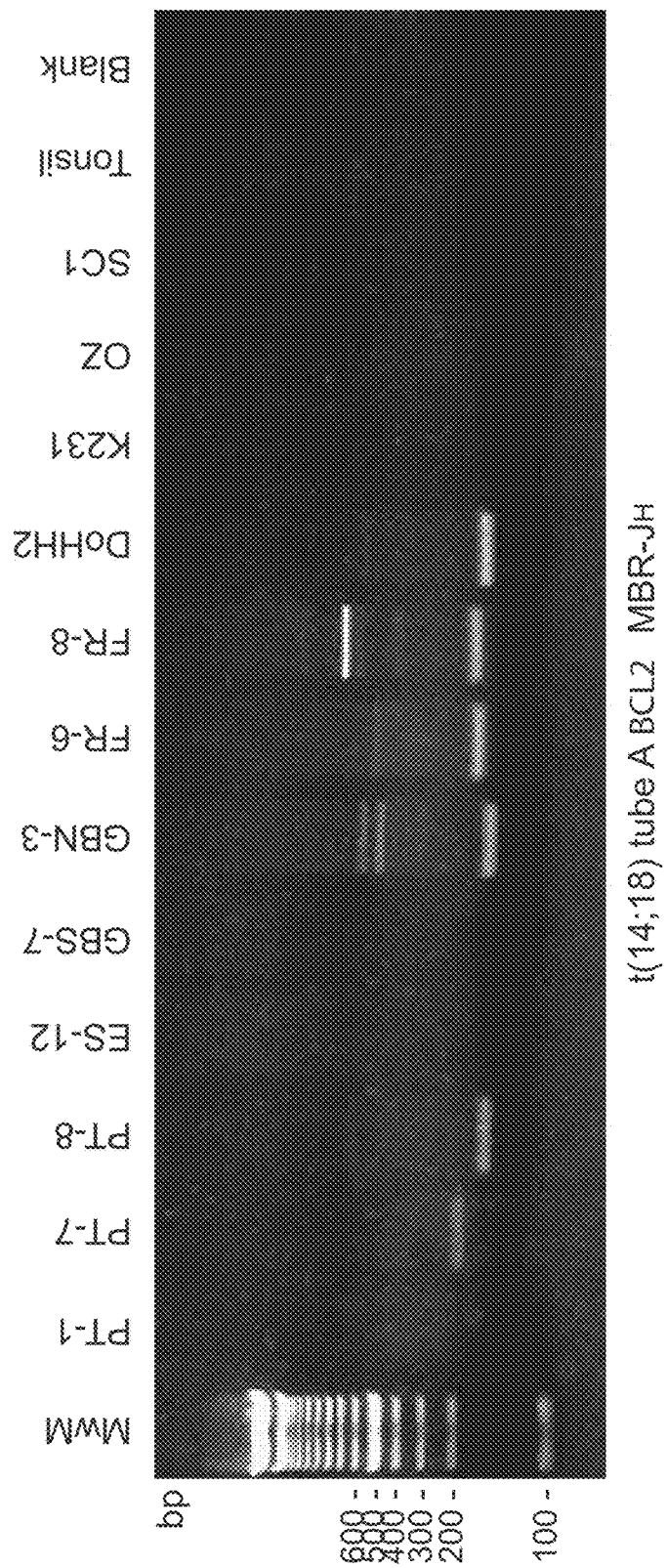
Figure 11C:
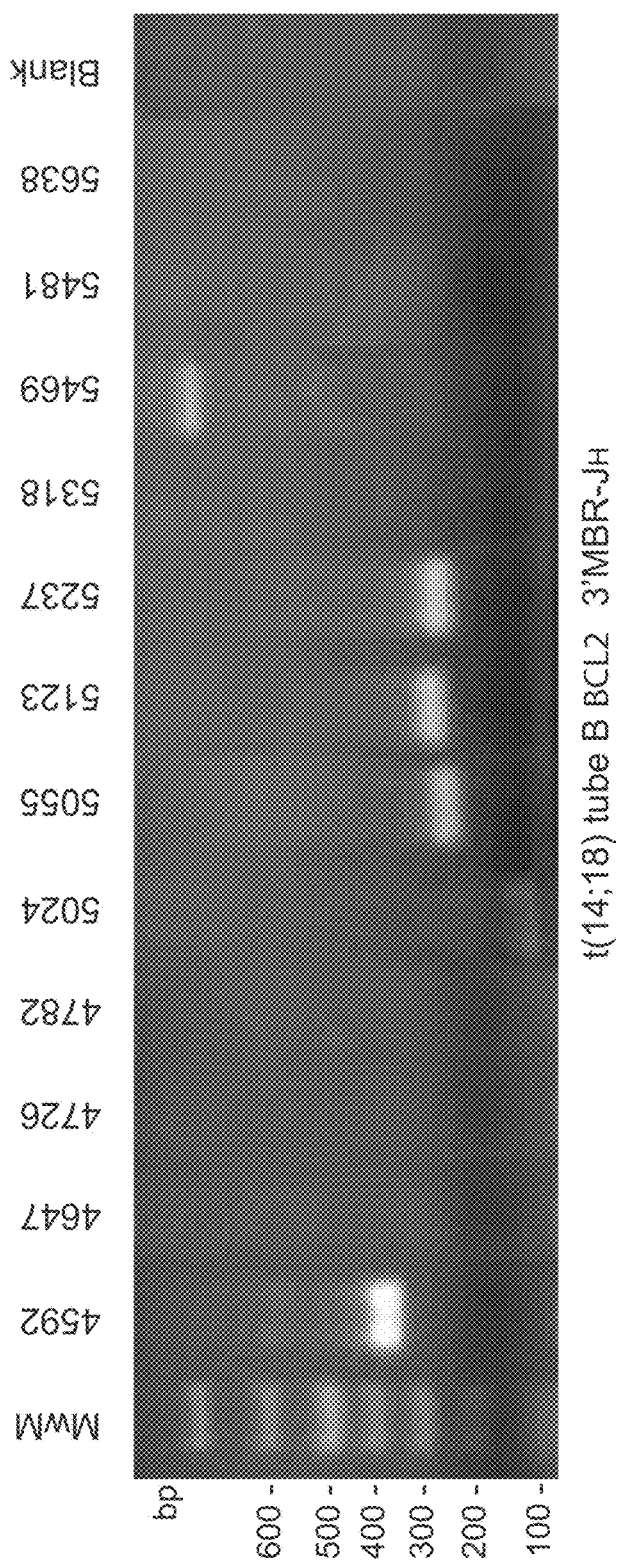
Figure 11D:
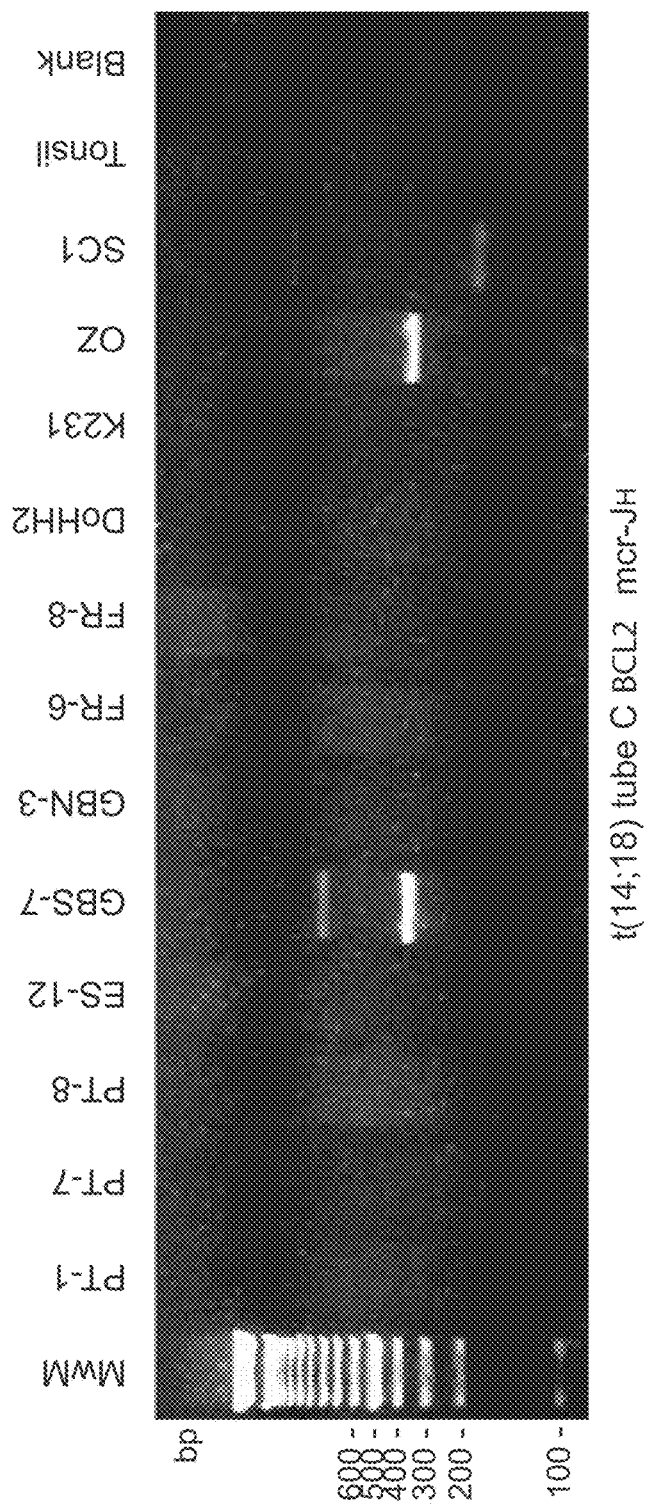

Inter-laboratory variations feature significantly in diagnostic PCR strategies. To evaluate this, 11 groups participated in an extensive external quality control exercise. DNA was extracted from a series of 90 histologically defined malignant and reactive lymphoproliferations were analyzed using the t(14;18) multiplex protocol (FIGS. 11B, C, and D). All cases were defined for their status at the Ig and TCR loci using Southern hybridization techniques. Karyotypic confirmation of the t(14;18) was not available on this series. We therefore adopted an approach requiring greater than 70% concordance between members of the network for acceptance of the t(14;18). Of the 90 cases, 11 were characterized histologically as follicular lymphoma. All 11 cases were shown to have a clonal IGH rearrangement by Southern hybridization. Assessment of rearrangements within the BCL2 gene was also performed by Southern hybridization using specific probes to the MBR, mcr and 3'MBR in 10/11 cases. 4/10 cases showed a rearrangement within the MBR that was concordant with the PCR result. A single case, GBS-7, shown to be mcr multiplex positive, gave an inconclusive SB result with the mcr probe. Immunophenotypically this case demonstrated two distinct clonal populations, representing approximately 5% and 15% of the original diagnostic material. The discrepancy between the two techniques in this case probably represents the reduced sensitivity of SB compared with PCR. There was no evidence of a 3'MBR rearrangement in any of the remaining cases by SB.

Of the six SB negative FCL cases, a single case; ES-7, showed a t(14;18) using the MBR multiplex. 5/11 FCL cases showed no evidence of a t(14; 18) by either SB or PCR. A t(14;18) was detected in two further cases by PCR; FR-6, a case of DLBCL showed an MBR breakpoint and was identified by all 11 laboratories, this finding is compatible with previous studies that have detected a t(14;18) in 20-40% of DLBCL cases.[161,162] Using the 3'MBR multiplex, 10/11 laboratories reported a positive result for sample ES-12, this was a case of Hodgkin's disease which contained very few B cells. It is difficult to explain this result in the absence of an IGH rearrangement by Southern blotting. Contamination or incorrect labeling of the sample at source is the most likely explanation.

Overall there was excellent concordance throughout the network, although small numbers of both false positive and false negative results were encountered. Overall 12 false positive results were identified, representing less than 0.4% (12/3036) of the total number of analyses. These were reported by five laboratories and involved six of the samples. The majority of the false positives (9/12) were found in three cases. Five false negative results, representing a 6% (5/88) failure rate, were reported by three laboratories, ES-7 was not detected by two laboratories, three further groups within the network commented that this case had shown weak amplification signals with the MBR multiplex. The remaining three false negative cases were reported in isolation by individual laboratories. The results of diagnoses using this approach are very encouraging and suggest that the definition of common approaches and reaction conditions can minimize erroneous results.

Conclusion

In conclusion, we have designed and evaluated a robust three-tube multiplex PCR in order to maximize the detection of the t(14;18). This strategy is capable of amplifying across the breakpoint region in the majority of cases of FCL with a cytogenetically defined translocation. Although the sensitivity of this strategy is lower than conventional single round or nested PCR approaches, it is still perfectly acceptable for diagnostic procedures. The widespread adoption of standardized reagents and methodologies has helped to minimize inaccurate results within this large multi-center network. However, it is noteworthy from the general testing phase of this study that it is impossible to detect a t(14;18) in all cases. This is certainly influenced by additional molecular mechanisms capable of deregulating the BCL2 gene.[153,164]

Example 10: Use of DNA Extracted from Paraffin-Embedded Tissue Biopsies and Development of Control Gene Primer Set Background Fresh/frozen tissue is considered to be the ideal sample type for extraction of DNA for use in PCR-based clonality analysis. However, fresh/frozen material is not always available to diagnostic laboratories and in many laboratories throughout Europe, paraffin-embedded tissue samples constitute the majority of diagnostic biopsies submitted for analysis. DNA extracted from paraffin-embedded material is often of poor quality and so PCR protocols need to be evaluated for use with these sample types before they can be widely used in diagnostic laboratories.

The integrity of DNA extracted from paraffin-embedded samples and its amplification by PCR are affected by a number of factors such as thickness of tissue, fixative type, fixative time, length of storage before analysis, DNA extraction procedures and the co-extraction of PCR inhibitors.[165-172] Ten percent neutral buffered formalin (10% NBF) is the most commonly used fixative, although laboratories also use a number of other fixatives, including unbuffered formalin and Bouins. The use of 10% NBF permits the amplification of DNA fragments of a wide range of sizes whereas Bouins appears to be the least amenable for use in PCR analysis.[167,168,171,173] The integrity of DNA fragments extracted from paraffin-embedded samples also depends on the length of time the blocks have been stored with the best results usually obtained from blocks less than 2 years old, while blocks over 15 years old tend to yield very degraded fragments.[174]

Primer Design

Initially, five pairs of control gene PCR primers were designed to amplify products of exactly 100, 200, 400, 600 and 1,000 bp in order to assess the quality of DNA submitted for analysis. The target genes were selected on the basis of having large exons with open reading frames to reduce the risk of selecting polymorphic regions and the primers were designed for multiplex usage in the standardized protocols. The following target genes were selected: human thromboxane synthase gene (TBXAS1, Exon 9; GenBank Accession No D34621), human recombination activating gene (RAG1, Exon 2; GenBank Accession No M29474), human promyelocytic leukemia zinc finger gene (PLZF, Exon 1; GenBank Accession No AF060568), and human AF4 gene (Exon 3; GenBank Accession No Z83679, and Exon 11; GenBank Accession No Z83687).

Results of Initial Testing Phase

The primer pairs were tested in separate reactions and subsequently in multiple reactions using high molecular weight DNA. Due to the large size range of the products (100 to 1,000 bp), it was necessary to vary the ratio of primer concentrations to obtain bands of equal intensities in the multiplex reactions. However, it proved extremely difficult to be able to amplify all the bands reproducibly and it was decided that the 1,000 bp product was probably unnecessary, since all the PCR protocols according to the invention give products of less than 600 bp. It was therefore decided to exclude the 1,000 bp product in order to improve the reproducibility of the assay. By increasing the MgCl$_2$ concentration to 2 mM and adding the primers in a 1:1:1:2 ratio, it was possible to reproducibly amplify four bands (100, 200, 400 and 600 bp) of equal intensity from high molecular weight DNA samples. However, for DNA extracted from paraffin blocks, it was thought that an extra size marker at 300 bp would be extremely informative and that the 600 bp marker might not be necessary. Using the gene sequence for the 1,000 bp marker (PLZF), primers were redesigned to generate a 300 bp product. These were tested successfully both in monoplex reactions and in multiplex reactions combining the 100, 200, 300, 400 and 600 bp primers (see FIG. 12A).

Thus two primer sets are available for assessing the quality of DNA for amplification: The 100, 200, 300 and 400 bp primers used at 2.5 pmol each can be used for assessing DNA from paraffin-embedded tissues. The addition of the 600 bp primers at 5 pmol allows this set to be used to check the quality of any DNA sample for use with the primers and protocols according to the invention. Both primer sets can be used with ABI Buffer II and 2.0 mM MgCl$_2$ under standardized amplification conditions. Products can be analyzed on 6% PAGE or 2% agarose (see FIG. 12B).

Results of General Testing Phase

Forty five paraffin-embedded biopsies were collected corresponding to 30 of the B-cell malignancies, eight of the T-cell malignancies and seven of the reactive lymphoproliferations submitted as fresh/frozen tissue samples. The age of the paraffin blocks as well as the methods of fixation and embedding of the samples varied between National Networks. The ES samples were submitted as pre-cut sections, NL-14, 15 and 16 were submitted as DNA samples and the remaining biopsies were submitted as paraffin blocks. Five sections (10 μm each) were cut from the paraffin blocks and DNA was extracted using the QIAamp DNA Mini Kit (QIAGEN) following the manufacturer's protocol for isolation of genomic DNA from paraffin-embedded tissue. This method of DNA extraction was chosen since the kit can be used to rapidly extract good quality DNA from blood, fresh/frozen tissue and paraffin-embedded tissue and thus enables the parallel processing of a variety of sample types with assured quality control. Numerous protocols for extraction of DNA from paraffin-embedded tissue for PCR analysis have been published.[171,172,175-177] Many of these aim to reduce DNA degradation and co-extraction of PCR inhibitors, but many of these methods require prolonged extraction procedures and can be unsuitable for use in the routine diagnostic laboratory.[166,170,179] DNA sample concentration and integrity were estimated by spectrophotometry and by comparison of sample DNA with known standards on agarose gel electrophoresis.

DNA samples (100 ng) were then analyzed for integrity and amplifiability using the control gene PCR primers (100-400 bp) and assessed for clonality at all target loci using the PCR protocols.

In the control gene PCR reaction of 24/45 cases the amplified products were at least 300 bp, whereas in the remaining 21 samples the amplified products were 200 bp or less. No clear correlation between the quality of the DNA and the age of the block or fixation method could be demonstrated. Therefore it is likely that a combination of factors is responsible for the DNA quality in these samples.

The DNA samples were evaluated for clonality using the 18 multiplex PCR reactions and were analyzed by both HD and GS. The number of paraffin samples showing clonality and translocations at the nine target loci were compared with the corresponding fresh/frozen sample data. In samples with control gene PCR products of up to 200 bp, the overall detection of clonality at the nine target loci was 9/55 (16%). Of the 46 missed rearrangements, 45 could be explained by the fact that the expected clonal PCR products had a molecular weight higher than the maximum size amplified by the sample in the control gene PCR. The remaining sample (PT-9) amplified to 100 bp in the control gene PCR but the expected 81 bp TCRG clonal product was not detected. In samples with control gene PCR products of at least 300 bp, the overall detection of clonality at the nine target loci was 42/55 (76%). Of the 13 missed rearrangements, five could again be explained by the fact that the expected clonal PCR products were larger than the maximum size amplified by the sample in the control gene PCR. The remaining eight missed rearrangements could not be explained directly by the quality of the DNA. One false positive clonal result (GBN-9; IGL) was detected in a reactive lymph node which may represent pseudoclonality.

PCR inhibitors are known to be present in DNA extracted from paraffin samples. Dilution of the DNA sample may reduce the concentration of these inhibitors to levels that allow successful amplification to occur. To investigate the effect of diluting DNA samples on the efficiency of amplification, four different concentrations of DNA were tested in the control gene PCR reaction: 5, 50, 100 and 500 ng. We observed that dilution of the DNA samples has a significant effect on the size of the PCR products in the control gene PCR. Overall, 24/45 cases (53%) showed an increased efficiency of amplification when diluted from 100 ng to 50 ng. The optimal DNA concentration appears to be between 50 to 100 ng whereas the use of 500 ng appears to inhibit the amplification of large products (300 bp or above). Although the use of 5 ng of DNA gives acceptable results with the control gene PCR, this can lead to false positivity in PCR-based clonality assays due to the low representation of total lymphoid cell DNA.[180,181] More importantly, 5 ng of DNA has no advantage over a dilution to 50 ng of DNA.

To assess Whether the use of 50 ng of DNA would also increase the detection of clonality, all the samples were retested at the IGH V-J locus using this DNA concentration. The number of clonal rearrangements detected in the three IGH V-J tubes using 100 ng of DNA was 12, compared with 23 using the corresponding fresh/frozen samples. The overall detection of clonality at this locus increased to 17 out of 23 when 50 ng of DNA was used, with an additional 9 FR1, 6 FR2 and 4 FR3 clonal products being detected. Thus dilution of the DNA can increase the detection of clonal products, presumably because of dilution of PCR inhibitors. Logically, dilution of DNA is only likely to improve both control gene PCR results and the detection of clonality, if PCR inhibitors are present, not if the DNA sample is highly degraded. Therefore it is recommended that at least two dilutions of DNA are tested using the control gene PCR and that the dilution that gives the better result is used in subsequent clonality analysis.

Nine clonal rearrangements remained undetected after initial analysis, which could not be explained by DNA quality (TCRG in PT-9 and NL-11; TCRB in GBS-4; TCRD in NL-15; IGK in GBN-4, NL-4 and NL-5; IGH V-J$_H$ in GBS-6 and GBS-8). These samples were retested using 50 ng of DNA, but only one sample (GBS8; IGH) showed improved detection, suggesting that other, unknown, factors can prevent amplification of specific targets in a small number of cases. However, it should be noted that for seven of these samples (NL-11, GBS-4, NL-15, GBN-4, NL-5, GBS-6 & GBS-8) clonal products were detected in at least one other locus. This demonstrates that testing for clonality at multiple target loci increases the likelihood of detecting clonal lymphocyte populations.

Conclusion

In conclusion, the protocols as provided herein work well with DNA extracted from paraffin-embedded material provided that the DNA can amplify products of 300 bp or more in the control gene PCR. Two concentrations of DNA are preferably tested in the control gene PCR and the more 'amplifiable' concentration should be used in further testing, although with the proviso that concentrations of DNA less than 20 ng may contribute to the detection of pseudoclonality due to the low representation of target lymphoid DNA.[180,181] Overall the data show that assessment of DNA quality using the control gene PCR provides a good indication of the suitability of the DNA for clonality analysis using the protocols provided. It is also important to note that the control gene PCR will give no indication of the amount of lymphoid cell DNA present in the sample and therefore good quality DNA may still produce negative results for clonality analysis. To ensure monoclonal results are reproducible (and to avoid potential pseudoclonality), all clonality assays, particularly using paraffin-extracted DNA, are preferably performed in duplicate and analyzed by HD and GS, wherever possible.

REFERENCES

1. Van Dongen J J M and Wolvers-Tettero I L M. Analysis of immunoglobulin and T cell receptor genes. Part II: Possibilities and limitations in the diagnosis and management of lymphoproliferative diseases and related disorders. *Clin Chim Acta* 1991; 198: 93-174.
2. Jaffe E S, Harris N L, Stein H, Vardiman J W, eds. *World Health Organization classification of tumours. Pathology and genetics of tumours of haematopoietic and lymphoid tissues.* 2001, IARC Press: Lyon.
3. Tonegawa S. Somatic generation of antibody diversity. *Nature* 1983; 802: 575-581.
4. Davis M M and Björkman P J. T-cell antigen receptor genes and T-cell recognition. *Nature* 1988; 334: 395-402.
5. Van Dongen J J M, Szczepanski T, Adriaansen H J, *Immunobiology of leukemia, in Leukemia*, E. S. Henderson, T A. Lister, and M. F. Greaves, Editors. 2002, WB Saunders Company: Philadelphia. p. 85-129.
6. Szczepanski T, Pongers-Willemse M J, Langerak A W, van Dongen J J M. Unusual immunoglobulin and T-cell receptor gene rearrangement patterns in acute lymphoblastic leukemias. *Curr Top Microbiol Immunol* 1999; 246: 205-215.
7. Küppers R, Klein U, Hansmann M L, Rajewsky K Cellular origin of human B-cell lymphomas. *N Engl J Med* 1999; 341: 1520-1529.
8. Smith B R, Weinberg Dδ, Robert N J, Towle M, Luther E, Pinkus G S, Ault K A. Circulating monoclonal B lymphocytes in non-Hodgkin's lymphoma. *N Engl J Med* 1984; 311: 1476-1481.

9. Letwin B W, Wallace P K, Muirhead K A, Hensler G L, Kashatus W H, Horan P K. An improved clonal excess assay using flow cytometry and B-cell gating. *Blood* 1990; 75: 1178-1185.
10. Fukushima P I, Nguyen P K, O'Grady P, Stetler-Stevenson M. Flow cytometric analysis of kappa and lambda light chain expression in evaluation of specimens for B-cell neoplasia. *Cytometry* 1996; 26: 243-252.
11. McCoy J P, Jr., Overton W R, Schroeder K, Blumatein L, Donaldson M H. Immunophenotypic analysis of the T cell receptor V beta repertoire in CD4+ and CD8+ lymphocytes from normal peripheral blood. *Cytometry* 1996; 26: 148-153.
12. Van Dongen J J M, van den Beemd M W M, Schellekens M, Wolvers-Tettero I L M, Langerak A W, Groeneveld K Analysis of malignant T cells with the Vβ antibody panel. *Immunologist* 1996; 4: 37-40.
13. Van den Beemd M W M, Boor P P C, Van Lochem E G, Hop W C J, Langerak A W, Wolvers-Tettero I L M, Hooijkaas H, Van Dongen J J M. Flow ctometric analysis of the Vβ repertoire in healthy controls. *Cytometry* 2000; 40: 336-345.
14. Lima M, Almeida J, Santos A H, dos Anjos Teixeira M, Alguero M C, Queiroes M L, Balanzategui A, Justica B, Gonzalez M, San Miguel J F, Orfao A. Immunophenotypic analysis of the TCR-Vbeta repertoire in 98 persistent expansions of CD3(+)/TCR-alphabeta(+) large granular lymphocytes: utility in assessing clonality and insights into the pathogenesis of the disease. *Am J Pathol* 2001; 159: 1861-1868.
15. Langerak A W, Wolvers-Tettero I L M, van den Beemd M W M, van Wering E R, Ludwig W-D, Hählen K, Necker A, van Dongen J J M. Immunophenotypic and immunogenotypic characteristics of TCRgd+ T cell acute lymphoblastic leukemia. *Leukemia* 1999; 13: 206-214.
16. Langerak A W, van Den Beemd R, Wolvers-Tettero I L M, Boor P P, van Lochem E G, Hooijkaas H, van Dongen J J M. Molecular and flow cytometric analysis of the Vbeta repertoire for clonality assessment in mature TCRalphabeta T-cell proliferations. *Blood* 2001; 98: 165-173.
17. Semenzato G, Zambello R, Starkebaum G, Oshimi K, Loughran T P, Jr. The lymphoproliferative disease of granular lymphocytes: updated criteria for diagnosis. *Blood* 1997; 89: 256-260.
18. Triebel F, Faure F, Graziani M, Jitsukawa S, Lefranc M P, Hercend T. A unique V-J-C-rearranged gene encodes a gamma protein expressed on the majority of CD3+ T cell receptor-alpha/beta-circulating lymphocytes. *J Exp Med* 1988; 167: 694-699.
19. Breit T M, Wolvers-Tettero I L, van Dongen J J. Unique selection determinant in polyclonal V delta 2-J delta 1 junctional regions of human peripheral gamma delta T lymphocytes. *J Immunol* 1994; 152: 2860-2864.
20. Breit T M, Wolvers-Tettero I L M, Hählen K, Van Wering E R, Van Dongen J J M. Limited combinatorial repertoire of gd T-cell receptors expressed by T-cell acute lymphoblastic leukemias. *Leukemia* 1991; 5: 116-124.
21. Van Dongen J J M and Wolvers-Tettero I L M. Analysis of immunoglobulin and T cell receptor genes. Part I: Basic and technical aspects. *Clin Chim Acta* 1991; 198: 1-91.
22. Beishuizen A, Verhoeven M A, Mol E J, Breit T M, Wolvers-Tettero I L M, van Dongen J J M. Detection of immunoglobulin heavy-chain gene rearrangements by Southern blot analysis: recommendations for optimal results. *Leukemia* 1993; 7: 2045-2053.
23. Breit T M, Wolvers-Tettero I L M, Beishuizen A, Verhoeven M-A J, van Wering E R, van Dongen J J M. Southern blot patterns, frequencies and junctional diversity of T-cell receptor d gene rearrangements in acute lymphoblastic leukemia. *Blood* 1993; 82: 3063-3074.
24. Beishuizen A, Verhoeven M A, Mol E J, van Dongen J J M. Detection of immunoglobulin kappa light-chain gene rearrangement patterns by Southern blot analysis. *Leukemia* 1994; 8: 2228-2236.
25. Tüimkaya T, Comans-Bitter W M, Verhoeven M A, van Dongen J J M. Southern blot detection of immunoglobulin lambda light chain gene rearrangements for clonality studies. *Leukemia* 1995; 9: 2127-2132.
26. Tümkaya T, Beishuizen A, Wolvers-Tettero I L M, van Dongen J J M. Identification of immunoglobulin lambda isotype gene rearrangements by Southern blot analysis. *Leukemia* 1996; 10: 1834-1839.
27. Moreau E J, Langerak A W, van Gastel-Mol E J, Wolvers-Tettero I L M, Zhan M, Zhou Q, Koop B F, van Dongen J J M. Easy detection of all T cell receptor gamma (TCRG) gene rearrangements by Southern blot analysis: recommendations for optimal results. *Leukemia* 1999; 13: 1620-1626.
28. Langerak A W, Wolvers-Tettero I L M, van Dongen J J M. Detection of T cell receptor beta (TCRB) gene rearrangement patterns in T cell malignancies by Southern blot analysis. *Leukemia* 1999; 13: 965-974.
29. Hara J, Benedict S H, Mak T W, Gelfand E W. T cell receptor alpha-chain gene rearrangements in B-precursor leukemia are in contrast to the findings in T cell acute lymphoblastic leukemia. Comparative study of T cell receptor gene rearrangement in childhood leukemia. *J Clin Invest* 1987; 80: 1770-1777.
30. Szczepanski T, Beishuizen A, Pongers-Willemse M J, Hählen K, van Wering E R, Wijkhuijs J M, Tibbe G J M, De Bruijn M A C, van Dongen J J M. Cross-lineage T-cell receptor gene rearrangements occur in more than ninety percent of childhood precursor-B-acute lymphoblastic leukemias: alternative PCR targets for detection of minimal residual disease. *Leukemia* 1999; 13: 196-205.
31. Szczepanski T, Langerak A W, van Dongen J J, van Krieken J H. Lymphoma with multi-gene rearrangement on the level of immunoglobulin heavy chain, light chain, and T-cell receptor beta chain. *Am J Hematol* 1998; 59: 99-100.
32. Przybylski G, Oettle H, Ludwig W D, Siegert W, Schmidt C A. Molecular characterization of illegitimate TCR delta gene rearrangements in acute myeloid leukaemia. *Br J Haematol* 1994; 87: 301-307.
33. Boeckx N, Willemse M J, Szczepanski T, van Der Velden V H J, Langerak A W, Vandekerckhove P, van Dongen J J M. Fusion gene transcripts and Ig/TCR gene rearrangements are complementary but infrequent targets for PCR-based detection of minimal residual disease in acute myeloid leukemia. *Leukemia* 2002; 16: 368-375.
34. Szczepanski T, Pongers-Willemse M J, Langerak A W, Harts W A, Wijkhuijs J M, van Wering E R, van Dongen J J M. Ig heavy chain gene rearrangements in T-cell acute lymphoblastic leukemia exhibit predominant DH6-19 and DH7-27 gene usage, can result in complete V-D-J rearrangements, and are rare in T-cell receptor ab lineage. *Blood* 1999; 98: 4079-4085.
35. Kluin-Nelemans H C, Kester M G, van deCorput L, Boor P P, Landegent J E, van Dongen J J, Willemze R, Falkenburg J H. Correction of abnormal T-cell receptor repertoire during interferon-alpha therapy in patients with hairy cell leukemia. *Blood* 1998; 91: 4224-4231.

36. Sarzotti M, Patel D D, Li X, Ozaki D A, Cao S, Langdon S, Parrott R E, Coyne K, Buckley R H. T cell repertoire development in humans with SCID after nonablative allogeneic marrow transplantation. *J Immunol* 2003; 170: 2711-2718.
37. Mariani S, Coscia M, Even J, Peola S, Foglietta M, Boccadoro M, Sbaiz L, Restagno G, Pileri A, Massaia M. Severe and long-lasting disruption of T-cell receptor diversity in human myeloma after high-dose chemotherapy and autologous peripheral blood progenitor cell infusion. *Br J Haematol* 2001; 118: 1051-1059.
38. Davis T H, Yockey C E, Balk S P. Detection of clonal immunoglobulin gene rearrangements by polymerase chain reaction amplification and single-strand conformational polymorphism analysis. *Am J Pathol* 1993; 142: 1841-1847.
39. Bourguin A, Tung R, Galili N, Sklar J. Rapid, nonradioactive detection of clonal T-cell receptor gene rearrangements in lymphoid neoplasms. *Proc Natl Acad Sci USA* 1990; 87: 8536-8540.
40. Bottaro M, Berti E, Biondi A, Migone N, Crosti L. Heteroduplex analysis of T-cell receptor gamma gene rearrangements for diagnosis and monitoring of cutaneous T-cell lymphomas. *Blood* 1994; 88: 3271-3278.
41. Langerak A W, Szczepanski T, van der Burg M, Wolvers-Tettero I L M, van Dongen J J M. Heteroduplex PCR analysis of rearranged T cell receptor genes for clonality assessment in suspect T cell proliferations. *Leukemia* 1997; 11: 2192-2199.
42. Kneba M, Bolz I, Linke B, Hiddemann W. Analysis of rearranged T-cell receptor beta-chain genes by polymerase chain reaction (PCR) DNA sequencing and automated high resolution PCR fragment analysis. *Blood* 1995; 86: 3930-3937.
43. Linke B, Bolz I, Fayyazi A, von Hofen M, Pott C, Bertram J, Hiddemann W, Kneba M. Automated high resolution PCR fragment analysis for identification of clonally rearranged immunoglobulin heavy chain genes. *Leukemia* 1997; 11: 1055-1062.
44. Szczepanski T, Flohr T, van der Velden V H, Bartram C R, van Dongen J J. Molecular monitoring of residual disease using antigen receptor genes in childhood acute lymphoblastic leukaemia. *Best Pract Res Clin Haematol* 2002; 15: 37-57.
45. Willemse M J, Seriu T, Hettinger K, d'Aniello E, Hop W C, Panzer-Grumayer E R, Biondi A, Schrappe M, Kamps W A, Masera G, Gadner H, Riehm H, Bartram C R, van Dongen J J. Detection of minimal residual disease identifies differences in treatment response between T-ALL and precursor B-ALL. *Blood* 2002; 99: 4386-4393.
46. Lefranc M P. IMGT, the international ImMunoGeneTics database. *Nucleic Acids Res* 2003; 81: 307-310.
47. Lefranc M P. IMGT databases, web resources and tools for immunoglobulin and T cell receptor sequence analysis, http://imet.cinee.fr. *Leukemia* 2003; 17: 260-266.
48. Ignatovich O, Tomlinson I M, Jones P T, Winter G. The creation of diversity in the human immunoglobulin V(lambda) repertoire. *J Mol Biol* 1997; 268: 69-77.
49. Tümkaya T, van der Burg M, Garcia Sanz R, Gonzalez Diaz M, Langerak A W, San Miguel J F, van Dongen J J M. Immunoglobulin lambda isotype gene rearrangements in B-cell malignancies. *Leukemia* 2001; 15: 121-127.
50. Arden B, Clark S P, Kabelitz D, Mak T W. Human T-cell receptor variable gene segment families. *Immunogenetics* 1995; 42: 455-500.
51. Rowen L, Koop B F, Hood L. The complete 685-kilobase DNA sequence of the human beta T cell receptor locus. *Science* 1996; 272: 1755-1762.
52. Quertermous T, Strauss W M, Van Dongen J J, Seidman J G. Human T cell gamma chain joining regions and T cell development. *J Immunol* 1987; 188: 2687-2690.
53. Rabbitte P, Douglas J, Fischer P, Nacheva E, Karpas A, Catovsky D, Melo J, Baer R, Stinson M, Rabbitts T. Chromosome abnormalities at 11q13 in B cell tumours. *Oncogene* 1988; 8: 99-103.
54. Williams M E, Swerdlow S H, Meeker T C. Chromosome t(11;14)(q13;q32) breakpoints in centrocytic lymphoma are highly localized at the bcl-1 major translocation cluster. *Leukemia* 1993; 7: 1437-1440.
55. Segal G H, Masih A S, Fox A C, Jorgensen T, Scott M, Braylan R C. CD5-expressing B-cell non-Hodgkin's lymphomas with bcl-1 gene rearrangement have a relatively homogeneous immunophenotype and are associated with an overall poor prognosis. *Blood* 1995; 85: 1570-1579.
56. Matsuda F, Ishii K, Bourvagnet P, Kuma K, Hayashida H, Miyata T, Honjo T. The complete nucleotide sequence of the human immunoglobulin heavy chain variable region locus. *J Exp Med* 1998; 188: 2151-2162.
57. Ghia P, ten Boekel E, Rolink A G, Melchers F. B-cell development: a comparison between mouse and man. *Immunol Today* 1998; 19: 480-485.
58. Corbett S J, Tomlinson I M, Sonnhammer E L L, Buck D, Winter G. Sequence of the human immunoglobulin diversity (D) segment locus: a systematic analysis provides no evidence for the use of DIR segments, inverted D segments, "minor" D segments or D-D recombination. *J Mol Biol* 1997; 270: 587-597.
59. Ichihara Y, Matsuoka H, Kurosawa Y. Organization of human immunoglobulin heavy chain diversity gene loci. *EMBO J* 1988; 7: 4141-4150.
60. Bertrand F E, III, Billips L G, Burrows P D, Gartland G L, Kubagawa H, Schroeder H W, Jr. Ig D(H) gene segment transcription and rearrangement before surface expression of the pan-B-cell marker CD19 in normal human bone marrow. *Blood* 1997; 90: 736-744.
61. Ghia P, ten Boekel E, Sanz E, de la Hera A, Rolink A, Melchere F. Ordering of human bone marrow B lymphocyte precursors by single-cell polymerase chain reaction analyses of the rearrangement status of the immunoglobulin H and L chain gene loci. *J Exp Med* 1996; 184: 2217-2229.
62. Szczepanski T, Willemse M J, van Wering E R, Weerden J F, Kamps W A, van Dongen J J M. Precursor-B-ALL with DH-JH gene rearrangements have an immature immunogenotype with a high frequency of oligoclonality and hyperdiploidy of chromosome 14. *Leukemia* 2001; 15: 1415-1423.
63. Davi F, Faili A, Gritti C, Blanc C, Laurent C, Sutton L, Schmitt C, Merle-Beral H. Early onset of immunoglobulin heavy chain gene rearrangements in normal human bone marrow CD34+ cells. *Blood* 1997; 90: 4014-4021.
64. Szczepanski T, van't Veer M B, Wolvers-Tettero I L M, Langerak A W, van Dongen J J M. Molecular features responsible for the absence of immunoglobulin heavy chain protein synthesis in an IgH(-) subgroup of multiple myeloma. *Blood* 2000; 96: 1087-1093.
65. Schroeder H W, Jr. and Wang J Y. Preferential utilization of conserved immunoglobulin heavy chain variable gene segments during human fetal life. *Proc Natl Acad Sci USA* 1990; 87: 6146-6150.
66. Raaphorst F M, Raman C S, Tami J, Fischbach M, Sanz I. Human Ig heavy chain CDR3 regions in adult bone 66. marrow pre-B cells display an adult phenotype of diversity: evidence for structural selection of DH amino acid sequences. *Int Immunol* 1997; 9: 1503-1515.
67. Lebecque S G and Gearhart P J. Boundaries of somatic mutation in rearranged immunoglobulin genes: 5' boundary is near the promoter, and 3' boundary is approximately 1 kb from V(D)J gene. *J Exp Med* 1990; 172: 1717-1727.
68. Fukita Y, Jacobs H, Rajewsky K. Somatic hypermutation in the heavy chain locus correlates with transcription. *Immunity* 1998; 9: 105-114.
69. Zachau H G. *The Immunologist* 1996; 4: 49-54.
70. Schäble K F and Zachau H G. The variable genes of the human immunoglobulin kappa locus. *Biol Chem Hoppe Seyler* 1993; 374: 1001-1022.
71. Weichhold G M, Ohnheiser R, Zachau H G. The human immunoglobulin kappa locus consists of two copies that are organized in opposite polarity. *Genomics* 1993; 16: 503-511.
72. Siminovitch K A, Bakhshi A, Goldman P, Korsmeyer S J. A uniform deleting element mediates the loss of kappa genes in human B cells. *Nature* 1985; 316: 260-262.
73. Szczepanski T, Langerak A W, Wolvers-Tettero I L M, Ossenkoppele G J, Verhoef G, Stul M, Petersen E J, de Bruijn MAC, van't Veer M B, van Dongen J J M. Immunoglobulin and T cell receptor gene rearrangement patterns in acute lymphoblastic leukemia are less mature in adults than in children: implications for selection of PCR targets for detection of minimal residual disease. *Leukemia* 1998; 12: 1081-1088.
74. Van der Velden V H J, Willemse M J, van der Schoot C E, van Wering E R, van Dongen J J M. Immunoglobulin kappa deleting element rearrangements in precursor-B acute lymphoblastic leukemia are stable targets for detection of minimal residual disease by real-time quantitative PCR *Leukemia* 2002; 16: 928-936.
75. van der Burg M, Tumkaya T, Boerma M, de Bruin-Versteeg S, Langerak A W, van Dongen J J M. Ordered recombination of immunoglobulin light chain genes occurs at the IGK locus but seems less strict at the IGL locus. *Blood* 2001; 97: 1001-1008.
76. Cannell P K, Amlot P, Attard M, Hoffbrand A V, Foroni L Variable kappa gene rearrangement in lymphoproliferative disorders: an analysis of V kappa gene usage, V J joining and somatic mutation. *Leukemia* 1994; 8: 1139-1145.
77. Frippiat J P, Williams S C, Tomlinson I M, Cook G P, CherifD, Le Paslier D, Collins J E, Dunham I, Winter G, Lefranc M P. Organization of the human immunoglobulin lambda light-chain locus on chromosome 22q11.2. *Hum Mol Genet* 1995; 4: 983-991.
78. Williams S C, Frippiat J P, Tomlinson I M, Ignatovich O, Lefranc M P, Winter G. Sequence and evolution of the human germline V lambda repertoire. *J Mol Biol* 1996; 264: 220-232.
79. Kawasaki K, Minoshima S, Nakato E, Shibuya K, Shintani A, Schmeits J L, Wang J, Shimizu N. One-megabase sequence analysis of the human immunoglobulin lambda gene locus. *Genome Res* 1997; 7: 250-261.
80. Hieter P A, Korsmeyer S J, Waldmann T A, Leder P. Human immunoglobulin kappa light-chain genes are deleted or rearranged in lambda-producing B cells. *Nature* 1981; 290: 368-372.
81. Vasicek T J and Leder P. Structure and expression of the human immunoglobulin lambda genes. *J Exp Med* 1990; 172: 609-620.
82. Taub R A, Hollis G F, Hieter P A, Korsmeyer S, Waldmann T A, Leder P. Variable amplification of immunoglobulin lambda light-chain genes in human populations. *Nature* 1983; 304: 172-174.
83. van der Burg M, Barendregt B H, van Gastel-Mol E J, Tumkaya T, Langerak A W, van Dongen J J. Unraveling of the polymorphic C lambda 2-C lambda 3 amplification and the Ke+Oz-polymorphism in the human Ig lambda locus. *J Immunol* 2002; 169: 271-276.
84. Bridges S L, Jr. Frequent N addition and clonal relatedness among immunoglobulin lambda light chains expressed in rheumatoid arthritis synovia and PBL, and the influence of V lambda gene segment utilization on CDR3 length. *Mol Med* 1998; 4: 525-553.
85. Kiyoi H, Naito K, Ohno R, Saito H, Naoe T. Characterization of the immunoglobulin light chain variable region gene expressed in multiple myeloma. *Leukemia* 1998; 12: 601-609.
86. Farner N L, Dorner T, Lipsky P E. Molecular mechanisms and selection influence the generation of the human V lambda J lambda repertoire. *J Immunol* 1999; 162: 2137-2145.
87. Ignatovich O, Tomlinson I M, Popov A V, Bruggemann M, Winter G. Dominance of intrinsic genetic factors in shaping the human immunoglobulin Vlambda repertoire. *J Mol Biol* 1999; 294: 457-465.
88. Wei S, Charmley P, Robinson M A, Concannon P. The extent of the human germline T-cell receptor V beta gene segment repertoire. *Immunogenetics* 1994; 40: 27-36.
89. Charmley P, Wei S, Concannon P. Polymorphisms in the TCRB-V2 gene segments localize the Tcrb orphon genes to human chromosome 9p21. *Immunogenetics* 1993; 38: 283-286.
90. Robinson M A, Mitchell M P, Wei S, Day C E, Zhao T M, Concannon P. Organization of human T-cell receptor beta-chain genes: clusters of V beta genes are present on chromosomes 7 and 9. *Proc Nat Acad Sci USA* 1993; 90: 2433-2437.
91. Toyonaga B, Yoshikai Y, Vadasz V, Chin B, Mak T W. Organization and sequences of the diversity, joining, and constant region genes of the human T-cell receptor beta chain. *Proc Natl Acad Sci* USA 1985; 82: 8624-8628.
92. Liu D, Callahan J P, Dau P C. Intrafamily fragment analysis of the T cell receptor beta chain CDR3 region. *J Immunol Methods* 1995; 187: 139-150.
93. Tsuda S, Rieke S, Hashimoto Y, Nakauchi H, Takahama Y. 11-7 supports D-J but not V-D J rearrangement of TCR-beta gene in fetal liver progenitor cells. *J Immunol* 1996; 156: 3233-3242.
94. Weidmann E, Whiteside T L, Giorda R, Herberman R B, Trucco M. The T-cell receptor V beta gene usage in tumor-infiltrating lymphocytes and blood of patients with hepatocellular carcinoma. *Cancer Res* 1992; 52: 5913-5920.
95. Jores R and Meo T. Few V gene segments dominate the T cell receptor beta-chain repertoire of the human thymus. *J Immunol* 1993; 151: 6110-6122.
96. Rosenberg W M, Moss P A, Bell J I. Variation in human T cell receptor V beta and J beta repertoire: analysis using anchor polymerase chain reaction. *Eur J Immunol* 1992; 22: 541-549.
97. Pongers-Willemse M J, Seriu T, Stolz F, d'Aniello E, Gameiro P, Pisa P, Gonzalez M, Bartram C R, Panzer-Grumayer E R, Biondi A, San Miguel J F, van Dongen J J M. Primers and protocols for standardized MRD detection in ALL using immunoglobulin and T cell receptor gene rearrangements and TAL1 deletions as PCR targets.

Report of the BIOMED-1 Concerted Action: Investigation of minimal residual disease in acute leukemia. *Leukemia* 1999; 18: 110-118.
98. Hansen-Hagge T E, Yokota S, Bartram C R. Detection of minimal residual disease in acute lymphoblastic leukemia by in vitro amplification of rearranged T-cell receptor delta chain sequences. *Blood* 1989; 74: 1762-1767.
99. Cave H, Guidal C, Rohrlich P, Delfau M H, Broyart A, Lescoeur B, Rahimy C, Fenneteau O, Monplaisir N, d'Auriol L, Elion J, Vilmer E, Grandchamp B. Prospective monitoring and quantitation of residual blasts in childhood acute lymphoblastic leukemia by polymerase chain reaction study of delta and gamma T-cell receptor genes. *Blood* 1994; 83: 1892-1902.
100. Goreki J, Yassai M, Zhu X, Kissela B, Kissella B, Keever C, Flomenberg N. Circulating T cell repertoire complexity in normal individuals and bone marrow recipients analyzed by CDR3 size spectratyping. Correlation with immune status. *J Immunol* 1994; 152: 5109-1519.
101. McCarthy K P, Sloane J P, Kabarowski J H, Matutes E, Wiedemann L M. The rapid detection of clonal T-cell proliferations in patients with lymphoid disorders. *Am J Pathol* 1991; 188: 821-828.
102. Assaf C, Hummel M, Dippel E, Goerdt S, Muller H H, Anagnostopoulos I, Orfanos C E, Stein H. High detection rate of T-cell receptor beta chain rearrangements in T-cell lymphoproliferations by family specific polymerase chain reaction in combination with the GeneScan technique and DNA sequencing. *Blood* 2000; 96: 640-646.
103. O'Shea U, Wyatt J I, Howdle P D. Analysis of T cell receptor beta chain CDR3 size using RNA extracted from formalin fixed paraffin wax embedded tissue. *J Clin Pathol* 1997; 50: 811-814.
104. Duby A D and Seidman J G. Abnormal recombination products result from aberrant DNA rearrangement of the human T-cell antigen receptor beta-chain gene. *Proc Natl Acad Sci USA* 1986; 83: 4890-4894.
105. Alatrakchi N, Farace F, Frau E, Carde P, Munck J N, Triebel F. T-cell clonal expansion in patients with B-cell lymphoproliferative disorders. *J Immunother* 1998; 21: 363-370.
106. Blom B, Verschuren M C, Heemakerk M H, Bakker A Q, van Gastel-Mol E J, Wolvers-Tettero I L, van Dongen J J M, Spits H. TCR gene rearrangements and expression of the pre-T cell receptor complex during human T-cell differentiation. *Blood* 1999; 98: 3033-3043.
107. Chen Z, Font M P, Loiseau P, Bories J C, Degos L, Lefranc M P, Sigaux F. The human T-cell V gamma gene locus: cloning of new segments and study of V gamma rearrangements in neoplastic T and B cells. *Blood* 1988; 72: 776-783.
108. Zhang X M, Tonnelle C, Lefranc M P, Huck S. T cell receptor gamma cDNA in human fetal liver and thymus: variable regions of gamma chains are restricted to V gamma I or V9, due to the absence of splicing of the V10 and V11 leader intron. *Eur J Immnunol* 1994; 24: 571-578.
109. Huck S and Lefranc M P. Rearrangements to the Jβ1, J P and Jβ2 segments in the human T-cell rearranging gamma gene (TRG gamma) locus. *FEBS Lett* 1987; 224: 291-296.
110. Delfau M H, Hance A J, Lecossier D, Vilmer E, Grandchamp B. Restricted diversity of V gamma 9-J P rearrangements in unstimulated human gamma/delta T lymphocytes. *Eur J Immunol* 1992; 22: 2437-2443.
111. Porcelli S, Brenner M B, Band H. Biology of the human gamma delta T-cell receptor. *Immunol Rev* 1991; 120: 137-183.
112. Van der Velden V H J, Wijkhuijs J M, Jacobs D C H, van Wering E R, van Dongen J J M. T cell receptor gamma gene rearrangements as targets for detection of minimal residual disease in acute lymphoblastic leukemia by real-time quantitative PCR analysis. *Leukemia* 2002; 16: 1372-1380.
113. Szczepanski T, Langerak A W, Willemse M J, Wolvers-Tettero I L M, van Wering E R, van Dongen J J M. T cell receptor gamma (TCRG) gene rearrangements in T cell acute lymphoblastic leukemia reflect "end-stage" recombinations: implications for minimal residual disease monitoring. *Leukemia* 2000; 14: 1208-1214.
114. Delabesse E, Burtin M L, Millien C, Madonik A, Arnulf B, Beldjord K, Valensi F, Macintyre E A. Rapid, multifluorescent TCRG Vgamma and Jgamma typing-application to T cell acute lymphoblastic leukemia and to the detection of minor clonal populations. *Leukemia* 2000; 14: 1143-1152.
115. Verschuren M C, Wolvers-Tettero I L, Breit T M, van Dongen J J. T-cell receptor V delta-J alpha rearrangements in human thymocytes: the role of V delta-J alpha rearrangements in T-cell receptor-delta gene deletion. *Immunology* 1998; 98: 208-212.
116. Nomenclature for T-cell receptor (TCR) gene segments of the immune system. WHO-IUIS Nomenclature Sub-Committee on TCR Designation. *Immunogenetics* 1995; 42: 451-453.
117. Kabelitz D, Wesch D, Hinz T. Gamma delta T cells, their T cell receptor usage and role in human diseases. *Springer Semin Immunopathol* 1999; 21: 55-75.
118. Shen J, Andrews D M, Pandolfi F, Boyle L A, Kersten C M, Blatman R N, Kurnick J T. Oligoclonality of Vdelta1 and Vdelta2 cells in human peripheral blood mononuclear cells: TCR selection is not altered by stimulation with gram-negative bacteria. *J Immunol* 1998; 160: 3048-3055.
119. Breit T M, Wolvers-Tettero I L M, Hihlen K, Van Wering E R, Van Dongen J J M. Extensive junctional diversity of gd T-cell receptors expressed by T-cell acute lymphoblastic leukemias: implications for the detection of minimal residual disease. *Leukemia* 1991; 5: 1076-1086.
120. Langlands K, Eden O B, Micallef-Eynaud P, Parker A C, Anthony R S. Direct sequence analysis of TCR V delta 2-D delta 3 rearrangements in common acute lymphoblastic leukaemia and application to detection of minimal residual disease. *Br J Haematol* 1993; 84: 648-655.
121. Schneider M, Panzer S, Stolz F, Fischer S, Gadner H, Panzer-Grumayer E R. Crosslineage TCR delta rearrangements occur shortly after the D J joinings of the IgH genes in childhood precursor B ALL and display age-specific characteristics. *Br J Haematol* 1997; 99: 115-121.
122. Hettinger K, Fischer S, Panzer S, Panzer-Grumayer E R. Multiplex PCR for TCR delta rearrangements: a rapid and specific approach for the detection and identification of immature and mature rearrangements in ALL. *Br J Haematol* 1998; 102: 1050-1054.
123. Theodorou I, Raphael M, Bigorgne C, Fourcade C, Lahet C, Cochet G, Lefranc M P, Gaulard P, Farcet J P. Recombination pattern of the TCR gamma locus in human peripheral T-cell lymphomas. *J Pathol* 1994; 174: 233-242.
124. Kanavaros P, Farcet J P, Gaulard P, Haioun C, Divine M, Le Couedic J P, Lefranc M P, Reyes F. Recombinative 125. Przybylski G K, Wu H, Macon W R, Finan J, Leonard D G, Felgar R E, DiGiuseppe J A, Nowell P C, Swerdlow S H, Kadin M E, Wasik M A, Salhany K E. Hepatosplenic and subcutaneous panniculitis-like gamma/delta T cell lymphomas are derived from different Vdelta subsets of gamma/delta T lymphocytes. *J Mol Diagn* 2000; 2: 11-19.

126. Kadin M E. Cutaneous gamma delta T-cell lymphomas—how and why should they be recognized? *Arch Dermatol* 2000; 136: 1052-1054.

127. Hodges E, Quin C, Farrell A M, Christmas S, Sewell H F, Doherty M, Powell R J, Smith J L. Arthropathy, leucopenia and recurrent infection associated with a TcR gamma delta population. *Br J Rheumatol* 1995; 34: 978-983.

128. Van Oostveen J W, Breit T M, de Wolf J T, Brandt R M, Smit J W, van Dongen J J M, Borst J, Melief C J. Polyclonal expansion of T-cell receptor-gd+T lymphocytes associated with neutropenia and thrombocytopenia. *Leukemia* 1992; 6: 410-418.

129. Triebel F, Faure F, Mami-Chouaib F, Jitsukawa S, Griscelli A, Genevee C, Roman-Roman S, Hercend T. A novel human V delta gene expressed predominantly in the Ti gamma A fraction of gamma/delta+peripheral lymphocytes. *Eur J Immunol* 1988; 18: 2021-2027.

130. De Boer C J, van Krieken J H, Schuuring E, Kluin P M. Bcl-1/cyclin D1 in malignant lymphoma. *Ann Oncol* 1997; 8: 109-117.

131. Tsujimoto Y, Yunis J, Onorato-Showe L, Erikson J, Nowell P C, Croce C M. Molecular cloning of the chromosomal breakpoint of B-cell lymphomas and leukemias with the t(11;14) chromosome translocation. *Science* 1984; 224: 1403-1406.

132. Vaandrager J W, Kleiverda J K, Schuuring E, Kluin-Nelemans J C, Raap A K, Kluin P M. Cytogenetics on released DNA fibers. *Verh Dtsch Ges Pathol* 1997; 81: 306-311.

133. Vaandrager J W, Schuuring E, Zwikstra E, de Boer C J, Kleiverda K K, van Krieken J H, Kluin-Nelemans H C, van Ommen G J, Raap A K, Kluin P M. Direct visualization of dispersed 11q13 chromosomal translocations in mantle cell lymphoma by multicolor DNA fiber fluorescence in situ hybridization. *Blood* 1996; 88: 1177-1182.

134. Pott C, Tiemann M, Linke B, Ott M M, von Hofen M, Bolz I, Hiddemann W, Parwaresch R, Kneba M. Structure of Bcl-1 and IgH-CDR3 rearrangements as clonal markers in mantle cell lymphomas. *Leukemia* 1998; 12: 1630-1637.

135. Luthra R, Hai S, Pugh W C. Polymerase chain reaction detection of the t(11;14) translocation involving the bcl-1 major translocation cluster in mantle cell lymphoma. *Diagn Mol Pathol* 1995; 4: 4-7.

136. de Boer C J, Schuuring E, Dreef E, Peters G, Bartek J, Kluin P M, van Krieken J H. Cyclin D1 protein analysis in the diagnosis of mantle cell lymphoma. *Blood* 1995; 86: 2715-2723.

137. Haralambieva E, Kleiverda K, Mason D Y, Schuuring E, Kluin P M. Detection of three common translocation breakpoints in non-Hodgkin's lymphomas by fluorescence in situ hybridization on routine paraffin-embedded tissue sections. *J Pathol* 2002; 198: 163-170.

138. Janssen J W, Vaandrager J W, Heuser T, Jauch A, Kluin P M, Geelen E, Bergsagel P L, Kuehl W M, Drexler H G, Otsuki T, Bartram C R, Schuuring E. Concurrent activation of a novel putative transforming gene, myeov, and cyclin D1 in a subset of multiple myeloma cell lines with t(11;14)(q13;q32). *Blood* 2000; 95: 2691-2698.

139. Troussard X, Mauvieux L, Radford-Weiss I, Rack K, Valensi F, Garand R, Vekemans M, Flandrin G, Macintyre E A. Genetic analysis of splenic lymphoma with villous lymphocytes: a Groupe Francais d'Hematologie Cellulaire (GFHC) study. *Br J Haematol* 1998; 101: 712-721.

140. Limpens J, Stad R, Vos C, de Vlaam C, de Jong D, van Ommen G J, Schuuring E, Kluin P M. Lymphoma-associated translocation t(14;18) in blood B cells of normal individuals. *Blood* 1995; 85: 2528-2536.

141. Fukuhara S, Rowley J D, Variakojis D, Golomb H M. Chromosome abnormalities in poorly differentiated lymphocytic lymphoma. *Cancer Res* 1979; 89: 3119-3128.

142. Weiss L M, Warnke R A, Sklar J, Cleary M L. Molecular analysis of the t(14;18) chromosomal translocation in malignant lymphomas. *N Engl J Med* 1987; 317: 1185-1189.

143. Bakhshi A, Jensen J P, Goldman P, Wright J J, McBride O W, Epstein A L, Korsmeyer S J. Cloning the chromosomal breakpoint of t(14; 18) human lymphomas: clustering around JH on chromosome 14 and near a transcriptional unit on 18. *Cell* 1985; 41: 899-906.

144. Cleary M L and Sklar J. Nucleotide sequence of a t(14;18) chromosomal breakpoint in follicular lymphoma and demonstration of a breakpoint-cluster region near a transcriptionally active locus on chromosome 18 *Proc Natl Acad Sci USA* 1985; 82: 7439-7443.

145. Korsmeyer S J. BCL-2 gene family and the regulation of programmed cell death. *Cancer Res* 1999; 59: 1693-1700.

146. Lithgow T, van Driel R, Bertram J F, Strasser A. The protein product of the oncogene bcl-2 is a component of the nuclear envelope, the endoplasmic reticulum, and the outer mitochondrial membrane. *Cell Growth Differ* 1994; 5: 411-417.

147. Woodland R T, Schmidt M R, Korsmeyer S J, Gravel K A. Regulation of B cell survival in xid mice by the proto-oncogene bcl-2. *J Immunol* 1996; 156: 2143-2154.

148. Hsu S Y, Lai R J, Finegold M, Hsueh A J. Targeted overexpression of Bcl-2 in ovaries of tranagenic mice leads to decreased follicle apoptosis, enhanced folliculogenesis, and increased germ cell tumorigenesis. *Endocrinology* 1996; 137: 4837-4843.

149. Lee M S, Chang K S, Cabanillas F, Freireich E J, Trujillo J M, Stass S A. Detection of minimal residual cells carrying the t(14;18) by DNA sequence amplification. *Science* 1987; 237: 175-178.

150. Crescenzi M, Seto M, Herzig G P, Weiss P D, Griffith R C, Korsmeyer S J. Thermostable DNA polymerase chain amplification of t(14;18) chromosome breakpoints and detection of minimal residual disease. *Proc Natl Acad Sci USA* 1988; 85: 4869-4873.

151. Lee M S. Molecular aspects of chromosomal translocation t(14;18). *Semin Hematol* 1993; 30: 297-305.

152. Buchonnet G, Lenain P, Ruminy P, Lepretre S, Stamatoullas A, Parmentier F, Jardin F, Duval C, Tilly H, Bastard C. Characterisation of BCL2-JH rearrangements in follicular lymphoma: PCR detection of 3' BCL2 breakpoints and evidence of a new cluster. *Leukemia* 2000; 14: 1563-1569.

153. Cleary M L, Galili N, Sklar J. Detection of a second t(14;18) breakpoint cluster region in human follicular lymphomas. *J Exp Med* 1986; 164: 315-320.

154. Akasaka T, Akasaka H, Yonetani N, Ohno H, Yamabe H, Fukuhara S, Okuma M. Refinement of the BCL2/immunoglobulin heavy chain fusion gene in t(14;18)(q32;

155. Willis T G, Jadayel D M, Coignet L J, Abdul-Rauf M, Treleaven J G, Catovsky D, Dyer M J. Rapid molecular cloning of rearrangements of the IGHJ locus using long-distance inverse polymerase chain reaction. *Blood* 1997; 90: 2456-2464.

156. Yabumoto K, Akasaka T, Muramatsu M, Kadowaki N, Hayashi T, Ohno H, Fukuhara S, Okuma M. Rearrangement of the 5' cluster region of the BCL2 gene in lymphoid neoplasm: a summary of nine cases. *Leukemia* 1996; 10: 970-977.

157. Pezzella F, Ralfkiaer E, Gatter K C, Mason D Y. The 14;18 translocation in European cases of follicular lymphoma: comparison of Southern blotting and the polymerase chain reaction. *Br JHaematol* 1990; 76: 58-64.

158. Turner G E, Ross F M, Krajewski A S. Detection of t(14;18) in British follicular lymphoma using cytogenetics, Southern blotting and the polymerase chain reaction. *Br J Haematol* 1995; 89: 223-225.

159. Vaandrager J W, Schuuring E, Raap T, Philippo K, Kleiverda K, Kluin P. Interphase FISH detection of BCL2 rearrangement in follicular lymphoma using breakpoint-flanking probes. *Genes Chromosomes Cancer* 2000; 27: 85-94.

160. Vaandrager J W, Schuuring E, Kluin-Nelemans H C, Dyer M J, Raap A K, Kluin P M. DNA fiber fluorescence in situ hybridization analysis of immunoglobulin class switching in B-cell neoplasia: aberrant CH gene rearrangements in follicle center-cell lymphoma. *Blood* 1998; 92: 2871-2878.

161. Jacobson J O, Wilkes B M, Kwaiatkowski D J, Medeiros L J, Aisenberg A C, Harris N L. bcl-2 rearrangements in de novo diffuse large cell lymphoma. Association with distinctive clinical features. *Cancer* 1993; 72: 231-236.

162. Hill M E, MacLennan K A, Cunningham D C, Vaughan Hudson B, Burke M, Clarke P, Di Stefano F, Anderson L, Vaughan Hudson G, Mason D, Selby P, Linch D C. Prognostic significance of BCL-2 expression and bcl-2 major breakpoint region rearrangement in diffuse large cell non-Hodgkin's lymphoma: a British National Lymphoma Investigation Study. *Blood* 1996; 88: 1046-1051.

163. Vaandrager J W, Schuuring E, Philippo K, Kluin P M. V(D)J recombinase-mediated transposition of the BCL2 gene to the IGH locus in follicular lymphoma. *Blood* 2000; 96: 1947-1952.

164. Fenton J A, Vaandrager J W, Aarts W M, Bende R J, Heering K, van Dijk M, Morgan G, van Noesel C J, Schuuring E, Kluin P M. Follicular lymphoma with a novel t(14;18) breakpoint involving the immunoglobulin heavy chain switch mu region indicates an origin from germinal center B cells. *Blood* 2002; 99: 716-718.

165. Alaibac M, Filotico R, Giannella C, Paradiso A, Labriola A, Marzullo F. The effect of fixation type on DNA extracted from paraffin-embedded tissue for PCR studies in dermatopathology. *Dermatology* 1997; 195: 105-107.

166. An S F and Fleming K A. Removal of inhibitor(s) of the polymerase chain reaction from formalin fixed, paraffin wax embedded tissues. *J Clin Pathol* 1991; 44: 924-927.

167. Camilleri-Broet S, Devez F, Tissier F, Ducruit V, Le Tourneau A, Diebold J, Audouin J, Molina T. Quality control and sensitivity of polymerase chain reaction techniques for the assessment of immunoglobulin heavy chain gene rearrangements from fixed- and paraffin-embedded samples. *Ann Diagn Pathol* 2000; 4: 71-76.

168. Greer C E, Peterson S L, Kiviat N B, Manos M M. PCR amplification from paraffin-embedded tissues. Effects of fixative and fixation time. *Am J Clin Pathol* 1991; 95: 117-124.

169. Legrand B, Mazancourt P, Durigon M, Khalifat V, Crainic K. DNA genotyping of unbuffered formalin fixed paraffin embedded tissues. *Forensic Sci Int* 2002; 125: 205-211.

170. Lo Y M, Mehal W Z, Fleming K A. In vitro amplification of hepatitis B virus sequences from liver tumour DNA and from paraffin wax embedded tissues using the polymerase chain reaction. *J Clin Pathol* 1989; 42: 840-846.

171. Longy M, Duboue B, Soubeyran P, Moynet D. Method for the purification of tissue DNA suitable for PCR after fixation with Bouin's fluid. Uses and limitations in microsatellite typing. *Diagn Mol Pathol* 1997; 6: 167-173.

172. Sato Y, Sugie R, Tauchiya B, Kameya T, Natori M, Mukai K. Comparison of the DNA extraction methods for polymerase chain reaction amplification from formalin-fixed and parafin-embedded tissues. *Diagn Mol Pathol* 2001; 10: 265-271.

173. Tbakhi A, Totos G, Pettay J D, Myles J, Tubbs R R. The effect of fixation on detection of B-cell clonality by polymerase chain reaction. *Mod Pathol* 1999; 12: 272-278.

174. Goelz S E, Hamilton S R, Vogelstein B. Purification of DNA from formaldehyde fixed and paraffin embedded human tissue. *Biochem Biophys Res Commun* 1985; 130: 118-126.

175. Chan P K Chan D P, To K F, Yu M Y, Cheung J L, Cheng A F. Evaluation of extraction methods from paraffin wax embedded tissues for PCR amplification of human and viral DNA. *J Clin Pathol* 2001; 54: 401-403.

176. Coombs N J, Gough A C, Primrose J N. Optimisation of DNA and RNA extraction from archival formalin-fixed tissue. *Nucleic Acids Res* 1999; 27: e12.

177. Wickham C L, Boyce M, Joyner M V, Sarsfield P, Wilkins B S, Jones D B, Ellard S. Amplification of PCR products in excess of 600 base pairs using DNA extracted from decalcified, paraffin wax embedded bone marrow trephine biopsies. *Mol Pathol* 2000; 58: 19-23.

178. Cawkwell L and Quirke P. Direct multiplex amplification of DNA from a formalin fixed, paraffin wax embedded tissue section. *Mol Pathol* 2000; 58: 51-52.

179. Diaz-Cano S J and Brady S P. DNA extraction from formalin-fixed, paraffin-embedded tissues: protein digestion as a limiting step for retrieval of high-quality DNA. *Diagn Mol Pathol* 1997; 6: 342-346.

180. Hoeve M A, Krol A D, Philippo K, Derksen P W, Veenendaal R A, Schuuring E, Kluin P M, van Krieken J H. Limitations of clonality analysis of B cell proliferations using CDR3 polymerase chain reaction. *Mol Pathol* 2000; 58: 194-200.

181. Zhou X G, Sandvej K, Gregersen N, Hamilton-Dutoit S J. Detection of clonal B cells in microdissected reactive lymphoproliferations: possible diagnostic pitfalls in PCR analysis of immunoglobulin heavy chain gene rearrangement. *Mol Pathol* 1999; 52: 104-110.

TABLE 1

B, T, and NK lineage of lymphoid malignancies[a]

| Lineage | ALL childhood | ALL adult | Chronic lymphocytic leukemias | Non-Hodgkin lymphomas nodal | Non-Hodgkin lymphomas extranodal | Non-Hodgkin lymphomas skin | Multiple myeloma |
|---|---|---|---|---|---|---|---|
| B  | 82-86% | 75-80% | 95-97% | 95-97% | 90-95% | 30-40% | 100% |
| T  | 14-18% | 20-25% | 3-5%   | 3-5%   | 5-10%  | 60-70% | 0%   |
| NK | <1%    | <1%    | 1-2%   | <2%    | <2%    | <2%    | 0%   |

[a]See Van Dongen et al. 1991[1], Jaffe et al. 2001[2], and Van Dongen et al. 2002[3]

TABLE 2

Estimated number of non-polymorphic human V, D, and J gene segments that can potentially be involved in Ig or TCR gene rearrangements[a]

| Gene segment | IGH | IGK | IGL | TCRA | TCRB | TCRG | TCRD |
|---|---|---|---|---|---|---|---|
| V segments | | | | | | | |
| functional (family) | 44 (7) | 43 (7) | 38 (10) | 46 (32) | 47 (23) | 6 (4) | 8 |
| rearrangeable (family) | 66 (7)[b] | 76 (7) | 56 (11) | 54 (32) | 67 (30) | 9 (4) | 8 |
| D segments | | | | | | | |
| rearrangeable (family) | 27 (7) | — | — | — | 2 | — | 3 |
| J segments | | | | | | | |
| functional | 6[c] | 5[d] | 4 | 53 | 13 | 5 | 4 |
| rearrangeable | 6[c] | 5[d] | 5[e] | 61 | 13 | 5 | 4 |

[a]Only non-polymorphic gene segments with a suitable RSS are included in this table.
[b]This estimation does not include the recently discovered (generally truncated) VH pseudogenes, which are clustered in three clans
[c]The six JH gene segments are highly homologous over a stretch of ~20 nucleotides, which is sufficient for the design of a consensus primer.
[d]The Jκ segments have a high homology, which allows the design of 2 to 3 Jκ consensus primers.
[e]Five of the seven Jλ gene segments have a suitable RSS.

TABLE 3

Standardized PCR protocol

Reaction conditions.
  buffer: ABI Buffer II or ABI Gold Buffer
  50 µl final volume
  100 ng DNA
  10 pmol of each primer (unlabeled or 6-FAM labeled)
  (irrespective of total numbers of primers in each multiplex PCR tube)
  dNTP: 200 µM final concentration
  MgCl$_2$ : 1.5 mM final concentration (to be optimized per target)
  Taq enzyme[a]: 1 U in most tubes; 2 U in tubes with many primers (>15)

Cycling conditions
  pre-activation 7 min. at 95° C.
  annealing temperature: 60° C.

| cycling times: | "classical" PCR equipment | "newer" PCR equipment |
|---|---|---|
| denaturation | 45 sec. | 30 sec. |
| annealing | ≥45 sec. | ≥30 sec. |
| extension | 1.30 min. | ≥30 sec. |
| final extension | ≥10 min. | ≥10 min. |
| number of cycles: 35 | | |
| hold 15° C. (or room temperature) | | |

[a]AmpliTaq Gold (Applied Biosystems, Foster City, CA) was used in combination with 1x ABI Buffer II or 1x ABI Gold Buffer (Applied Biosystems), depending on the target.

TABLE 4

Standardized protocol for heteroduplex analysis of PCR products

PCR product preparation
  tube with 10-20 µl of PCR product
  denaturation of PCR product: 5 min. at 95° C.
  re-annealing of PCR product: 60 min. at 4° C.
Electrophoresis conditions (non-commercial polyacrylamide gels)
  gel: 6% non-denaturing polyacrylamide (acrylamide:bisacrylamide 29:1)
  buffer: 0.5x TBE
  loading buffer: 5 µl ice-cold non-denaturing bromophenol blue loading buffer
  electrophoresis: typically 2-3 hours at 110 V or overnight at 40-50 V[a]
Electrophoresis conditions (commercial polyacrylamide gels)
  gel: non-denaturing polyacrylamide (e.g. BioRad PreCast Gel System or Amersham Pharmacia Biotech Gene Gel Excel Kit)
  buffer: 1x TBE
  loading buffer: ice-cold non-denaturing bromophenol blue loading buffer
  electrophoresis: 1.5 hours at 100 V
Visualization
  staining: 5-10 min, in 0.5 µg/ml EtBr in H$_2$O
  destaining/washing: 2x 5-10 min. in H$_2$O
  visualization: UV illumination
  alternative: silver staining using Amersham Pharmacia Biotech DNA Silver stain kit

[a]Voltage and electrophoresis time depend on PCR amplicon sizes, thickness of polyacrylamide gel, and type of PCR equipment, and should be adapted accordingly.

TABLE 5

Standardized protocol for GeneScanning of PCR products

A. Gel-based sequencers
PCR product preparation
1. PCR product dilution: initially 1:10 in formamide or H$_2$O (can be altered if fluorescent signal is outside optimal range; see electrophoresis conditions)
2. sample volume: 2 µl diluted PCR product
3. loading buffer volume: 0.5 µl blue dextran loading buffer + 0.5 µl TAMRA internal standard + 2 µl deionized formamide
4. denaturation of PCR product: 2 min. at 95° C. or higher temperature
5. cooling of PCR product at 4° C.
Electrophoresis conditions
6. gel: 5% denaturing polyacrylamide
7. buffer: 1x TBE
8. electrophoresis: 2-3.5 hours[a] (see Table 25)
9. optimal fluorescent signal intensity:
    600-4,000 fluorescent units (373 platforms)
    400-7,000 fluorescent units (377 platforms)
B. Capillary sequencers (to be optimized per sequencer)
PCR product preparation
1. 1 µl PCR product (volume of PCR product or sampling times can be altered if fluorescent signal is outside optimal range; see electrophoresis conditions)
2. sample volume: 1 µl PCR product + 9.5 µl (Hi-Di) formamide + 0.5 µl ROX-400 heteroduplex analysis internal standard
3. denaturation of PCR product: 2 min. at 95° C. or higher temperature
4. cooling of PCR product at 4° C. for an hour
Electrophoresis conditions
5. gel: 3100 POP4 polymer
6. buffer: 1x 3100 buffer with EDTA
7. electrophoresis: 45 minutes[b]
8. optimal fluorescent signal intensity:
    up to 10,000 fluorescent units

[a]Electrophoresis time depends on amplicon sizes and on employed platform.
[b]For 36 cm capillary; time taken depends on capillary used.

TABLE 6

Sensitivity of detection of clonal TCRB rearrangements

| TCRB tube | Involved primer pair V | J | Clonal Control | Size of PCR product | Sensitivity of detection single PCR[a] | multiplex PCR |
|---|---|---|---|---|---|---|
| tube A | Vβ2 | Jβ1.2 | patient | 261 nt | 1-5% | 5% |
| | Vβ2 | Jβ1.3 | patient | 267 nt | 5% | 5% |
| | Vβ2 | Jβ1.6 | patient | 267 nt | | <5% |
| | Vβ7 | Jβ2.2 | patient | 254 nt | | 10% |
| | Vβ8a | Jβ1.2 | Jurkat | 267 nt | 0.1% | 0.5-1% |
| | Vβ8a | Jβ2.7 | patient | 264 nt | | 10% |
| | Vβ10 | Jβ2.7 | PEER | 263 nt | | 20% |
| | Vβ3/12a/13a/15 | Jβ1.6 | patient | 278 nt | <5% | 5% |
| | Vβ3/12a/13a/15 | Jβ2.7 | patient | 286 nt | | 10% |
| | Vβ17 | Jβ2.7 | RPMI-8402 | 260 nt | | 10% |
| | Vβ17 | Jβ1.1 | patient | 260 nt | 1% | 10% |
| | Vβ18 | Jβ1.2 | DND41 | 261 nt | 1% | 10% |
| | Vβ22 | Jβ1.1 | patient | 265 nt | 0.1% | 10% |
| | Vβ8b/23 | Jβ1.2 | H9 | 257 nt | 0.1% | 0.5% |
| | Vβ24 | Jβ1.5 | RPMI-8402 | 264 nt | 0.5% | 10% |
| tube B | Vβ2 | Jβ2.1 | Molt-4 | 267 nt | 5% | 5% |
| | Vβ1/5 | Jβ2.1 | patient | 266 nt | 5% | 1-5% |
| | Vβ6a/11 | Jβ2.1 | patient | 265 nt | 1% | 5% |
| | Vβ6a/11 | Jβ2.5 | patient | 258 nt | | 5% |
| | Vβ7 | Jβ2.3 | PEER | 271 nt | | <5% |
| | Vβ8a | Jβ2.1 | patient | 293 nt | 0.1% | 1% |
| | Vβ3/12a/13a/15 | Jβ2.1 | patient | 258 nt | 5% | 10% |
| | Vβ3/12a/13a/15 | Jβ2.3 | patient | 258 nt | | <5% |
| | Vβ16 | Jβ2.1 | patient | 258 nt | 0.5% | 10% |
| tube C | Vβ17 | Jβ2.5 | CML-T1 | 270 nt | 0.1-1% | 1% |
| | Vβ21 | Jβ2.3 | patient | 282 nt | 0.5% | <10% |
| | Dβ1 | Jβ1.1 | patient | 304 nt | 0.10% | <5% |
| | Dβ1 | Jβ1.2 | patient | 306 nt | 5% | 5% |
| | Dβ1 | Jβ1.4 | patient | 310 nt | | 5-10% |
| | Dβ1 | Jβ1.6 | patient | 320 nt | | 20% |
| | Dβ1 | Jβ2.1 | patient | 309 nt | 5% | 20% |
| | Dβ1 | Jβ2.7 | patient | 307 nt | | <5% |
| | Dβ1 | Jβ2.5 | patient | 310 nt | | <1% |
| | Dβ2 | Jβ1.4 | patient | 182 nt | | <1% |
| | Dβ2 | Jβ2.1 | patient | 185 nt | 1% | <5% |
| | Dβ2 | Jβ2.5 | patient | 191 nt | | 5% |

[a]The dilution experiment for assessing the sensitivity of the single PCR was not performed in each case.

TABLE 7

Sensitivity of detection of clonal TCRD gene rearrangements

| TCRD rearrangement | Clonal control sample | (approximate size) | Sensitivity of detection by heteroduplex |
|---|---|---|---|
| Vδ1-Jδ1 | patient | (200 nt) | 5% |
| | patient | (190 nt) | 1-5% |
| | patient | (200 nt) | 5% |
| Vδ2-Jδ1 | patient | (200 nt) | 5% |
| | patient | (220 nt) | 5% |
| | patient | (210 nt) | 5% |
| Vδ2-Jδ3 | patient | (220 nt) | 5% |
| Vδ3-Jδ1 | patient | (270 nt) | 5% |
| Vδ6-Jδ2 | Loucy | (210 nt) | 0.5% |
| | patient | (210 nt) | 10% |
| Dδ2-Jδ1 | Loucy | (150 nt) | 0.2% |
| | patient | (160 nt) | 0.5% |
| | patient | (135 nt) | 0.5% |
| Dδ2-Jδ3 | patient | (150 nt) | 5% |
| Dδ2-Dδ3 | NALM-16 | (170 nt) | 1% |
| | patient | (200 nt) | 1% |
| | patient | (190 nt) | 0.5% |
| | patient | (170 nt) | 0.5% |
| Vδ2-Dδ3 | REH | (240 nt) | 5-10% |
| | NALM-16 | (230 nt) | 1-5% |
| | patient | (250 nt) | 5% |

TABLE 8

Concordance between multiplex PCR results and Southern blot (SB) analysis results (PCR/SB) on Ig/TCR gene rearrangements per (sub)category of included frozen samples

| Diagnosis | IGH[a] | IGK | IGL | TCRB | TCRG | TCRD |
|---|---|---|---|---|---|---|
| pre-follicular | C[b]: 8/8 | C: 8/8 | C: 4/4 | C: 2/4[b] | C: 0/0 | C: 0/0 |
| (n = 8) | P[b]: 0/0 | P: 0/0 | P: 4/4 | P: 4/4 | P: 8/8 | P: 8/8[e] |
| B-CLL (n = 16) | C: 15/16 | C: 16/16 | C: 5/5 | C: 1/1 | C: 0/0 | C: 2/2 |
|  | P: 0/0 | P: 0/0 | P: 9/11 | P: 15/15 | P: 16/16 | P: 14/14 |
| (post-)follicular | C: 22/25[b] | C: 19/24[c] | C: 3/5 | C: 2/4 | C: 0/1 | C: 0/0 |
| (n = 25) | P: 0/0 | P: 0/1 | P: 19/20 | P: 21/21[d,e] | P: 22/24 | P: 24/25[e] |
| All B-cell | C: 45/49 | C: 43/48 | C: 12/14 | C: 4/8 | C: 0/1 | C: 2/2 |
| malignancies | P: 0/0 | P: 0/1 | P: 32/35 | P: 41/41 | P: 46/48 | P: 46/47 |
| (n = 49) |  |  |  |  |  |  |
| T-cell | C: 2/2 | C: 0/0 | C: 0/0 | C: 17/17[c] | C: 15/16[b] | C: 2/3 |
| malignancies | P: 15/16[e] | P: 17/18 | P: 17/18 | P: 1/1 | P: 1/2 | P: 14/15[e] |
| (n = 18) |  |  |  |  |  |  |
| Reactive samples | C: 0/0 | C: 0/0 | C: 0/0 | C: 0/0 | C: 0/0 | C: 0/0 |
| (n = 15) | P: 15/15 | P: 15/15 | P: 15/15 | P: 14/15 | P: 15/15 | P: 15/15 |
| Miscellaneous | C: 3/3 | C: 2/2 | C: 0/0 | C: 3/3 | C: 1/1 | C: 1/1 |
| (n = 8) | P: 3/5 | P: 4/6 | P: 6/8 | P: 5/5[d,d] | P: 6/7 | P: 5/7 |
| All samples | C: 50/54 | C: 45/50 | C: 12/14 | C: 25/29 | C: 16/18 | C: 5/6 |
| (n = 90) | P: 33/36 | P: 36/40 | P: 70/76 | P: 60/61 | P: 68/72 | P: 80/84 |

[a]Includes both VH-JH and DH-JH PCR analysis
[b]C, clonal rearrangements; P, polyclonal rearrangements
[c]In one sample clonality in GeneScanning only
[d]In one sample clonality in heteroduplex analysis only
[e]In one sample polyclonality in GeneScanning only
[f]In one sample polyclonality in heteroduplex analysis only

TABLE 9

Complementarity of different Ig multiplex PCR targets for clonality detection in Southern blot-defined B-cell malignancies

| Multiplex PCR tubes | Pre-germinal center B (n = 8) | B-CLL (n = 16) | (post-)germinal center B (n = 25) | all B-cell malignancies (n = 49) |
|---|---|---|---|---|
| IGH VH-JH FR1 | 8/8[b] (100%) | 14/16[c] (88%) | 15/25[b] (60%) | 37/49 (76%) |
| IGH VH-JH FR2 | 8/8 (100%) | 15/16 (94%) | 14/25[b] (56%) | 37/49 (76%) |
| IGH VH-JH FR3 | 8/8 (100%) | 14/16 (88%) | 11/25[c] (44%) | 33/49 (67%) |
| IGH VH-JH 3FR | 8/8 (100%) | 15/16 (94%) | 17/25 (68%) | 40/49 (82%) |
| IGH $D_H$-$J_H$ | 0/8 (0%) | 11/16 (69%) | 11/25 (44%) | 22/49 (45%) |
| IGH VH-JH + IGH DH-JH | 8/8 (100%) | 15/16 (94%) | 22/25 (88%) | 45/49 (92%) |
| IGK | 8/8 (100%) | 16/16 (100%) | 21/25[d] (84%) | 45/49 (92%) |
| IGL | 4/8 (50%) | 7/16[e] (44%) | 4/25[f] (16%) | 15/49 (31%) |
| IGH VH-JH + IGK | 8/8 (100%) | 16/16 (100%) | 21/25 (84%) | 45/49 (92%) |
| IGH VH-JH + IGL | 8/8 (100%) | 15/16 (94%) | 17/25 (68%) | 40/49 (82%) |
| IGH VH-JH + IGH DH-JH + IGK | 8/8 (100%) | 16/16 (100%) | 24/25 (96%) | 48/49 (98%) |
| IGH VH-JH + IGH DH-JH + IGK + IGL | 8/8 (100%) | 16/16 (100%) | 24/25 (96%) | 48/49 (98%) |

[a]All samples have clonal gene rearrangements in at least the IGH locus as determined by Southern blot analysis
[b]Two cases showed clonal products in GeneScanning, but polyclonal products in heteroduplex analysis
[c]One case showed clonal products in GeneScanning, but polyclonal products in heteroduplex analysis
[d]Including case 25-NL-4 with weak clonal IGH but polyclonal IGK gene rearrangements in Southern blot analysis
[e]Including cases 11-NL-19 and 12-ES-1 with clonal IGH + IGK but polyclonal IGL gene rearrangements in Southern blot analysis

TABLE 10

Conditions and control samples for multiplex PCR analysis of Ig/TCR gene rearrangements and translocations t(11; 14) and t(14; 18)

| Multiplex PCR | Tubes | Buffer | TaqGold (U) | MgCl$_2$ (mM) | Positive controls (examples) polyclonal | Positive controls (examples) monoclonal[a] |
|---|---|---|---|---|---|---|
| IGH VH-JH | A/B/C | Gold/II | 1 | 1.5 | tonsil | A: NALM-6; SU-DHL-5; SU-DHL-6 B: NALM-6; SU-DHL-5; SU-DHL-6 C: NALM-6; SU-DHL-5; SU-DHL-6 |
| IGH DH-JH | D/E | Gold | 1 | 1.5 | tonsil | D: KCA; ROS15 E: HSB-2, HPB-ALL |
| IGK | A/B | Gold/II | 1 | 1.5 | tonsil | A: KCA; ROS15 B: ROS15, 380 |
| IGL | A | Gold/II | 1 | 2.5 | tonsil | A: CLL-1; EB-4B; KCA |
| TCRB | A/B/C | II | 2 (A, B)[b] 1 (C) | 3.0 (A, B) 1.5 (C) | PB-MNC[c] | A: RPMI-8402; Jurkat; PEER; DND-41 B: PEER; CML-T1, MOLT-3 C: Jurkat |
| TCRG | A/B | II | 1 | 1.5 | PB-MNC[c] | A: MOLT-3; RPMI-8402; Jurkat; PEER B: Jurkat; PEER |
| TCRD | A | II | 1 | 2.0 | PB-MNC[c] | A: PEER, REH |
| BCL1-IGH | A | II | 1 | 2.0 | NA[c] | A: JVM 2 |
| BCL2-IGH | A/B/C | II | 1 | 1.5 | NA[c] | A: DoHH2; SU-DHL-6 B: K231[d] |

[a]Most clonal cell line controls can be obtained via the Deutsche Sammlung von Mikroorganismen und Zellkulturen GmbH; contact person: dr. H. G. Drexler (address: Department of Human and Animal Cell Cultures, Mascheroder Weg 1B, 38124 Braunschweig, Germany).[192,193]
[b]In most multiplex tubes only 1 U TaqGold is needed, but 2 U TaqGold are needed in TCRB tubes A and B because they contain >15 different primers.
[c]Abbreviations: PB-MNC, mononuclear cells from peripheral blood; NA, not applicable.
[d]The t(14; 18) positive cell lines K231, OZ, and SC1 were kindly provided by prof. Martin Dyer, University of Leicester, Leicester, GB.

TABLE 11

Size ranges, non-specific bands, and detection method in multiplex PCR analysis of Ig/TCR gene rearrangements and chromosome aberrations t(11; 14) and t(14; 18)

| Multiplex PCR | Size range (bp) | Nonspecific bands (bp) | Preferred method of analysis | GeneScan running time: gel/capillary |
|---|---|---|---|---|
| IGH VH-JH | Tube A: 310-360 Tube B: 250-295 Tube C: 100-170 | Tube A: ~85 Tube B: — Tube C: — | GeneScanning and heteroduplex analysis equally suitable | 3-3.5 h/45 min |
| IGH DH-JH | Tube D: 110-290 (D$_H$1/2/4/5/6-J$_H$) + 390-420 (D$_H$3-J$_H$) Tube E: 100-130 | Tube D: 350[a] Tube E: 211[b] | heteroduplex analysis slightly preferred over GeneScanning (variation of product sizes hampers GeneScanning) | 3-3.5 h/45 min |
| IGK | Tube A: 120-160 (Vκ1f/6/Vκ7-Jκ) + 190-210 (Vκ3f-Jκ) + 260-300 (Vκ2f/Vκ4/Vκ5-Jκ) | Tube A: — Tube B: ~404 | heteroduplex analysis slightly preferred over GeneScanning (small junction | 3-3.5 h/45 min |

TABLE 11-continued

Size ranges, non-specific bands, and detection method in multiplex PCR analysis of Ig/TCR gene rearrangements and chromosome aberrations t(11; 14) and t(14; 18)

| Multiplex PCR | Size range (bp) | Nonspecific bands (bp) | Preferred metbhod of analysis | GeneScan running time: gel/capillary |
|---|---|---|---|---|
| | Tube B: 210-250 Vκ1f/6/Vκ7-Kde + 270-300 (Vκ3f/intron-Kde) + 350-390 (Vκ2f/Vκ4/Vκ5-Kde) | | size + variation of product sizes hampers GeneScanning | |
| IGL | Tube A: 140-165 | Tube A: — | heteroduplex analysis clearly preferred over GeneScanning (small junction size hampers GeneScanning) | 2 h/45 min |
| TCRB | Tube A: 240-285 Tube B: 240-285 Tube C: 170-210 (Dβ2) + 285-325 (Dβ1) | Tube A: (273)[c] Tube B: <150, 221[d] Tube C: 128, 337[d] | heteroduplex analysis slightly preferred over GeneScanning (limited repertoire, particularly in case of ψVγ10 and ψVγ11 usage) | 2 h/45 min |
| TCRG | Tube A: 145-255 Tube B: 80-220 | Tube A: — Tube B: — | GeneScanning and heteroduplex analysis equally suitable | 2 h/45 min |
| TCRD | Tube A: 120-280 | Tube A: ~90 | heteroduplex analysis clearly preferred over GeneScanmng (low amount of template + variation of product sizes hampers GeneScanning) | 2 h/45 min |
| BCL1-IGH | Tube A: 150-2000 | Tube A: ~550 (weak) | agarose | NA[e] |
| BCL2-IGH | Tube A: variable Tube B: variable Tube C: variable | Tube A: — Tube B: — Tube C: — | agarose | NA[e] |

[a]The nonspecific 350 bp band is the result of cross-annealing of the $D_H2$ primer to a sequence in the region upstream of $J_H4$. In GeneScanning this nonspecific band does not comigrate with D-J products (see FIG. 5B).
[b]The 211 bp PCR product represents the smallest background band derived from the germline $D_H7$-$J_H1$ region. When the PCR amplification is very efficient, also longer PCR products might be obtained because of primer annealing to downstream $J_H$ gene rearrangements; e.g. 419 bp ($D_H7$-$J_H2$), 1031 bp ($D_H7$-$J_H3$), etc.
[c]The 273 bp band (mainly visible by GeneScanning) is particularly seen in samples with low numbers of contaminating lymphoid cells.
[d]Intensity of non-specific band depends on primer quality.
[e]NA, not applicable

The invention claimed is:

1. A method for detecting a Vβ-Jβ TCRB rearrangement, comprising amplifying a TCRB locus in a sample, said amplification comprising using a set of 23 forward primers, each forward primer of said set comprising a different one of SEQ ID NOs: 42-64 or variant thereof differing by 1 to 3 nucleotides in size and/or sequence, and a set of 13 reverse primers, each reverse primer of said set comprising a different one of SEQ ID NOs: 65-77 or variant thereof differing by 1 to 3 nucleotides in size and/or sequence.

2. The method of claim 1, wherein each forward primer of said set consists of a different one of SEQ ID NOs: 42-64 or variant thereof differing by 1 to 3 nucleotides in size and/or sequence, and wherein each reverse primer of said set consists of a different one of SEQ ID NOs: 65-77 or variant thereof differing by 1 to 3 nucleotides in size and/or sequence.

3. The method of claim 1, wherein each forward primer of said set comprises a different one of SEQ ID NOs: 42-64, and wherein each reverse primer of said set comprises a different one of SEQ ID NOs: 65-77.

4. The method of claim 1, wherein each forward primer of said set consists of a different one of SEQ ID NOs: 42-64, and wherein each reverse primer of said set consists of a different one of SEQ ID NOs: 65-77.

5. The method of claim 1, wherein each forward primer of said set comprises a different one of SEQ ID NOs: 42-64 or variant thereof differing by 1 to 3 nucleotides in sequence, and a set of 13 reverse primers, each reverse primer of said set comprising a different one of SEQ ID NOs: 65-77 or variant thereof differing by 1 to 3 nucleotides in sequence.

6. A method for detecting a Vβ-Jβ TCRB rearrangement, comprising amplifying a TCRB locus in a sample, wherein said method comprises a multiplex PCR assay performed in at least two PCR reactions,
wherein a first PCR reaction comprises a set of 23 forward primers, each forward primer of said set comprising a different one of SEQ ID NOs: 42-64 or variant thereof differing by 1 to 3 nucleotides in size and/or sequence, and a set of 9 reverse primers, each reverse primer of said set comprising a different one of SEQ ID NOs: 65-73 or variant thereof differing by 1 to 3 nucleotides in size and/or sequence, and
wherein a second PCR reaction comprises a set of 23 forward primers, each forward primer of said set comprising a different one of SEQ ID NOs: 42-64 or variant thereof differing by 1 to 3 nucleotides in size and/or sequence, and a set of 4 reverse primers, each reverse primer of said set comprising a different one of SEQ ID NOs: 74-77 or variant thereof differing by 1 to 3 nucleotides in size and/or sequence.

7. The method of claim 6, further comprising a third PCR reaction for detecting a Dβ-Jβ TCRB rearrangement, the third PCR reaction comprising a set of 2 forward primers, each forward primer of said set comprising a different one of SEQ ID NOs: 78 and 79 or variant thereof differing by 1 to 3 nucleotides in size and/or sequence, and a set of 13 reverse primers, each reverse primer of said set comprising a different one of SEQ ID NOs: 65-77 or variant thereof differing by 1 to 3 nucleotides in size and/or sequence.

8. The method of claim 7, wherein the third PCR reaction comprises a set of 2 forward primers, each forward primer of said set comprising a different one of SEQ ID NOs: 78 and 79 or variant thereof differing by 1 to 3 nucleotides in sequence, and a set of 13 reverse primers, each reverse primer of said set comprising a different one of SEQ ID NOs: 65-77 or variant thereof differing by 1 to 3 nucleotides sequence.

9. The method of claim 6,
wherein said first PCR reaction comprises a set of 23 forward primers, each forward primer of said set consisting of a different one of SEQ ID NOs: 42-64 or variant thereof differing by 1 to 3 nucleotides in size and/or sequence, and a set of 9 reverse primers, each reverse primer of said set consisting of a different one of SEQ ID NOs: 65-73 or variant thereof differing by 1 to 3 nucleotides in size and/or sequence, and
wherein said second PCR reaction comprises a set of 23 forward primers, each forward primer of said set consisting of a different one of SEQ ID NOs: 42-64 or variant thereof differing by 1 to 3 nucleotides in size and/or sequence, and a set of 4 reverse primers, each reverse primer of said set consisting of a different one of SEQ ID NOs: 74-77 or variant thereof differing by 1 to 3 nucleotides in size and/or sequence.

10. The method of claim 9, further comprising a third PCR reaction for detecting a Dβ-Jβ TCRB rearrangement, the third PCR reaction comprising a set of 2 forward primers, each forward primer of said set consisting of a different one of SEQ ID NOs: 78 and 79 or variant thereof differing by 1 to 3 nucleotides in size and/or sequence, and a set of 13 reverse primers, each reverse primer of said set consisting of a different one of SEQ ID NOs: 65-77 or variant thereof differing by 1 to 3 nucleotides in size and/or sequence.

11. The method of claim 6,
wherein said first PCR reaction comprises a set of 23 forward primers, each forward primer of said set comprising a different one of SEQ ID NOs: 42-64, and a set of 9 reverse primers, each reverse primer of said set comprising a different one of SEQ ID NOs: 65-73, and
wherein said second PCR reaction comprises a set of 23 forward primers, each forward primer of said set comprising a different one of SEQ ID NOs: 42-64, and a set of 4 reverse primers, each reverse primer of said set comprising a different one of SEQ ID NOs: 74-77.

12. The method of claim 11, further comprising a third PCR reaction for detecting a Dβ-Jβ TCRB rearrangement, the third PCR reaction comprising a set of 2 forward primers, each forward primer of said set comprising a different one of SEQ ID NOs: 78 and 79, and a set of 13 reverse primers, each reverse primer of said set comprising a different one of SEQ ID NOs: 65-77.

13. The method of claim 6,
wherein said first PCR reaction comprises a set of 23 forward primers, each forward primer of said set consisting of a different one of SEQ ID NOs: 42-64, and a set of 9 reverse primers, each reverse primer of said set consisting of a different one of SEQ ID NOs: 65-73, and
wherein said second PCR reaction comprises a set of 23 forward primers, each forward primer of said set consisting of a different one of SEQ ID NOs: 42-64, and a set of 4 reverse primers, each reverse primer of said set consisting of a different one of SEQ ID NOs: 74-77.

14. The method of claim 13, further comprising a third PCR reaction for detecting a Dβ-Jβ TCRB rearrangement, the third PCR reaction comprising a set of 2 forward primers, each forward primer of said set consisting of a different one of SEQ ID NOs: 78 and 79, and a set of 13 reverse primers, each reverse primer of said set consisting of a different one of SEQ ID NOs: 65-77.

15. The method of claim 6, wherein the first PCR reaction comprises a set of 23 forward primers, each forward primer of said set comprising a different one of SEQ ID NOs: 42-64 or variant thereof differing by 1 to 3 nucleotides in sequence, and a set of 9 reverse primers, each reverse primer of said set comprising a different one of SEQ ID NOs: 65-73 or variant thereof differing by 1 to 3 nucleotides in sequence, and
wherein the second PCR reaction comprises a set of 23 forward primers, each forward primer of said set comprising a different one of SEQ ID NOs: 42-64 or variant thereof differing by 1 to 3 nucleotides in sequence, and a set of 4 reverse primers, each reverse primer of said set comprising a different one of SEQ ID NOs: 74-77 or variant thereof differing by 1 to 3 nucleotides sequence.

16. A method for the detection of minimal residual disease (MRD) or for identification of PCR targets to be used for MRD detection comprising:
obtaining a sample from a subject, and
utilizing a set of 25 forward primers, each forward primer of said set comprising a different one of SEQ ID NOs: 42-64, 78 and 79 or variant thereof differing by 1 to 3 nucleotides in size and/or sequence, and a set of 13 reverse primers, each reverse primer of said set comprising a different one of SEQ ID NOs: 65-77 or variant thereof differing by 1 to 3 nucleotides in size and/or sequence, to amplify a nucleic acid in said sample.

17. The method of claim 16, wherein each forward primer of said consists of a different one of SEQ ID NOs: 42-64, 78 and 79 or variant thereof differing by 1 to 3 nucleotides in size and/or sequence, and wherein each reverse primer of said set consists of a different one of SEQ ID NOs: 65-77 or variant thereof differing by 1 to 3 nucleotides in size and/or sequence.

18. The method of claim 16, wherein each forward primer of said set comprises a different one of SEQ ID NOs: 42-64, 78 and 79, and wherein each reverse primer of said set comprises a different one of SEQ ID NOs: 65-77 to amplify a nucleic acid in said sample.

19. The method of claim 16, wherein each forward primer of said set consists of a different one of SEQ ID NOs: 42-64, 78 and 79, wherein each reverse primer of said set consists of a different one of SEQ ID NOs: 65-77 to amplify a nucleic acid in said sample.

20. A method for the detection of minimal residual disease (MRD) or for identification of PCR targets to be used for MRD detection comprising:
obtaining a sample from a subject, and
amplifying a nucleic acid in said sample, wherein said amplifying comprises a multiplex PCR assay performed in at least three PCR reactions wherein a first PCR reaction comprises a set of 23 forward primers, each forward primer of said set comprising a different one of SEQ ID NOs: 42-64 or variant thereof differing by 1 to 3 nucleotides in size and/or sequence, and a set of 9 reverse primers, each reverse primer of said set comprising a different one of SEQ ID NOs: 65-73 or variant thereof differing by 1 to 3 nucleotides in size and/or sequence, wherein a second PCR reaction comprises a set of 23 forward primers, each forward primer of said set comprising a different one of SEQ ID NOs: 42-64 or variant thereof differing by 1 to 3 nucleotides in size and/or sequence, and a set of 4 reverse primers, each reverse primer of said set comprising a different one of SEQ ID NOs: 74-77 or variant thereof differing by 1 to 3 nucleotides in size and/or sequence, and wherein a third PCR reaction comprises a set of 2 forward primers, each forward primer of said set comprising a different one of SEQ ID NOs: 78 and 79 or variant thereof differing by 1 to 3 nucleotides in size and/or sequence, and a set of 13 reverse primers, each reverse primer of said set comprising a different one of SEQ ID NOs: 65-77 or variant thereof differing by 1 to 3 nucleotides in size and/or sequence.

21. The method of claim 20, wherein said first PCR reaction comprises a set of 23 forward primers, each forward primer of said set consisting of a different one of SEQ ID NOs: 42-64 or variant thereof differing by 1 to 3 nucleotides in size and/or sequence, and a set of 9 reverse primers, each reverse primer of said set consisting of a different one of SEQ ID NOs: 65-73 or variant thereof differing by 1 to 3 nucleotides in size and/or sequence, wherein said second PCR reaction comprises a set of 23 forward primers, each forward primer of said set consisting of a different one of SEQ ID NOs: 42-64 or variant thereof differing by 1 to 3 nucleotides in size and/or sequence, and a set of 4 reverse primers, each reverse primer of said set consisting of a different one of SEQ ID NOs: 74-77 or variant thereof differing by 1 to 3 nucleotides in size and/or sequence, and wherein said third PCR reaction comprises a set of 2 forward primers, each forward primer of said set consisting of a different one of SEQ ID NOs: 78 and 79 or variant thereof differing by 1 to 3 nucleotides in size and/or sequence, and a set of 13 reverse primers, each reverse primer of said set consisting of a different one of SEQ ID NOs: 65-77 or variant thereof differing by 1 to 3 nucleotides in size and/or sequence.

22. The method of claim 20, wherein said first PCR reaction comprises a set of 23 forward primers, each forward primer of said set comprising a different one of SEQ ID NOs: 42-64, and a set of 9 reverse primers, each reverse primer of said set comprising a different one of SEQ ID NOs: 65-73, wherein said second PCR reaction comprises a set of 23 forward primers, each forward primer of said set comprising a different one of SEQ ID NOs: 42-64, and a set of 4 reverse primers, each reverse primer of said set comprising a different one of SEQ ID NOs: 74-77, and wherein said third PCR reaction comprises a set of 2 forward primers, each forward primer of said set comprising a different one of SEQ ID NOs: 78 and 79, and a set of 13 reverse primers, each reverse primer of said set comprising a different one of SEQ ID NOs: 65-77.

23. The method of claim 20, wherein said first PCR reaction comprises a set of 23 forward primers, each forward primer of said set consisting of a different one of SEQ ID NOs: 42-64, and a set of 9 reverse primers, each reverse primer of said set consisting of a different one of SEQ ID NOs: 65-73, wherein said second PCR reaction comprises a set of 23 forward primers, each forward primer of said set consisting of a different one of SEQ ID NOs: 42-64, and a set of 4 reverse primers, each reverse primer of said set consisting of a different one of SEQ ID NOs: 74-77, and wherein said third PCR reaction comprises a set of 2 forward primers, each forward primer of said set consisting of a different one of SEQ ID NOs: 78 and 79, and a set of 13 reverse primers, each reverse primer of said set consisting of a different one of SEQ ID NOs: 65-77.

24. A method for detecting a Dβ-Jβ TCRB rearrangement, comprising using a set of 2 forward primers, each forward primer of said set comprising a different one of SEQ ID NOs: 78 and 79 or variant thereof differing by 1 to 3 nucleotides in size and/or sequence, and a set of 13 reverse primers, each reverse primer of said set comprising a different one of SEQ ID NOs: 65-77 or variant thereof differing by 1 to 3 nucleotides in size and/or sequence to amplify the TCRB locus in a sample.

25. The method of claim 24, wherein each forward primer of said set consists of a different one of SEQ ID NOs: 78 and 79 or variant thereof differing by 1 to 3 nucleotides in size and/or sequence, and wherein each reverse primer of said set consists of a different one of SEQ ID NOs: 65-77 or variant thereof differing by 1 to 3 nucleotides in size and/or sequence.

26. The method of claim 24, wherein each forward primer of said set comprises a different one of SEQ ID NOs: 78 and 79, and wherein each reverse primer of said set comprises a different one of SEQ ID NOs: 65-77.

27. The method of claim 24, wherein each forward primer of said set consists of a different one of SEQ ID NOs: 78 and 79, and wherein each reverse primer of said set consists of a different one of SEQ ID NOs: 65-77.

* * * * *